United States Patent
Crowe et al.

(10) Patent No.: US 11,401,327 B2
(45) Date of Patent: Aug. 2, 2022

(54) POLYPEPTIDES WHICH BIND TO INTERLEUKIN-6 RECEPTOR (IL-6R)

(71) Applicant: Sorriso Pharmaceuticals, Inc., San Diego, CA (US)

(72) Inventors: Scott Crowe, Babraham (GB); Tim Carlton, Babraham (GB); Marion Cubitt, Babraham (GB); Kevin Roberts, Babraham (GB); Luana Maggiore, Babraham (GB); Mike West, Babraham (GB); Keith Ray, Babraham (GB)

(73) Assignee: SORRISO PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 16/750,516

(22) Filed: Jan. 23, 2020

(65) Prior Publication Data

US 2020/0291108 A1  Sep. 17, 2020

Related U.S. Application Data

(63) Continuation of application No. 16/041,652, filed on Jul. 20, 2018, now abandoned, which is a continuation of application No. PCT/EP2017/051237, filed on Jan. 20, 2017.

(30) Foreign Application Priority Data

Jan. 21, 2016  (EP) .................................... 16152321
Sep. 30, 2016  (EP) .................................... 16191988

(51) Int. Cl.
  *C07K 16/28* (2006.01)
  *A61P 29/00* (2006.01)
  *A61K 9/00* (2006.01)
  *C07K 16/24* (2006.01)
  *A61K 39/00* (2006.01)

(52) U.S. Cl.
  CPC .......... *C07K 16/248* (2013.01); *A61K 9/0053* (2013.01); *A61P 29/00* (2018.01); *C07K 16/2866* (2013.01); *A61K 2039/505* (2013.01); *A61K 2039/542* (2013.01); *C07K 2317/22* (2013.01); *C07K 2317/33* (2013.01); *C07K 2317/565* (2013.01); *C07K 2317/567* (2013.01); *C07K 2317/569* (2013.01); *C07K 2317/73* (2013.01); *C07K 2317/76* (2013.01); *C07K 2317/92* (2013.01); *C07K 2317/94* (2013.01)

(58) Field of Classification Search
  CPC .............. C07K 16/248; C07K 16/2866; C07K 2317/76; C07K 2317/22; C07K 2317/33; C07K 2317/565; C07K 2317/567; C07K 2317/569; C07K 2317/73; C07K 2317/92; C07K 2317/94; A61P 29/00; A61K 9/0053; A61K 2039/505; A61K 2039/542
  See application file for complete search history.

(56) References Cited

FOREIGN PATENT DOCUMENTS

WO   WO-2008020079 A1   2/2008
WO   WO-2008149143 A2   12/2008
WO   WO-2010115998 A2   10/2010

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Arbabi-Ghahroudi et al.: Selection and identification of single domain antibody fragments from camel heavy-chain antibodies. FEBS Letters 414(3):521-526 (1997).
Biancheri et al.: Proteolytic cleavage and loss of function of biologic agents that neutralize tumor necrosis factor in the mucosa of patients with inflammatory bowel disease. Gastroenterology 149(6):1564-1574 (2015).
Blattler et al. New heterobifunctional protein crosslinking reagent that forms an acid-labile link. Biochemistry 24(6):1517-1524 (1985).
Chomczynski, et al. Single-step method of RNA isolation by acid guanidinium thiocyanate-phenol-chloroform extraction. Anal Biochem. 162(1):156-9 (1987).
Faisst et al.: Isolation of a fully infectious variant of parvovirus H-1 supplanting the standard strain in human cells. Journal of Virology 69(7):4538-4543 (1995).
Frenken et al.: Isolation of antigen specific llama VHH antibody fragments and their high level secretion by *Saccharomyces cerevisiae*. J Biotechnol 78(1):11-21 (2000).
Griffiths et al.: Shark Variable New Antigen Receptor (VNAR) Single Domain Antibody Fragments: Stability and Diagnostic Applications. Antibodies 2(1):66-81 (2013).
Grundstrom et al.: Oligonucleotide-directed mutagenesis by microscale 'shot-gun' gene synthesis. Nucleic Acids Research 13(9):3305-3316 (1985).
Gustot et al.: Profile of soluble cytokine receptors in Crohn's disease. Gut. 54(4):488-495 (2005).
Hamers-Casterman et al. Naturally occurring antibodies devoid of light chains. Nature 363(6428):446-8 (1993).
Harmsen et al.: Effect of a pmr 1 disruption and different signal sequences on the intracellular processing and secretion of Cyamopsis tetragonoloba alpha-galactosidase by *Saccharomyces cerevisiae*. Gene 125(2):115-123 (1993).

(Continued)

*Primary Examiner* — Robert S Landsman
(74) *Attorney, Agent, or Firm* — Wilson Sonsini Goodrich & Rosati

(57) ABSTRACT

There is provided inter alia a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein CDR1-CDR3 and FR1-FR4 are as defined in the specification.

8 Claims, 33 Drawing Sheets

Specification includes a Sequence Listing.

(56) References Cited

OTHER PUBLICATIONS

Harmsen et al. Properties, production, and applications of camelid single-domain antibody fragments. Appl. Microbiol. Biotechnol. 77:13-22 (2007).
Harmsen et al.: Selection and Optimization of Proteolytically Stable Llama Single-Domain Antibody Fragments for Oral Immunotherapy. Applied Microbiology and Biotechnology 72(3):544-551 (2006).
Hendrickson et al.: Clinical aspects and pathophysiology of inflammatory bowel disease. Clinical Microbiology Reviews 15(1):79-94 (2002).
Hoogenboom et al. Multi-subunit proteins on the surface of filamentous phage: methodologies for displaying antibody (Fab) heavy and light chains. Nucleic Acids Res. 19(15):4133-4137 (1991).
Hosokawa et al.: Interleukin-6 and soluble interleukin-6 receptor in the colonic mucosa of inflammatory bowel disease. Journal of Gastroenterology and Hepatology 14(10):987-996 (1999).
Huse et al. Generation of a large combinatorial library of the immunoglobulin repertoire in phage lambda. Science 246(4935):1275-1281 (1989).
Hussack et al. Engineered Single-Domain Antibodies with High Protease Resistance and Thermal Stability. PLoS One 6(11):e28218 (2011).
Ito et al.: A pilot randomized trial of a human anti-interleukin-6 receptor monoclonal antibody in active Crohn's disease. Gastroenterology 126(4):989-996 (2004).
Katoh et al.: MAFFT multiple sequence alignment software version 7: improvements in performance and usability. Mol Biol Evol. 30(4):772-780 (2013).
Koh et al.: Generation of a family-specific phage library of llama single chain antibody fragments that neutralize HIV-1. Journal of Biological Chemistry 285(25):19116-19124 (2010).
Kohler et al. Continuous cultures of fused cells secreting antibody of predefined specificity. Nature256(5517):495-497 (1975).
Kusugami et al.: Elevation of interleukin-6 in inflammatory bowel disease is macrophage- and epithelial cell-dependent. Dig Dis Sci. 40(5):949-959 (1995).
Ling et al.: Approaches to DNA Mutagenesis: An Overview. Analytical Biochemistry 254(2):157-178 (1997).
McCoy et al.: Neutralisation of HIV-1 cell-cell spread by human and llama antibodies. Retrovirology 11:83 (2014).
Merchlinsky et al.: Construction of an infectious molecular clone of the autonomous parvovirus minute virus of mice. Journal of Virology 47(1):227-232 (1983).
Miethe et al.: Production of Single Chain Fragment Variable (scFv) Antibodies in *Escherichia coli* Using the LEX TM Bioreactor. Journal of Biotechnology 163(2):105-111 (2012).
Mitsuyama et al.: Therapeutic strategies for targeting the IL-6/STAT3 cytokine signaling pathway in inflammatory bowel disease. Anticancer Research 27(6A):3749-3756 (2007).
Muyldermans. Nanobodies: natural single-domain antibodies. Annu Rev Biochem 82:775-797 (2013).
Muyldermans et al. Sequence and structure of VH domain from naturally occurring camel heavy chain immunoglobulins lacking light chains. Protein Engineering 7(9):1129-1133 (1994).
Nambiar, et al. Total synthesis and cloning of a gene coding for the ribonuclease S protein. Science 223(4642):1299-301 (1984).
Nelson et al.: Monoclonal antibodies. Mol Pathol. 53(3):111-117 (2000).
Nguyen et al.: Functional heavy-chain antibodies in Camelidae. Advances in Immunology 79:261-296 (2001).
Ortonne. Recent developments in the understanding of the pathogenesis of psoriasis. British Journal of Dermatology 140(Suppl 54):1-7 (1999).
Padlan. Anatomy of the Antibody Molecule. Mol Immunol 31(3):169-217 (1994).
PCT/EP2017/051237 International Search Report and Written Opinion dated Jun. 1, 2017.
Reimund et al.: Increased production of tumour necrosis factor-alpha interleukin-1 beta, and interleukin-6 by morphologically normal intestinal biopsies from patients with Crohn's disease. Gut 39(5):684-689 (1996).
Reimund et al.: Mucosal inflammatory cytokine production by intestinal biopsies in patients with ulcerative colitis and Crohn's disease. Journal of Clinical Immunology 16(3):144-150 (1996).
Reinecker et al., Enhanced secretion of tumor necrosis factor-alpha, IL-6 and IL-1 beta by isolated lamina propia mononuclear cells from patients with ulcerative colitis and Crohn's disease Clin Exp Immunol 94:174-181 (1993).
Rose-John: IL-6 trans-signaling via the soluble IL-6 receptor: importance for the pro-inflammatory activities of IL-6. Int. J. Biol. Sci. 8(9):1237-1247 (2012).
Roux et al.: Structural analysis of the nurse shark (new) antigen receptor (NAR): molecular convergence of NAR and unusual mammalian immunoglobulins. PNAS USA 95(20):11804-11809 (1998).
Sakmar et al.: Total synthesis and expression of a gene for the alpha-subunit of bovine rod outer segment guanine nucleotide-binding protein (transducin). Nucleic Acids Research 16(14A):6361-6372 (1988).
Skerra et al. Assembly of a functional Immunoglobulin Fv fragment in *Escherichia coli*. Science 240(4855):1038-1041 (1988).
Tanha et al.: Selection by phage display of llama conventional V(H) fragments with heavy chain antibody V(H)H properties. Journal of Immunological Methods 263(1-2):97-109 (2002).
Thomassen et al.: Large-scale production of VHH antibody fragments by *Saccharomyces cerevisiae*. Enzyme and Microbial Technology 30(3):273-278 (2002).
U.S. Appl. No. 16/041,652 Office Action dated Aug. 29, 2019.
Vandenbroucke et al. Orally administered L. lactis secreting an anti-TNF nanobody demonstrate efficacy in chronic colitis. Mucosal Immunology 3(1):49-56 (2010).
Verma et al. Modified oligonucleotides: synthesis and strategy for users. Annu Rev Biochem 67:99-134 (1998).
Vossenkamper et al.: A CD3-specific antibody reduces cytokine production and alters phosphoprotein profiles in intestinal tissues from patients with inflammatory bowel disease. Gastroenterology 147(1):172-183 (2014).
Waetzig et al.: Hitting a complex target: an update on interleukin-6 trans-signalling. Expert Opin Ther Targets. 16(2):225-236 (2012).
Ward et al. Binding activities of a repertoire of single immunoglobulin variable domains secreted from *Escherichia coli*. Nature 341(6242):544-546 (1989).
Wells et al. Cassette mutagenesis: an efficient method for generation of multiple mutations at defined sites. Gene 34:315-323 (1985).

\* cited by examiner

Figure 24

Inhibition of Phosphoproteins in Crohn's Biopsy Tissue by IL-6R Neutralising ICVD ID-142V

Figure 26

POLYPEPTIDES WHICH BIND TO INTERLEUKIN-6 RECEPTOR (IL-6R)

CROSS REFERENCE

This application is a continuation of U.S. application Ser. No. 16/041,652 filed on Jul. 20, 2018 (Jul. 20, 2018), now abandoned, which is a continuation of international application PCT/EP2017/051237 filed on Jan. 20, 2017 which derives priority from EP 16152321.2 filed on Jan. 21, 2016 and EP 16191988.1 filed on Sep. 30, 2016, the contents of each of which are herein incorporated by reference in their entirety.

FIELD OF THE INVENTION

The present invention relates to polypeptides comprising an immunoglobulin chain variable domain (or 'ICVD') which binds to the interleukin-6 receptor (IL-6R) as well as to constructs and pharmaceutical compositions comprising these polypeptides. The present invention also relates to nucleic acids encoding such polypeptides, to methods for preparing such polypeptides, to cDNA and vectors comprising nucleic acids encoding such polypeptides, to host cells expressing or capable of expressing such polypeptides and to uses of such polypeptides, pharmaceutical compositions or constructs.

BACKGROUND OF THE INVENTION

IL-6 induces cell activation via a receptor system that consists of two receptor chains: a ligand-specific non-signalling transmembrane IL-6 receptor alpha subunit (the membrane-bound form of IL-6R, also known as mIL-6R, IL-6Rα, gp80 and CD126) and a second trans-membrane receptor chain gp130 that is required for signal transduction. In classical (cis) IL-6 signalling, IL-6 first binds to the membrane IL-6Ra subunit, which in turn associates with gp130 to form an IL-6-receptor complex that is able to induce cell activation. The restricted expression of membrane IL-6Rα receptors limits this classical IL-6 signalling mechanism to a few cell types including hepatocytes, neutrophils, monocyte/macrophages, some lymphocyte subtypes and intestinal epithelial cells. A second form of the IL-6R comprising the extracellular ligand-binding region of the IL-6Ra-subunit has also been identified. The soluble form of the IL-6R (sIL-6R) is generated by protease mediated shedding of IL-6Rα ecto-domains from membrane IL-6R expressing cells or is secreted from the cells as an alternatively spliced product. Importantly, IL-6 can still bind to the sIL-6R and the IL-6/sIL-6R complexes formed can associate with gp130-receptor chains to induce signalling. As a wide range of cells express gp130 but not the IL-6R, this process termed "trans-signalling" provides a mechanism for extending the range of cell types that are capable of responding to IL-6 and this process appears to be particularly important for the development and perpetuation of chronic inflammation (Rose-John 2012).

Inhibition of the IL-6R has potential for therapeutic benefit in autoimmune diseases such as Crohn's disease (CD) and ulcerative colitis (UC). Systemically administered IL-6 pathway antagonists including both IL-6 and IL-6R blocking antibodies have demonstrated efficacy without major toxicity in inflammatory diseases including rheumatoid arthritis and Castleman's disease. Tocilizumab, a humanised IL-6R monoclonal antibody that targets both membrane and soluble IL-6Rs (cis/trans signalling inhibitor) has also shown evidence of clinical efficacy in a pilot clinical study in patients with Crohn's disease (Ito et al., 2004).

CD and UC are diseases of the gastrointestinal tract in which excessive production of IL-6 and the release of sIL-6R are both localised within inflamed mucosal and sub-mucosal intestinal tissues. Preclinical studies have shown that the production of IL-6 in ex vivo cultures of inflamed IBD tissue greatly exceeds the release of sIL-6Rs. The ability to deliver an oral therapeutic agent with exposure and IL-6R antagonist activity limited to the gut offers potential for efficacy similar to (or greater than) tocilizumab, but with potentially improved safety due to the reduced systemic exposure. Unlike tocilizumab (or other systemically administered anti-IL-6R targeted antibodies), an orally delivered IL-6R antagonist would not be required to neutralise the large pool of sIL-6R that is present in the circulation in addition to the neutralisation of tissue sIL-6R production.

In inflamed IBD tissue, the production of IL-6 and shedding of IL-6Rs from activated macrophages results in the formation of soluble IL-6/sIL-6R complexes that can activate trans-signalling in cells that express only the IL-6R gp130 subunit. This mechanism, which extends IL-6 responsiveness to an increased number of target cells, is considered to play an important role in the orchestration of mucosal inflammatory processes. The mechanism of IL-6 induced intestinal epithelial cell proliferation and regeneration is thought to involve signal transduction mediated via membrane bound IL-6 receptors (cis-signalling) (Rose-John, 2012). The anti-human IL-6R antibody tocilizumab blocks both IL-6R classic signalling and IL-6/sIL-6R mediated trans-signalling and therefore blocks both pro-inflammatory and potentially protective activities of IL-6. A rationale for the development of selective antagonists of IL6-trans-signalling has been proposed based on the concept that this might avoid the inhibition of potential beneficial epithelial regenerative effects of IL-6 (see Rose-John, 2012; Waetzig et al., 2012) that are mediated via mIL-6Rs (cis-signalling). An oral IL-6R antagonist with this profile could have safety and efficacy advantages over existing IL-6 neutralising antibodies for the treatment of Crohn's disease based on anti-inflammatory and improved mucosal healing properties.

WO2008020079, WO2008071685, WO2009095489, WO2010115995, WO2010115998 and WO2013041722 (herein incorporated by reference in their entirety) disclose single domain antibodies directed against IL-6R and related aspects.

Polypeptides of the present invention may, in at least some embodiments, have one or more of the following advantages compared to anti-IL-6R substances of the prior art:

(i) increased affinity for IL-6R;
(ii) increased specificity for IL-6R;
(iii) increased neutralising capability against IL-6R;
(iv) increased cross-reactivity with I L-6R from different species such as human and cynomolgus monkey;
(v) reduced immunogenicity, for example when administered to a mouse, cynomolgus monkey or human;
(vi) increased stability in the presence of proteases, for example (a) in the presence of proteases found in the small and/or large intestine and/or IBD inflammatory proteases, for example trypsin, chymotrypsin, MMP3, MMP10, MMP12, other MMPs and cathepsin and/or (b) in the presence of proteases from gut commensal microflora and/or pathogenic bacteria, actively secreted and/or released by lysis of microbial cells found in the small and/or large intestine;
(vii) increased stability to protease degradation during production (for example resistance to yeast proteases);
(viii) increased suitability for oral administration;
(ix) increased suitability for local delivery to the intestinal tract and lamina propria following oral administration;
(x) increased suitability for expression, in a heterologous host such as bacteria such as *Escherichia coli*, or a yeast or mould (e.g. those belonging to the genera *Aspergillus, Saccharomyces, Kluyveromyces, Hansenula* or *Pichia*, such as *Saccharomyces cerevisiae* or *Pichia pastoris*);
(xi) suitability for, and improved properties for, use in a pharmaceutical;
(xii) suitability for, and improved properties for, use in a functional food;
(xiii) improved tissue penetration such as penetration of inflamed colonic mucosal epithelium and submucosal tissues to access the sub mucosal lamina propria;
(xiv) increased suitability for formatting in a multispecific format;
(xv) increased selectivity for inhibition of IL-6R trans-signalling over cis-signalling;
(xvi) binding to novel epitopes.

Advantages (i) to (xvi) above may potentially be realised by the polypeptides of the present invention in a monovalent format or in a multivalent format such as a bihead format (for example homobihead or heterobihead formats).

SUMMARY OF THE INVENTION

The present inventors have produced surprisingly advantageous polypeptides comprising immunoglobulin chain variable domains which bind to IL-6R. These polypeptides in particular benefit from surprisingly high potency. In some embodiments, they are also capable of cross-reacting with cynomolgus monkey IL-6R and in some embodiments, remain stable on exposure to proteases of the small and large intestine.

In one embodiment, these polypeptides have undergone further enhancement by engineering. These further enhanced polypeptides benefit from the above advantages, retain their IL-6R-neutralising activity during passage through the intestinal tract and further resist degradation and/or inactivation by proteases of the intestinal tract, for example, digestive, inflammatory and microbial proteases from, for example, multiple mammalian species (rodent, pig, non-human primate and human).

It may be expected that these polypeptides have particular utility in the prevention or treatment of autoimmune and or inflammatory disease such as inflammatory bowel disease (for example Crohn's disease or ulcerative colitis), or in the prevention or treatment of mucositis, particularly when administered orally.

The present invention provides a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein CDR3 comprises a sequence sharing 75% or greater sequence identity with SEQ ID NO: 3.

The present invention also provides a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein CDR3 comprises a sequence sharing 50% or greater sequence identity with SEQ ID NO: 3 and wherein the immunoglobulin chain variable domain comprises one or more amino acids selected from V33, G52, G56 and Y93, and optionally one or more amino acids selected from T18, T21 and F62, according to Kabat numbering.

DESCRIPTION OF THE FIGURES

FIG. 24—Phosphoprotein signals (% inhibition vs control) in Crohn's disease biopsy tissue (ID-142V, phosphoproteins ALK to Axl)

FIG. 26—Phosphoprotein signals in ulcerative colitis biopsy tissue (ID-142V, phosphoproteins ErbB1 to Ret)

DESCRIPTION OF THE SEQUENCES

Figure 1:
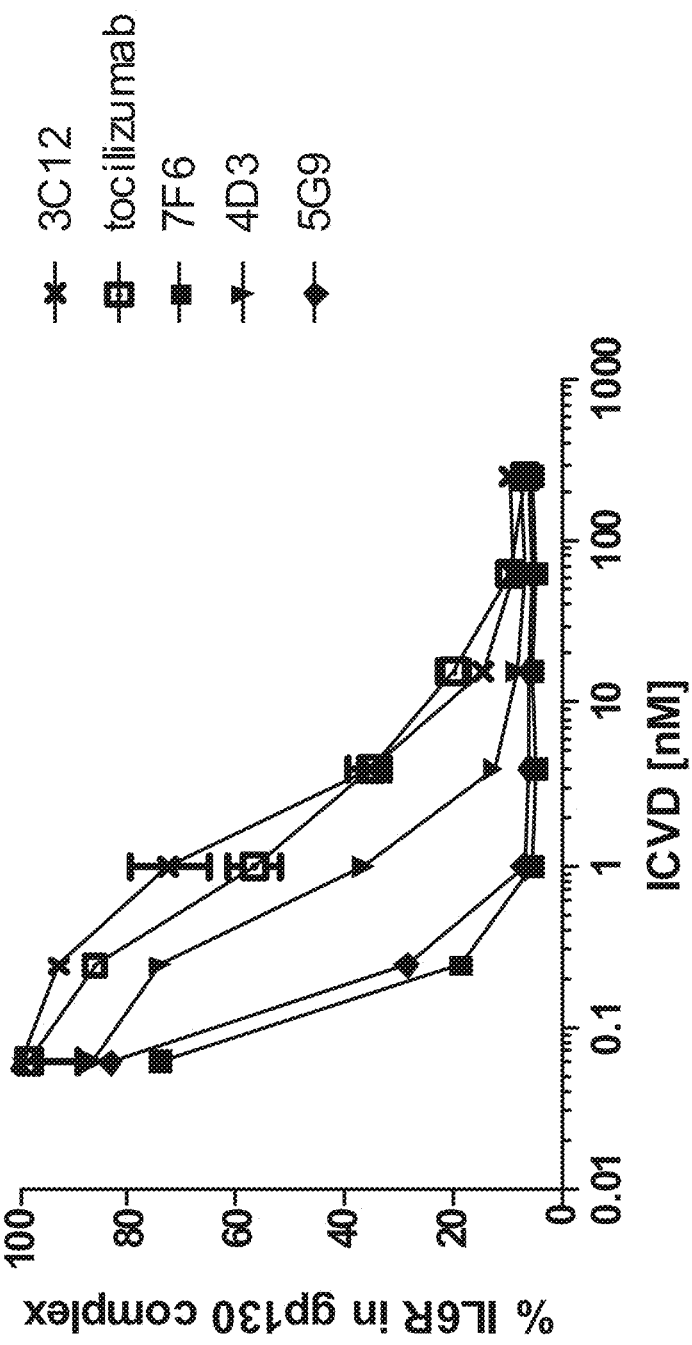
FIG. 1—Inhibition of IL-6/IL-6R/gp130 interaction by ICVDs (3C12, tocilizumab, 7F6, 4D3 and 5G9)

SEQ ID NO: 1—Polypeptide sequence of ID-142V CDR1
SEQ ID NO: 2—Polypeptide sequence of ID-142V CDR2
SEQ ID NO: 3—Polypeptide sequence of ID-142V CDR3
SEQ ID NO: 4—Polypeptide sequence of ID-142V FR1
SEQ ID NO: 5—Polypeptide sequence of ID-142V FR2
SEQ ID NO: 6—Polypeptide sequence of ID-142V FR3
SEQ ID NO: 7—Polypeptide sequence of ID-142V FR4
SEQ ID NO: 8—Polypeptide sequence of ID-40V CDR1
SEQ ID NO: 9—Polypeptide sequence of ID-40V CDR2
SEQ ID NO: 10—Polypeptide sequence of ID-40V FR1
SEQ ID NO: 11—Polypeptide sequence of ID-40V FR2
SEQ ID NO: 12—Polypeptide sequence of ID-40V FR3
SEQ ID NO: 13—Polynucleotide sequence of 3' primer
SEQ ID NO: 14—Polypeptide sequence of ID-40V CDR3
SEQ ID NO: 15—Polypeptide sequence of 5G9
SEQ ID NO: 16—Polypeptide sequence of ID-52V
SEQ ID NO: 17—Polypeptide sequence of ID-53V
SEQ ID NO: 18—Polypeptide sequence of ID-54V
SEQ ID NO: 19—Polypeptide sequence of ID-55V
SEQ ID NO: 20—Polypeptide sequence of ID-56V
SEQ ID NO: 21—Polypeptide sequence of ID-57V
SEQ ID NO: 22—Polypeptide sequence of ID-58V
SEQ ID NO: 23—Polypeptide sequence of ID-59V
SEQ ID NO: 24—Polypeptide sequence of ID-112V
SEQ ID NO: 25—Polypeptide sequence of ID-114V
SEQ ID NO: 26—Polypeptide sequence of ID-122V
SEQ ID NO: 27—Polypeptide sequence of ID-123V
SEQ ID NO: 28—Polypeptide sequence of ID-141V
SEQ ID NO: 29—Polypeptide sequence of ID-142V
SEQ ID NO: 30—Polypeptide sequence of ID-143V
SEQ ID NO: 31—Polypeptide sequence of ID-144V
SEQ ID NO: 32—Polypeptide sequence of 7F6
SEQ ID NO: 33—Polypeptide sequence of ID-3V
SEQ ID NO: 34—Polypeptide sequence of ID-6V
SEQ ID NO: 35—Polypeptide sequence of ID-40V
SEQ ID NO: 36—Polypeptide sequence of ID-47V
SEQ ID NO: 37—Polypeptide sequence of ID-49V
SEQ ID NO: 38—Polypeptide sequence of ID-50V
SEQ ID NO: 39—Polypeptide sequence of 21E6
SEQ ID NO: 40—Polypeptide sequence of 4D3
SEQ ID NO: 41—Polypeptide sequence of 3C12
SEQ ID NO: 42—Polypeptide sequence of 20A11
SEQ ID NO: 43—Polypeptide sequence of ID-74V
SEQ ID NO: 44—Polypeptide sequence of ID-75V
SEQ ID NO: 45—Polypeptide sequence of ID-2A
SEQ ID NO: 46—Polypeptide sequence of ID-58V CDR2
SEQ ID NO: 47—Polypeptide sequence of ID-59V CDR2
SEQ ID NO: 48—Polypeptide sequence of CDR3 of multiple ICVDs including 5G9
SEQ ID NO: 49—Polypeptide sequence of ID-53V CDR3
SEQ ID NO: 50—Polypeptide sequence of CDR3 of multiple ICVDs including ID-143V
SEQ ID NO: 51—Polypeptide sequence of 7F6 CDR3
SEQ ID NO: 52—Polypeptide sequence of ID-3V CDR3
SEQ ID NO: 53—Polypeptide sequence of ID-6V CDR3
SEQ ID NO: 54—Polynucleotide sequence encoding human IL-6R
SEQ ID NO: 55—Polypeptide sequence of ID-47V CDR3
SEQ ID NO: 56—Polypeptide sequence of ID-49V CDR3
SEQ ID NO: 57—Polypeptide sequence of ID-50V CDR3
SEQ ID NO: 58—Polypeptide sequence of 21E6 CDR3
SEQ ID NO: 59—Polynucleotide sequence encoding 5G9
SEQ ID NO: 60—Polynucleotide sequence encoding 5G9 (codon optimised for *S. cerevisiae*)
SEQ ID NO: 61—Polynucleotide sequence encoding 7F6
SEQ ID NO: 62—Polynucleotide sequence encoding 21E6
SEQ ID NO: 63—Polynucleotide sequence encoding ID-52V
SEQ ID NO: 64—Polynucleotide sequence encoding ID-53V
SEQ ID NO: 65—Polynucleotide sequence encoding ID-54V
SEQ ID NO: 66—Polynucleotide sequence encoding ID-55V
SEQ ID NO: 67—Polynucleotide sequence encoding ID-56V
SEQ ID NO: 68—Polynucleotide sequence encoding ID-57V
SEQ ID NO: 69—Polynucleotide sequence encoding ID-58V
SEQ ID NO: 70—Polynucleotide sequence encoding ID-59V
SEQ ID NO: 71—Polynucleotide sequence encoding ID-74V
SEQ ID NO: 72—Polynucleotide sequence encoding ID-75V
SEQ ID NO: 73—Polynucleotide sequence encoding ID-112V
SEQ ID NO: 74—Polynucleotide sequence encoding ID-114V
SEQ ID NO: 75—Polynucleotide sequence encoding ID-122V
SEQ ID NO: 76—Polynucleotide sequence encoding ID-123V
SEQ ID NO: 77—Polynucleotide sequence encoding ID-141V
SEQ ID NO: 78—Polynucleotide sequence encoding ID-142V
SEQ ID NO: 79—Polynucleotide sequence encoding ID-143V
SEQ ID NO: 80—Polynucleotide sequence encoding ID-144V
SEQ ID NO: 81—Polypeptide sequence of human IL-6R (NCBI Reference Sequence NP_000556.1)
SEQ ID NO: 82—Polypeptide sequence of mature human IL-6R (cleaved at L20)
SEQ ID NO: 83—Polypeptide sequence of soluble human IL-6R isoform produced by differential mRNA splicing
SEQ ID NO: 84—Polypeptide sequence of soluble human IL-6R isoform produced by protease shedding
SEQ ID NO: 85—Polypeptide sequence of predicted full length precursor cynomolgous monkey IL-6R (NCBI Reference Sequence: XP_005541720.1)
SEQ ID NO: 86—Polypeptide sequence of FR1 of ID-141V, ID-142V, ID-143V and ID-144V SEQ ID NO: 87—Polypeptide sequence of FR2 of ID-141V, ID-142V, ID-143V and ID-144V SEQ ID NO: 88—Polypeptide sequence of FR3 of ID-141V and ID-143V SEQ ID NO: 89—Polypeptide sequence of FR3 of ID-142V and ID-144V SEQ ID NO: 90—Polypeptide sequence of FR4 of ID-141V, ID-142V, ID-143V and ID-144V SEQ ID NO: 91—Polypeptide VHHR sequence of 7F6

SEQ ID NO: 92—Polypeptide VHHR sequence of 5G9

SEQ ID NO: 93—Polypeptide VHHR sequence of 21E6

SEQ ID NO: 94—Polypeptide germline equivalent sequence of 7F6

SEQ ID NO: 95—Polypeptide germline equivalent sequence of 5G9

SEQ ID NO: 96—Polypeptide germline equivalent sequence of 21E6

DETAILED DESCRIPTION OF THE INVENTION

Polypeptides Including Antibodies and Antibody Fragments Including the VH and VHH A conventional antibody or immunoglobulin (Ig) is a protein comprising four polypeptide chains: two heavy (H) chains and two light (L) chains. Each chain is divided into a constant region and a variable domain. The heavy chain variable domains are abbreviated herein as VHC, and the light (L) chain variable domains are abbreviated herein as VLC. These domains, domains related thereto and domains derived therefrom, are referred to herein as immunoglobulin chain variable domains. The VHC and VLC domains can be further subdivided into regions of hypervariability, termed "complementarity determining regions" ("CDRs"), interspersed with regions that are more conserved, termed "framework regions" ("FRs"). The framework and complementarity determining regions have been precisely defined (Kabat et al., 1991, herein incorporated by reference in its entirety). In a conventional antibody, each VHC and VLC is composed of three CDRs and four FRs, arranged from amino-terminus to carboxy-terminus in the following order: FR1, CDR1, FR2, CDR2, FR3, CDR3, FR4. The conventional antibody tetramer of two heavy immunoglobulin chains and two light immunoglobulin chains is formed with the heavy and the light immunoglobulin chains inter-connected by e.g. disulfide bonds, and the heavy chains similarity connected. The heavy chain constant region includes three domains, CH1, CH2 and CH3. The light chain constant region is comprised of one domain, CL. The variable domain of the heavy chains and the variable domain of the light chains are binding domains that interact with an antigen. The constant regions of the antibodies typically mediate the binding of the antibody to host tissues or factors, including various cells of the immune system (e.g. effector cells) and the first component (C1 q) of the classical complement system. The term antibody includes immunoglobulins of types IgA, IgG, IgE, IgD, IgM (as well as subtypes thereof), wherein the light chains of the immunoglobulin may be kappa or lambda types. The overall structure of immunoglobulin-gamma (IgG) antibodies assembled from two identical heavy (H)-chain and two identical light (L)-chain polypeptides is well established and highly conserved in mammals (Padlan 1994).

An exception to conventional antibody structure is found in sera of Camelidae. In addition to conventional antibodies, these sera possess special IgG antibodies. These IgG antibodies, known as heavy-chain antibodies (HCAbs), are devoid of the L chain polypeptide and lack the first constant domain (CH1). At its N-terminal region, the H chain of the homodimeric protein contains a dedicated immunoglobulin chain variable domain, referred to as the VHH, which serves to associate with its cognate antigen (Muyldermans 2013, Hamers-Casterman et al., 1993, Muyldermans et al., 1994, herein incorporated by reference in their entirety).

An antigen-binding fragment (or "antibody fragment", "immunoglobulin fragment" or "antigen-binding polypeptide") as used herein refers to a portion of an antibody that specifically binds to IL-6R (e.g. a molecule in which one or more immunoglobulin chains is not full length, but which specifically binds to IL-6R). Examples of binding fragments encompassed within the term antigen-binding fragment include:

(i) a Fab fragment (a monovalent fragment consisting of the VLC, VHC, CL and CH1 domains);

(ii) a F(ab')2 fragment (a bivalent fragment comprising two Fab fragments linked by a disulfide bridge at the hinge region);

(iii) a Fd fragment (consisting of the VHC and CH1 domains);

(iv) a Fv fragment (consisting of the VLC and VHC domains of a single arm of an antibody);

(v) an scFv fragment (consisting of VLC and VHC domains joined, using recombinant methods, by a synthetic linker that enables them to be made as a single protein chain in which the VLC and VHC regions pair to form monovalent molecules);

(vi) a VH (an immunoglobulin chain variable domain consisting of a VHC domain (Ward et al., 1989);

(vii) a VL (an immunoglobulin chain variable domain consisting of a VLC domain);

(viii) a V-NAR (an immunoglobulin chain variable domain consisting of a VHC domain from chondrichthyes IgNAR (Roux et al., 1998 and Griffiths et al., 2013, herein incorporated by reference in their entirety)

(ix) a VHH.

The total number of amino acid residues in a VHH or VH may be in the region of 110-140, is suitably 115-130, more suitably 120-125, most suitably 123.

Immunoglobulin chain variable domains of the invention may for example be obtained by preparing a nucleic acid encoding an immunoglobulin chain variable domain using techniques for nucleic acid synthesis, followed by expression of the nucleic acid thus obtained According to a specific embodiment, an immunoglobulin chain variable domain of the invention does not have an amino acid sequence which is exactly the same as (i.e. shares 100% sequence identity with) the amino acid sequence of a naturally occurring polypeptide such as a VH or VHH domain of a naturally occurring antibody.

The examples provided herein relate to immunoglobulin chain variable domains per se which bind to IL-6R. The principles of the invention disclosed herein are, however, equally applicable to any polypeptide comprising an immunoglobulin chain variable domain which binds to IL-6R, such as antibodies and antibody fragments. For example, the anti-IL-6R immunoglobulin chain variable domains disclosed herein may be incorporated into a polypeptide such as a full length antibody. Such an approach is demonstrated by McCoy et al., 2014, who provide an anti-HIV VHH engineered as a fusion with a human Fc region (including hinge, CH2 and CH3 domains), expressed as a dimer construct.

Substituting at least one amino acid residue in the framework region of a non human immunoglobulin variable domain with the corresponding residue from a human variable domain is humanisation. Humanisation of a variable domain may reduce immunogenicity in humans.

Suitably, the polypeptide of the present invention consists of an immunoglobulin chain variable domain. Suitably, the polypeptide of the present invention is an antibody or an antibody fragment. Suitably the antibody fragment is a VHH, a VH, a VL, a V-NAR, a Fab fragment, a VL or a F(ab')2 fragment (such as a VHH or VH, most suitably a VHH).

Specificity, Affinity, Avidity and Cross-Reactivity

Specificity refers to the number of different types of antigens or antigenic determinants to which a particular antigen-binding polypeptide can bind. The specificity of an antigen-binding polypeptide is the ability of the antigen-binding polypeptide to recognise a particular antigen as a unique molecular entity and distinguish it from another.

Affinity, represented by the equilibrium constant for the dissociation of an antigen with an antigen-binding polypeptide (Kd), is a measure of the binding strength between an antigenic determinant and an antigen-binding site on the antigen-binding polypeptide: the lesser the value of the Kd, the stronger the binding strength between an antigenic determinant and the antigen-binding polypeptide (alternatively, the affinity can also be expressed as the affinity constant (Ka), which is 1/Kd). Affinity can be determined by known methods, depending on the specific antigen of interest.

Avidity is the measure of the strength of binding between an antigen-binding polypeptide and the pertinent antigen. Avidity is related to both the affinity between an antigenic determinant and its antigen binding site on the antigen-binding polypeptide and the number of pertinent binding sites present on the antigen-binding polypeptide.

Suitably, antigen-binding polypeptides of the invention will bind with an equilibrium dissociation constant (Kd) of at least $1\times10^{-6}$ M, more suitably at least $1\times10^{-7}$ M, more suitably at least $1\times10^{-8}$ M, more suitably at least $1\times10^{-9}$ M.

Any Kd value less than $10^{-6}$ is considered to indicate binding. Specific binding of an antigen-binding polypeptide to an antigen or antigenic determinant can be determined in any suitable known manner, including, for example, Scatchard analysis and/or competitive binding assays, such as radioimmunoassays (RIA), enzyme immunoassays (EIA) and sandwich competition assays, and the different variants thereof known in the art.

An anti-IL-6R polypeptide, a polypeptide which interacts with IL-6R, or a polypeptide against IL-6R, are all effectively polypeptides which bind to IL-6R. A polypeptide of the invention may bind to a linear or conformational epitope on IL-6R. The term "binds to IL-6R" means binding to IL-6R wherein, for example, IL-6R may be comprised within the IL-6 receptor complex wherein the IL-6R receptor comprises gp130 and/or IL-6.

Suitably, the polypeptide of the invention will bind to both soluble and membrane IL-6R and more suitably with higher affinity to soluble IL-6R than membrane IL-6R. Suitably, the polypeptide of the invention will bind to human IL-6R. More suitably, the polypeptide of the invention will bind to both human and at least one additional primate IL-6R selected from the group consisting of baboon IL-6R, marmoset IL-6R, cynomolgus IL-6R and rhesus IL-6R. Most suitably, the polypeptide of the invention binds to both human and cynomolgus IL-6R.

Suitably, the polypeptide of the invention will neutralise both soluble and membrane IL-6R or more suitably only soluble IL-6R. Suitably, the polypeptide of the invention will neutralise human IL-6R. More suitably, the polypeptide of the invention will neutralise both human and at least one additional primate IL-6R selected from the group consisting of baboon IL-6R, marmoset IL-6R, cynomolgus IL-6R and rhesus IL-6R. Most suitably, the polypeptide of the invention neutralises both human and cynomolgus IL-6R.

Suitably, IL-6R is human or cynomolgous monkey soluble or membrane IL-6R. More suitably, IL-6R is IL-6R is human membrane or soluble IL-6R. More suitably, IL-6R is human soluble IL-6R.

Suitably IL-6R is a polypeptide comprising or more suitably consisting of any one of SEQ ID NO: 81-85. More suitably IL-6R is a polypeptide comprising or more suitably consisting of any one of SEQ ID NO: 81-84. Most suitably IL-6R is a polypeptide comprising or more suitably consisting of any one of SEQ ID NO: 82-84.

Polypeptides capable of reacting with IL-6R from humans and IL-6R from another species ("cross-reacting"), such as with cynomolgus monkey IL-6R, are advantageous because they allow preclinical studies to be more readily performed in animal models.

Suitably the polypeptide of the invention is directed against epitopes on IL-6R (and in particular epitopes on IL-6R which are exposed when IL-6R is comprised in an IL-6/IL-6R complex) that lie in and/or form part of the gp130-binding site(s) of the IL-6/IL-6R complex, such that said polypeptide of the invention, upon binding to IL-6R, results in inhibiting or reducing signalling mediated by the IL-6/IL-6R complex via gp130 association.

The polypeptides of the present invention bind to one or more epitope(s) on IL-6R. In one aspect of the invention there is provided a polypeptide which binds to at least a part of the same epitope on IL-6R, more suitably substantially the whole or the same epitope or most suitably the whole of the same epitope on IL-6R as 5G9, ID-52V, 1D-53V, ID-54V, ID-55V, ID-56V, ID-57V, ID-58V, ID-59V, ID-112V, ID-114V, 1D-122V, ID-123V, ID-141V, ID-142V, ID-143V, ID-144V, 7F6, ID-3V, ID-6V, ID-40V, ID-47V, ID-49V or ID-50V.

Suitably, the polypeptide of the invention is isolated. An "isolated" polypeptide is one that is removed from its original environment. For example, a naturally-occurring polypeptide of the invention is isolated if it is separated from some or all of the coexisting materials in the natural system.

Potency, Inhibition and Neutralisation

Potency is a measure of the activity of a therapeutic agent expressed in terms of the amount required to produce an effect of given intensity. A highly potent agent evokes a greater response at low concentrations compared to an agent of lower potency that evokes a smaller response at low concentrations. Potency is a function of affinity and efficacy. Efficacy refers to the ability of therapeutic agent to produce a biological response upon binding to a target ligand and the quantitative magnitude of this response. The term half maximal effective concentration (EC50) refers to the concentration of a therapeutic agent which causes a response halfway between the baseline and maximum after a specified exposure time. The therapeutic agent may cause inhibition or stimulation. It is commonly used, and is used herein, as a measure of potency.

A neutralising polypeptide for the purposes of the invention is a polypeptide which interferes in the binding of a sIL-6/IL-6R complex to gp130 as measured by ELISA. Alternatively, or in addition, a neutralising polypeptide for the purposes of the invention is a polypeptide which reduces the proliferation of cells presenting surface IL-6R (such as TF-1 cells) which are exposed to exogenous IL-6, by preventing formation of IL-6/IL-6R/gp130 cis-signalling complexes.

A method for determining the potency of an anti-IL-6R agent in neutralising IL-6R is as follows:

1. Standard gp 130 ELISA Assay

The objective of this assay is to measure the potency of anti-IL-6R ICVDs by measuring interference in the binding to gp130 of a sIL-6/IL-6R complex. This assay detects binding of hIL-6R/hIL-6 complexes to recombinant human gp130. This interaction can be competitively inhibited by anti-IL-6R ICVDs, causing reduced binding of hIL-6R-hIL-6 complexes to gp130. Therefore, high signal in this ELISA represents a low concentration or low affinity of anti-IL-6R ICVD, and vice versa.

Materials
Solutions required:
1× PBS
PBST (1× PBS, 0.05% Tween 20)
Block buffer (1% BSA in 1× PBS, pH 7.3-7.5)
0.5 M Sulphuric acid ($H_2SO_4$)
Reagents required:
Recombinant soluble human gp130 at known concentration
ICVD stock (preferably 250 ug/mL diluted to 20 ug/mL in protease testing solution)
Recombinant soluble human IL-6 at known concentration
Recombinant soluble human IL-6R at known concentration
Biotinylated goat anti-IL-6R polyclonal antibody (R&D systems BAF227); resuspended at 250 ug/ml in sterile PBS.
ExtrAvidin-Peroxidase (Sigma E2886)
TMB substrate (Microwell Peroxidase substrate System 2-C, KPL, 50-70-00)
Procedure
Preparation:
1. Determine number of plates required for the assay.
2. Prepare the relevant volume (up to 3 plates at a time) of 0.2 μg/ml recombinant soluble human gp130 in PBS with 5 ug/mL BSA in 1× PBS.
3. Working quickly, dispense 50 μl/well into Maxisorp 96-well ELISA plates (Nunc), loading a maximum of 3 plates in one batch.
4. Shake plate briefly, seal and incubate at 4° C. overnight.

Assay:
1. Wash the ELISA plate using a plate washer (4× ~380 μl PBST). Bang the plate on towel to remove residual liquid.
2. Apply 200 μl/well block buffer. Seal and incubate on a rotary plate shaker for ≥1 hour.
3. Prepare a dilution series of ICVD standards between 0.004 nM to 80 nM in minimum final volumes of 70 μl using block buffer as a diluent.
4. Prepare appropriate dilutions of samples to be tested in block buffer, such that their estimated final concentration on the plate will fall in the range of 0.001 nM to 250 nM ICVD.
5. Prepare a 40 ng/ml IL-6R solution in block buffer.
6. In a separate 96-well plate, mix together 50 μl of each ICVD dilution with 50 μl IL-6R solution. In each dilution series include one well with no ICVD. Incubate for 1 hour on a rotary plate shaker.
7. Prepare a 100 ng/ml IL-6 solution in block buffer.
8. In a further additional 96-well plate, mix together 85 μl ICVD-IL-6R mixture from step 6 with 85 μl IL-6 solution prepared in step 7. Include wells containing block buffer only, such that the following controls are applied to each plate: IL-6 only, and no ICVD (IL6+IL6R only). Incubate for 10 minutes on rotary plate shaker.
9. Wash blocked ELISA plate as in step 1.
10. Transfer 50 μl of the mixtures prepared in step 8 to the washed ELISA plate in triplicate. Seal and incubate on a rotary plate shaker for 2 hours.
11. Wash blocked ELISA plate as in step 1.
12. Prepare 5.2 ml/plate 125 ug/mL of BAF227 anti-hIL-6R antibody made up in block buffer. Add 50 μl/well, seal, shake briefly, and incubate for 1 hour at room temperature or overnight at 4° C.
13. Wash blocked ELISA plate as in step 1.
14. Prepare 5.2 ml/plate of 1/1,000-1/3000 dilution of Extravidin in block buffer. Add 50 μl/well, seal, and incubate on a rotary shaker for 30 mins.
15. Wash blocked ELISA plate as in step 1.
16. Prepare 10 ml/plate TM B substrate (1:1 ratio of substrate A and B). Add 100 μl/well, seal and incubate on a rotary plate shaker until a mid blue colour evolves in the lowest dilution wells or up to a maximum of 30 mins. Shield from light.
17. Stop reaction with 50 μl/well 0.5 M $H_2SO_4$.
18. Read plate at 450 nm.
19. Use standard curve to interpolate concentrations of active ICVD. Raw OD450 values are adjusted with readings taken from blank control wells. Standard curves are plotted using appropriate software (e.g. Graphpad Prism using Log (inhibitor) vs. response—variable slope (four parameters)). ICVD concentrations in the test samples are calculated in the software using the standard curve.

A method for determining the potency of an anti-IL-6R agent in neutralising cynomolgous monkey IL-6R is as follows:

2. Standard Anti-Cynomolgus Monkey IL-6R gp130 ELISA Assay

The objective of this assay is to measure the potency of anti-IL-6R antibodies in neutralising cynomolgus monkey IL-6R activity by inhibiting the formation of a cynomolgus monkey IL-6R, human gp130, and human IL-6 complex. This assay detects binding of IL-6R/hIL-6 complexes to recombinant human gp130. This interaction can be competitively inhibited by anti-IL-6R ICVDs, causing reduced binding of IL-6R/hIL-6 complexes to gp130. Therefore, high signal in this ELISA represents a low concentration or low affinity of anti-IL-6R ICVD, and vice versa.

Materials
Solutions required:
1× PBS
1% BSA in PBS
PBST (1× PBS, 0.05% Tween 20)
Block buffer (1% BSA in 1× PBS, pH 7.3-7.5)
Assay buffer (1% BSA, 2× protease inhibitor* in 1× PBS)
0.5 M Sulphuric acid ($H_2SO_4$)
*2× protease inhibitor=1 tablet per 50 ml buffer
Reagents required:
Recombinant soluble human gp130 at known concentration
SigmaFast protease inhibitor tablets (S8820)
ICVD stock of known concentration
Recombinant soluble human IL-6 at known concentration
Recombinant soluble human IL-6R at known concentration
Cynomolgus monkey serum
Biotinylated goat anti-IL-6R polyclonal antibody (R&D systems BAF227); resuspended at 250 ug/ml in sterile PBS.
ExtrAvidin-Peroxidase (Sigma E2886)
TMB substrate (Microwell Peroxidase substrate System 2-C, KPL, 50-70-00)

Procedure

Preparation:
1. Determine number of plates required for the assay.
2. Prepare the relevant volume (up to 3 plates at a time) of 1 µg/ml recombinant soluble human gp130 in PBS+5 µg/ml BSA, which are for use for the cynomolgus monkey serum. Coat the same number of plates with 0.2 ug/mL gp130 with +5 µg/ml BSA for the human IL6R control.
3. Working quickly, dispense 50 µl/well into Maxisorp 96-well ELISA plates (Nunc), loading a maximum of 4 plates in one batch.
4. Shake plate briefly, seal and incubate at 4° C. overnight.

Assay:
1. Wash the ELISA plate using a plate washer (4× ~380 µl PBST). Bang the plate on towel to remove residual liquid.
2. Apply 200 µl/well block buffer. Seal and incubate on a rotary plate shaker for ≥1 hour.
3. Prepare a dilution series of ICVD standards between 0.004 nM to 1000 nM in minimum final volumes of 70 µl using assay buffer as a diluent.
4. Prepare a 20 ng/ml IL-6R solution in assay buffer.
5. Prepare a 2.5× dilution of normal cynomolgus monkey serum in assay buffer.
6. In a separate 96-well plate, mix together 50 µl of each ICVD dilution with 50 µl IL-6R solution or monkey serum. In each dilution series include one well with no ICVD. Incubate for 1 hour on a rotary plate shaker.
7. Prepare a 100 ng/ml IL-6 solution in block buffer.
8. In a further additional 96-well plate, mix together 85 µl ICVD-IL-6R mixture from step 6 with 85 µl IL-6 solution prepared in step 7. Include wells containing block buffer only, such that the following controls are applied to each plate: IL-6 only, and no ICVD (IL6+1L6R only). Incubate for 10 minutes on rotary plate shaker.
9. Wash blocked ELISA plate as in step 1.
10. Transfer 50 µl of the mixtures prepared in step 8 to the washed ELISA plate in triplicate. Seal and incubate on a rotary plate shaker for 2 hours.
11. Wash, blocked ELISA plate as in step 1.
12. Prepare 5.2 ml/plate 125 ug/mL of BAF227 anti-hIL-6R antibody made up in block buffer. Add 50 µl /well, seal, shake briefly, and incubate overnight at 4° C.
13. Wash blocked. ELISA plate as in step 1.
14. Prepare 5.2 ml/plate of 1/3000 dilution of Extravidin in block buffer. Add 50 µl/well, seal, and incubate on a rotary shaker for 30 mins.
15. Wash blocked ELISA plate as in step 1.
16. Prepare 10 ml/plate TMB substrate (1:1 ratio of substrate A and B). Add 100 µl/well, seal and incubate on a rotary plate shaker until a mid blue colour evolves in the lowest dilution wells or up to a maximum of 30 mins. Shield from light.
17. Stop reaction with 50 µl/well 0.5 M $H_2SO_4$.
18. Read plate at 450 nm.
19. Use standard curve to interpolate concentrations of active ICVD. Raw OD450 values are adjusted with readings taken from blank control wells. Standard curves are plotted using appropriate software (e.g. Graphpad Prism using Log (inhibitor) vs. response—variable slope (four parameters)). ICVD concentrations in the test samples are calculated in the software using the standard curve.

A method for determining the potency of ah anti-IL-6R agent in inhibiting membrane bound IL-6R mediated IL-6 cis-signalling is as follows:

3. The Standard TF1 Cell Assay

This assay detects the activity of exogenous IL-6 on TF1 cell proliferation. TF1 cells are a human erythroblast immortal cell line that expresses the membrane-bound IL-6 receptor on their surface. In the presence of exogenously added IL-6, the cells are stimulated via the IL-6 cis-signalling pathway to proliferate. Anti membrane-bound IL-6R compounds prevent the formation of the complete IL-6/IL-6R/gp130 complex that is required for signalling, reducing IL-6-stimulated proliferation in dose-dependent manner. Cell proliferation is measured after two days using resazurin, a blue dye that is irreversibly reduced to the pink coloured and highly red fluorescent resorufin by cellular metabolic processes.

Materials

Standard components:

Cell line: TF-1 (Public Health England, Cat. No. 93022307). Exponentially growing cells (<5×10^5 cells/mL) cultivated in Advanced RPMI with 5% heat-inactivated foetal bovine serum and 2.5 ng/mL GM-CSF (Human Granulocyte Macrophage Colony Stimulating Factor).

Assay medium: Advanced RMPI (LifeTech 12633-012) with 2 mM L-glutamine, Pen/Strep

1×PBS

3% SDS

Sterile MQ water

Sterile 96 well micro-titre plates for cell culture, flat bottomed, optically clear 12 multi-channel pipette and filtered tips Reagents:

Recombinant soluble human IL-6 at known concentration
Anti-IL-6R antibodies or ICVD of known concentration
Resazurin (Alamar Blue; LifeTech, DAL1100)

Procedure

Cell Preparation:
a. Pre-warm media and 1×PBS in a 37° C. water bath.
b. Determine the number of plates required for the assay.
c. Fill the outside wells with 320 uL of sterile MilliQ water.
d. Fill the spaces between the wells with 160 uL of the same water.
e. Calculate the volume of the cell culture you will need to have 20,000 cells/well using the equation:

(60 wells per plate x# plates×20,000 cells/well×1.2 (for 20% overage)=total cells/Cell count (cells/ml)

f. Transfer cells to falcon tube. Take to maximum tube volume with 1×PBS. Spin 5' at 1.1 k×rpm at 20 degrees C.
g. Remove medium from cell pellet with a 10 mL stripette, leave ~200 uL on the cells, ensuring no cells are aspirated. Tap cells in residual volume to resuspend.
h. Wash cells in full tube volume of 1×PBS spin as before.
i. Remove 1×PBS with a 10 mL stripette, leave ~200 uL on the cells, ensuring no cells are aspirated. Remove residual with P200.
j. Resuspend cell pellet by tapping then add assay medium using the equation below to calculate the volume required:

60 wells per plate x# plates×0.05 mL volume per well×1.2 (for 20% overage)=total volume k. Fill plates with 50 ul cells per well proceeding row by row. Place filled plates in the incubator. Agitate the cells by pipetting or shaking the trough intermittently during this process.

ICVD/Antibody Preparation:
a. Prepare the assay stock of IL-6 at 20 ng/mL (4× the assay concentration) in a volume of assay medium sufficient to add 25 ul per well.

b. Prepare a 9 point serial dilution series of ICVD reference standards at 4×the assay concentration (being between 0.04 nM and 2500 nM in minimum final volumes of 100 µl using assay medium as a diluent. In a tenth well, add assay medium only. For example, starting in well A1 make the dilutions series along to plate to well A9. In well A10, add medium only.

c. In a fresh microtitre plate, add a minimum volume of 85 uL of IL-6 to the equivalent 9 wells used in the dilution series. In the tenth well add either assay medium or IL-6 to the effect that each final assay plate will have wells with IL-6 only (maximum proliferation) and media only (minimum proliferation).

d. To the IL-6 mix plate prepared above, add an equivalent volume (e.g. 85 uL) of each ICVD/antibody serial dilution. At this stage both IL-6 and ICVD will be at 2× the assay concentration.

Assay:

a. Mix the ICVD/Antibody & IL-6 mixtures by pipetting and add 50 ul of each mix to the cells.

b. Incubate the cells for 2 days at 37° C., 5% $CO_2$.

c. Add 10 uL of AlamarBlue to cells. Protect from light.

d. Shake the cells gently for 30 s on a plate shaker to mix e. Incubate 37° C., 5% $CO_2$ for 2 hours.

f. Stop cellular processes with 50 uL 3% SDS. Protect from light g. Read on plate reader (e.g. BMG Fluorstar) at Ex 544 nm–Em 590 nm h. Use calibration curve to interpolate unknown sample concentrations. Raw OD450 values are adjusted with readings taken from blank control wells. Standard curves are plotted using appropriate software (e.g. Graphpad Prism using Log(inhibitor) vs. response—variable slope (four parameters)). ICVD concentrations in the test samples are calculated in the software using the standard curve.

Suitably the polypeptide or construct of the invention neutralizes sIL-6R-IL-6 binding to gp130 in an ELISA assay such as the standard gp130 ELISA with an $EC_{50}$ of 100 nM or less, such as 75 nM or less, such as 50 nM or less, such as 40 nM or less, such as 30 nM or less, such as 25 nM or less, such as 20 nM or less, such as 10 nM or less, such as 5 nM or less, such as 2 nM or less, such as 1.5 nM or less, such as 1 nM or less, such as 0.9 nM or less, such as 0.8 nM or less, such as 0.7 nM or less, such as 0.6 nM or less, such as 0.5 nM or less, such as 0.45 nM or less, such as 0.4 nM or less, such as 0.35 nM or less, such as 0.3 nM or less, such as 0.25 nM or less, such as 0.2 nM or less, such as 0.16 nM or less, such as 0.15 nM or less, such as 0.1 nM or less.

Suitably the polypeptide or construct of the invention neutralizes cynomolgous IL-6R-human IL-6 binding to human gp130 in an ELISA assay such as the standard anti-cynomolgus monkey IL-6R gp130 ELISA assay with an $EC_{50}$ of 20 nM or less, such as 10 nM or less, such as 5 nM or less, such as 2 nM or less, such as 1.5 nM or less, such as 1 nM or less, such as 0.9 nM or less, such as 0.8 nM or less, such as 0.7 nM or less, such as 0.6 nM or less, such as 0.5 nM or less, such as 0.45 nM or less, such as 0.4 nM or less, such as 0.35 nM or less, such as 0.3 nM or less, such as 0.25 nM or less, such as 0.2 nM or less, such as 0.16 nM or less, such as 0.15 nM or less, such as 0.1 nM or less.

Suitably the polypeptide or construct of the invention prevents proliferation of TF-1 cells in the standard TF-1 assay with an $EC_{50}$ of 20 nM or less, such as 10 nM or less, such as 5 nM or less, such as 2 nM or less, such as 1.5 nM or less, such as 1 nM or less, such as 0.9 nM or less, such as 0.8 nM or less, such as 0.7 nM or less, such as 0.6 nM or less, such as 0.5 nM or less, such as 0.45 nM or less, such as 0.4 nM or less, such as 0.35 nM or less, such as 0.3 nM or less, such as 0.25 nM or less, such as 0.2 nM or less, such as 0.16 nM or less, such as 0.15 nM or less, such as 0.1 nM or less.

Suitably the polypeptide of the invention inhibits IL-6R trans-signalling to a higher extent than it inhibits IL-6R cis-signalling, i.e. the polypeptide is 'trans-selective'.

Polypeptide and Polynucleotide Sequences

For the purposes of comparing two closely-related polypeptide sequences, the "% sequence identity" between a first polypeptide sequence and a second polypeptide sequence may be calculated using NCBI BLAST v2.0, using standard settings for polypeptide sequences (BLASTP). For the purposes of comparing two closely-related polynucleotide sequences, the "% sequence identity" between a first nucleotide sequence and a second nucleotide sequence may be calculated using NCBI BLAST v2.0, using standard settings for nucleotide sequences (BLASTN).

Polypeptide or polynucleotide sequences are said to be the same as or identical to other polypeptide or polynucleotide sequences, if they share 100% sequence identity over their entire length. Residues in sequences are numbered from left to right, i.e. from N- to C-terminus for polypeptides; from 5' to 3' terminus for polynucleotides.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced % sequence identity. For example, if the identical sequences are 9 amino acid residues long, one substitution in the second sequence results in a sequence identity of 88.9%. If the identical sequences are 17 amino acid residues long, two substitutions in the second sequence results in a sequence identity of 88.2%. If the identical sequences are 7 amino acid residues long, three substitutions in the second sequence results in a sequence identity of 57.1%. If first and second polypeptide sequences are 9 amino acid residues long and share 6 identical residues, the first and second polypeptide sequences share greater than 66% identity (the first and second polypeptide sequences share 66.7% identity). If first and second polypeptide sequences are 17 amino acid residues long and share 16 identical residues, the first and second polypeptide sequences share greater than 94% identity (the first and second polypeptide sequences share 94.1% identity). If first and second polypeptide sequences are 7 amino acid residues long and share 3 identical residues, the first and second polypeptide sequences share greater than 42% identity (the first and second polypeptide sequences share 42.9% identity).

Alternatively, for the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

For the purposes of comparing a first, reference polynucleotide sequence to a second, comparison polynucleotide sequence, the number of additions, substitutions and/or deletions made to the first sequence to produce the second sequence may be ascertained. An addition is the addition of one nucleotide residue into the sequence of the first polynucleotide (including addition at either terminus of the first polynucleotide). A substitution is the substitution of one nucleotide residue in the sequence of the first polynucleotide with one different nucleotide residue. A deletion is the deletion of one nucleotide residue from the sequence of the first polynucleotide (including deletion at either terminus of the first polynucleotide).

A "conservative" amino acid substitution is an amino acid substitution in which an amino acid residue is replaced with another amino acid residue of similar chemical structure and which is expected to have little influence on the function, activity or other biological properties of the polypeptide. Such conservative substitutions suitably are substitutions in which one amino acid within the following groups is substituted by another amino acid residue from within the same group:

| Group | Amino acid residue |
|---|---|
| Non-polar aliphatic | Glycine |
| | Alanine |
| | Valine |
| | Leucine |
| | Isoleucine |
| Aromatic | Phenylalanine |
| | Tyrosine |
| | Tryptophan |
| Polar uncharged | Serine |
| | Threonine |
| | Asparagine |
| | Glutamine |

-continued

| Group | Amino acid residue |
|---|---|
| Negatively charged | Aspartate |
| | Glutamate |
| Positively charged | Lysine |
| | Arginine |

Suitably, a hydrophobic amino acid residue is a non-polar amino acid. More suitably, a hydrophobic amino acid residue is selected from V, I, L, M, F, W or C.

As used herein, numbering of polypeptide sequences and definitions of CDRs and FRs are as defined according to the Kabat system (Kabat et al., 1991, herein incorporated by reference in its entirety). A "corresponding" amino acid residue between a first and second polypeptide sequence is an amino acid residue in a first sequence which shares the same position according to the Kabat system with an amino acid residue in a second sequence, whilst the amino acid residue in the second sequence may differ in identity from the first. Suitably corresponding residues will share the same number (and letter) if the framework and CDRs are the same length according to Kabat definition. Alignment can be achieved manually or by using, for example, a known computer algorithm for sequence alignment such as NCBI BLAST v2.0 (BLASTP or BLASTN) using standard settings.

Polypeptide Sequences

Suitably, the polypeptide sequence of the present invention contains at least one alteration with respect to a native sequence. Suitably, the polynucleotide sequences of the present invention contain at least one alteration with respect to a native sequence. Suitably the alteration to the polypeptide sequence or polynucleotide sequence is made to increase stability of the polypeptide or encoded polypeptide to proteases present in the intestinal tract (for example trypsin and chymotrypsin).

The Kabat numbering system applied to particular immunoglobulin chain variable domains of the invention:

| 5G9 | H1 | H2 | H3 | H4 | H5 | H6 | H7 | H8 | H9 | H10 | H11 | H12 | H13 |
|---|---|---|---|---|---|---|---|---|---|---|---|---|---|
| | E | V | Q | L | V | E | S | G | G | G | L | V | Q |
| | 1 | 2 | 3 | 4 | 5 | 6 | 7 | 8 | 9 | 10 | 11 | 12 | 13 |

| | H14 | H15 | H16 | H17 | H18 | H19 | H20 | H21 | H22 | H23 | H24 | H25 | H26 |
|---|---|---|---|---|---|---|---|---|---|---|---|---|---|
| | A | G | G | S | T | R | L | T | C | K | A | S | G |
| | 14 | 15 | 16 | 17 | 18 | 19 | 20 | 21 | 22 | 23 | 24 | 25 | 26 |

| | | | | | | | | CDR-H1 | | | | | |
|---|---|---|---|---|---|---|---|---|---|---|---|---|---|
| | H27 | H28 | H29 | H29A | H29B | H29O | H30 | H31 | H32 | H33 | H34 | H35 | H36 |
| | S | I | F | N | I | N | S | I | N | V | M | A | W |
| | 27 | 28 | 29 | 30 | 31 | 32 | 33 | 34 | 35 | 36 | 37 | 38 | 39 |

| | H37 | H38 | H39 | H40 | H41 | H42 | H43 | H44 | H45 | H46 | H47 | H48 | H49 |
|---|---|---|---|---|---|---|---|---|---|---|---|---|---|
| | Y | R | Q | A | P | G | K | Q | R | E | L | V | A |
| | 40 | 41 | 42 | 43 | 44 | 45 | 46 | 47 | 48 | 49 | 50 | 51 | 52 |

-continued

| | | | | | CDR-H2 | | | | | | | |
|---|---|---|---|---|---|---|---|---|---|---|---|---|
| | H50 | H51 | H52 | H53 | H54 | H55 | H56 | H57 | H58 | H59 | H60 | H61 | H62 |
| | I | I | G | K | G | G | G | T | N | Y | A | D | F |
| | 53 | 54 | 55 | 56 | 57 | 58 | 59 | 60 | 61 | 62 | 63 | 64 | 65 |

| CDR2-H2 | | | | | | | | | | | | |
|---|---|---|---|---|---|---|---|---|---|---|---|---|
| H63 | H64 | H65 | H66 | H67 | H68 | H69 | H70 | H71 | H72 | H73 | H74 | H75 |
| V | K | G | R | F | T | I | S | R | D | A | A | K |
| 66 | 67 | 68 | 69 | 70 | 71 | 72 | 73 | 74 | 75 | 76 | 77 | 78 |

| H76 | H77 | H78 | H79 | H80 | H81 | H82 | H82A | H82B | H82C | H83 | H84 | H85 |
|---|---|---|---|---|---|---|---|---|---|---|---|---|
| N | T | V | N | L | Q | M | N | S | L | K | P | E |
| 79 | 80 | 81 | 82 | 83 | 84 | 85 | 86 | 87 | 88 | 89 | 90 | 91 |

| | | | | | | | | | CDR-H3 | | | |
|---|---|---|---|---|---|---|---|---|---|---|---|---|
| H86 | H87 | H88 | H89 | H90 | H91 | H92 | H93 | H94 | H95 | H96 | H97 | H98 |
| D | T | A | V | Y | Y | C | Y | A | D | Y | E | D |
| 92 | 93 | 94 | 95 | 96 | 97 | 98 | 99 | 100 | 101 | 102 | 103 | 104 |

| | | | CRD-H3 | | | | | | | |
|---|---|---|---|---|---|---|---|---|---|---|
| H99 | H100 | H100A | H100B | H100C | H100D | H101 | H102 | H103 | H104 | H105 |
| R | D | S | P | F | N | A | S | W | G | Q |
| 105 | 106 | 107 | 108 | 109 | 110 | 111 | 112 | 113 | 114 | 115 |

| H106 | H107 | H108 | H109 | H110 | H111 | H112 | H113 |
|---|---|---|---|---|---|---|---|
| G | T | Q | V | T | V | S | S |
| 116 | 117 | 118 | 119 | 120 | 121 | 122 | 123 |

| | H1 | H2 | H3 | H4 | H5 | H6 | H7 | H8 | H9 | H10 | H11 | H12 | H13 |
|---|---|---|---|---|---|---|---|---|---|---|---|---|---|
| 7F6 | E | V | Q | L | V | E | S | G | G | G | L | V | Q |
| | 1 | 2 | 3 | 4 | 5 | 6 | 7 | 8 | 9 | 10 | 11 | 12 | 13 |

| H14 | H15 | H16 | H17 | H18 | H19 | H20 | H21 | H22 | H23 | H24 | H25 | H26 |
|---|---|---|---|---|---|---|---|---|---|---|---|---|
| A | G | G | S | T | R | L | T | C | L | A | S | G |
| 14 | 15 | 16 | 17 | 18 | 19 | 20 | 21 | 22 | 23 | 24 | 25 | 26 |

| | | | | CDR-H1 | | | | | | | |
|---|---|---|---|---|---|---|---|---|---|---|---|
| H27 | H28 | H29 | H30 | H31 | H32 | H33 | H34 | H35 | H36 | H37 | H38 | H39 |
| S | I | S | S | I | N | V | I | G | W | Y | R | Q |
| 27 | 28 | 29 | 30 | 31 | 32 | 33 | 34 | 35 | 36 | 37 | 38 | 39 |

| | | | | | | | | | CDR2-H2 | | |
|---|---|---|---|---|---|---|---|---|---|---|---|
| H40 | H41 | H42 | H43 | H44 | H45 | H46 | H47 | H48 | H49 | H50 | H51 | H52 |
| A | P | G | K | Q | R | E | L | V | A | M | I | G |
| 40 | 41 | 42 | 43 | 44 | 45 | 46 | 47 | 48 | 49 | 50 | 51 | 52 |

| CDR2-H2 | | | | | | | | | | | | |
|---|---|---|---|---|---|---|---|---|---|---|---|---|
| H53 | H54 | H55 | H567 | H57 | H58 | H59 | H60 | H61 | H62 | H63 | H64 | H65 |
| R | G | E | G | A | N | Y | G | D | F | A | K | G |
| 53 | 54 | 55 | 56 | 57 | 58 | 59 | 60 | 61 | 62 | 63 | 64 | 65 |

| H66 | H67 | H68 | H69 | H70 | H71 | H72 | H73 | H74 | H75 | H76 | H77 | H78 |
|---|---|---|---|---|---|---|---|---|---|---|---|---|
| R | F | T | I | S | R | D | N | S | K | N | T | V |
| 66 | 67 | 68 | 69 | 70 | 71 | 72 | 73 | 74 | 75 | 76 | 77 | 78 |

| H79 | H80 | H81 | H82 | H82A | H82B | H82C | H83 | H84 | H85 | H86 | H87 | H88 |
|---|---|---|---|---|---|---|---|---|---|---|---|---|
| Y | L | Q | M | N | S | L | K | P | E | D | T | A |
| 79 | 80 | 81 | 82 | 83 | 84 | 85 | 86 | 87 | 88 | 89 | 90 | 91 |

|  |  |  |  |  |  | CDR-H3 | | | | | |
|---|---|---|---|---|---|---|---|---|---|---|---|
| H89 | H90 | H91 | H92 | H93 | H94 | H95 | H96 | H97 | H98 | H99 | H100 | H100A |
| V | Y | Y | C | Y | A | D | Y | E | D | R | D | S |
| 92 | 93 | 94 | 95 | 96 | 97 | 98 | 99 | 100 | 101 | 102 | 103 | 104 |

| CDR-H3 | | | | | | | | | |
|---|---|---|---|---|---|---|---|---|---|
| H100B | H100C | H100D | H101 | H102 | H103 | H104 | H105 | H106 | H107 | H108 |
| P | F | N | G | S | W | G | Q | G | T | Q |
| 105 | 106 | 107 | 108 | 109 | 110 | 111 | 112 | 113 | 114 | 115 |

| H109 | H110 | H111 | H112 | H113 |
|---|---|---|---|---|
| V | T | V | S | S |
| 116 | 117 | 118 | 119 | 120 |

| 21E6 | H1 | H2 | H3 | H4 | H5 | H6 | H7 | H8 | H9 | H10 | H11 | H12 | H13 |
|---|---|---|---|---|---|---|---|---|---|---|---|---|---|
|  | E | V | Q | L | V | E | S | G | G | G | L | V | L |
|  | 1 | 2 | 3 | 4 | 5 | 6 | 7 | 8 | 9 | 10 | 11 | 12 | 13 |

| H14 | H15 | H16 | H17 | H18 | H19 | H20 | H21 | H22 | H23 | H24 | H25 | H26 |
|---|---|---|---|---|---|---|---|---|---|---|---|---|
| A | G | G | S | T | R | L | T | C | L | A | S | G |
| 14 | 15 | 16 | 17 | 18 | 19 | 20 | 21 | 22 | 23 | 24 | 25 | 26 |

|  |  |  |  | CDR-H1 | | | | | | | |
|---|---|---|---|---|---|---|---|---|---|---|---|
| H27 | H28 | H29 | H30 | H31 | H32 | H33 | H34 | H35 | H36 | H37 | H38 | H39 |
| S | I | S | S | I | N | V | I | G | W | Y | R | Q |
| 27 | 28 | 29 | 30 | 31 | 32 | 33 | 34 | 35 | 36 | 37 | 38 | 39 |

|  |  |  |  |  |  |  |  |  | CDR2-H2 | | |
|---|---|---|---|---|---|---|---|---|---|---|---|
| H40 | H41 | H42 | H43 | H44 | H45 | H46 | H47 | H48 | H49 | H50 | H51 | H52 |
| A | P | G | K | Q | R | E | L | V | A | M | I | G |
| 40 | 41 | 42 | 43 | 44 | 45 | 46 | 47 | 48 | 49 | 50 | 51 | 52 |

| CDR2-H2 | | | | | | | | | | | |
|---|---|---|---|---|---|---|---|---|---|---|---|
| H53 | H54 | H55 | H567 | H57 | H58 | H59 | H60 | H61 | H62 | H63 | H64 | H65 |
| R | G | E | G | A | N | Y | G | D | F | A | K | G |
| 53 | 54 | 55 | 56 | 57 | 58 | 59 | 60 | 61 | 62 | 63 | 64 | 65 |

| H66 | H67 | H68 | H69 | H70 | H71 | H72 | H73 | H74 | H75 | H76 | H77 | H78 |
|---|---|---|---|---|---|---|---|---|---|---|---|---|
| R | F | T | I | S | R | D | N | S | K | N | T | V |
| 66 | 67 | 68 | 69 | 70 | 71 | 72 | 73 | 74 | 75 | 76 | 77 | 78 |

| H79 | H80 | H81 | H82 | H82A | H82B | H820 | H83 | H84 | H85 | H86 | H87 | H88 |
|---|---|---|---|---|---|---|---|---|---|---|---|---|
| Y | L | Q | M | N | S | L | K | P | E | D | T | A |
| 79 | 80 | 81 | 82 | 83 | 84 | 85 | 86 | 87 | 88 | 89 | 90 | 91 |

|  |  |  |  |  |  | CDR-H3 | | | | | |
|---|---|---|---|---|---|---|---|---|---|---|---|
| H89 | H90 | H91 | H92 | H93 | H94 | H95 | H96 | H97 | H98 | H99 | H100 | H100A |
| V | Y | Y | C | Y | A | D | Y | E | D | R | D | S |
| 92 | 93 | 94 | 95 | 96 | 97 | 98 | 99 | 100 | 101 | 102 | 103 | 104 |

| CDR-H3 | | | | | | | | | |
|---|---|---|---|---|---|---|---|---|---|
| H100B | H100C | H100D | H101 | H102 | H103 | H104 | H105 | H106 | H107 | H108 |
| P | L | N | G | S | W | G | Q | G | T | Q |
| 105 | 106 | 107 | 108 | 109 | 110 | 111 | 112 | 113 | 114 | 115 |

-continued

|  | H109 | H110 | H111 | H112 | H113 |  |  |  |  |  |  |
|---|---|---|---|---|---|---|---|---|---|---|---|
|  | V 116 | T 117 | V 118 | S 119 | S 120 |  |  |  |  |  |  |
| ID-141V | H1 | H2 | H3 | H4 | H5 | H6 | H7 | H8 | H9 | H10 | H11 | H12 | H13 |
|  | D 1 | V 2 | Q 3 | L 4 | V 5 | E 6 | S 7 | G 8 | G 9 | G 10 | L 11 | V 12 | Q 13 |
|  | H14 | H15 | H16 | H17 | H18 | H19 | H20 | H21 | H22 | H23 | H24 | H25 | H26 |
|  | A 14 | G 15 | G 16 | S 17 | T 18 | R 19 | L 20 | T 21 | C 22 | K 23 | A 24 | S 25 | G 26 |

|  |  |  |  |  |  |  |  | CDR-H1 | | | | |
|---|---|---|---|---|---|---|---|---|---|---|---|---|
| H27 | H28 | H29 | H29A | H29B | H29C | H30 | H31 | H32 | H33 | H34 | H35 | H36 |
| S 27 | I 28 | S 29 | N 30 | I 31 | N 32 | S 33 | I 34 | N 35 | V 36 | M 37 | A 38 | W 39 |
| H37 | H38 | H39 | H40 | H41 | H42 | H43 | H44 | H45 | H46 | H47 | H48 | H49 |
| Y 40 | R 41 | Q 42 | A 43 | P 44 | G 45 | K 46 | G 47 | R 48 | E 49 | L 50 | V 51 | A 52 |

|  |  |  |  |  | CDR2-H2 | | | | | | |
|---|---|---|---|---|---|---|---|---|---|---|---|
| H50 | H51 | H52 | H53 | H54 | H55 | H56 | H57 | H58 | H59 | H60 | H61 | H62 |
| I 53 | I 54 | G 55 | K 56 | G 57 | G 58 | G 59 | T 60 | N 61 | Y 62 | A 63 | D 64 | F 65 |

| CDR2-H2 | | | | | | | | | | | | |
|---|---|---|---|---|---|---|---|---|---|---|---|---|
| H63 | H64 | H65 | H66 | H67 | H68 | H69 | H70 | H71 | H72 | H73 | H74 | H75 |
| V 66 | K 67 | G 68 | R 69 | F 70 | T 71 | I 72 | S 73 | R 74 | D 75 | A 76 | A 77 | K 78 |
| H76 | H77 | H78 | H79 | H80 | H81 | H82 | H82A | H82B | H82C | H83 | H84 | H85 |
| N 79 | T 80 | L 81 | Y 82 | L 83 | Q 84 | M 85 | N 86 | S 87 | L 88 | R 89 | P 90 | E 91 |

|  |  |  |  |  |  |  |  | CDR-H3 | | | |
|---|---|---|---|---|---|---|---|---|---|---|---|
| H86 | H87 | H88 | H89 | H90 | H91 | H92 | H93 | H94 | H95 | H96 | H97 | H98 |
| D 92 | T 93 | A 94 | V 95 | Y 96 | Y 97 | C 98 | Y 99 | A 100 | D 101 | Y 102 | E 103 | D 104 |

| CDR-H13 | | | | | | | | | |
|---|---|---|---|---|---|---|---|---|---|
| H99 | H100 | H100A | H100B | H100C | H100D | H101 | H102 | H103 | H104 |
| H 105 | D 106 | S 107 | P 108 | H 109 | N 110 | A 111 | S 112 | W 113 | G 114 |
| H105 | H106 | H107 | H108 | H109 | H110 | H111 | H112 | H113 |  |
| Q 115 | G 116 | T 117 | Q 118 | V 119 | T 120 | V 121 | S 122 | S 123 |  |

| ID-142V | H1 | H2 | H3 | H4 | H5 | H6 | H7 | H8 | H9 | H10 | H11 | H12 | H13 |
|---|---|---|---|---|---|---|---|---|---|---|---|---|---|
|  | D 1 | V 2 | Q 3 | L 4 | V 5 | E 6 | S 7 | G 8 | G 9 | G 10 | L 11 | V 12 | Q 13 |
|  | H14 | H15 | H16 | H17 | H18 | H19 | H20 | H21 | H22 | H23 | H24 | H25 | H26 |
|  | A 14 | G 15 | G 16 | S 17 | T 18 | R 19 | L 20 | T 21 | C 22 | K 23 | A 24 | S 25 | G 26 |

-continued

|  |  |  |  |  |  |  | CDR-H1 | | | | |
|---|---|---|---|---|---|---|---|---|---|---|---|
| H27 | H28 | H29 | H29A | H29B | H29C | H30 | H31 | H32 | H33 | H34 | H35 | H36 |
| S | I | S | N | I | N | S | I | N | V | M | A | W |
| 27 | 28 | 29 | 30 | 31 | 32 | 33 | 34 | 35 | 36 | 37 | 38 | 39 |

| H37 | H38 | H39 | H40 | H41 | H42 | H43 | H44 | H45 | H46 | H47 | H48 | H49 |
|---|---|---|---|---|---|---|---|---|---|---|---|---|
| Y | R | Q | A | P | G | K | G | R | E | L | V | A |
| 40 | 41 | 42 | 43 | 44 | 45 | 46 | 47 | 48 | 49 | 50 | 51 | 52 |

|  |  |  |  |  | CDR2-H2 | | | | | | |
|---|---|---|---|---|---|---|---|---|---|---|---|
| H50 | H51 | H52 | H53 | H54 | H55 | H56 | H57 | H58 | H59 | H60 | H61 | H62 |
| I | I | G | K | G | G | G | T | N | Y | A | D | F |
| 53 | 54 | 55 | 56 | 57 | 58 | 59 | 60 | 61 | 62 | 63 | 64 | 65 |

| CDR2-H2 | | | | | | | | | | | |
|---|---|---|---|---|---|---|---|---|---|---|---|
| H63 | H64 | H65 | H66 | H67 | H68 | H69 | H70 | H71 | H72 | H73 | H74 | H75 |
| V | K | G | R | F | T | I | S | R | D | A | A | K |
| 66 | 67 | 68 | 69 | 70 | 71 | 72 | 73 | 74 | 75 | 76 | 77 | 78 |

| H76 | H77 | H78 | H79 | H80 | H81 | H82 | H82A | H82B | H82C | H83 | H84 | H85 |
|---|---|---|---|---|---|---|---|---|---|---|---|---|
| N | T | V | Y | L | Q | M | N | S | L | R | P | E |
| 79 | 80 | 81 | 82 | 83 | 84 | 85 | 86 | 87 | 88 | 89 | 90 | 91 |

|  |  |  |  |  |  |  |  |  | CDR-H3 | | |
|---|---|---|---|---|---|---|---|---|---|---|---|
| H86 | H87 | H88 | H89 | H90 | H91 | H92 | H93 | H94 | H95 | H96 | H97 | H98 |
| D | T | A | V | Y | Y | C | Y | A | D | Y | E | D |
| 92 | 93 | 94 | 95 | 96 | 97 | 98 | 99 | 100 | 101 | 102 | 103 | 104 |

| CDR-H3 | | | | | | | | | |
|---|---|---|---|---|---|---|---|---|---|
| H99 | H100 | H100A | H100B | H100C | H100D | H101 | H102 | H103 | H104 |
| H | D | S | P | H | N | A | S | W | G |
| 105 | 106 | 107 | 108 | 109 | 110 | 111 | 112 | 113 | 114 |

| H105 | H106 | H107 | H108 | H109 | H110 | H111 | H112 | H113 |
|---|---|---|---|---|---|---|---|---|
| Q | G | T | Q | V | T | V | S | S |
| 115 | 116 | 117 | 118 | 119 | 120 | 121 | 122 | 123 |

| ID-143V | H1 | H2 | H3 | H4 | H5 | H6 | H7 | H8 | H9 | H10 | H11 | H12 | H13 |
|---|---|---|---|---|---|---|---|---|---|---|---|---|---|
|  | D | V | Q | L | V | E | S | G | G | G | L | V | Q |
|  | 1 | 2 | 3 | 4 | 5 | 6 | 7 | 8 | 9 | 10 | 11 | 12 | 13 |

| H14 | H15 | H16 | H17 | H18 | H19 | H20 | H21 | H22 | H23 | H24 | H25 | H26 |
|---|---|---|---|---|---|---|---|---|---|---|---|---|
| A | G | G | S | T | R | L | T | C | K | A | S | G |
| 14 | 15 | 16 | 17 | 18 | 19 | 20 | 21 | 22 | 23 | 24 | 25 | 26 |

|  |  |  |  |  |  |  | CDR-H1 | | | | |
|---|---|---|---|---|---|---|---|---|---|---|---|
| H27 | H28 | H29 | H29A | H29B | H29C | H30 | H31 | H32 | H33 | H34 | H35 | H36 |
| S | I | S | N | I | N | S | I | N | V | M | A | W |
| 27 | 28 | 29 | 30 | 31 | 32 | 33 | 34 | 35 | 36 | 37 | 38 | 39 |

| H37 | H38 | H39 | H40 | H41 | H42 | H43 | H44 | H45 | H46 | H47 | H48 | H49 |
|---|---|---|---|---|---|---|---|---|---|---|---|---|
| Y | R | Q | A | P | G | K | G | R | E | L | V | A |
| 40 | 41 | 42 | 43 | 44 | 45 | 46 | 47 | 48 | 49 | 50 | 51 | 52 |

|  |  |  |  |  | CDR2-H2 | | | | | | |
|---|---|---|---|---|---|---|---|---|---|---|---|
| H50 | H51 | H52 | H53 | H54 | H55 | H56 | H57 | H58 | H59 | H60 | H61 | H62 |
| I | I | G | K | G | G | G | T | N | Y | A | D | F |
| 53 | 54 | 55 | 56 | 57 | 58 | 59 | 60 | 61 | 62 | 63 | 64 | 65 |

|  | CDR2-H2 | | | | | | | | | | | |
|---|---|---|---|---|---|---|---|---|---|---|---|---|
|  | H64 | H64 | H65 | H66 | H67 | H68 | H69 | H70 | H71 | H72 | H73 | H74 | H75 |
|  | V<br>66 | K<br>67 | G<br>68 | R<br>69 | F<br>70 | T<br>71 | I<br>72 | S<br>73 | R<br>74 | D<br>75 | A<br>76 | A<br>77 | K<br>78 |
|  | H76 | H77 | H78 | H79 | H80 | H81 | H82 | H82A | H82B | H82C | H83 | H84 | H85 |
|  | N<br>79 | T<br>80 | L<br>81 | Y<br>82 | L<br>83 | Q<br>84 | M<br>85 | N<br>86 | S<br>87 | L<br>88 | R<br>89 | P<br>90 | E<br>91 |
|  |  | | | | | | | | CDR-H3 | | | |
|  | H86 | H87 | H88 | H89 | H90 | H91 | H92 | H93 | H94 | H95 | H96 | H97 | H98 |
|  | D<br>92 | T<br>93 | A<br>94 | V<br>95 | Y<br>96 | Y<br>97 | C<br>98 | Y<br>99 | A<br>100 | D<br>101 | Y<br>102 | E<br>103 | D<br>104 |
|  | CDR-H3 | | | | | | | | |
|  | H99 | H100 | H100A | H100B | H100C | H100D | H101 | H102 | H103 | H104 |
|  | H<br>105 | D<br>106 | S<br>107 | P<br>108 | F<br>109 | N<br>110 | A<br>111 | S<br>112 | W<br>113 | G<br>114 |
|  | H105 | H106 | H107 | H108 | H109 | H110 | H111 | H112 | H113 |
|  | Q<br>115 | G<br>116 | T<br>117 | Q<br>118 | V<br>119 | T<br>120 | V<br>121 | S<br>122 | S<br>123 |

| | | | | | | | | | | | | |
|---|---|---|---|---|---|---|---|---|---|---|---|---|
| ID-144V | H1 | H2 | H3 | H4 | H5 | H6 | H7 | H8 | H9 | H10 | H11 | H12 | H13 |
|  | D<br>1 | V<br>2 | Q<br>3 | L<br>4 | V<br>5 | E<br>6 | S<br>7 | G<br>8 | G<br>9 | G<br>10 | L<br>11 | V<br>12 | Q<br>13 |
|  | H14 | H15 | H16 | H17 | H18 | H19 | H20 | H21 | H22 | H23 | H24 | H25 | H26 |
|  | A<br>14 | G<br>15 | G<br>16 | S<br>17 | T<br>18 | R<br>19 | L<br>20 | T<br>21 | C<br>22 | K<br>23 | A<br>24 | S<br>25 | G<br>26 |
|  |  | | | | | | | CDR-H1 | | | | |
|  | H27 | H28 | H29 | H29A | H29B | H29O | H30 | H31 | H32 | H33 | H34 | H35 | H36 |
|  | S<br>27 | I<br>28 | S<br>29 | N<br>30 | I<br>31 | N<br>32 | S<br>33 | I<br>34 | N<br>35 | V<br>36 | M<br>37 | A<br>38 | W<br>39 |
|  | H37 | H38 | H39 | H40 | H41 | H42 | H43 | H44 | H45 | H46 | H47 | H48 | H49 |
|  | Y<br>40 | R<br>41 | Q<br>42 | A<br>43 | P<br>44 | G<br>45 | K<br>46 | G<br>47 | R<br>48 | E<br>49 | L<br>50 | V<br>51 | A<br>52 |
|  | CDR-H2 | | | | | | | | | | | | |
|  | H50 | H51 | H52 | H53 | H54 | H55 | H56 | H57 | H58 | H59 | H60 | H61 | H62 |
|  | I<br>53 | I<br>54 | G<br>55 | K<br>56 | G<br>57 | G<br>58 | G<br>59 | T<br>60 | N<br>61 | Y<br>62 | A<br>63 | D<br>64 | F<br>65 |
|  | CDR-H2 | | | | | | | | | | | | |
|  | H63 | H64 | H65 | H66 | H67 | H68 | H69 | H70 | H71 | H72 | H73 | H74 | H75 |
|  | V<br>66 | K<br>67 | G<br>68 | R<br>69 | F<br>70 | T<br>71 | I<br>72 | S<br>73 | R<br>74 | D<br>75 | A<br>76 | A<br>77 | K<br>78 |
|  | H76 | H77 | H78 | H79 | H80 | H81 | H82 | H82A | H82B | H82C | H83 | H84 | H85 |
|  | N<br>79 | T<br>80 | V<br>81 | Y<br>82 | L<br>83 | Q<br>84 | M<br>85 | N<br>86 | S<br>87 | L<br>88 | R<br>89 | P<br>90 | E<br>91 |
|  |  | | | | | | | | CDR-H3 | | | |
|  | H86 | H87 | H88 | H89 | H90 | H91 | H92 | H93 | H94 | H95 | H96 | H97 | H98 |
|  | D<br>92 | T<br>93 | A<br>94 | V<br>95 | Y<br>96 | Y<br>97 | C<br>98 | Y<br>99 | A<br>100 | D<br>101 | Y<br>102 | E<br>103 | D<br>104 |

|  | | | | | | CDR-H3 | | | | |
|---|---|---|---|---|---|---|---|---|---|---|
|  | H99 | H100 | H100A | H100B | H100C | H100D | H101 | H102 | H103 | H104 |
|  | H | D | S | P | F | N | A | S | W | G |
|  | 105 | 106 | 107 | 108 | 109 | 110 | 111 | 112 | 113 | 114 |
|  | H105 | H106 | H107 | H108 | H109 | H110 | H111 | H112 | H113 | |
|  | Q | G | T | Q | V | T | V | S | S | |
|  | 115 | 116 | 117 | 118 | 119 | 120 | 121 | 122 | 123 | |

| ID-112V | H1 | H2 | H3 | H4 | H5 | H6 | H7 | H8 | H9 | H10 | H11 | H12 | H13 |
|---|---|---|---|---|---|---|---|---|---|---|---|---|---|
|  | E | V | Q | L | V | E | S | G | G | G | L | V | Q |
|  | 1 | 2 | 3 | 4 | 5 | 6 | 7 | 8 | 9 | 10 | 11 | 12 | 13 |
|  | H14 | H15 | H16 | H17 | H18 | H19 | H20 | H21 | H22 | H23 | H24 | H25 | H26 |
|  | A | G | G | S | T | R | L | T | C | K | A | S | G |
|  | 14 | 15 | 16 | 17 | 18 | 19 | 20 | 21 | 22 | 23 | 24 | 25 | 26 |

|  | | | | | | | CDR-H1 | | | | |
|---|---|---|---|---|---|---|---|---|---|---|---|
| H27 | H28 | H29 | H29A | H29B | H29C | H30 | H31 | H32 | H33 | H34 | H35 | H36 |
| S | I | S | N | I | N | S | I | N | V | M | A | W |
| 27 | 28 | 29 | 30 | 31 | 32 | 33 | 34 | 35 | 36 | 37 | 38 | 39 |
| H37 | H38 | H39 | H40 | H41 | H42 | H43 | H44 | H45 | H46 | H47 | H48 | H49 |
| Y | R | Q | A | P | G | K | G | R | E | L | V | A |
| 40 | 41 | 42 | 43 | 44 | 45 | 46 | 47 | 48 | 49 | 50 | 51 | 52 |

|  | | | | CDR2-H2 | | | | | | | |
|---|---|---|---|---|---|---|---|---|---|---|---|
| H50 | H51 | H52 | H53 | H54 | H55 | H56 | H57 | H58 | H59 | H60 | H61 | H62 |
| I | I | G | K | G | G | G | T | N | Y | A | D | F |
| 53 | 54 | 55 | 56 | 57 | 58 | 59 | 60 | 61 | 62 | 63 | 64 | 65 |

| CDR2-H2 | | | | | | | | | | | | |
|---|---|---|---|---|---|---|---|---|---|---|---|---|
| H63 | H64 | H65 | H66 | H67 | H68 | H69 | H70 | H71 | H72 | H73 | H74 | H75 |
| V | K | G | R | F | T | I | S | R | D | A | A | K |
| 66 | 67 | 68 | 69 | 70 | 71 | 72 | 73 | 74 | 75 | 76 | 77 | 78 |
| H76 | H77 | H78 | H79 | H80 | H81 | H82 | H82A | H82B | H82C | H83 | H84 | H85 |
| N | T | V | Y | L | Q | M | N | S | L | R | P | E |
| 79 | 80 | 81 | 82 | 83 | 84 | 85 | 86 | 87 | 88 | 89 | 90 | 91 |

|  | | | | | | | | | CDR-H3 | | |
|---|---|---|---|---|---|---|---|---|---|---|---|
| H86 | H87 | H88 | H89 | H90 | H91 | H92 | H93 | H94 | H95 | H96 | H97 | H98 |
| D | T | A | V | Y | Y | C | Y | A | D | Y | E | D |
| 92 | 93 | 94 | 95 | 96 | 97 | 98 | 99 | 100 | 101 | 102 | 103 | 104 |

|  | | | | | | CDR-H3 | | | | |
|---|---|---|---|---|---|---|---|---|---|---|
|  | H99 | H100 | H100A | H100B | H100C | H100D | H101 | H102 | H103 | H104 |
|  | H | D | S | P | H | N | A | S | W | G |
|  | 105 | 106 | 107 | 108 | 109 | 110 | 111 | 112 | 113 | 114 |
|  | H105 | H106 | H107 | H108 | H109 | H110 | H111 | H112 | H113 | |
|  | Q | G | T | Q | V | T | V | S | S | |
|  | 115 | 116 | 117 | 118 | 119 | 120 | 121 | 122 | 123 | |

| ID-114V | H1 | H2 | H3 | H4 | H5 | H6 | H7 | H8 | H9 | H10 | H11 | H12 | H13 |
|---|---|---|---|---|---|---|---|---|---|---|---|---|---|
|  | E | V | Q | L | V | E | S | G | G | G | L | V | Q |
|  | 1 | 2 | 3 | 4 | 5 | 6 | 7 | 8 | 9 | 10 | 11 | 12 | 13 |

|     | H14 | H15 | H16 | H17 | H18 | H19 | H20 | H21 | H22 | H23 | H24 | H25 | H26 |
|-----|-----|-----|-----|-----|-----|-----|-----|-----|-----|-----|-----|-----|-----|
|     | A   | G   | G   | S   | T   | R   | L   | T   | C   | K   | A   | S   | G   |
|     | 14  | 15  | 16  | 17  | 18  | 19  | 20  | 21  | 22  | 23  | 24  | 25  | 26  |

|     |     |     |     |     |     |     |     | CDR-H1 | | | | |
|-----|-----|-----|-----|-----|-----|-----|-----|-----|-----|-----|-----|-----|-----|
|     | H27 | H28 | H29 | H29A | H29B | H29C | H30 | H31 | H32 | H33 | H34 | H35 | H36 |
|     | S   | I   | S   | N    | I    | N    | S   | I   | N   | V   | M   | A   | W   |
|     | 27  | 28  | 29  | 30   | 31   | 32   | 33  | 34  | 35  | 36  | 37  | 38  | 39  |

|     | H37 | H38 | H39 | H40 | H41 | H42 | H43 | H44 | H45 | H46 | H47 | H48 | H49 |
|-----|-----|-----|-----|-----|-----|-----|-----|-----|-----|-----|-----|-----|-----|
|     | Y   | R   | Q   | A   | P   | G   | K   | G   | R   | E   | L   | V   | A   |
|     | 40  | 41  | 42  | 43  | 44  | 45  | 46  | 47  | 48  | 49  | 50  | 51  | 52  |

|     |     |     |     | CDR2-H2 | | | | | | | | |
|-----|-----|-----|-----|-----|-----|-----|-----|-----|-----|-----|-----|-----|-----|
|     | H50 | H51 | H52 | H53 | H54 | H55 | H56 | H57 | H58 | H59 | H60 | H61 | H62 |
|     | I   | I   | G   | K   | G   | G   | G   | T   | N   | Y   | A   | D   | F   |
|     | 53  | 54  | 55  | 56  | 57  | 58  | 59  | 60  | 61  | 62  | 63  | 64  | 65  |

|     | CDR2-H2 | | | | | | | | | | | |
|-----|-----|-----|-----|-----|-----|-----|-----|-----|-----|-----|-----|-----|-----|
|     | H63 | H64 | H65 | H66 | H67 | H68 | H69 | H70 | H71 | H72 | H73 | H74 | H75 |
|     | V   | K   | G   | R   | F   | T   | I   | S   | R   | D   | A   | A   | K   |
|     | 66  | 67  | 68  | 69  | 70  | 71  | 72  | 73  | 74  | 75  | 76  | 77  | 78  |

|     | H76 | H77 | H78 | H79 | H80 | H81 | H82 | H82A | H82B | H82C | H83 | H84 | H85 |
|-----|-----|-----|-----|-----|-----|-----|-----|------|------|------|-----|-----|-----|
|     | N   | T   | V   | Y   | L   | Q   | M   | N    | S    | L    | R   | P   | E   |
|     | 79  | 80  | 81  | 82  | 83  | 84  | 85  | 86   | 87   | 88   | 89  | 90  | 91  |

|     |     |     |     |     |     |     |     |     | CDR-H3 | | | |
|-----|-----|-----|-----|-----|-----|-----|-----|-----|-----|-----|-----|-----|-----|
|     | H86 | H87 | H88 | H89 | H90 | H91 | H92 | H93 | H94 | H95 | H96 | H97 | H98 |
|     | D   | T   | A   | V   | Y   | Y   | C   | Y   | A   | D   | Y   | E   | D   |
|     | 92  | 93  | 94  | 95  | 96  | 97  | 98  | 99  | 100 | 101 | 102 | 103 | 104 |

|     |     |     | CDR-H3 | | | | | | |
|-----|-----|-----|-----|-----|-----|-----|-----|-----|-----|
|     | H99 | H100 | H100A | H100B | H100C | H100D | H101 | H102 | H103 | H104 |
|     | H   | D    | S     | P     | F     | N     | A    | S    | W    | G    |
|     | 105 | 106  | 107   | 108   | 109   | 110   | 111  | 112  | 113  | 114  |

|     | H105 | H106 | H107 | H108 | H109 | H110 | H111 | H112 | H113 |
|-----|------|------|------|------|------|------|------|------|------|
|     | Q    | G    | T    | Q    | V    | T    | V    | S    | S    |
|     | 115  | 116  | 117  | 118  | 119  | 120  | 121  | 122  | 123  |

| ID-122V | H1 | H2 | H3 | H4 | H5 | H6 | H7 | H8 | H9 | H10 | H11 | H12 | H13 |
|---------|----|----|----|----|----|----|----|----|----|-----|-----|-----|-----|
|         | E  | V  | Q  | L  | V  | E  | S  | G  | G  | G   | L   | V   | Q   |
|         | 1  | 2  | 3  | 4  | 5  | 6  | 7  | 8  | 9  | 10  | 11  | 12  | 13  |

|     | H14 | H15 | H16 | H17 | H18 | H19 | H20 | H21 | H22 | H23 | H24 | H25 | H26 |
|-----|-----|-----|-----|-----|-----|-----|-----|-----|-----|-----|-----|-----|-----|
|     | A   | G   | G   | S   | T   | R   | L   | T   | C   | K   | A   | S   | G   |
|     | 14  | 15  | 16  | 17  | 18  | 19  | 20  | 21  | 22  | 23  | 24  | 25  | 26  |

|     |     |     |     |     |     |     |     | CDR-H1 | | | | |
|-----|-----|-----|-----|-----|-----|-----|-----|-----|-----|-----|-----|-----|-----|
|     | H27 | H28 | H29 | H29A | H29B | H29C | H30 | H31 | H32 | H33 | H34 | H35 | H36 |
|     | S   | I   | S   | N    | I    | N    | S   | I   | N   | V   | M   | A   | W   |
|     | 27  | 28  | 29  | 30   | 31   | 32   | 33  | 34  | 35  | 36  | 37  | 38  | 39  |

|     | H37 | H38 | H39 | H40 | H41 | H42 | H43 | H44 | H45 | H46 | H47 | H48 | H49 |
|-----|-----|-----|-----|-----|-----|-----|-----|-----|-----|-----|-----|-----|-----|
|     | Y   | R   | Q   | A   | P   | G   | K   | G   | R   | E   | L   | V   | A   |
|     | 40  | 41  | 42  | 43  | 44  | 45  | 46  | 47  | 48  | 49  | 50  | 51  | 52  |

| CDR2-H2 | | | | | | | | | | | | |
|---|---|---|---|---|---|---|---|---|---|---|---|---|
| H50 | H51 | H52 | H53 | H54 | H55 | H56 | H57 | H58 | H59 | H60 | H61 | H62 |
| I 53 | I 54 | G 55 | K 56 | G 57 | G 58 | G 59 | T 60 | N 61 | Y 62 | A 63 | D 64 | F 65 |

| CDR2-H2 | | | | | | | | | | | |
|---|---|---|---|---|---|---|---|---|---|---|---|
| H63 | H64 | H65 | H66 | H67 | H68 | H69 | H70 | H71 | H72 | H73 | H74 | H75 |
| V 66 | K 67 | G 68 | R 69 | F 70 | T 71 | I 72 | S 73 | R 74 | D 75 | A 76 | A 77 | K 78 |

| H76 | H77 | H78 | H79 | H80 | H81 | H82 | H82A | H82B | H82C | H83 | H84 | H85 |
|---|---|---|---|---|---|---|---|---|---|---|---|---|
| N 79 | T 80 | V 81 | N 82 | L 83 | Q 84 | M 85 | N 86 | S 87 | L 88 | R 89 | P 90 | E 91 |

| | | | | | | | | CDR-H3 | | | |
|---|---|---|---|---|---|---|---|---|---|---|---|
| H86 | H87 | H88 | H89 | H90 | H91 | H92 | H93 | H94 | H95 | H96 | H97 | H98 |
| D 92 | T 93 | A 94 | V 95 | Y 96 | Y 97 | C 98 | Y 99 | A 100 | D 101 | Y 102 | E 103 | D 104 |

| CDR-H3 | | | | | | | | | |
|---|---|---|---|---|---|---|---|---|
| H99 | H100 | H100A | H100B | H100C | H100D | H101 | H102 | H103 | H104 |
| H 105 | D 106 | S 107 | P 108 | H 109 | N 110 | A 111 | S 112 | W 113 | G 114 |

| H105 | H106 | H107 | H108 | H109 | H110 | H111 | H112 | H113 |
|---|---|---|---|---|---|---|---|---|
| Q 115 | G 116 | T 117 | Q 118 | V 119 | T 120 | V 121 | S 122 | S 123 |

| ID-123V | H1 | H2 | H3 | H4 | H5 | H6 | H7 | H8 | H9 | H10 | H11 | H12 | H13 |
|---|---|---|---|---|---|---|---|---|---|---|---|---|---|
| | E 1 | V 2 | Q 3 | L 4 | V 5 | E 6 | S 7 | G 8 | G 9 | G 10 | L 11 | V 12 | Q 13 |

| H14 | H15 | H16 | H17 | H18 | H19 | H20 | H21 | H22 | H23 | H24 | H25 | H26 |
|---|---|---|---|---|---|---|---|---|---|---|---|---|
| A 14 | G 15 | G 16 | S 17 | T 18 | R 19 | L 20 | T 21 | C 22 | K 23 | A 24 | S 25 | G 26 |

| | | | | | | | CDR-H1 | | | | |
|---|---|---|---|---|---|---|---|---|---|---|---|
| H27 | H28 | H29 | H29A | H29B | H29C | H30 | H31 | H32 | H33 | H34 | H35 | H36 |
| S 27 | I 28 | S 29 | N 30 | I 31 | N 32 | S 33 | I 34 | N 35 | V 36 | M 37 | A 38 | W 39 |

| H37 | H38 | H39 | H40 | H41 | H42 | H43 | H44 | H45 | H46 | H47 | H48 | H49 |
|---|---|---|---|---|---|---|---|---|---|---|---|---|
| Y 40 | R 41 | Q 42 | A 43 | P 44 | G 45 | K 46 | G 47 | R 48 | E 49 | L 50 | V 51 | A 52 |

| CDR2-H2 | | | | | | | | | | | | |
|---|---|---|---|---|---|---|---|---|---|---|---|---|
| H50 | H51 | H52 | H53 | H54 | H55 | H56 | H57 | H58 | H59 | H60 | H61 | H62 |
| I 53 | I 54 | G 55 | K 56 | G 57 | G 58 | G 59 | T 60 | N 61 | Y 62 | A 63 | D 64 | F 65 |

| CDR2-H2 | | | | | | | | | | | |
|---|---|---|---|---|---|---|---|---|---|---|---|
| H63 | H64 | H65 | H66 | H67 | H68 | H69 | H70 | H71 | H72 | H73 | H74 | H75 |
| V 66 | K 67 | G 68 | R 69 | F 70 | T 71 | I 72 | S 73 | R 74 | D 75 | A 76 | A 77 | K 78 |

| H76 | H77 | H78 | H79 | H80 | H81 | H82 | H82A | H82B | H82C | H83 | H84 | H85 |
|---|---|---|---|---|---|---|---|---|---|---|---|---|
| N 79 | T 80 | V 81 | Y 82 | L 83 | Q 84 | M 85 | N 86 | S 87 | L 88 | R 89 | P 90 | E 91 |

| | H86 | H87 | H88 | H89 | H90 | H91 | H92 | H93 | H94 | CDR-H3 H95 | H96 | H97 | H98 |
|---|---|---|---|---|---|---|---|---|---|---|---|---|---|
| | D | T | A | V | Y | Y | C | Y | A | D | Y | E | D |
| | 92 | 93 | 94 | 95 | 96 | 97 | 98 | 99 | 100 | 101 | 102 | 103 | 104 |

| CDR-H3 | | | | | | | | |
|---|---|---|---|---|---|---|---|---|
| H99 | H100 | H100A | H100B | H100C | H100D | H101 | H102 | H103 | H104 |
| H | D | S | P | H | N | A | S | W | G |
| 105 | 106 | 107 | 108 | 109 | 110 | 111 | 112 | 113 | 114 |
| H105 | H106 | H107 | H108 | H109 | H110 | H111 | H112 | H113 | |
| Q | G | T | Q | V | T | V | S | S | |
| 115 | 116 | 117 | 118 | 119 | 120 | 121 | 122 | 123 | |

Note that the ICVDs of the invention provided above all share similar CDR3s. It should also be noted that the 5G9-related ICVDs above all share a 'NIN' insert in FR1 (29A-29C in Kabat numbering).

The Kabat numbering system applied to other immunoglobulin chain variable domains referred to in the examples:

| 4D3 | H1 | H2 | H3 | H4 | H5 | H6 | H7 | H8 | H9 | H10 | H11 | H12 | H13 |
|---|---|---|---|---|---|---|---|---|---|---|---|---|---|
| | E | V | Q | L | V | E | S | G | G | G | L | V | Q |
| | 1 | 2 | 3 | 4 | 5 | 6 | 7 | 8 | 9 | 10 | 11 | 12 | 13 |

| H14 | H15 | H16 | H17 | H18 | H19 | H20 | H21 | H22 | H23 | H24 | H25 | H26 |
|---|---|---|---|---|---|---|---|---|---|---|---|---|
| A | G | E | S | L | T | L | S | C | V | A | S | I |
| 14 | 15 | 16 | 17 | 18 | 19 | 20 | 21 | 22 | 23 | 24 | 25 | 26 |

| | | | | CDR-H1 | | | | | | | | |
|---|---|---|---|---|---|---|---|---|---|---|---|---|
| H27 | H28 | H29 | H30 | H31 | H32 | H33 | H34 | H35 | H36 | H37 | H38 | H39 |
| S | T | F | S | Q | N | A | M | G | W | F | R | Q |
| 27 | 28 | 29 | 30 | 31 | 32 | 33 | 34 | 35 | 36 | 37 | 38 | 39 |

| | | | | | | | | | | CDR2-H2 | | |
|---|---|---|---|---|---|---|---|---|---|---|---|---|
| H40 | H41 | H42 | H43 | H44 | H45 | H46 | H47 | H48 | H49 | H50 | H51 | H52 |
| A | A | G | K | R | R | E | S | V | A | R | I | S |
| 40 | 41 | 42 | 43 | 44 | 45 | 46 | 47 | 48 | 49 | 50 | 51 | 52 |

| CDR-H2 | | | | | | | | | | | | |
|---|---|---|---|---|---|---|---|---|---|---|---|---|
| H53 | H54 | H55 | H56 | H57 | H58 | H59 | H60 | H61 | H62 | H63 | H64 | H65 |
| S | S | G | N | V | G | Y | T | D | A | V | K | G |
| 53 | 54 | 55 | 56 | 57 | 58 | 59 | 60 | 61 | 62 | 63 | 64 | 65 |

| H66 | H67 | H68 | H69 | H70 | H71 | H72 | H73 | H74 | H75 | H76 | H77 | H78 |
|---|---|---|---|---|---|---|---|---|---|---|---|---|
| R | F | T | M | S | R | D | N | A | K | K | T | V |
| 66 | 67 | 68 | 69 | 70 | 71 | 72 | 73 | 74 | 75 | 76 | 77 | 78 |

| H79 | H80 | H81 | H82 | H82A | HB82B | H82C | HB3 | HB4 | H85 | H86 | H87 | H88 |
|---|---|---|---|---|---|---|---|---|---|---|---|---|
| Y | I | Q | M | N | S | L | K | P | E | D | T | A |
| 79 | 80 | 81 | 82 | 83 | 84 | 85 | 86 | 87 | 88 | 89 | 90 | 91 |

| | | | | | | CDR-H3 | | | | | |
|---|---|---|---|---|---|---|---|---|---|---|---|
| H89 | H90 | H91 | H92 | H93 | H94 | H95 | H96 | H97 | H98 | H99 | H100 | H100A |
| V | Y | Y | C | N | A | Y | S | M | S | G | E | L |
| 92 | 93 | 94 | 95 | 96 | 97 | 98 | 99 | 100 | 101 | 102 | 103 | 104 |

-continued

| | | | | CDR-H3 | | | | | | |
|---|---|---|---|---|---|---|---|---|---|---|
| H100B | H101 | H102 | H103 | H104 | H105 | H106 | H107 | H108 | H109 | H110 |
| A 105 | A 106 | P 107 | W 108 | G 109 | Q 110 | G 111 | T 112 | Q 113 | V 114 | T 115 |

| H111 | H112 | H113 |
|---|---|---|
| V 116 | S 117 | S 118 |

| 3C12 | H1 | H2 | H3 | H4 | H5 | H6 | H7 | H8 | H9 | H10 | H11 | H12 | H13 |
|---|---|---|---|---|---|---|---|---|---|---|---|---|---|
| | E 1 | V 2 | Q 3 | L 4 | V 5 | E 6 | S 7 | G 8 | G 9 | G 10 | L 11 | V 12 | Q 13 |

| H14 | H15 | H16 | H17 | H18 | H19 | H20 | H21 | H22 | H23 | H24 | H25 | H26 |
|---|---|---|---|---|---|---|---|---|---|---|---|---|
| L 14 | G 15 | G 16 | S 17 | L 18 | R 19 | L 20 | S 21 | C 22 | V 23 | A 24 | S 25 | G 26 |

| | | | | CDR-H1 | | | | | | | | |
|---|---|---|---|---|---|---|---|---|---|---|---|---|
| H27 | H28 | H29 | H30 | H31 | H32 | H33 | H34 | H35 | H36 | H37 | H38 | H39 |
| N 27 | I 28 | F 29 | S 30 | S 31 | N 32 | T 33 | A 34 | G 35 | W 36 | F 37 | R 38 | Q 39 |

| | | | | | | | | | | CDR2-H2 | |
|---|---|---|---|---|---|---|---|---|---|---|---|
| H40 | H41 | H42 | H43 | H44 | H45 | H46 | H47 | H48 | H49 | H50 | H51 | H52 |
| A 40 | P 41 | G 42 | K 43 | Q 44 | R 45 | E 46 | W 47 | V 48 | A 49 | G 50 | I 51 | S 52 |

| | | | | CDR-H2 | | | | | | | | |
|---|---|---|---|---|---|---|---|---|---|---|---|---|
| H53 | H54 | H55 | H56 | H57 | H58 | H59 | H60 | H61 | H62 | H63 | H64 | H65 |
| I 53 | G 54 | G 55 | M 56 | P 57 | A 58 | Y 59 | A 60 | D 61 | S 62 | V 63 | K 64 | G 65 |

| H66 | H67 | H68 | H69 | H70 | H71 | H72 | H73 | H74 | H75 | H76 | H77 | H78 |
|---|---|---|---|---|---|---|---|---|---|---|---|---|
| R 66 | F 67 | T 68 | I 69 | S 70 | R 71 | D 72 | N 73 | A 74 | K 75 | N 76 | T 77 | V 78 |

| H79 | H80 | H81 | H82 | H82A | HB82B | H82C | HB3 | HB4 | H85 | H86 | H87 | H88 |
|---|---|---|---|---|---|---|---|---|---|---|---|---|
| Y 79 | L 80 | Q 81 | M 82 | N 83 | S 84 | L 85 | K 86 | P 87 | E 88 | D 89 | T 90 | A 91 |

| | | | | | | CDR-H3 | | | | | |
|---|---|---|---|---|---|---|---|---|---|---|---|
| H89 | H90 | H91 | H92 | H93 | H94 | H95 | H96 | H97 | H98 | H99 | H101 | H102 |
| V 92 | Y 93 | Y 94 | C 95 | A 96 | T 97 | G 98 | G 99 | T 100 | E 101 | Y 102 | D 103 | Y 104 |

| H103 | H104 | H105 | H106 | H107 | H108 | H109 | H110 | H111 | H112 | H113 |
|---|---|---|---|---|---|---|---|---|---|---|
| W 105 | G 106 | Q 107 | G 108 | T 109 | Q 110 | V 111 | T 112 | V 113 | S 114 | S 115 |

Note that the ICVDs above which fall outside the scope of the invention share distinct CDR3s from ICVDs falling within the scope of the invention. The CDRs of the polypeptides labelled above as 'CDR-H1'/'CDR1-H1', 'CDR-H2'/'CDR2-H2' and 'CDR-H3'/'CDR3-H3' relate to 'CDR1', 'CDR2' and 'CDR3' respectively, as discussed herein. Numbering in the figures above with the prefix 'H' is Kabat numbering, while numbering below the amino acid sequence is numbering of amino acids consecutively from N- to C-terminus. The residues of each CDR or FR can also be numbered from the N- to the C-terminus of that CDR or FR. For example, it can be seen that CDR3 of 5G9 contains S at position 107 numbered from N- to C-terminus of the full length polypeptide, which is also position 100A according to Kabat, which is also residue number 7 of CDR3 of 5G9.

Also highlighted above are insertion sequences NIN (H29A-H29C), NSL (H82A-H82C), SPFN/SPHN (H100A-H100D) and H100A-H100B (LA).

CDR3 Sequences

Suitably CDR3 of the polypeptide of the present invention comprises or more suitably consists of a sequence sharing 50%, 55%, 60%, more suitably 65%, 70%, 75%, 80%, 85%, 90% or greater sequence identity with SEQ ID NO: 3.

Alternatively, CDR3 of the polypeptide of the present invention comprises or more suitably consists of a sequence having no more than 6, more suitably no more than 5, more suitably no more than 4, more suitably no more than 3, more suitably no more than 2, more suitably no more than 1 addition(s) compared to SEQ ID NO: 3. Suitably, CDR3 of the polypeptide of the present invention comprises or more suitably consists of a sequence having no more than 6, more suitably no more than 5, more suitably no more than 4, more suitably no more than 3, more suitably no more than 2, more suitably no more than 1 substitution(s) compared to SEQ ID NO: 3. Suitably, CDR3 of the polypeptide of the present invention comprises or more suitably consists of a sequence having no more than 6, more suitably no more than 5, more suitably no more than 4, more suitably no more than 3, more suitably no more than 2, more suitably no more than 1 deletion(s) compared to SEQ ID NO: 3. Suitably, any substitutions are conservative, with respect to their corresponding residues in SEQ ID NO: 3.

Suitably any residues of CDR3 differing from their corresponding residues in SEQ ID NO: 3 are conservative substitutions with respect to their corresponding residues.

Suitably the residue of CDR3 corresponding to residue number 5 of SEQ ID NO: 3 is R or H, most suitably H. Suitably the residue of CDR3 corresponding to residue number 5 of SEQ ID NO: 3 is R or H, most suitably H, and any other residues of CDR3 differing from their corresponding residues in SEQ ID NO: 3 are conservative substitutions with respect to their corresponding residues.

Suitably the residue of CDR3 corresponding to residue number 9 of SEQ ID NO: 3 is F, L or H, more suitably F or H, most suitably H. Suitably the residue of CDR3 corresponding to residue number 9 of SEQ ID NO: 3 is F, L or H, most suitably H, and any other residues of CDR3 differing tom their corresponding residues in SEQ ID NO: 3 are conservative substitutions with respect to their corresponding residues.

Suitably the residue of CDR3 corresponding to residue number 11 of SEQ ID NO: 3 is A, G, or a conservative substitution thereof. Suitably the residue of CDR3 corresponding to residue number 11 of SEQ ID NO: 3 is A or G, most suitably A. Suitably the residue of CDR3 corresponding to residue number 11 of SEQ ID NO: 3 is A or G, most suitably A, and any other residues of CDR3 differing from their corresponding residues in SEQ ID NO: 3 are conservative substitutions with respect to their corresponding residues.

Suitably CDR3 comprises or more suitably consists of SEQ ID NO: 3.

CDR1 and CDR2 Sequences Derived from 5G9

Suitably CDR1 of the polypeptide of the present invention comprises or more suitably consists of a sequence sharing 50%, 55%, 60%, 65%, 70%, 75%, 80%, 85%, 90% or greater sequence identity, with SEQ ID NO: 1.

Alternatively, CDR1 of the polypeptide of the present invention comprises or more suitably consists of a sequence having no more than 4, more suitably no more than 3, more suitably no more than 2, more suitably no more than 1 addition(s) compared to SEQ ID NO: 1. Suitably, CDR1 of the polypeptide of the present invention comprises or more suitably consists of a sequence having no more than 4, more suitably no more than 3, more suitably no more than 2, more suitably no more than 1 substitution(s) compared to SEQ ID NO: 1. Suitably, CDR1 of the polypeptide of the present invention comprises or more suitably consists of a sequence having no more than 4, more suitably no more than 3, more suitably no more than 2, more suitably no more than 1 deletion(s) compared to SEQ ID NO: 1.

Suitably any residues of CDR1 differing from their corresponding residues in SEQ ID NO: 1 are conservative substitutions with respect to their corresponding residues. Suitably CDR1 comprises or more suitably consists of SEQ ID NO: 1.

Suitably CDR2 of the polypeptide of the present invention comprises or more suitably consists of a sequence sharing 50%, 55%, 60%, 65%, 70%, 75%, 80%, 85%, 90% or greater sequence identity, with SEQ ID NO: 2.

Alternatively, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 2. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 2. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 2.

Suitably any residues of CDR2 differing from their corresponding residues in SEQ ID NO: 2 are conservative substitutions with respect to their corresponding residues. Suitably CDR2 comprises or more suitably consists of SEQ ID NO: 2.

CDR1 and CDR2 Sequences Derived from 7F6

Suitably CDR1 of the polypeptide of the present invention comprises or more, suitably consists of a sequence sharing 20%, 40%, 60%, 80% or greater sequence identity, with SEQ ID NO: 8.

Alternatively, CDR1 of the polypeptide of the present invention comprises or more suitably consists of a sequence having no more than 4, more suitably no more than 3, more suitably no more than 2, more suitably no more than 1 addition(s) compared to SEQ ID NO: 8. Suitably, CDR1 of the polypeptide of the present invention comprises or more suitably consists of a sequence having no more than 4, more suitably no more than 3, more suitably no more than 2, more suitably no more than 1 substitution(s) compared to SEQ ID NO: 8. Suitably, CDR1 of the polypeptide of the present invention comprises or more suitably consists of a sequence having no more than 4, more suitably no more than 3, more suitably no more than 2, more suitably no more than 1 deletion(s) compared to SEQ ID NO: 8.

Suitably any residues of CDR1 differing from their corresponding residues in SEQ ID NO: 8 are conservative substitutions with respect to their corresponding residues. Suitably CDR1 comprises or more suitably consists of SEQ ID NO: 8.

Suitably CDR2 of the polypeptide of the present invention comprises or more suitably consists of a sequence sharing 50%, 55%, 60%, 65%, 70%, 75%, 80%, 85%, 90% or greater sequence identity, with SEQ ID NO: 9.

Alternatively, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 9. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 9. Suitably, CDR2 of the polypeptide of the present invention comprises or more suitably consists of a sequence having no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 9.

Suitably any residues of CDR2 differing from their corresponding residues in SEQ ID NO: 9 are conservative substitutions with respect to their corresponding residues. Suitably CDR2 comprises or more suitably consists of SEQ ID NO: 9.

Specific CDR Sequences

Some particularly suitable CDR sequences are shown in the table below. Suitably, CDR1 of the polypeptide of the invention is one of the CDR1 sequences listed below. Suitably, CDR2 of the polypeptide of the invention is one of the CDR2 sequences listed below. Suitably, CDR3 of the polypeptide of the invention is one of the CDR3 sequences listed below. Suitably, the polypeptide of the invention comprises a combination of two, or more suitably three, of the CDR sequences listed below.

Particular CDRs of the polypeptide of the invention:

| CDR1 | CDR2 | CDR3 |
|---|---|---|
| INVMA (CDR1 of multiple ICVDs including ID-142V, SEQ ID NO: 1) | IIGKGGGTNYADFVKG (CDR2 of multiple ICVDs including ID-142V, SEQ ID NO: 2) | DYEDRDSPFNAS (CDR3 of multiple ICVDs including 5G9, SEQ ID NO: 48) |
| INVI Framework Sequences Suitably FR1 of the polypeptide of the present invention comprises or more suitably consists of a sequence sharing 5%, 12%, 18%, 26%, 32%, 38%, 46%, 52%, 58%, 62%, 66%, 68%, 72%, 75%, 78%, 82%, 85%, 90%, 95% or greater sequence identity, with SEQ ID NO: 4 or SEQ ID NO: 10.

Alternatively, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 4 or SEQ ID NO: 10. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 4 or SEQ ID NO: 10. Suitably, FR1 of the polypeptide of the present invention comprises or more suitably consists of a sequence having no more than 28, more suitably no more than 26, more suitably no more than 24, more suitably no more than 22, more suitably no more than 20, more suitably no more than 18, more suitably no more than 16, more suitably no more than 14, more suitably no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 4 or SEQ ID NO: 10.

Suitably any residues of FR1 differing from their corresponding residues in SEQ ID NO: 4 or SEQ ID NO: 10 are conservative substitutions with respect to their corresponding residues.

Suitably the residue of FR1 corresponding to residue number 1 of SEQ ID NO: 4 or SEQ ID NO: 10 is G, A, V, L, I, F, P, S, T, Y, C, M, K, R, H, W, D, E or N (more suitably D or E, most suitably D). Suitably the residue of FR1 corresponding to residue number 23 of SEQ ID NO: 4 or SEQ ID NO: 10 is K or L. Suitably the residues of FR1 corresponding to residue numbers 2 to 5 of SEQ ID NO: 4 or SEQ ID NO: 10 are VQLV. Suitably the residue of FR1 corresponding to residue number 29 of SEQ ID NO: 4 or SEQ ID NO: 10 is F or S, most suitably S. Suitably the residue of FR1 corresponding to residue number 30 of SEQ ID NO: 4 or SEQ ID NO: 10 is N or S. Suitably FR1 comprises or more suitably consists of SEQ ID NO: 4 or SEQ ID NO: 10.

Suitably FR1 comprises the sequence NIN or three consecutive amino acids wherein one or more of the amino acids is a conservative substitution of the corresponding amino acid in the sequence NIN. Most suitably FR1 comprises the sequence NIN. More suitably the last four C-terminal residues of FR1 are NINX or four consecutive amino acids wherein one or more of the amino acids is a conservative substitution of the corresponding amino acid in the sequence NINX, wherein X is any amino acid. Suitably X is S or a conservative substitution of S, most suitably X is S. More suitably FR1 consists of 33 residues and the last four residues of FR1 are NINS.

Suitably FR2 of the polypeptide of the present invention comprises or more suitably consists of a sequence sharing 10%, 15%, 25%, 30%, 40%, 45%, 55%, 60%, 70%, 75%, 85%, 90% or greater sequence identity, with SEQ ID NO: 5 or SEQ ID NO: 11, Alternatively, FR2 of the polypeptide of the present invention comprises or more, suitably consists of a sequence having no more than 13, more suitably no more than 12, more suitably no more than 1.1, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 5 or SEQ ID NO: 11. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 5 or SEQ ID NO: 11. Suitably, FR2 of the polypeptide of the present invention comprises or more suitably consists of a sequence having no more than 13, more suitably no more than 12, more suitably no more than 11, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 5 or SEQ ID NO: 11.

Suitably any residues of FR2 differing from their corresponding residues in SEQ ID NO: 5 or SEQ ID NO: 11 are conservative substitutions with respect to their corresponding residues. Suitably the residue of FR2 corresponding to residue number 9 of SEQ ID NO: 5 or SEQ ID NO: 11 is G or Q. Suitably the residues of FR2 corresponding to residue numbers 8 to 11 of SEQ ID NO: 5 or SEQ ID NO: 11 are KERE, KELE, KGRE or KQRE; most suitably KGRE or KQRE. Suitably FR2 comprises or more suitably consists of SEQ ID NO: 5 or SEQ ID NO: 11.

Suitably FR3 of the polypeptide of the present invention comprises or more suitably consists of a sequence sharing 8%, 15%, 20%, 26%, 32%, 40%, 45%, 52%, 58%, 65%, 70%, 76%, 80%, 82%, 85%, 90%, 92%, 95% or greater sequence identity, with SEQ ID NO: 6 or SEQ ID NO: 12.

Alternatively, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 addition(s) compared to SEQ ID NO: 6 or SEQ ID NO: 12. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 6 or SEQ ID NO: 12. Suitably, FR3 of the polypeptide of the present invention comprises or more suitably consists of a sequence having no more than 29, more suitably no more than 27, more suitably no more than 25, more suitably no more than 23, more suitably no more than 21, more suitably no more than 19, more suitably no more than 17, more suitably no more than 15, more suitably no more than 13, more suitably no more than 11, more suitably no more than 9, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 6 or SEQ ID NO: 12.

Suitably the residue of FR3 corresponding to residue number 8 of SEQ ID NO: 6 or SEQ ID NO: 12 is an amino acid which is hydrophobic (suitably A or N, more suitably A). Suitably the residue of FR3 corresponding to residue number 9 of SEQ ID NO: 6 or SEQ ID NO: 12 is an amino acid which is hydrophobic (suitably A or S, more suitably A). Suitably the residue of FR3 corresponding to residue number 13 of SEQ ID NO: 6 or SEQ ID NO: 12 is V or L, most suitably V. Suitably the residue of FR3 corresponding to residue number 14 of SEQ ID NO: 6 or SEQ ID NO: 1.2 is N or Y, most suitably Y. Suitably the residue of FR3 corresponding to residue number 21 of SEQ ID NO: 6 or SEQ ID NO: 12 is R or K, most suitably R.

Suitably any residues of FR3 differing from their corresponding residues in SEQ ID NO: 6 or SEQ ID NO: 12 are conservative substitutions with respect to their corresponding residues. Suitably FR3 comprises or more suitably consists of SEQ ID NO: 6 or SEQ ID NO: 12.

Suitably FR4 of the polypeptide of the present invention comprises or more suitably consists of a sequence sharing 5%, 10%, 20%, 30%, 40%, 50%, 60%, 70%, 80%, 90% or greater sequence identity, with SEQ ID NO: 7.

Alternatively, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NO: 7. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NO: 7. Suitably, FR4 of the polypeptide of the present invention comprises or more suitably consists of a sequence having no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to SEQ ID NO: 7.

Suitably any residues of FR4 differing from their corresponding residues in SEQ ID NO: 7 are conservative substitutions with respect to their corresponding residues. Suitably FR4 comprises or more suitably consists of SEQ ID NO: 7.

The particularly preferred framework sequences of ICVDs ID-141V, ID-142V, ID-143V and ID-144V are listed below.

```
DVQLVESGGGLVQAGGSTRLTCKASGSISNINS
(FR1 of ID-141V, ID-142V, ID-143V
and ID-144V, SEQ ID NO: 86)

VVYRQAPGKGRELVA
(FR2 of ID-141V, ID-142V, ID-143V
and ID-144V, SEQ ID NO: 87)

RFTISRDAAKNTLYLQMNSLRPEDTAVYYCYA
(FR3 of ID-141V and ID-143V, SEQ ID NO: 88)

RFTISRDAAKNTVYLQMNSLRPEDTAVYYCYA
(FR3 of ID-142V and ID-144V, SEQ ID NO: 89)

WGQGTQVTVSS
(FR4 of ID-141V, ID-142V, ID-143V
and ID-144V, SEQ ID NO: 90)
```

Suitably FR1 of the polypeptide of the invention comprises or more suitably consists of SEQ ID NO: 86. Suitably FR2 of the polypeptide of the invention comprises or more suitably consists of SEQ ID NO: 87. Suitably FR3 of the polypeptide of the invention comprises or more suitably consists of SEQ ID NO: 88 or SEQ ID NO: 89. Suitably FR4 of the polypeptide of the invention comprises of more suitably consists of SEQ ID NO: 90.

Full Length Sequences Derived from 5G9

Suitably the polypeptide of the present invention comprises or more suitably consists of a sequence sharing 50%, 55%, 60%, 65%, 70%, 75%, 80%, 85%, 90%, 95%, 96%, 97%, 98%, 99% or greater sequence identity, with any one of SEQ ID NOs: 15 to 31, 43 or 44, more suitably SEQ ID NOs: 24-31, more suitably SEQ ID NO: 29 or SEQ ID NO: 30.

Alternatively, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to any one of SEQ. ID NOs: 15 to 31, 43 or 44, more suitably SEQ ID NOs: 24-31, more suitably SEQ ID NO: 29 or SEQ ID NO: 30. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to any one of SEQ ID NOs: 15 to 31, 43 or 44, more suitably SEQ ID NOs: 24-31, more suitably SEQ ID NO: 29 or SEQ ID NO: 30. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to any one of SEQ ID NOs: 15 to 31, 43 or 44, more suitably SEQ ID NOs: 24-31, more suitably SEQ ID NO: 29 or SEQ ID NO: 30.

Suitably the N-terminus of the polypeptide is D. Suitably the polypeptide comprises or more suitably consists of any one of SEQ ID NOs: 15 to 31, 43 or 44, more suitably SEQ ID NOs: 24-31, more suitably SEQ ID NO: 29 or SEQ ID NO: 30.

Full Length Sequences Derived from 7F6

Suitably the polypeptide of the present invention comprises or more suitably consists of a sequence sharing 50%, 55%, 60%, 65%, 70%, 75%, 80%, 85%, 90%, 95%, 96%, 97%, 98%, 99% or greater sequence identity, with any one of SEQ ID NOs: 32 to 39, more suitably SEQ ID NOs: 33-38, more suitably SEQ ID NO: 33, SEQ ID NO: 34 or SEQ ID NO: 35, more suitably SEQ ID NO: 35.

Alternatively, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 addition(s) compared to SEQ ID NOs: 32 to 39, more suitably SEQ ID NOs: 33-38, more suitably SEQ ID NO: 33, SEQ ID NO: 34 or SEQ ID NO: 35, more suitably SEQ ID NO: 35. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 substitution(s) compared to SEQ ID NOs: 32 to 39, more suitably SEQ ID NOs: 33-38, more suitably SEQ ID NO: 33, SEQ ID NO: 34 or SEQ ID NO: 35, more suitably SEQ ID NO: 35. Suitably, the polypeptide of the present invention comprises or more suitably consists of a sequence having no more than 20, more suitably no more than 15, more suitably no more than 10, more suitably no more than 9, more suitably no more than 8, more suitably no more than 7, more suitably no more than 6, more suitably no more than 5, more suitably no more than 4, more suitably no more than 3, more suitably no more than 2, more suitably no more than 1 deletion(s) compared to any one of SEQ ID NOs: 32 to 39, more suitably SEQ ID NOs: 33-38, more suitably SEQ ID NO: 33, SEQ ID NO: 34 or SEQ ID NO: 35; more suitably SEQ ID NO: 35.

Suitably the N-terminus of the polypeptide is D. Suitably the polypeptide comprises or more suitably consists of any one of SEQ ID NOs: 32 to 39, more suitably SEQ ID NOs: 33-38, more suitably SEQ ID NO: 33, SEQ ID NO: 34 or SEQ ID NO: 35; more suitably SEQ ID NO: 35.

A comparison of the full length percentage identity and the number of identical residues between some of the polypeptides described herein is provided below. Polypeptides of the invention are highlighted in bold.

Full length percentage identity comparison and number of identical residues between ICVDs described herein:

Full length BLASTP polypeptide % Identity (# of identical amino acids/total length of alignment)

| Subject | ID-144V | ID-143V | ID-142V | ID-141V | 5G9 |
|---|---|---|---|---|---|
| 3C12 | 68 (84/123) | 67 (83/123) | 68 (84/123) | 67 (83/123) | 69 (86/123) |
| 4D3 | 63 (78/123) | 62 (77/123) | 63 (78/123) | 62 (77/123) | 65 (80/123) |
| 21E6 | 82 (102/123) | 82 (102/123) | 82 (102/123) | 82 (101/123) | 84 (104/123) |
| 7F6 | 84 (104/123) | 83 (103/123) | 83 (103/123) | 82 (102/123) | 86 (106/123) |
| 5G9 | 95 (117/123) | 94 (116/123) | 94 (116/123) | 93 (115/123) | 100 |
| ID-141V | 98 (121/123) | 99 (122/123) | 99 (122/123) | 100 | — |
| ID-142V | 99 (122/123) | 98 (121/123) | 100 | — | — |
| ID-143V | 99 (122/123) | 100 | — | — | — |
| ID-144V | 100 | — | — | — | — |

| Subject | 7F6 | 21E6 | 403 | 3C12 | — |
|---|---|---|---|---|---|
| 3C12 | 70 (84/120) | 69 (83/120) | 70 (83/118) | 100 | — |
| 4D3 | 64 (77/120) | 64 (77/120) | 100 | — | — |
| 21E6 | 98 (112/120) | 100 | — | — | — |
| 7F6 | 100 | — | — | — | — |

Polynucleotide Sequences

Suitably, the polynucleotides used in the present invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

In one aspect of the invention there is provided a polynucleotide encoding the polypeptide or construct of the invention. Suitably the polynucleotide comprises or consists of a sequence sharing 70% or greater, such as 80% or greater, such as 90% or greater, such as 95% or greater, such, as 99% or greater sequence identity with any one of SEQ ID NOs: 59 to 80. More suitably the polynucleotide comprises or consists of any one of SEQ ID NOs: 59 to 80. In a further aspect there is provided a cDNA comprising said polynucleotide.

In one aspect of the invention there is provided a polynucleotide comprising or consisting of a sequence sharing 70% or greater, such as 80% or greater, such as 90% or greater, such as 95% or greater, such as 99% or greater sequence identity with any one of the portions of any one of SEQ ID NOs: 59 to 80 which encodes CDR1, CDR2 or CDR3 of the encoded immunoglobulin chain variable domain.

Sequence Analysis

Sequence analysis as detailed in Example 17 has revealed that particularly preferred ICVDs of the invention contain one or more conserved differences from their germline equivalent sequence (i.e. maturated residues that, in particular ICVDs of the invention, are maintained during the maturation process, due to their contribution to binding cognate antigen). These conserved amino acids are highlighted in respect of the 5G9 and 7F6 sequences illustrated below (T18, T21, V33, G52, G56, F62 and Y93; according to Kabat numbering). The residues believed to be particularly important for maintenance of optimal potency are V33, G52, G56 and Y93.

Also highlighted below are insertion sequences NIN (H29A-H29C), NSL (H82A-H82C) and SPFN/SPHN (H100A-H100D.

| 5G9 | H1 | H2 | H3 | H4 | H5 | 1-16 | H7 | H8 | H9 | H10 | H11 | H12 | H13 |
|---|---|---|---|---|---|---|---|---|---|---|---|---|---|
|  | E | V | Q | L | V | E | S | G | G | G | L | V | Q |
|  | 1 | 2 | 3 | 4 | 5 | 6 | 7 | 8 | 9 | 10 | 11 | 12 | 13 |
|  | H14 | H15 | H16 | H17 | H18 | H19 | H20 | H21 | H22 | H23 | H24 | H25 | H26 |
|  | A | G | G | S | T | R | L | T | C | K | A | S | G |
|  | 14 | 15 | 16 | 17 | 18 | 19 | 20 | 21 | 22 | 23 | 24 | 25 | 26 |

|  |  |  |  |  |  |  |  | CDR-H1 |  |  |  |  |
|---|---|---|---|---|---|---|---|---|---|---|---|---|
| H27 | H28 | H29 | H29A | H29C | H29C | H30 | H31 | H32 | H33 | H34 | H35 | H36 |
| S | I | F | N | I | N | S | I | N | V | M | A | W |
| 27 | 28 | 29 | 30 | 31 | 32 | 33 | 34 | 35 | 36 | 37 | 38 | 39 |
| H37 | H38 | H39 | H40 | H41 | H42 | H43 | H44 | H45 | H46 | H47 | H48 | H49 |
| Y | R | Q | A | P | G | K | Q | R | E | L | V | A |
| 40 | 41 | 42 | 43 | 44 | 45 | 46 | 47 | 48 | 49 | 50 | 51 | 52 |

|  |  |  | CDR-H2 |  |  |  |  |  |  |  |  |  |
|---|---|---|---|---|---|---|---|---|---|---|---|---|
| H50 | H51 | H52 | H53 | H54 | H55 | H56 | H57 | H58 | H59 | H60 | H61 | H62 |
| I | I | G | K | G | G | G | T | N | Y | A | D | F |
| 53 | 54 | 55 | 56 | 57 | 58 | 59 | 60 | 61 | 62 | 63 | 64 | 65 |

| CDR2-H2 |  |  |  |  |  |  |  |  |  |  |  |  |
|---|---|---|---|---|---|---|---|---|---|---|---|---|
| H63 | H64 | H65 | H66 | H67 | H68 | H69 | H70 | H71 | H72 | H73 | H74 | H75 |
| V | K | G | R | F | T | I | S | R | D | A | A | K |
| 66 | 67 | 68 | 69 | 70 | 71 | 72 | 73 | 74 | 75 | 76 | 77 | 78 |
| H76 | H77 | H78 | H79 | H80 | H81 | H82 | H82A | H82B | H82C | H83 | H84 | H85 |
| N | T | V | N | L | Q | M | N | S | L | K | P | E |
| 79 | 80 | 81 | 82 | 83 | 84 | 85 | 86 | 87 | 88 | 89 | 90 | 91 |

|  |  |  |  |  |  |  |  | CDR-H3 |  |  |  |  |
|---|---|---|---|---|---|---|---|---|---|---|---|---|
| H86 | H87 | H88 | H89 | H90 | H91 | H92 | H93 | H94 | H95 | H96 | H97 | H98 |
| D | T | A | V | Y | Y | C | Y | A | D | Y | E | D |
| 92 | 93 | 94 | 95 | 96 | 97 | 98 | 99 | 100 | 101 | 102 | 103 | 104 |

| CDR-H3 |  |  |  |  |  |  |  |  |  |  |  |  |
|---|---|---|---|---|---|---|---|---|---|---|---|---|
| H99 | H100 | H100A | H100B | H100C | H100D | H101 | H102 | H103 | H104 | H105 | H106 | H107 |
| R | D | S | P | F | N | A | S | W | G | Q | G | T |
| 105 | 106 | 107 | 108 | 109 | 110 | 111 | 112 | 113 | 114 | 115 | 116 | 117 |
| H108 | H109 | H110 | H111 | H112 | H113 |  |  |  |  |  |  |  |
| Q | V | T | V | S | S |  |  |  |  |  |  |  |
| 118 | 119 | 120 | 121 | 122 | 123 |  |  |  |  |  |  |  |

| 7F6 | H1 | H2 | H3 | H4 | H5 | H6 | H7 | H8 | H9 | H10 | H11 | H12 | H13 |
|---|---|---|---|---|---|---|---|---|---|---|---|---|---|
|  | E | V | Q | L | V | E | S | G | G | G | L | V | Q |
|  | 1 | 2 | 3 | 4 | 5 | 6 | 7 | 8 | 9 | 10 | 11 | 12 | 13 |
|  | H14 | H15 | H16 | H17 | H18 | H19 | H20 | H21 | H22 | H23 | H24 | H25 | H26 |
|  | A | G | G | S | T | R | L | T | C | L | A | S | G |
|  | 14 | 15 | 16 | 17 | 18 | 19 | 20 | 21 | 22 | 23 | 24 | 25 | 26 |

|  |  |  |  |  | CDR-H1 | | | | | | | |
| --- | --- | --- | --- | --- | --- | --- | --- | --- | --- | --- | --- | --- |
| H27 | H28 | H29 | H30 | H31 | H32 | H33 | H34 | H35 | H36 | H37 | H38 | H39 |
| S | I | S | S | I | N | V | I | G | W | Y | R | Q |
| 27 | 28 | 29 | 30 | 31 | 32 | 33 | 34 | 35 | 36 | 37 | 38 | 39 |

|  |  |  |  |  |  |  |  |  |  | CDR-H2 | | |
| --- | --- | --- | --- | --- | --- | --- | --- | --- | --- | --- | --- | --- |
| H40 | H41 | H42 | H43 | H44 | H45 | H46 | H47 | H48 | H49 | H50 | H51 | H52 |
| A | P | G | K | Q | R | E | L | V | A | M | I | G |
| 40 | 41 | 42 | 43 | 44 | 45 | 46 | 47 | 48 | 49 | 50 | 51 | 52 |

| CDR2-H2 | | | | | | | | | | | | |
| --- | --- | --- | --- | --- | --- | --- | --- | --- | --- | --- | --- | --- |
| H53 | H54 | H55 | H56 | H57 | H58 | H59 | H60 | H61 | H62 | H63 | H64 | H65 |
| R | G | E | G | A | N | Y | G | D | F | A | K | G |
| 53 | 54 | 55 | 56 | 57 | 58 | 59 | 60 | 61 | 62 | 63 | 64 | 65 |
| H66 | H67 | H68 | H69 | H70 | H71 | H72 | H73 | H74 | H75 | H76 | H77 | H78 |
| R | F | T | I | S | R | D | N | S | K | N | T | V |
| 66 | 67 | 68 | 69 | 70 | 71 | 72 | 73 | 74 | 75 | 76 | 77 | 78 |
| H79 | H80 | H81 | H82 | H82A | H82B | H82C | H83 | H84 | H85 | H86 | H87 | H88 |
| Y | L | Q | M | N | S | L | K | P | E | D | T | A |
| 79 | 80 | 81 | 82 | 83 | 84 | 85 | 86 | 87 | 88 | 89 | 90 | 91 |

|  |  |  |  |  |  |  |  |  | CDR-H3 | | | |
| --- | --- | --- | --- | --- | --- | --- | --- | --- | --- | --- | --- | --- |
| H89 | H90 | H91 | H92 | H93 | H94 | H95 | H96 | H97 | H98 | H99 | H100 | H100A |
| V | Y | Y | C | Y | A | D | Y | E | D | R | D | S |
| 92 | 93 | 94 | 95 | 96 | 97 | 98 | 99 | 100 | 101 | 102 | 103 | 104 |

| CDR-H3 | | | | | | | | | | |
| --- | --- | --- | --- | --- | --- | --- | --- | --- | --- | --- |
| H100B | H100C | H100D | H101 | H102 | H103 | H104 | H105 | H106 | H107 | H108 |
| P | F | N | G | S | W | G | Q | G | T | Q |
| 105 | 106 | 107 | 108 | 109 | 110 | 111 | 112 | 113 | 114 | 115 |
| H109 | H110 | H111 | H112 | H113 | | | | | | |
| V | T | V | S | S | | | | | | |
| 116 | 117 | 118 | 119 | 120 | | | | | | |

In one aspect of the invention there is provided a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein the immunoglobulin chain variable domain originates from a llama V gene which is either the Vo or Vq gene and from a llama J gene which is either the J6 or J6.1 gene and which differs from an immunoglobulin chain variable domain encoded by said genes by comprising one or more amino acids selected from T18, T21, V33, G52, G56, F62 and Y93 and conservative substitutions of said amino acids at these positions, according to Kabat numbering.

In one aspect of the invention there is provided a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein the immunoglobulin chain variable domain originates from a llama V gene which is either the Vo or Vq gene and from a llama J gene which is either the J6 or J6.1 gene and which differs from an immunoglobulin chain variable domain encoded by said genes by comprising one or more amino acids selected from V33, G52, G56 and Y93, and optionally one or more amino acids selected from T18, T21 and F62, according to Kabat numbering.

In one aspect of the invention there is provided a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein CDR3 comprises a sequence sharing 50% or greater sequence identity with SEQ ID NO: 3 and, wherein the immunoglobulin chain variable domain comprises one or more amino acids selected from T18, T21, V33, G52, G56, F62 and Y93 and conservative substitutions of said amino acids at these positions, according to Kabat numbering.

In one aspect of the invention there is provided a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein CDR3 comprises a sequence sharing 50% or greater sequence identity with SEQ ID NO: 3 and, wherein the immunoglobulin chain variable domain comprises one or more amino acids selected from V33, G52, G56 and Y93, and optionally one or more amino acids selected from T18, T21 and F62, according to Kabat numbering.

In one aspect of the invention there is provided a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein CDR3 comprises a sequence sharing 50% or greater sequence identity with SEQ ID NO: 3 and wherein the immunoglobulin chain variable domain comprises one or more amino acids selected from amino acids at positions which correspond to T18, T21, V36, G55, G59, F65 and Y99 of SEQ ID NO. 29 and conservative substitutions of the said amino acids at these positions.

In one aspect of the invention there is provided a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein CDR3 comprises a sequence sharing 50% or greater sequence identity with SEQ ID NO: 3 and wherein the immunoglobulin chain variable domain comprises one or more amino acids selected from amino acids at positions which correspond to V36, G55, G59 and Y99 of SEQ ID NO. 29, and optionally one or more amino acids selected from amino acids at positions which correspond to T18, T21 and F65 of SEQ ID NO. 29.

In one aspect of the invention there is provided a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein CDR3 comprises a sequence sharing 50% or greater sequence identity with SEQ ID NO: 3 and wherein the immunoglobulin chain variable domain comprises one or more amino acids selected from amino acids at positions which correspond to T18, T21, V33 G52, G56, F62 and Y96 of SEQ ID NO: 35 and conservative substitutions of the said amino acids at these positions.

In one aspect of the invention there is provided a polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein CDR3 comprises a sequence sharing 50% or greater sequence identity with SEQ ID NO: 3 and wherein the immunoglobulin chain variable domain comprises one or more amino acids selected from amino acids at positions which correspond to V33, G52, G56 and Y96 of SEQ ID NO: 35, and optionally one or more amino acids selected from amino acids at positions which correspond to T18, T21 and F62 of SEQ ID NO: 35.

Suitably the immunoglobulin chain variable domain comprises two or more, more suitably three or more, more suitably four or more, more suitably five or more, more suitably six or more, most suitably all of these amino acids, or conservative substitutions thereof, at these positions. More suitably still, the immunoglobulin chain variable domain comprises all of these amino acids.

Suitably CDR3 comprises a sequence sharing 55% or greater sequence identity with the sequences recited above, more suitably 65% or greater sequence identity or more suitably 75% or greater sequence identity.

Linkers and Multimers

A construct according to the invention comprises multiple polypeptides and therefore may suitably be multivalent. Such a construct may comprise at least two identical polypeptides according to the invention. A construct consisting of two identical polypeptides according to the invention is a "homobihead". In one aspect of the invention there is provided a construct comprising two or more identical polypeptides of the invention.

Alternatively, a construct may comprise at least two polypeptides which are different, but are both still polypeptides according to the invention (a "heterobihead").

Alternatively, such a construct may comprise (a) at least one polypeptide according to the invention and (b) at least one polypeptide such as an antibody or antigen-binding fragment thereof, which is not a polypeptide of the invention (also a "heterobihead").

The at least one polypeptide of (b) may bind IL-6R (for example via a different epitope to that of (a)), or alternatively may bind to a target other than IL-6R. Suitably the different polypeptide (b) binds to, for example, another pro inflammatory cytokine or chemokine or their respective receptors, other inflammatory mediators or immunologically relevant ligands involved in human pathological processes.

Constructs can be multivalent and/or multispecific. A multivalent construct (such as a bivalent construct) comprises two or more binding polypeptides therefore presents two or more sites at which attachment to one or more antigens can occur. An example of a multivalent construct could be a homobihead or a heterobihead. A multispecific construct (such as a bispecific construct) comprises two or more different binding polypeptides which present two or more sites at which either (a) attachment to two or more different antigens can occur or (b) attachment to two or more different epitopes on the same antigen can occur. An example of a multispecific construct could be a heterobihead. A multispecific construct is multivalent.

Suitably, the polypeptides comprised within the construct are antibody fragments. More suitably, the polypeptides comprised within the construct are selected from the list consisting of: a VHH, a VH, a VL, a V-NAR, a Fab fragment and a F(ab')2 fragment. More suitably, the polypeptides comprised within the construct are VHHs.

The polypeptides of the invention can be linked to each other directly (i.e. without use of a linker) or via a linker. Suitably, the linker is a protease-labile or a non-protease-labile linker.

The linker is suitably a polypeptide and will be selected so as to allow binding of the polypeptides to their epitopes. If used for therapeutic purposes, the linker is suitably non-immunogenic in the subject to which the polypeptides are administered. Suitably the polypeptides are all connected by non-protease-labile linkers. Suitably the non-protease-labile linkers are of the format $(G4S)_x$. Suitably x is 1 to 10, most suitably x is 6. Suitably the protease-labile linker is of the format $[-(G_aS)_x-B-(G_bS)_y-]_z$ wherein a is 1 to 10; b is 1 to 10; x is 1 to 10; y is 0.1 to 10, z is 1 to 10 and B is K or R. Suitably a is 2 to 5, more suitably a is 4. Suitably b is 2 to 5, more suitably b is 4. Suitably x is 1 to 5, more suitably x is 1. Suitably y is 1 to 5, more suitably y is 1. Suitably z is 1 to 3, more suitably z is 1. Suitably B is K.

Vectors and Hosts

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian and yeast vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g. replication defective retroviruses. adenoviruses and adeno-associated viruses), which serve equivalent functions, and also bacteriophage and phagemid systems. The invention also relates to nucleotide sequences that encode polypeptide sequences or multivalent and/or multispecific constructs. The term "recombinant host cell" (or simply "host cell"), as used herein, is intended to refer to a cell into which a recombinant expression vector has been introduced. Such terms are intended to refer not only to the particular subject cell but to the progeny of such a cell. In one aspect of the invention there is provided a vector comprising the polynucleotide encoding the polypeptide or construct of the invention or cDNA comprising said polynucleotide. In a further aspect of the invention there is provided a host cell transformed with said vector, which is capable of expressing the polypeptide or construct of the invention. Suitably the host cell is a bacterium such as *Escherchia coli* a yeast or mould belonging to the genera *Aspergillus, Saccharomyces, Kluyveromyces, Hansenula* or *Pichia*, such as *Saccharomyces cerevisiae* or *Pichia pastoris*. Suitably the recombinant host is a yeast. Suitably the recombinant host is a mould. Suitably the yeast belongs to the genera *Saccharomyces, Kluyveromyces, Hansenula* or *Pichia*. Further examples of yeasts are those belonging to the genera *Candida* and *Torulopsis*. Suitably the mould belongs to the genus *Aspergillus*. Further examples of moulds are those belonging to the genera *Acremonium, Alternaria, Chrysosporium, Cladosporium, Dictyostelium, Fusarium, Mucor, Penicillium, Rhizopus*, Stachybotys, *Trichoderma* and *Trichophyton*.

Stability

For the provision of an oral medicament, it is desirable to predict the stability of an ICVD in the intestinal tract of a model organism (such as mouse or cynomolgus monkey) and a target organism (such as a human). The activities of the major small intestinal proteases, trypsin and chymotrypsin, are conserved across mammalian species, whereas proteases present in the large intestine are likely to be produced by host species-specific gut microflora. To generate testing solutions (or testing 'matrices') that reflect these two environments, pooled mouse small intestinal supernatants and pooled human faecal supernatants may be prepared and used as outlined below. Both of these solutions are highly digestive towards unselected, un-engineered ICVDs.

Accordingly, suitable methods for determining the stability of an anti-IL6R agent in the intestinal tract include:

1A. The Standard Mouse Small Intestinal Supernatant Digestion Assay

An anti-IL6R agent can be assayed for stability in the intestinal tract by exposure to supernatant extract prepared from the pooled small intestinal contents of several mice. Following incubation of the anti-I L6R agent in the presence of the intestinal extract for a given time period, IL6R-binding activities of the "digested" samples are assayed using the anti-IL-6R gp130 ELISA provided below, and compared to the binding activity of "undigested" samples.

To produce mouse small intestinal supernatant, mouse small intestines are excised, the solid contents removed and the intestines rinsed with 1 ml of 0.9% saline. The solid and liquid parts are combined in 1.5 mL microfuge tubes, vortexed to homogeny and centrifuged at 16k×rcf for 10 minutes at 4 degrees C. The supernatants are removed and stored at −80 degrees C. before being assayed further.

1B. The Standard Human Faecal Extract Digestion Assay

Alternatively, an anti-IL6R agent can be assayed for stability in the intestinal tract by exposure to human faecal supernatant prepared from pooled faecal supernatants of several humans. Following incubation of the anti-IL6R agent in the presence of the faecal supernatant for different time periods, IL6R-binding activities of the "digested" samples are assayed using the anti-IL-6R gp130 ELISA provided below, and compared to the binding activity of "undigested" samples.

To produce pooled human faecal supernatant, several faecal samples are turned into slurries with addition of 1× PBS. The slurries are then pooled, centrifuged and the supernatants removed, aliquoted and stored at −80 degrees C. This process removes the faecal matrix, including any cellular, material.

2. The Standard Anti-IL-6R Gp130 ELISA Performed on Samples Previously Exposed to Proteolytic Material The objective of this assay is to measure the remaining concentration of active anti-IL-6R ICVDs which have previously been incubated in the presence of proteolytic material, such as mouse small intestinal supernatant or human faecal extract, thereby elucidating the impact on the ICVD of any proteolysis which may have taken place during incubation and therefore the proteolytic stability of the anti-IL-6R ICVDs. This assay detects binding of hIL-6R/hIL-6 complexes to recombinant human gp130. This interaction can be competitively inhibited by anti-IL-6R ICVDs, causing reduced binding of hIL-6R-hIL-6 complexes to gp130. Therefore, high signal in this ELISA represents a low concentration or low affinity of anti-IL-6R ICVD remaining active, and vice versa. The % survival is the percentage concentration of active ICVD, interpolated using the standard curve, maintained between a sample before and after digestion.

Materials
Solutions required:
1× PBS
1% BSA in PBS
PBST (1× PBS, 0.05% Tween 20)
Block buffer (1% BSA in 1× PBS, pH 7.3-7.5)
Assay buffer (1% BSA, 2× protease inhibitor* in 1× PBS)
0.5 M Sulphuric acid ($H_2SO_4$)
*2× protease inhibitor=1 tablet per 50 ml buffer
Reagents required:
Recombinant soluble human gp130 at known concentration
SigmaFast protease inhibitor tablets (S8820)
ICVD stock of known concentration (preferably 250 ug/mL diluted to 20 ug/mL in protease testing solution)
Soluble human IL-6 at known concentration
Soluble human IL-6R at known concentration Biotinylated goat anti-IL-6R polyclonal antibody (R&D systems BAF227); resuspended at 250 ug/ml in sterile PBS.

ExtrAvidin-Peroxidase (Sigma E2886)

TMB substrate (Microwell Peroxidase substrate System 2-C, KPL, 50-70-00)

Procedure

Preparation:
1. Determine number of plates required for the assay.
2. Prepare the relevant volume (up to 3 plates at a time) of 0.2 μg/ml recombinant soluble human gp130 in PBS+5 μg/ml BSA.
3. Working quickly, dispense 50 μl/well into Maxisorp 96-well ELISA plates (Nunc), loading a maximum of 4 plates in one batch.
4. Shake plate briefly, seal and incubate at 4° C. overnight.

Assay:
1. Wash the ELISA plate using a plate washer (4× ~380 μl PBST). Bang the plate on towel to remove residual liquid.
2. Apply 200 μl/well block buffer. Seal and incubate on a rotary plate shaker for ≥1 hour.
3. Prepare a dilution series of ICVD standards between 0.004 nM to 1000 nM in minimum final volumes of 70 μl using assay buffer as a diluent.
4. Prepare appropriate dilutions of samples to be tested in assay buffer, such that their estimated final concentration on the plate will fall in the range of 0.001 nM to 250 nM ICVD. Ensure that samples containing GI/faecal material are kept on ice as much as possible.
5. Prepare a 400 ng/ml IL-6 solution in assay buffer.
6. Prepare a 40 ng/ml IL-6R solution in assay buffer.
7. In a separate 96-well plate, mix together 50 μl of each ICVD dilution with 50 μl IL-6 solution. In each dilution series include one well with no ICVD.
8. In a further additional 96-well plate, mix together 85 μl ICVD-IL-6 mixture from step 7 with 85 μl IL-6R solution prepared in step 6. Include wells containing assay buffer only, such that the following controls are applied to each plate: IL-6 only, and no ICVD (IL6+IL6R only). Incubate for 5 minutes on rotary plate shaker.
9. Wash blocked ELISA plate as in step 1.
10. Transfer 50 μl of the mixtures prepared in step 8 to the washed ELISA, plate in triplicate. Seal and incubate on a rotary plate shaker for 2 hours.
11. Wash blocked ELISA plate as in step 1.
12. Prepare 5 ml/plate 125 ng/mL of BAF227 anti-hIL-6R antibody made up in block buffer. Add 50 μl/well, seal, shake briefly, and incubate for 1 hour at room temperature or overnight at 4° C.
13. Wash blocked ELISA plate as in step 1.
14. Prepare 5 ml/plate 1/1000-1/3000 dilution of Extravidin in block buffer. Add 50 μl/well, seal, and incubate on a rotary shaker ≤30 mins
15. Wash blocked ELISA plate as in step 1.
16. Prepare 10 ml/plate TM B substrate (1:1 ratio of substrate A and B). Add 100 μl/well, seal and incubate on a rotary plate shaker until a mid blue colour evolves in the lowest dilution wells or up to a maximum of 30 mins. Shield from light.
17. Stop reaction with 50 μl/well 0.5 M $H_2SO_4$.
18. Read plate at 450 nm.
19. Use standard curve to interpolate concentrations of active ICVD. Raw OD450 values are adjusted with readings taken from blank control wells. Standard curves are plotted using appropriate software (e.g. Graphpad Prism using Log (inhibitor) vs. response—variable slope (four parameters)). ICVD concentrations in the test samples are calculated in the software using the standard curve. The active ICVD concentration in the test sample is expressed as a % of that in the 0 h sample to give % survival Suitably the polypeptide or construct of the present invention retains 10%, more suitably 20%, more suitably 30%, more suitably 40%, more suitably 50%, more suitably 60%, more suitably 70%, more suitably 80%, more suitably 90%, more suitably 95%, more suitably 100% or more of the original potency of the polypeptide of the invention or construct after exposure to proteases present in the small and/or large intestine and/or IBD inflammatory proteases, such as after at least 6 hours', suitably after at least 16 hours' exposure to human faecal extract, for example in the standard human faecal extract assay.

Suitably the polypeptide or construct of the present invention retains 10%, more suitably 20%, more suitably 30%, more suitably 40%, more suitably 50%, more suitably 60%, more suitably 70%, more suitably 80%, more suitably 90%, more suitably 95%, more suitably 100% or more of the original potency of the polypeptide of the invention or construct after exposure to proteases present in the small and/or large intestine and/or IBD inflammatory proteases, such as after at least 1 hour's, suitably after at least 4 hours', suitably after at least 7 hours' exposure to mouse small intestinal supernatant, for example in the standard mouse small intestinal supernatant assay.

Suitably the polypeptide or construct of the present invention substantially retains neutralisation ability when exposed to proteases present in the small and/or large intestine and/or IBD inflammatory proteases when suitably 10%, more suitably 20%, more suitably 30%, more suitably 40%, more suitably 50%, more suitably 60%, more suitably 70%, more suitably 80%, more suitably 90%, more suitably 95%, more suitably 100% or more of the original potency of the polypeptide of the invention or construct is retained after exposure to proteases present in the small and/or large intestine and/or IBD inflammatory proteases, such as after at least 6 hours', suitably after at least 16 hours' exposure to human faecal extract, for example in the standard human faecal extract assay.

Suitably the polypeptide or construct of the present invention substantially retains neutralisation ability when exposed to proteases present in the small and/or large intestine and/or IBD inflammatory proteases when suitably 10%, more suitably 20%, more suitably 30%, more suitably 40%, more suitably 50%, more suitably 60%, more suitably 70%, more suitably 80%, more suitably 90%, more suitably 95%, more suitably 100% or more of the original potency of the polypeptide of the invention or construct is retained after exposure to proteases present in the small and/or large intestine and/or IBD inflammatory proteases, such as after at least 1 hour's, suitably after at least 4 hours', suitably after at least 7 hours' exposure to mouse small intestinal supernatant, for example in the standard mouse small intestinal supernatant assay.

Suitably 10% or more, more suitably 20% or more, more suitably 30% or more, more suitably 40% or more, more suitably 50% or more, more suitably 60% or more, more suitably 70% or more of the administered dose of polypeptides or constructs of the invention retains neutralisation ability against IL-6R and remain in the faeces of a mouse, cynomolgus monkey and/or human (suitably excreted faeces or faeces removed from the intestinal tract) after 1, 2, 3, 4, 5, 6, 7, 8, 9, 10, 11, 12, 13, 14, 15 or 16 hours of exposure to conditions of the intestinal tract.

A polypeptide of the invention or construct of the present invention remains substantially intact when suitably 10%, more suitably 20% or more, more suitably 30% or more, more suitably 40% or more, more suitably 50% or more, more suitably 60% or more, more suitably 70% or more, more suitably 80% or more, more suitably 90% or more, more suitably 95% or more, more suitably 99% or more, most suitably 100% of the administered quantity of polypeptide of the invention or construct remains intact after exposure to proteases present in the small and/or large intestine and/or IBD inflammatory proteases.

Suitably, the polypeptide or construct of the present invention substantially retains neutralisation ability and/or potency when delivered orally and after exposure to the intestinal tract (for example, after exposure to proteases of the small and/or large intestine and/or IBD inflammatory proteases). Such proteases include enteropeptidase, trypsin, chymotrypsin, and irritable bowel disease inflammatory proteases (such as MMP3, MMP12 and cathepsin). Proteases of, or produced in, the small and/or large intestine include proteases sourced from intestinal commensal microflora and/or pathogenic bacteria, for example wherein the proteases are cell membrane-attached proteases, excreted proteases and proteases released on cell lysis). Most suitably the proteases are trypsin and chymotrypsin.

Suitably the intestinal tract is the intestinal tract of a dog, pig, human, monkey or mouse. Suitably the intestinal tract is the intestinal tract of a dog, pig, human, cynomolgus monkey or mouse. The small intestine suitably consists of the duodenum, jejunum and ileum. The large intestine suitably consists of the cecum, colon, rectum and anal canal. Suitably the polypeptide or construct of the invention is substantially resistant to one or more proteases. The intestinal tract, as opposed to the gastrointestinal tract, consists of only the small intestine and the large intestine.

Therapeutic Use and Delivery

A therapeutically effective amount of a polypeptide, pharmaceutical composition or construct of the invention, is an amount which is effective, upon single or multiple dose administration to a subject, in neutralising IL-6R to a significant extent in a subject. A therapeutically effective amount may vary according to factors such as the disease state, age, sex, and weight of the individual, and the ability of the polypeptide, pharmaceutical composition or construct to elicit a desired response in the individual. A therapeutically effective amount is also one in which any toxic or detrimental effects of the polypeptide of the invention, pharmaceutical composition or construct are outweighed by the therapeutically beneficial effects. The polypeptide or construct of the invention can be incorporated into pharmaceutical compositions suitable for administration to a subject. The polypeptide or construct of the invention can be in the form of a pharmaceutically acceptable salt.

A pharmaceutical composition of the invention may suitably be formulated for oral, intramuscular, subcutaneous or intravenous delivery. The pharmaceutical compositions of the invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. Solid dosage forms are preferred. The polypeptide of the invention, pharmaceutical composition or construct may be incorporated with excipients and used in the form of ingestible tablets, buccal tablets, troches, capsules, elixirs, suspensions, syrups, wafers, and the like.

Typically, the pharmaceutical composition comprises a polypeptide or construct of the invention and a pharmaceutically acceptable diluent or carrier. Examples of pharmaceutically acceptable carriers include one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the polypeptide or construct of the invention. Pharmaceutical compositions may include antiadherents, binders, coatings, disintegrants, flavours, colours, lubricants, sorbents, preservatives, sweeteners, freeze dry excipients (including lyoprotectants) or compression aids.

Most suitably, the polypeptide of the invention, pharmaceutical composition or construct of the invention is administered orally. A key problem with oral delivery is ensuring that sufficient polypeptide, pharmaceutical composition or construct reaches the area of the intestinal tract where it is required. Factors which prevent a polypeptide, pharmaceutical composition or construct of the invention reaching the area of the intestinal tract where it is required include the presence of proteases in digestive secretions which may degrade a polypeptide, pharmaceutical composition or construct of the invention.

Suitably, the polypeptide, pharmaceutical composition or construct of the invention are substantially stable in the presence of one or more of such proteases by virtue of the inherent properties of the polypeptide or construct itself. Suitably, the polypeptide or construct of the invention is lyophilised before being incorporated into a pharmaceutical composition.

A polypeptide of the invention may also be provided with an enteric coating. An enteric coating is a polymer barrier applied on oral medication which helps to protect the polypeptide from the low pH of the stomach. Materials used for enteric coatings include fatty acids, waxes, shellac, plastics, and plant fibers. Suitable enteric coating components include methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), methyl methacrylate-methacrylic acid copolymers, sodium alginate and stearic acid. Suitable enteric coatings include pH-dependent release polymers. These are polymers which are insoluble at the highly acidic pH found in the stomach, but which dissolve rapidly at a less acidic pH. Thus, suitably, the enteric coating will not dissolve in the acidic juices of the stomach (pH ~3), but will do so in the higher pH environment present in the small intestine (pH above 6) or in the colon (pH above 7.0). The pH-dependent release polymer is selected such that the polypeptide or construct of the invention will be released at about the time that the dosage reaches the small intestine, particularly the jejunum and ileum.

A polypeptide, construct or pharmaceutical composition of the invention can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilisers, isotonic agents, suspending agents, emulsifying agents, stabilisers and preservatives. Acceptable carriers, excipients and/or stabilisers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof);

amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as polysorbates, POE ethers, poloxamers, Triton-X, or polyethylene glycol. Suitably the polypeptide of the invention is formulated and/or administered with a milk and bicarbonate mixture.

A pharmaceutical composition of the invention may be delivered topically to the skin (for example for use in the treatment of an autoimmune disease such as psoriasis or eczema). Such a pharmaceutical composition may suitably be in the form of a cream, ointment, lotion, gel, foam, transdermal patch, powder, paste or tincture and may suitably include vitamin D3 analogues (e.g calcipotriol and maxacalcitol), steroids (e.g. fluticasone propionate, betamethasone valerate and clobetasol propionate), retinoids (e.g. tazarotene), coal tar and dithranol. Topical medicaments are often used in combination with each other (e.g. a vitamin D3 and a steroid) or with further agents such as salicylic acid. If the pharmaceutical composition of the invention is to be delivered topically for the treatment of psoriasis or eczema, suitably a further substance considered to be effective in treating psoriasis or eczema may be included in the composition such as steroids especially Class 4 or Class 5 steroids such as hydrocortisone (eg 1% hydrocortisone cream); cyclosporin or similar macrolide agent or retinoids.

For all modes of delivery, the polypeptide, pharmaceutical composition or construct of the invention may be formulated in a buffer, in order to stabilise the pH of the composition, at a concentration between 5-50, or more suitably 15-40 or more suitably 25-30 g/litre. Examples of suitable buffer components include physiological salts such as sodium citrate and/or citric acid. Suitably buffers contain 100-200, more suitably 125-175 mM physiological salts such as sodium chloride. Suitably the buffer is selected to have a pKa close to the pH of the composition or the physiological pH of the patient.

Exemplary polypeptide or construct concentrations in a pharmaceutical composition may range from about 1 mg/mL to about 200 mg/mL or from about 50 mg/mL to about 200 mg/mL, or from about 150 mg/mL to about 200 mg/mL.

An aqueous formulation of the polypeptide, construct or pharmaceutical composition of the invention may be prepared in a pH-buffered solution, e.g., at pH ranging from about 4.0 to about 7.0, or from about 5.0 to about 6.0, or alternatively about 5.5. Examples of suitable buffers include phosphate-, histidine-, citrate-, succinate-, acetate-buffers and other organic acid buffers. The buffer concentration can be from about 1 mM to about 100 mM, or from about 5 mM to about 50 mM, depending, for example, on the buffer and the desired tonicity of the formulation.

The tonicity of the pharmaceutical composition may be altered by including a tonicity modifier. Such tonicity modifiers can be charged or uncharged chemical species. Typical uncharged tonicity modifiers include sugars or sugar alcohols or other, polyols, preferably trehalose, sucrose, mannitol, glycerol, 1,2-propanediol, raffinose, sorbitol or lactitol (especially trehalose, mannitol, glycerol or 1,2-propanediol). Typical charged tonicity modifiers include salts such as a combination of sodium, potassium or calcium ions, with chloride, sulfate, carbonate, sulfite, nitrate, lactate, succinate, acetate or maleate ions (especially sodium chloride or sodium sulphate); or amino acids such as arginine or histidine. Suitably, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 1 mM to 500 nM. Suitably, at least one isotonic agent is included in the composition.

A surfactant may also be added to the pharmaceutical composition to reduce aggregation of the formulated polypeptide or construct and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, and polysorbate 80. Exemplary concentrations of surfactant may range from about 0.001% to about 10% w/v.

A lyoprotectant may also be added in order to protect the polypeptide or construct of the invention against destabilizing conditions during the lyophilization process. For example, known lyoprotectants include sugars (including glucose, sucrose, mannose and trehalose); polyols (including mannitol, sorbitol and glycerol); and amino acids (including alanine, glycine and glutamic acid). Lyoprotectants can be included in an amount of about 10 mM to 500 mM.

The dosage ranges for administration of the polypeptide of the invention, pharmaceutical composition or construct of the invention are those to produce the desired therapeutic effect. The dosage range required depends on the precise nature of the polypeptide of the invention, pharmaceutical composition or construct, the route of administration, the nature of the formulation, the age of the patient, the nature, extent or severity of the patient's condition, contraindications, if any, and the judgement of the attending physician. Variations in these dosage levels can be adjusted using standard empirical routines for optimisation.

Suitable daily dosages of polypeptide of the invention, pharmaceutical composition or construct of the invention are in the range of 50 ng-50 mg per kg, such as 50 ug-40 mg per kg, such as 5-30 mg per kg of body weight. The unit dosage can vary from less than 100 mg, but typically will be in the region of 250-2000 mg per dose, which may be administered daily or more frequently, for example 2, 3 or 4 times per day or less frequently for example every other day or once per week, once per fortnight or once per month.

In one aspect of the invention there is provided the use of the polypeptide, pharmaceutical composition or construct of the invention in the manufacture of a medicament for the treatment of autoimmune disease. In a further aspect of the invention there is provided a method of treating autoimmune disease comprising administering to a person in need thereof a therapeutically effective amount of the polypeptide, pharmaceutical composition or construct of the invention.

The word 'treatment' is intended to embrace prophylaxis as well as therapeutic treatment. Treatment of diseases also embraces treatment of exacerbations thereof and also embraces treatment of patients in remission from disease symptoms to prevent relapse of disease symptoms.

Combination Therapy

A pharmaceutical composition of the invention may also comprise one or more active agents (e.g. active agents suitable for treating the diseases mentioned herein). It is within the scope of the invention to use the pharmaceutical composition of the invention in therapeutic methods for the treatment of autoimmune diseases as an adjunct to, or in conjunction with, other established therapies normally used in the treatment of autoimmune diseases.

For the treatment of IBD (such as Crohn's disease or ulcerative colitis), possible combinations include combinations with, for example, one or more active agents selected from the list comprising: 5-aminosalicylic acid, or a prodrug thereof (such as sulfasalazine, olsalazine or bisalazide); corticosteroids (e.g. prednisolone, methylprednisolone, or budesonide); immunosuppressants (e.g. cyclosporin, tacrolimus, methotrexate, azathioprine or 6-mercaptopurine); anti-IL-6R antibodies (e.g. tocilizumab), anti-IL-6 antibodies, anti-TNF-alpha antibodies (e.g., infliximab, adalimumab, certolizumab pegol or golimumab); anti-IL12/IL23 antibodies (e.g., ustekinumab); anti-IL6R antibodies or small molecule IL12/IL23 inhibitors (e.g., apilimod); Anti-alpha-4-beta-7 antibodies (e.g., vedolizumab); MAdCAM-1 blockers (e.g., PF-00547659); antibodies against the cell adhesion molecule alpha-4-integrin (e.g., natalizumab); antibodies against the IL2 receptor alpha subunit (e.g., daclizumab or basiliximab); JAK3 inhibitors (e.g., tofacitinib or R348); Syk inhibitors and prodrugs thereof (e.g., fostamatinib and R-406); Phosphodiesterase-4 inhibitors (e.g., tetomilast); HMPL-004; probiotics; Dersalazine; semapimod/CPSI-2364; and protein kinase C inhibitors (e.g. AEB-071). The most suitable combination agents are tocilizumab, infliximab, adalimumab, certolizumab pegol or golimumab.

Hence another aspect of the invention provides a pharmaceutical composition of the invention in combination with one or more further active agents, for example one or more active agents described above.

In a further aspect of the invention, the polypeptide, pharmaceutical composition or construct is administered sequentially, simultaneously or separately with at least one active agent selected from the list above.

Similarly, another aspect of the invention provides a combination product comprising:

(A) a polypeptide, pharmaceutical composition or construct of the present invention; and (B) one or more other active agents, wherein each of components (A) and (B) is formulated in admixture with a pharmaceutically-acceptable adjuvant, diluent or carrier. In this aspect of the invention, the combination product may be either a single (combination) formulation or a kit-of-parts. Thus, this aspect of the invention encompasses a combination formulation including a polypeptide, pharmaceutical composition or construct of the present invention and another therapeutic agent, in admixture with a pharmaceutically acceptable adjuvant, diluent or carrier.

The invention also encompasses a kit of parts comprising components:

(i) a polypeptide, pharmaceutical composition or construct of the present invention in admixture with a pharmaceutically acceptable adjuvant, diluent or carrier, and (ii) a formulation including one or more other active agents, in admixture with a pharmaceutically-acceptable adjuvant, diluent or carrier, which components (i) and (ii) are each provided in a form that is suitable for administration in conjunction with the other.

Component (i) of the kit of parts is thus component (A) above in admixture with a pharmaceutically acceptable adjuvant, diluent or carrier. Similarly, component (ii) is component (B) above in admixture with a pharmaceutically acceptable adjuvant, diluent or carrier. The one or more other active agents (i.e. component (B) above) may be, for example, any of the agents mentioned above in connection with the treatment of autoimmune diseases such as IBD (e.g. Crohn's disease and/or ulcerative colitis). If component (B) is more than one further active agent, these further active agents can be formulated with each other or formulated with component (A) or they may be formulated separately. In one embodiment component (B) is one other therapeutic agent. In another embodiment component (B) is two other therapeutic agents. The combination product (either a combined preparation or kit-of-parts) of this aspect of the invention may be used in the treatment or prevention of an autoimmune disease (e.g. the autoimmune diseases mentioned herein).

Suitably the polypeptide, pharmaceutical composition or construct of the invention is for use as a medicament and more suitably for use in the treatment of an autoimmune and/or inflammatory disease.

Autoimmune Diseases and/or Inflammatory Diseases

Autoimmune diseases develop when the immune system responds adversely to normal body tissues. Autoimmune disorders may result in damage to body tissues, abnormal organ growth and/or changes in organ function. The disorder may affect only one organ or tissue type or may affect multiple organs and tissues. Organs and tissues commonly affected by autoimmune disorders include blood components such as red blood cells, blood vessels, connective tissues, endocrine glands such as the thyroid or, pancreas, muscles, joints and skin. An inflammatory disease is a disease characterised by inflammation. Many inflammatory diseases are autoimmune diseases and vice-versa.

Autoimmune Diseases and/or Inflammatory Diseases of the GIT

The chronic inflammatory bowel diseases (IBD) Crohn's disease and ulcerative colitis, which afflict both children and adults, are examples of autoimmune and inflammatory diseases of the GIT (Hendrickson et al., 2002, herein incorporated by reference in its entirety). Ulcerative colitis is defined as a condition where the inflammatory response and morphologic changes remain confined to the colon. The rectum is involved in 95% of patients. Inflammation is largely limited to the mucosa and consists of continuous involvement of variable severity with ulceration, edema, and hemorrhage along the length of the colon (Hendrickson et al., 2002, herein incorporated by reference in its entirety). Ulcerative colitis is usually manifested by the presence of blood and mucus mixed with stool, along with lower abdominal cramping which is most severe during the passage of bowel movements. Clinically, the presence of diarrhoea with blood and mucus differentiates ulcerative colitis from irritable bowel syndrome, in which blood is absent. Unlike ulcerative colitis, the presentation of Crohn's disease is usually subtle, which leads to a later diagnosis. Factors such as the location, extent, and severity of involvement determine the extent of gastrointestinal symptoms. Patients who have ileocolonic involvement usually have postprandial abdominal pain, with tenderness in the right lower quadrant and an occasional inflammatory mass. Symptoms associated with gastroduodenal Crohn's disease include early satiety, nausea, emesis, epigastric pain, or dysphagia. Perianal disease is common, along with anal tags, deep anal fissures, and fistulae (Hendrickson et al., 2002, herein incorporated by reference in its entirety).

Crohn's disease and Ulcerative Colitis are primarily diseases of the intestinal tract and colon. Interleukin-6 is a proinflammatory cytokine that is considered to be involved in the pathogenesis of IBD and IL6-trans-signalling via soluble IL6-R is thought to play a particularly important role in mediating effects of IL-6 associated with the perpetuation of chronic intestinal inflammation (see Mitsuyama et al., 2007). High levels of IL-6 production have been found in cultured CD and UC intestinal mucosal biopsies (Gustot et al., 2005; Kusugami et al., 1995; Reimund et al., 1996; Hosokawa et al., 1999) associated with increased levels of sIL6R production (Hosokawa, 1999). Levels of IL-6 and sIL-6R production were greater in "involved" vs "non-involved" IBD tissue and were correlated with the severity of clinical disease. Lamina propria cells were found to be major producers of IL-6 (Reinecker et al., 1993; Kusugami et al., 1995; Reimund et al., 1996; Hosokawa et al., 1999) and sIL6Rs (Hosokawa et al., 1999). In cell cultures, IBD mucosal tissue-derived macrophages were the main cell type producing IL6 (Kusugami et al., 1995) and sIL6R (Hosokawa et al., 1999) on a per cell basis, while T cells, B cells and epithelial cells produced substantially lower amounts. Interestingly, the levels of IL6 production by IBD tissue and tissue derived cells far exceeded the levels of sIL6R production (see Hosokawa et al., 1999).

In these diseases the IL-6R is produced in the lamina propria underlying the gastrointestinal epithelium. This epithelium is disrupted in IBD and facilitates transport of the immunoglobulin chain variable domain into the lamina propria—the site of IL-6R production and biological action in these diseases (see Example 8). Other diseases of the GIT include for example the inflammatory disease mucositis (suitably drug- and radiation induced-mucositis) where inflammatory lesions are present in the mucosa disrupting the epithelial tight junctions which also allow the immunoglobulin chain variable domain access to the site of IL-6R production. In mucositis the lesions can occur anywhere from mouth to anus and for mouth and oesophagus lesions a mouthwash or cream preparation containing the variable domain may be used. For anal and rectal lesions, suppositories, creams or foams containing the variable domain would be suitable for topical application. The immunoglobulin chain variable domains will be cleared from the lamina propria or other inflammatory sites via absorption into the bloodstream at sites of inflammation or via lymphatic clearance and subsequent entry into the bloodstream. The domains will therefore reach the liver via the bloodstream and will be cleared via glomerular filtration in the kidney. There is therefore good rationale that the domains will function therapeutically in diseases such as autoimmune hepatitis, type II diabetes and glomerular nephritis.

In inflamed IBD tissue, the production of IL-6 and shedding of IL-6Rs from activated macrophages results in the formation of soluble IL-6/sIL-6R complexes that can activate trans-signalling in cells that express only the gp130 subunit. This mechanism, which extends IL-6 responsiveness to an increased number of target cells, is considered to play an important role in the orchestration of mucosal inflammatory processes. The mechanism of IL-6 induced intestinal epithelial cell proliferation and regeneration is thought to involve signal transduction mediated via membrane bound IL-6 receptors (cis-signalling) (Rose-John, 2012; Waetzig & Rose-John 2012). The anti-human IL-6R antibody tocilizumab blocks both IL-6R classical signalling and IL-6/sIL-6R mediated trans-signalling and therefore blocks both pro-inflammatory, and potentially protective activities of IL-6. A rationale for the development of selective antagonists of IL-6-trans-signalling has been proposed based on the concept that this might avoid the inhibition of beneficial epithelial regenerative effects of IL-6 (see Rose-John et al, 2012; Waetzig & Rose-John 2012) that are mediated via mIL-6Rs (cis-signalling). An oral ICVD product with this profile could have safety and efficacy advantages over existing IL-6 neutralising antibodies for the treatment on Crohn's disease based on anti-inflammatory and improved mucosal healing properties.

Suitably the polypeptide, pharmaceutical composition or construct of the invention is used in the treatment of an autoimmune and/or inflammatory disease of the GI (gastrointestinal) tract where IL-6R (via, for example, the IL-6/IL-6R complex binding gp130) contributes to the pathology of such disease.

Suitably the polypeptide, pharmaceutical composition or construct of the invention is for use in the treatment of an autoimmune and/or inflammatory disease of the GI tract selected from the list consisting of Crohn's disease, ulcerative colitis, irritable bowel disease, diabetes type II, glomerulonephritis, autoimmune hepatitis, Sjogren's syndrome, celiac disease and drug- or radiation-induced mucositis (most suitably Crohn's disease).

Oral delivery of the immunoglobulin chain variable domain will ideally treat inflammatory diseases where IL-6R contributes to at least a proportion of the pathology and the immunoglobulin chain variable domain can access the tissue where the IL-6R is biologically active.

Autoimmune Diseases and/or Inflammatory Diseases of the Skin

The polypeptide of the invention may be incorporated into a cream/ointment or other topical carrier for administration to inflammatory skin lesions where IL-6R contributes to the pathology of such lesions.

Suitably the polypeptide, pharmaceutical composition or construct of the invention is for use in the treatment of an autoimmune and/or inflammatory disease of the skin selected from the list consisting of pemphigus, psoriasis, eczema, scleroderma, atopic dermatitis and fibrosis and inflammation induced cancers of the skin.

Suitably the polypeptide, pharmaceutical composition or construct is for use in the treatment of other autoimmune/inflammatory diseases in which IL-6R is responsible for a proportion of the pathology observed.

Preparative Methods

Polypeptides of the invention can be obtained and manipulated using the techniques disclosed for example in Green and Sambrook 2012.

Monoclonal antibodies can be produced using hybridoma technology, by fusing a specific antibody-producing B cell with a myeloma (B cell cancer) cell that is selected for its ability to grow in tissue culture and for an absence of antibody chain synthesis (Kohler et al., 1975 and Nelson et al., 2000, herein incorporated by reference in their entirety).

A monoclonal antibody directed against a determined antigen can, for example, be obtained by:

a) immortalizing lymphocytes obtained from the peripheral blood of an animal previously immunized with a determined antigen, with an immortal cell and preferably with myeloma cells, in order to form a hybridoma, b) culturing the immortalized cells (hybridoma) formed and recovering the cells producing the antibodies having the desired specificity.

Alternatively, the use of a hybridoma cell is not required. Accordingly, monoclonal antibodies can be obtained by a process comprising the steps of:

a) cloning into vectors, especially into phages and more particularly filamentous bacteriophages, DNA or cDNA sequences obtained from lymphocytes especially peripheral blood lymphocytes of an animal (suitably previously immunized with determined antigens), b) transforming prokaryotic cells with the above vectors in conditions allowing the production of the antibodies, c) selecting the antibodies by subjecting them to antigen-affinity selection, d) recovering the antibodies having the desired specificity.

Methods for immunizing camelids, cloning the VHH repertoire of B cells circulating in blood (Chomezynnski et al., 1987), and isolation of antigen-specific VHHs from immune (Arbabi-Ghahroudi et al., 1997) and nonimmune (Tanha et al 2002) libraries using phage, yeast, or ribosome display are known (WO92/01047, Nguyen et al., 2001 and Harmsen et al., 2007. These references are herein incorporated by reference in their entirety.

Antigen-binding fragments of antibodies such as the scFv and Fv fragments can be isolated and expressed in *E. coli* (Miethe et al., 2013, Skerra et al., 1988 and Ward et al., 1989, herein incorporated by reference in their entirety).

Mutations can be made to the DNA or cDNA that encode polypeptides which are silent as to the amino acid sequence of the polypeptide, but which provide preferred codons for translation in a particular host. The preferred codons for translation of a nucleic acid in, e.g., *E. coli* and *S. cerevisiae*, are known.

Mutation of polypeptides can be achieved for example by substitutions, additions or deletions to a nucleic acid encoding the polypeptide. The substitutions, additions or deletions to a nucleic acid encoding the polypeptide can be introduced by many methods, including for example error-prone PCR, shuffling, oligonucleotide-directed mutagenesis, assembly PCR, PCR mutagenesis, in vivo mutagenesis, cassette mutagenesis, recursive ensemble mutagenesis, exponential ensemble mutagenesis, site-specific mutagenesis (Ling et al 1997, herein incorporated by reference in its entirety), gene reassembly, Gene Site Saturation Mutagenesis (GSSM), synthetic ligation reassembly (SLR) or a combination of these methods. The modifications, additions or deletions to a nucleic acid can also be introduced by a method comprising recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, ensemble mutagenesis, chimeric nucleic acid multimer creation, or a combination thereof.

In particular, artificial gene synthesis may be used (Nambiar et al 1984, Sakamar et al., 1988, Wells et al., 1985 and Grundstrom et al., 1985, herein incorporated by reference in their entirety). A gene encoding a polypeptide of the invention can be synthetically produced by, for example, solid-phase DNA synthesis. Entire genes may be synthesized de novo, without the need for precursor template DNA. To obtain the desired oligonucleotide, the building blocks are sequentially coupled to the growing oligonucleotide chain in the order required by the sequence of the product. Upon the completion of the chain assembly, the product is released from the solid phase to solution, deprotected, and collected. Products can be isolated by high-performance liquid chromatography (HPLC) to obtain the desired oligonucleotides in high purity (Verma et al., 1998) Expression of immunoglobulin chain variable domains such as VHs and VHHs can be achieved using a suitable expression vector such as a prokaryotic cell such as bacteria, for example *E. coli* (for example according to the protocols disclosed in WO94/04678, which is incorporated herein by reference and detailed further below). Expression of immunoglobulin chain variable domains such as VHs and VHHs can also be achieved using eukaryotic cells, for example insect cells, CHO cells, Vero cells or suitably yeast or mould cells such as yeasts or moulds belonging to the genera *Aspergillus, Saccharomyces, Kluyveromyces, Hansenula* or *Pichia*. Suitably *S. cerevisiae* is used (for example according to the protocols disclosed in WO94/025591, which is incorporated herein by reference and detailed further below).

Specifically, VHHs can be prepared according to the methods disclosed in WO94/04678 using *E. coli* cells by a process comprising the steps of:

a) cloning in a Bluescript vector (Agilent Technologies) a DNA or cDNA sequence coding for the VHH (for example obtained from lymphocytes of camelids or produced synthetically) optionally including a His-tag, b) recovering the cloned fragment after amplification using a 5' primer specific for the VHH containing an XhoI site and a 3' primer containing the SpeI site having the sequence TC TTA ACT AGT GAG GAG ACG GTG ACC TG (SEQ ID NO: 13), c) cloning the recovered fragment in phase in the Immuno PBS vector (Huse et al., 1989, herein incorporated by reference in its entirety) after digestion of the vector with XhoI and SpeI restriction enzymes, d) transforming host cells, especially *E. coli* by transfection with the recombinant Immuno PBS vector of step c, e) recovering the expression product of the VHH coding sequence, for instance by affinity purification such as by chromatography on a column using Protein A, cation exchange, or a nickel-affinity resin if the VHH includes a His-tag.

Alternatively, immunoglobulin chain variable domains such as VHs and VHHs are obtainable by a process comprising the steps of:

a) obtaining a DNA or cDNA sequence coding for a VHH, having a determined specific antigen binding site, b) amplifying the obtained DNA or cDNA, using a 5' primer containing an initiation codon and a HindIII site, and a 3' primer containing a termination codon having a XhoI site, c) recombining the amplified DNA or cDNA into the HindII (position 2650) and XhoI (position 4067) sites of a plasmid pMM984 (Merchlinsky et al., 1983, herein incorporated by reference in its entirety), d) transfecting permissive cells especially NB-E cells (Faisst et al., 1995, herein incorporated by reference in its entirety) with the recombinant plasmid, e) recovering the obtained products.

Further, immunoglobulin chain variable domains such as VHHs or VHs can be produced using *E. coli* or *S. cerevisiae* according to the methods disclosed in Frenken et al., 2000 and WO99/23221 (herein incorporated by reference in their entirety) as follows:

After taking a blood sample from an immunised llama and enriching the lymphocyte population via Ficoll (a neutral, highly branched, high-mass, hydrophilic polysaccharide which dissolves readily in aqueous solutions—Pharmacia) discontinuous gradient centrifugation, isolating total RNA by acid guanidium thiocyanate extraction (Chomezynnski et al., 1987), and first strand cDNA synthesis (e.g. using a cDNA kit such as RPN 1266 (Amersham)), DNA fragments encoding VHH and VH fragments and part of the short or long hinge region are amplified by PCR using the specific primers detailed on pages 22 and 23 of WO99/23221. Upon digestion of the PCR fragments with PstI and HindIII or BstEII, the DNA fragments with a length between about 300 and 450 bp are purified via agarose gel electrophoresis and ligated in the *E. coli* phagemid vector pUR4536 or the episomal *S. cerevisiae* expression vector pUR4548, respectively. pUR4536 is derived from pHEN (Hoogenboom et al., 1991, herein incorporated by reference in its entirety) and contains the lacI$^q$ gene and unique restriction sites to allow the cloning of the llama VHH and VH genes. pUR4548 is derived from pSY1 (Harmsen et al., 1993, herein incorporated by reference in its entirety). From this plasmid, the BstEII site in the leu2 gene is removed via PCR and the cloning sites between the SUC2 signal sequence and the terminator are replaced in order to facilitate the cloning of the VH/VHH gene fragments. The VH/VHHs have the c-myc tag at the C-terminus for detection. Individual *E. coli* JM109 colonies are transferred to 96 well microtiter plates containing 150 ml 2TY medium supplemented with 1% glucose and 100 mg L$^{-1}$ ampicillin. After overnight growth (37 degrees C.), the plates are duplicated in 2TY medium containing 100 mg L$^{-1}$ ampicillin and 0.1 mM IPTG. After another overnight incubation and optionally freezing and thawing, cells are centrifuged and pelleted and the supernatant can be used in an ELISA. Individual *S. cerevisiae* colonies are transferred to test tubes containing selective minimal medium (comprising 0.7% yeast nitrogen base, 2% glucose, supplemented with the essential amino acids and bases) and are grown for 48 h at 30 degrees C. Subsequently, the cultures are diluted ten times in YPGal medium (comprising 1% yeast extract, 2% bacto peptone and 5% galactose). After 24 and 48 h of growth, the cells are pelleted and the culture supernatant can be analysed in an ELISA. Absorbance at 600 nm (OD600) is optionally measured.

Further, immunoglobulin chain variable domains such as VH/VHHs can be produced using *S. cerevisiae* using the procedure as follows:

Isolate a naturally-occurring DNA sequence encoding the VH/VHH or obtain a synthetically produced DNA sequence encoding the VH/VHH, including a 5'-UTR, signal sequence, stop codons and flanked with SacI and HindIII sites (such a synthetic sequence can be produced as outlined above or for example may be ordered from a commercial supplier such as Geneart (Life Technologies)).

Use the restriction sites for transfer of the VH/VHH gene to the multi-copy integration (MCI) vector pUR8569 or pUR8542, as follows. Cut the DNA sequence encoding the VHH optionally contained within a shuttle vector, cassette or other synthetic gene construct and the MCI vector with SacI and HindIII using: 25 ul VHH DNA (Geneart plasmid or MCI vector), 1 ul SacI, 1 ul HindIII, 3 ul of a suitable buffer for double digestion such as NEB buffer 1 (New England Biolabs) overnight at 37 degrees C. Run 25 ul of digested DNA encoding the VHH and 25 ul of digested MCI vector on a 1.5% agarose gel with 1× TAE buffer and then perform gel extraction for example using QIAquick Gel Extraction Kit (Qiagen)). Set-up a ligation of digested MCI vector and digested DNA encoding the VH/VHH as follows: 100 ng vector, 30 ng VHH gene, 1.5 ul 10× ligase buffer, 1 ul T4 DNA ligase, and ddH$_2$O. Then perform ligation overnight at 16 degrees C.

Next transform the *E. coli* cells. For chemical competent XL-1 blue cells, thaw 200 ul heat competent XL-1 blue cells and add 5 ul ligation mix on ice for about 30 minutes followed by heat shock for 90 seconds at 42 degrees C. Then add 800 ul Luria-Bertani low salt medium supplemented with 2% glucose and recover cells for 2 hours at 37 degrees C. Plate cells on Luria-Bertani agar and ampicillin (100 ug/ml) plates and keep overnight at 37 degrees C. For electro competent TG1 *E. coli* cells, use an electroporation cuvette. In the electroporation cuvette: thaw 50 ul electro competent TG1 cells and 1 ul ligation mix on ice for about 15 minutes. Place the cuvette in the holder and pulse. Add 500 ul of 2TY medium and recover cells for 30 minutes at 37 degrees C. Plate 100 ul of cells on Luria-Bertani, agar, containing ampicillin (100 ug/ml) and 2% glucose plates. Keep plates at 37 degrees C. overnight.

After cloning of the VH/VHH gene into *E. coli* as detailed above, *S. cerevisiae* can be transformed with the linearized MCI vector. Before transformation is carried out, some steps are performed: (i) the DNA should be changed from circular to linear by digestion or else the DNA cannot be integrated into the yeast genome and (ii) the digested DNA should be cleaned of impurities by ethanol precipitation. Also, during the transformation process, the yeast cells are made semi-permeable so the DNA can pass the membrane.

Preparation for yeast transformation: perform a HpaI digestion of the midi-prep prepared from the selected *E. coli* colony expressing the VH/VHH gene as follows. Prepare a 100 ul solution containing 20 ng of midi-prep, 5 ul HpaI, 10 ul of appropriate buffer such as NEB4 buffer (BioLabs), and ddH$_2$O.

Cut the DNA with the HpaI at room temperature overnight. Next perform an ethanol precipitation (and put to one side a 5 ul sample from HpaI digestion). Add 300 ul ethanol 100% to 95 ul HpaI digested midiprep, vortex, and spin at full speed for 5 minutes. Carefully decant when a pellet is present, add 100 ul of ethanol 70%, then spin again for 5 minutes at full speed. Decant the sample again, and keep at 50-60 degrees C. until the pellet is dry. Re-suspend the pellet in 50 ul ddH$_2$O. Run 5 ul on a gel beside the 5 ul HpaI digested sample.

Yeast transformation: prepare YNBglu plates. Use 10 g agar+425 ml water (sterilised), 25 ml filtered 20× YNB (3.35 g YNB (yeast nitrogen base) in 25 ml sterilized H$_2$O) and 50 ml sterile 20% glucose and pour into petri dishes. Pick one yeast colony from the masterplate and grow in 3 ml YPD (Yeast Extract Peptone Dextrose) overnight at 30 degrees C. Next day prepare about 600 ml YPD and use to fill 3 flasks with 275 ml, 225 ml and 100 ml YPD. Add 27.5 ul yeast YPD culture to the first flask and mix gently. Take 75 ml from the first flask and put this in the second flask, mix gently. Take 100 ml from the second flask and put in the third one, mix gently. Grow until reaching an OD660 of between 1 and 2. Divide the flask reaching this OD over 4 Falcon tubes, ±45 ml in each. Spin for 2 minutes at 4200 rpm. Discard the supernatant. Dissolve the pellets in two Falcon tubes with 45 ml H$_2$O (reducing the number of tubes from 4 to 2). Spin for 2 minutes at 4200 rpm. Dissolve the pellets in 45 ml H$_2$O (from 2 tubes to 1). Spin for 2 minutes at 4200 rpm. Gently dissolve the pellets in 5 ml lithium acetate (LiAc) (100 mM), and spin for a few seconds. Carefully discard some LiAc, but retain over half of the LiAc in the tube. Vortex the cells, boil carrier DNA for 5 minutes and quickly chill in ice-water. Add to a 15 ml tube containing: 240 ul PEG, 50 ul cells, 36uLiAc (1M), 25 ul carrier DNA, 45 ul ethanol precipitated VH/VHH. Mix gently after each step (treat the blank sample the same, only without ethanol precipitated VH/VHH). Incubate for 30 minutes at 30 degrees C., gently invert the tube 3-4 times, then heat shock for 20-25 minutes at 42 degrees C. Spin up to 6000 rpm for a brief time. Gently remove the supernatant and add 250 ul ddH$_2$O and mix. Streak all of it on an YNBglu plate until plates are dry and grow for 4-5 days at 30 degrees C. Finally, prepare YNBglu plates by dividing plates in 6 equal parts, number the parts 1 to 6, inoculate the biggest colony and streak out number 1. Repeat for other colonies from big to small from 1 to 6. Grow at 30 degrees C. for 3-4 days large until colonies are produced. The VH/VHH clones are grown using glucose as a carbon source, and induction of VH/VHH expression is done by turning on the Galactose-7-promoter by adding 0.5% galactose. Perform a 3 mL small scale culture to test the colonies and choose which one shows the best expression of the VH or VHH. This colony is then used in purification.

Purification: the VH/VHH is purified by cation exchange chromatorgraphy with a strong anion resin (such as Capto S). On day 1, inoculate the selected yeast colony expressing the VH/VHH in 5 ml YPD medium (YP medium+2% glucose) and grow the cells in 25 mL sealed sterile tubes at 30 degrees C. overnight (shaking at 180 rpm). On day 2, dilute the 5 ml overnight culture in 50 mL freshly prepared YP medium+2% glucose+0.5% galactose, grow the cells in 250 ml aerated baffled flasks at 30 degrees C. for two nights (shaking at 180 rpm). On day 4, spin the cells down in a centrifuge at 4200 rpm for 20 min. Cation exchange purification step using a strong anion resin: adjust the pH of the supernatant containing the ligand to 3.5. Wash 0.75 ml resin (+/−0.5 mL slurry) per of 50 mL supernatant with 50 mL of ddH$_2$O followed by three washes with binding buffer. Add the washed resin to the supernatant and incubate the suspension at 4 degrees C. on a shaker for 1.5 hours. Pellet the resin-bound VH/VHH by centrifugation at 500 g for 2 minutes and wash it with wash buffer. Decant supernatant and re-suspend the resin with 10 mL of binding buffer. Put a filter in a PD-10 column, pour the resin in the column and let the resin settle for a while, then add a filter above the resin. Wait until all binding buffer has run through. Elute the VH/VHH with 6×0.5 ml elution buffer. Collect the elution fractions in eppendorf tubes. Measure the protein concentration of the 6 eluted fractions with a Nanodrop. Pool the fractions that contain the VHH and transfer the solution into a 3,500 Da cutoff dialysis membrane. Dialyze the purified protein solution against 3 L of PBS overnight at 4 degrees C. On day 5, dialyze the purified protein solution against 2 L of fresh PBS for an additional 2 hours at 4 degrees C. Finally, calculate the final concentration by BCA.

Although discussed in the context of the VH/VHH, the techniques described above could also be used for scFv, Fab, Fv and other antibody fragments if required.

Multiple antigen-binding fragments (suitably VH/VHHs) can be fused by chemical cross-linking by reacting amino acid residues with an organic derivatising agent such as described by Blattler et al., 1985 (herein incorporated by reference in its entirety).

Alternatively, the antigen-binding fragments may be fused genetically at the DNA level i.e. a polynucleotide construct formed which encodes the complete polypeptide construct comprising one or more antigen-binding fragments. One way of joining multiple antigen-binding fragments via the genetic route is by linking the antigen-binding fragment coding sequences either directly or via a peptide linker. For example, the carboxy-terminal end of the first antigen-binding fragment may be linked to the amino-terminal end of the next antigen-binding fragment. This linking mode can be extended in order to link antigen-binding fragments for the construction of tri-, tetra-, etc. functional constructs. A method for producing multivalent (such as bivalent) VHH polypeptide constructs is disclosed in WO 96/34103 (herein incorporated by reference in its entirety).

Suitably, the polypeptide of the invention (in particular, a VHH of the invention) can be produced in a fungus such as a yeast (for example, S. cerevisiae) comprising growth of the fungus on a medium comprising a carbon source wherein 50-100 wt % of said carbon source is ethanol, according to the methods disclosed in WO02/48382. Large scale production of VHH fragments in S. cerevisiae is described in Thomassen et al., 2002 (herein incorporated by reference in its entirety).

In one aspect of the invention there is provided a process for the preparation of the polypeptide or construct of the invention comprising the following steps:

i) cloning into a vector, such as a plasmid, the polynucleotide of the invention, ii) transforming a cell, such as a bacterial cell or a yeast cell capable of producing the polypeptide or construct of the invention, with said vector in conditions allowing the production of the polypeptide or construct, iii) recovering the polypeptide or construct, such as by affinity chromatography.

In one aspect of the invention there is provided a polypeptide comprising an immunoglobulin chain variable domain comprising three complementarity determining regions (CDR1-CDR3) and four framework regions; wherein the polypeptide has increased intestinal stability and/or potency relative to a corresponding polypeptide not having said insert, wherein FR1 comprises an insert of 4 to 5 amino acids, suitably 3 amino acids. Suitably the insert is the sequence NIN or three consecutive amino acids wherein one or more of the amino acids is a conservative substitution of the corresponding amino acid in the sequence NIN. Most suitably FR1 comprises the sequence NIN. More suitably the last four C-terminal residues of FR1 are NINX or four consecutive amino acids wherein one or more of the amino acids is a conservative substitution of the corresponding amino acid in the sequence NINX, wherein X is any amino acid. Suitably X is S or a conservative substitution of S, most suitably X is S. More suitably FR1 consists of 33 residues and the last four residues of FR1 are NINS.

In one aspect of the invention there is provided a method of increasing the intestinal stability of a polypeptide comprising an immunoglobulin chain variable domain, wherein the immunoglobulin chain variable domain comprises three complementarity determining regions (CDR1-CDR3) and four framework regions, wherein the method comprises the step of inserting into FR1 an insert of 4 to 5 amino acids, suitably 3 amino acids. Suitably the insert is the sequence NIN or three consecutive amino acids wherein one or more of the amino acids is a conservative substitution of the corresponding amino acid in the sequence NIN. Most suitably FR1 comprises the sequence NIN. More suitably the last four C-terminal residues of FR1 are NINX or four consecutive amino acids wherein one or more of the amino acids is a conservative substitution of the corresponding amino acid in the sequence NINX, wherein X is any amino acid. Suitably X is S or a conservative substitution of S, most suitably X is S. More suitably FR1 consists of 33 residues and the last four residues of FR1 are NINS.

In one aspect of the invention there is provided a method of making a polypeptide comprising an immunoglobulin chain variable domain, wherein the immunoglobulin chain variable domain comprises three complementarity determining regions (CDR1-CDR3) and four framework regions;

wherein the polypeptide has increased intestinal stability relative to a corresponding polypeptide not having said insertions, wherein the method comprises the step of inserting into FR1 an insert of 4 to 5 amino acids, suitably 3 amino acids. Suitably the insert is the sequence NIN or three consecutive amino acids wherein one or more of the amino acids is a conservative substitution of the corresponding amino acid in the sequence NIN. Most suitably FR1 comprises the sequence NIN. More suitably the last four C-terminal residues of FR1 are NINX or four consecutive amino acids wherein one or more of the amino acids is a conservative substitution of the corresponding amino acid in the sequence NINX, wherein X is any amino acid. Suitably X is S or a conservative substitution of S, most suitably X is S. More suitably FR1 consists of 33 residues and the last four residues of FR1 are NINS The present invention will now be further described by means of the following non-limiting examples.

EXAMPLES

Example 1: Llama Immunisation, Phage Display and Immunoglobulin Chain Variable Domain Selection Immunisation Two llamas (llama numbers 37 and 46) were each immunised with soluble human recombinant IL-6R, using two protocols to increase the chance of generating a range of ICVDs with significant sequence diversity and activity against the IL-6R. Blood cells collected from each llama at the end of each immunisation phase were used to generate six separate phage display libraries: one from each llama after the first round of immunisations and two from each llama after the second round of immunisations.

Immunisation Protocol 1

The llamas received an initial prime with 50 ug soluble human recombinant IL-6R (shIL-6R) mixed 1:1 with stimmune adjuvant on day 0. The llamas were boosted with 50 ug of the same at days 14, and 28, and with 40 ug on day 35. All injections were intra-muscular. Blood was drawn on day 44 for the isolation of peripheral blood lymphocytes and extraction of RNA for library construction.

Immunisation Protocol 2

After a resting period of 11 weeks after the first protocol, each llama received two more boosts of 50 ug shIL-6R one week apart and with blood drawn 9 days later. Serum immune responses to immunisations were assessed for each of the llamas at several time-points by measuring the binding of heavy chain antibodies to immobilised human IL-6R using a plate ELISA format and detection with rabbit anti-heavy chain and donkey anti-rabbit IgG coupled to horseradish peroxidase (HRP). Titration curves obtained showed that each of the llamas had responded to the first round of immunisations giving mid-range titres of IL-6R-binding IgG heavy chain antibodies. The serum antibody titres did not increase following the second round of immunisations.

Construction of Phage Libraries

Blood cells collected from each llama at the end of each immunisation phase were used to generate six separate phage display libraries. Total RNA was extracted from the peripheral blood lymphocytes that were isolated from each of the immunised llamas (llamas 37 and 46). The RNA was then used to generate cDNA and PCR was performed to amplify specifically the variable regions of antibodies. cDNA fragments encoding the heavy chain repertoire were cloned into a phagemid vector and the library introduced into E. coli. The phage libraries were produced by culturing the E. coli with helper phage, and precipitation of the resulting heavy chain-displaying phage. The numbers in each library were determined by titration and infection of log-phase. E. coli strain TG1 with the different dilutions. The libraries were estimated to contain $1 \times 10^5$ unique heavy chain sequences.

Libraries 37-2 and 46-2

These libraries are from PMBC harvested after the first immunisations. The PCR primers used amplified VH3 family heavy chains. ICVD sequences in this library were c-terminally fused to Flag and 6-His affinity tags.

Libraries 37-3/3r and 46-3/3r

These libraries are from PMBCs harvested after the second immunisations. The PCR primers used amplified VH3 and VH4 family heavy chains. The ICVD sequences in libraries 37-3 and 46-3 were c-terminally fused to Flag and 6-His affinity tags, whereas in libraries 37-3r and 46-3r were c-terminally fused to only 6-His affinity tags.

Library Selections for Phage with Human IL6R-Binding Activity

Library selection strategies were established to isolate ICVDs that bind to epitopes present on the extracellular domain of the IL-6R alpha subunit including ICVDs that interfere either with (i) the binding of IL-6 to sIL-6R or (ii) with the association of IL-6-IL-6R complexes with gp130 subunits. Complexes formed between IL-6 and soluble (sIL-6R) or membrane (mIL-6R) IL-6 receptor subunits can associate with gp130 to form trans- or cis-IL-6R signalling complexes, respectively. A class of ICVD that block the interaction of IL-6 with the receptor binding site would be expected to inhibit formation of both trans- and cis-IL-6R signalling complexes. ICVD that target other regions of the IL-6R involved in receptor complex formation and that are non-competitive with IL-6 binding may be more efficient (and effective) for inhibition of the IL-6 pathway at sites of inflammation. Furthermore, ICVDs capable of selectively binding to either IL-6-sIL-6R or IL-6-mIL-6R complexes may preferentially antagonise either trans- or cis-IL-6R signalling. Accordingly, several methods were used for the selective enrichment of phages displaying ICVDs with the binding characteristics described above. These methods included the following:

1) Ability to inhibit IL-6R-IL6-gp130 complex formation: Methods for the library selection were chosen that would enrich for ICVDs that are capable of binding to IL-6R at the IL-6 binding site because ICVDs with these properties are most likely to block biological activity of IL-6R. Antibodies capable of inhibiting the complex formation have previously been shown to block a range of biological effects of IL-6R. For example, tocilizumab is a clinically-effective, humanised mouse mAb that binds IL-6R at the IL-6-binding site with high affinity (Kishimoto T. et al. 2006). High concentrations of a tocilizumab Fab fragment or IL-6 were used for the selective elution of this particular group of ICVDs.

2) Ability to bind IL-6R a) in solution and b) when bound to IL-6: A method for selection was developed for ICVDs that bind to the natural epitopes of IL-6R in solution (instead of IL-6R adsorbed to a plastic substrate) in the presence and absence of IL-6. Selections on soluble antigen may isolate ICVDs unrelated to those binding surface-adsorbed antigen. In this method, biotinylated antigen is mixed with phage and the phage-antigen complex is pulled down using avidin. This format also allows pre-incubation of IL-6 with the biotinylated shIL-6R to create a complex.

3) Desirable binding kinetics: high-affinity ICVDs have a low $K_d$, which is a ratio of their speed of antigen-binding ($K_{on}$) and their slow rate of release ($K_{off}$). The length of the phage absorptions were decreased to select for a fast $K_{on}$, and both the number of washes and the length of incubations were increased to select for a slow $K_{off}$.

4) Improved stability against gastro-intestinal supernatants: the removal of unstable ICVDs from the phage libraries by digestion may improve the efficiency of the ICVD screening process. Proteolytic digestion of phage libraries has previously been used to select for stabilised proteins. These previous methods used low concentrations of protease due to the instability of the phage pill fusion protein. A new phagemid was developed showing increased protease stability of the pill fusion protein and used in short digestions with high concentrations of proteases or GI extracts.

First round library selections of phage displaying ICVDs with human IL-6R-binding activity Phage libraries were derived from the llamas after the first round immunisation (Library 37-2 and 46-2); a first selection was performed to isolate phage displaying ICVDs with IL-6R-binding activity by panning on human IL-6R. Soluble recombinant human IL-6R (1000 or 500 ng) was coated directly onto wells of a Maxisorp plate and phages were allowed to attach. After extensive washing, bound phages were collected using either (i) non-selective elution by alkaline pH shock using TEA or (ii) by selective displacement of ICVD by 1 ug IL-6. Phage from the 1000 ng first round selections were selected further on 100 or 10 ng IL-6R with the same washing and elution conditions as before.

Second round library selections of phage displaying ICVDs with human IL-6R-binding activity Phage libraries were derived from the llamas after $2^{nd}$ round immunisation (Libraries 37-3 and 46-3). In the first instance, libraries were selected on 200 or 40 ng shIL-6R coated directly onto wells of a maxisorp plate, subjected to multiple washes, prolonged incubations with 1× PBS, and elution with either IL-6, tocilizumab Fab fragment or TEA.

ICVD 4D3 from the llama 46-3 library was selected at this stage by capture on 200 ng shIL-6R, incubated for 2 h with 1 ug/mL IL-6 and then eluted in a 24 h incubation with 1 ug/mL tocilizumab Fab fragment. In between the incubation and elution step, the plate was washed 10× with 1× PBS, 0.05% Tween20.

Phage from the 200 ng wells were then selected further on 200 and 20 ng IL-6R-coated wells, washed and eluted in similar conditions. In the initial selection, phage captured on 200 ng shIL-6R were eluted in a 2 hour incubation with the 1 ug/mL IL-6, bulked up and put through a secondary selection by capture on 200 ng IL6R and a 6 h elution with 1 ug/mL IL6. The phage were washed 10× with 1×PBS, 0.05% Tween20 in between the capture and elution steps in both elutions. ICVDs 5G9 and 3C12 were isolated from the llama 37-3 library at this stage.

A second set of selections on soluble, biotinylated IL-6R were performed to isolate phage against epitopes on the soluble form of IL-6R when in complex with IL-6. The libraries were mixed with 200, 40 or 8 ng of sIL-6R or sIL-6R in complex with IL-6. ICVD 7F6 was isolated from the llama 37-3 here after capture on 40 ng biotinylated shIL-6R and elution with TEA. The phage were washed 10× with 1×PBS, 0.05% Tween20 in between the capture and elution. The sIL-6R and bound phage were captured on neutravidin coated microplates, and the plates washed prior to elution using TEA. The phage from 200 ng selections went through another selection in identical conditions.

Third round library selections of phage displaying ICVDs with human IL-6R-binding activity Phage Libraries from the llamas after 2nd round immunisation (Libraries 37-3r and 46-3r) were cloned into a newly developed phagemid that produces more protease-stable phage. The libraries were digested with either 1 mg/ml trypsin, 1 mg/mL trypsin and chymotrypsin or 20% rat GI extract before capturing the phage on 500 or 50 ng sIL6R-coated microwell plates. After the washing with 1×PBS, the phage were eluted in TEA. The rat GI digested phage captured on 500 ng IL-6R were further selected identical conditions after digestion in 20% rat GI extract.

Example 2: Generation and Screening of Periplasmic Extracts for Primary Evaluation Phages present in eluates from the selections were used to infect *E. coli* TG1 cells. Colonies were picked randomly into twelve 96-well master plates (76 clones and 88 clones from Libraries 37-2 and 46-2, respectively into master plates VIL-1 and VIL-2; 396 clones and 340 clones from Libraries 37-3 and 46-3, respectively into master plates VIL-3 to VIL-10; 92 clones each from Libraries 37-3r and 46-3r into masterplates VIL-14 and VIL-15) and propagated to generate clonal cultures. Bacterial cell outer membranes were lysed by freeze-thawing to release the ICVD-containing periplasmic fraction. Cell debris was removed by centrifugation and the periplasmic supernatants containing the selected monoclonal ICVDs were transferred to fresh 96-well plates and used for further primary evaluation studies to identify those ICVDs with the required characteristics.

Phages present in eluates from the different library selections were used to infect *E. coli* and individual colonies were picked into master-plates and propagated to generate clonal cultures. Periplasmic supernatants containing the selected monoclonal ICVD were used for primary evaluation studies to identify those with the required characteristics.

The neutralising activity of anti-IL-6R ICVDs was measured in a plate ELISA format as the ability to inhibit binding of the IL-6-sIL-6R complex to gp130, either by interference with IL-6 binding to the IL-6R or by inhibition of the IL-6-sIL-6R interaction with gp130.

ICVDs were also tested for intrinsic resistance to inactivation in the presence of small intestinal proteases. Following protease digestions, ICVDs showing residual activity in the gp130-based plate ELISA were identified.

Cross-reactivity of ICVDs with cynomolgus monkey IL-6R was assessed using the gp130-based plate ELISA assay format but with cynomolgus monkey serum as a source of monkey sIL-6R. ICVDs inhibiting the formation of a cyno-IL-6R complex with human IL-6 and human gp130 were identified.

Amino acid sequences of selected ICVDs were determined and aligned to assess diversity and family relationships. From a total of 900 library-selected clones picked into the original 12 master-plates a final set of primary clones was selected for production in *E. coli* and the ICVDs affinity purified for more detailed evaluation studies.

These primary clones included ICVDs 7F6, 3C12, 4D3 and 5G9. Sequencing revealed that 5G9 and 7F6 shared similar CDR3s. 3C12 and 4D3 had CDR3s distinct from each other and distinct from the 5G9 and 7F6 'family'. The remaining selected primary clones also had CDR3s distinct from the 5G9 and 7F6 'family'. These remaining selected primary clones are not discussed further. ICVDs sharing similar CDR3s to the 5G9 and 7F6 'family', and which are therefore polypeptides of the invention, are highlighted in bold in the tables below.

Example 3: Family Expansion to Produce 21E6

After the initial rounds of selecting primary clones, a family expansion approach was used (see Koh et al., 2010). Family expansion is a molecular biology technique that enriches for groups of related antibodies in display libraries. When these new libraries are subjected to selections and screens, a higher proportion of eluted antibodies will be related to the original clone, allowing for better sampling of the sequence diversity within a single family. In this case, a family expansion approach was therefore attempted to identify antibodies with similarly favourable antigen-binding characteristics to 7F6.

The family-expanded library was panned to capture the phage on IL6R, followed by a brief two hour elution with a competing protein (tocilizumab Fab/IL6) and then along (16 elution) with the same proteins. Masterplates were picked from the selected clones, which then were digested with 1 mg/mL trypsin for 6 hours. The resulting protease resistant, potent clones were patched into a new masterplate and then reanalyzed with 1 mg/mL trypsin+1 mg/mL chymotrypsin for 6 hours. Most ICVDs did not survive this treatment, but one ICVD which had not already been encountered appeared to survive better than the rest. This was 21E6. 21E6 is related to 7F6 and differs by two mutations: Q131, and F106L. 21E6 was expressed from a phagemid vector and purified for testing in digest and potency assays.

Example 4: Evaluation of the Potency and Maximal IL-6R Neutralising Activity of Purified E. coli Recombinant ICVDs Production of Selected ICVD Clones in E. coli Selected ICVDs were re-cloned into the vector pMEK222 (thus introducing C-terminal Flag and 6xHis tags) for production in E. coli and the ICVDs affinity purified for more detailed evaluation studies.

IL-6R-neutralising activities of the purified ICVDs were evaluated in several in vitro assay systems to assess potency and efficacy against soluble and membrane forms of human IL-6R and soluble cynomolgus monkey IL-6R.

Inhibition of gp130/IL-6/IL-6R Complex Formation—Potency in Neutralising Soluble Human IL6R The standard gp130 ELISA assay detailed above under 'Potency, inhibition and neutralisation' (referred to as 'the gp130 ELISA' hereon) was performed with the modifications described below to test the ability of anti-IL-6R ICVDs to neutralise sIL-6R-IL-6 binding to gp130, demonstrating the potency of the recombinant purified ICVDs. Briefly, Maxisorp 96-well plates were coated overnight with 50 µl/well 0.5 µg/ml gp130 then blocked. ICVDs were serially diluted and mixed 1:1 with 100 ng/ml recombinant human IL-6 then 1:1 with 40 ng/ml recombinant human sIL-6R, and incubated for 1 hour to allow binding before adding to the gp130-coated plates. Bound IL-6R was detected with 50 µl/well 0.250 µg/ml BAF227 and then 50 µl/well 1/1000 diluted Extravidin-HRP and the level of neutralisation by the ICVD of IL-6R binding to IL-6/gp130 was determined.

Dose response curves were obtained (dose response curves of particular ICVDs illustrated in FIG. 1). In particular, 7F6 and 5G9 appeared to be substantially more potent than tocilizumab. 3C12 was not more potent than tocilizumab. This was confirmed with curve-fitting software (Graphpad Prism), which fitted 4 parameter curves to the data and calculated the IC50s (Table 4.1, below).

TABLE 4.1

| IC50s of particular ICVDs and tocilizumab in the first assay with 20 ng/mL IL6R and 100 ng/mL IL6 | | | | | |
|---|---|---|---|---|---|
| ICVD Name | 7F6 | 3C12 | 4D3 | 5G9 | tocilizumab |
| IC50 (nM) | 0.11 | 1.89 | 0.66 | 0.16 | 0.97 |

7F6 and 5G9 were more potent than 3C12, 4D3 or tocilizumab in this assay.

Figure 2:
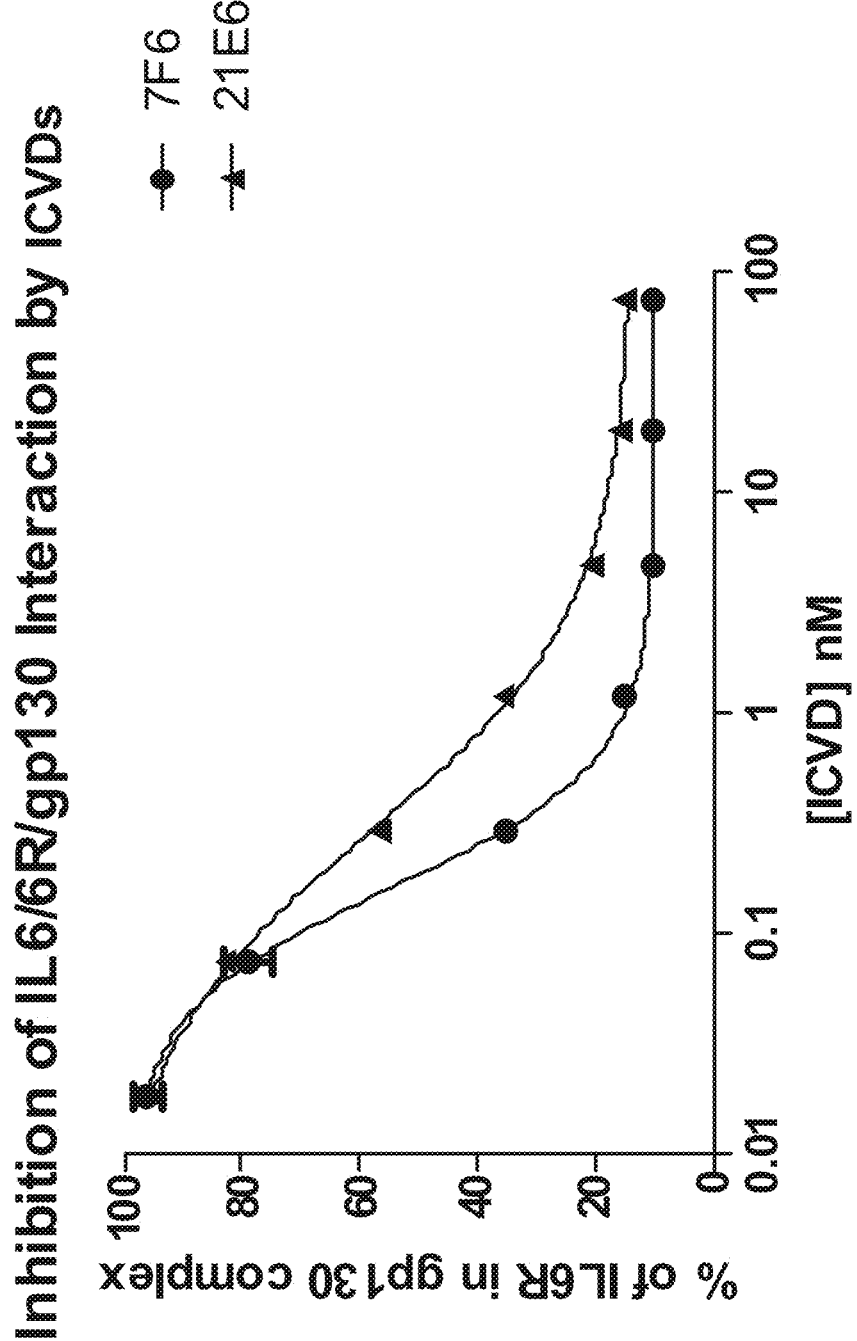
FIG. 2—Inhibition of IL-6/IL-6R/gp130 interaction by ICVDs (7F6 and 21E6)

A separate assay was performed on 21E6 and 7F6 using the same protocol as above with the exception that the ICVD/IL-6R/IL-6 where only incubated with shaking for 10 min before being added to the assay plates. The results of the assay are shown in FIG. 2 and Table 4.2. It was found that 21E6 was approximately two-fold less potent than 7F6.

TABLE 4.2

| IC50s of 7F6 and 21E6 in the second assay with 20 ng/mL IL6R and 100 ng/mL IL6 | | |
|---|---|---|
| ICVD Name | 7F6 | 21E6 |
| IC50 (nM) | 0.16 | 0.3 |

In summary, highly potent ICVDs 7F6, 5G9 and 21 E6, were identified. These ICVDs all share similar CDR3 sequences.

Cynomolqus Monkey sIL6R Cross-Reactivity

Cross-reactivity of anti-human IL6R ICVDs with cynomolgus monkey IL-6R would facilitate preclinical studies in this species. The cross-reactivity of the selected ICVDs was therefore investigated.

Figure 3:
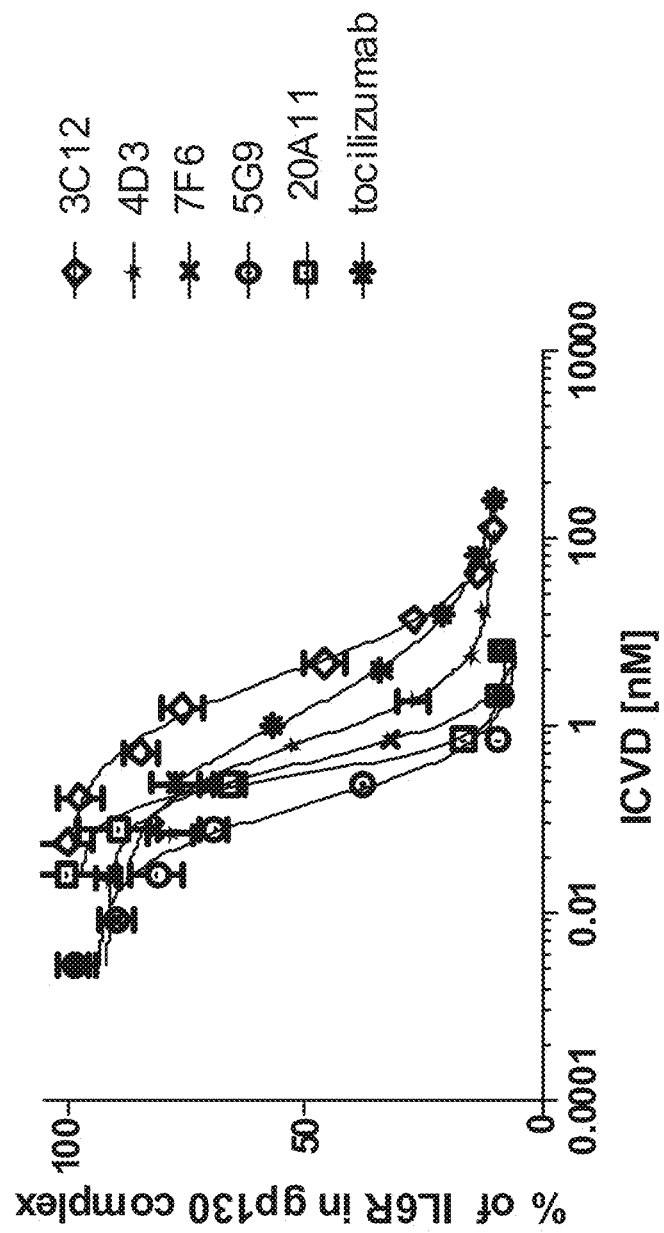
FIG. 3—Inhibition of gp130/IL-6/IL-6R interaction by ICVDs (3C12, 4D3, 7F6, 5G9, 20A11 and tocilizumab)
Figure 4:
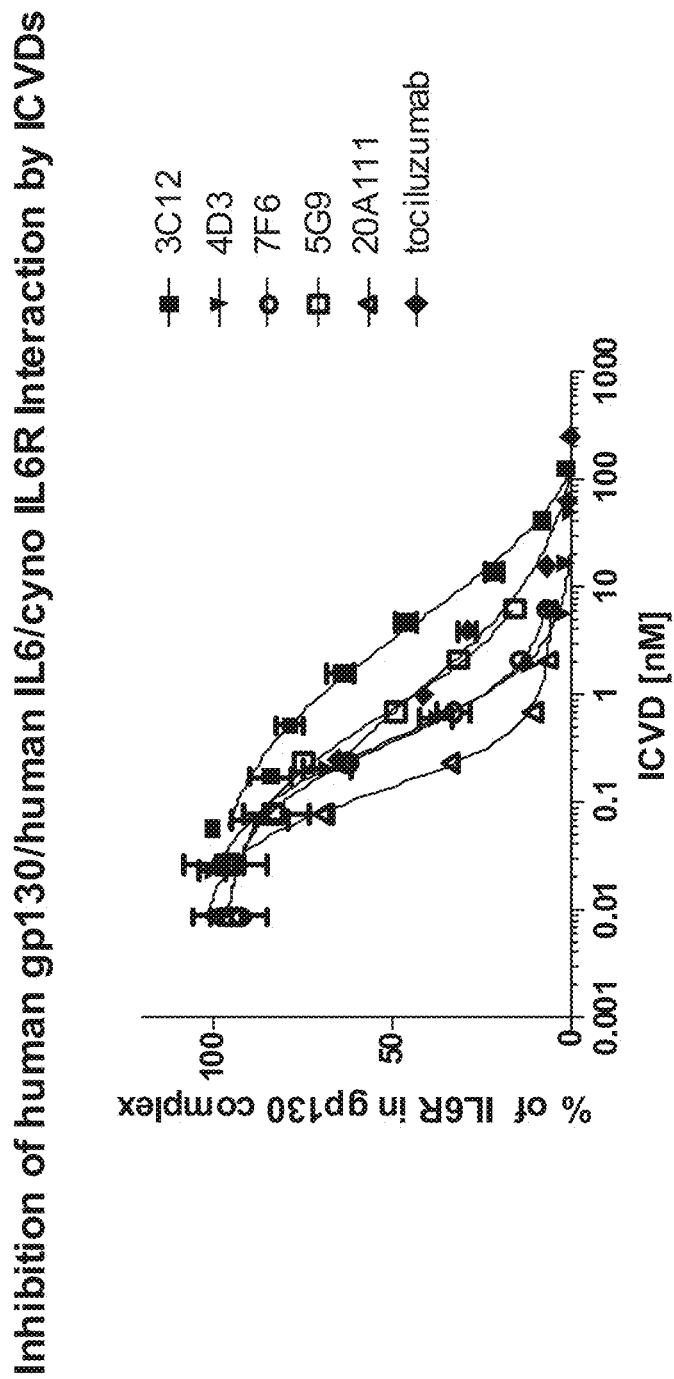
FIG. 4—Inhibition of human gp130/human IL-6/cynomolgous monkey IL6-R interaction by ICVDs (3C12, 4D3, 7F6, 5G9, 20A11 and tocilizumab)

The standard anti-cynomolgus monkey IL-6R gp130 ELISA assay detailed under 'Potency, neutralisation and inhibition' above was performed to assay the ICVDs in parallel for their ability to neutralise sIL6R in cynomolgous monkey serum and recombinant purified human sIL6R. Briefly, Maxisorp 96-well plates were coated overnight with 50 µl/well 1 µg/ml gp130 then blocked. ICVDs were serially diluted and mixed 1:1 with 200 ng/ml recombinant human IL-6, then 1:1 with either 20 ng/ml recombinant human sIL-6R or a 5-fold dilution of cynomolgus monkey serum and incubated for 1 hour to allow binding before adding to the gp130-coated plates. Bound cynomolgus monkey IL-6R was detected with 50 µl/well either 0.25 µg/ml (for human IL-6R) or 0.5 µg/ml (for monkey serum) BAF227 and then 50 µl/well 1/1000 Extravidin-HRP and the level of neutralisation by the ICVD of IL-6R binding to IL-6/gp130 was determined (dose response curves of particular ICVDs in inhibiting human gp130/IL-6/IL-6R interaction are illustrated in FIG. 3 and dose response curves of particular ICVDs in inhibiting human gp130/human IL-6/cynomolgous monkey IL-6R interaction are illustrated in FIG. 4).

To demonstrate the relative potencies of the ICVDs on the two sIL-6Rs, the IC50s were calculated as before, and the two IC50s were expressed as a ratio (i.e. how many fold more potent the ICVDs are in neutralising cynomolgous IL6R compared to human IL-6R. These ratios are shown in Table 4.3 below. In this iteration of the assay, 10 ng/mL human IL-6R was compared to 10× diluted cynomolgous serum in the presence of 50 ng/mL human IL-6.

Prior art anti-IL-6R polypeptide 20A11 was also included in this assay. 20A11 is disclosed in WO 2010/115998.

TABLE 4.3

Human and cynomolgous sIL-6R IC50 ratios of the ICVDs (human IC50 divided by cynomolgous IC50)

| ICVD Name | Cyno IL6R IC50 (nM) | Human IL6R IC50 (nM) | Ratio Cyno IC50/human IC50 |
|---|---|---|---|
| 3C12 | 4.142 | 3.531 | 0.9 |
| 4D3 | 0.372 | 0.6907 | 1.9 |
| 7F6 | 0.342 | 0.4243 | 1.2 |
| 5G9 | 0.8038 | 0.1477 | 0.2 |
| 20A11 (prior art comparative example) | 0.1058 | 0.2401 | 2.3 |
| tocilizumab Fab (prior art comparative example) | 1.131275 | 0.7044 | 0.6 |

7F6 and 5G9 were found to have cross-reactivity with cynomolgous sIL-6R.

Inhibition of Membrane-IL-6R Induced Cell Proliferation in the TF1 Assay

Selected ICVDs were tested in the TF-1 assay as detailed above under 'Potency, inhibition and neutralisation'; 'The standard TF-1 cell assay'. IL-6 stimulates the proliferation of human TF-1 human erythroleukemic cells via the activation of membrane IL-6 receptors. The clinical anti-IL-6R monoclonal antibody tocilizumab potently and effectively inhibits IL-6-indiced TF-1 cell proliferation by interfering with the binding of IL-6 to mIL-6Rs on the cells. Selected ICVD were tested in this assay to compare their potencies and maximal inhibitory effects on IL-6 induced proliferation with a Fab fragment of the clinical standard tocilizumab.

Briefly, TF1 cells were grown to log phase in Low-serum RPMI 1640+2 nM L-glu+pen/strep+5% FCS+2.5 ug/mL GM-CSF. The cells were washed 2× in prewarmed 1×PBS, and plated at $2 \times 10^4$ cells/well in 50 ul in 96 wells Costar micro-plates in assay medium (AM; Low-serum RPMI 1640+2 mM L-glu+Pen/Strep with no serum and no GM-CSF). The serial dilutions of anti-IL-6R ICVDs were prepared in AM at 4 times the assay concentration and mixed 1:1 with IL6 at 20 ng/mL (4 times the assay concentration) to have a 2× final concentration of ICVD and IL6. 50 uL of each solution were added to the cells. Plates were stored for 48 hours at 37° C. and 5% CO₂. The assay was read with 10 uL of resazurin and the cells were incubated for 2 h at 37° C. The assay was stopped with 50 uL of 3% SDS and the plates were then read with excitation at 540 nm and emission at 590 nm.

Figure 5:
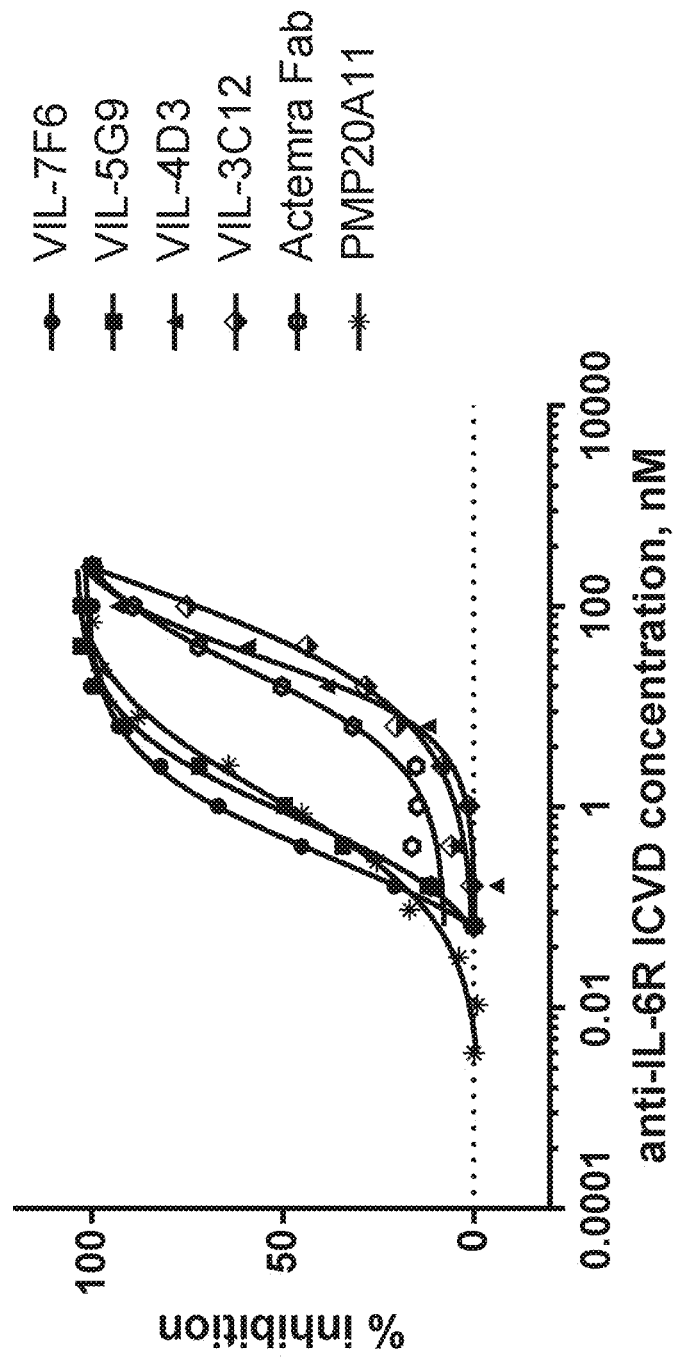
FIG. 5—Inhibition of IL-6-dependent proliferation of TF-1 cells (7F6, 5G9, 4D3, 3C12, tocilizumab Fab and 20A11)

FIG. 5 shows the inhibition of IL6-induced proliferation of TF1 cells following incubation with increasing concentration of anti-IL-6R ICVD (in the figure, VIL-7F6 refers to 7F6, VIL-5G9 refers to 5G9, VIL-4D3 refers to 4D3, VIL-3C12 refers to 3C12 and PMP20A11 refers to 20A11). A Prism GraphPad analysis using 4 parameter non-linear regression curve provided the IC50 values in Table 4.4. All of these tested ICVDs exhibited a complete inhibition of TF1 proliferation at the highest concentration tested or lower (16-250 nM).

TABLE 4.4

IC50 values of ICVDs in TF1 assay

| Anti-IL-6R ICVD | IC50 (nM) |
|---|---|
| 7F6 | 0.5 |
| 5G9 | 0.9 |
| 4D3 | 26.0 |
| 3C12 | 44.6 |
| tocilizumab Fab (prior art comparative example) | 15.9 |
| 20A11 (prior art comparative example) | 1.1 |

It can be seen that 7F6 and 5G9 are the most potent ICVDs in this assay with IC50 values of 0.5 nM and 0.9 nM respectively, which are lower than the tocilizumab Fab fragment, comparative example 20A11, 4D3 and 3C12.

Figure 6:
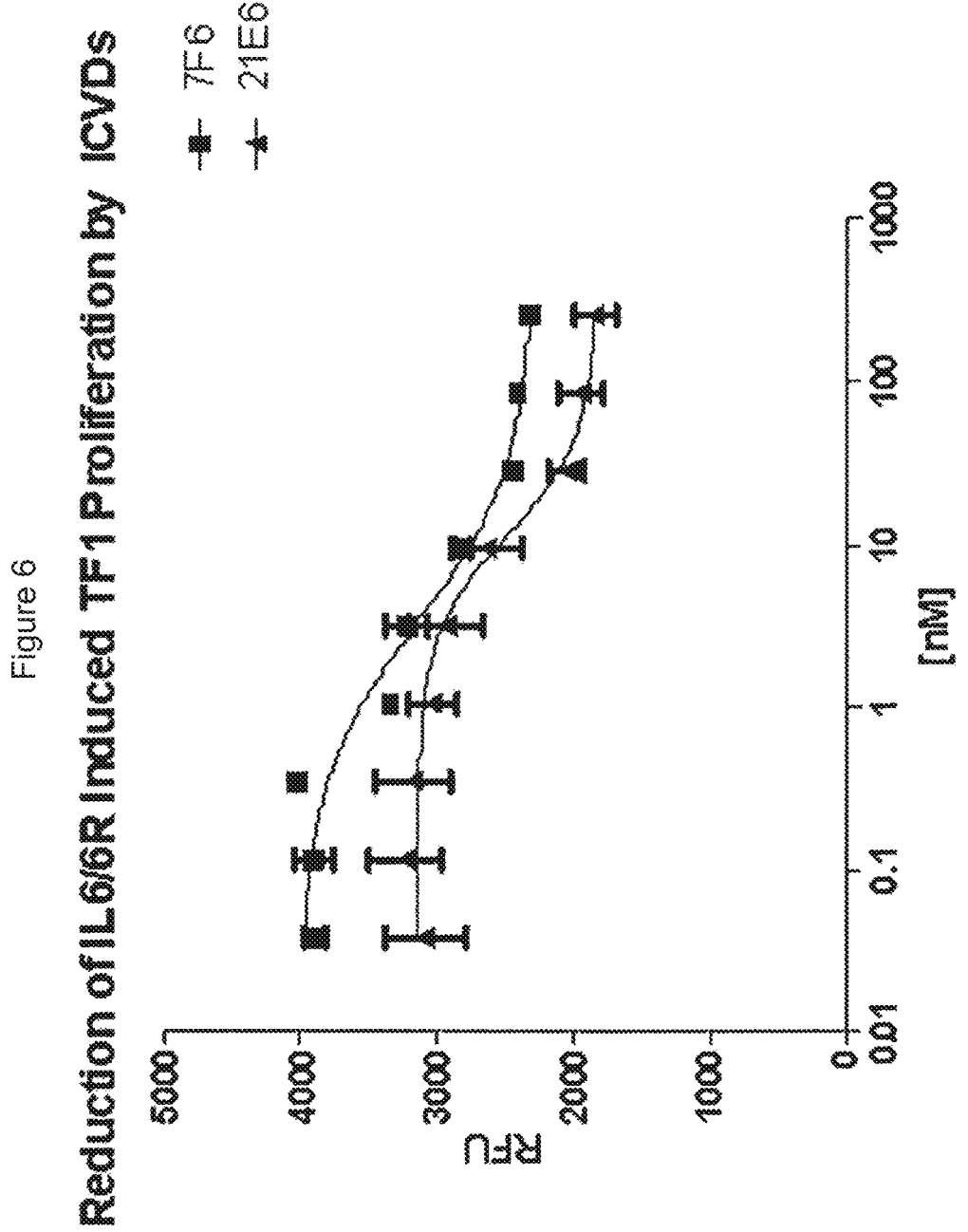
FIG. 6—Inhibition of IL-6-dependent proliferation of TF-1 cells (7F6 and 21E6)
Figure 7:
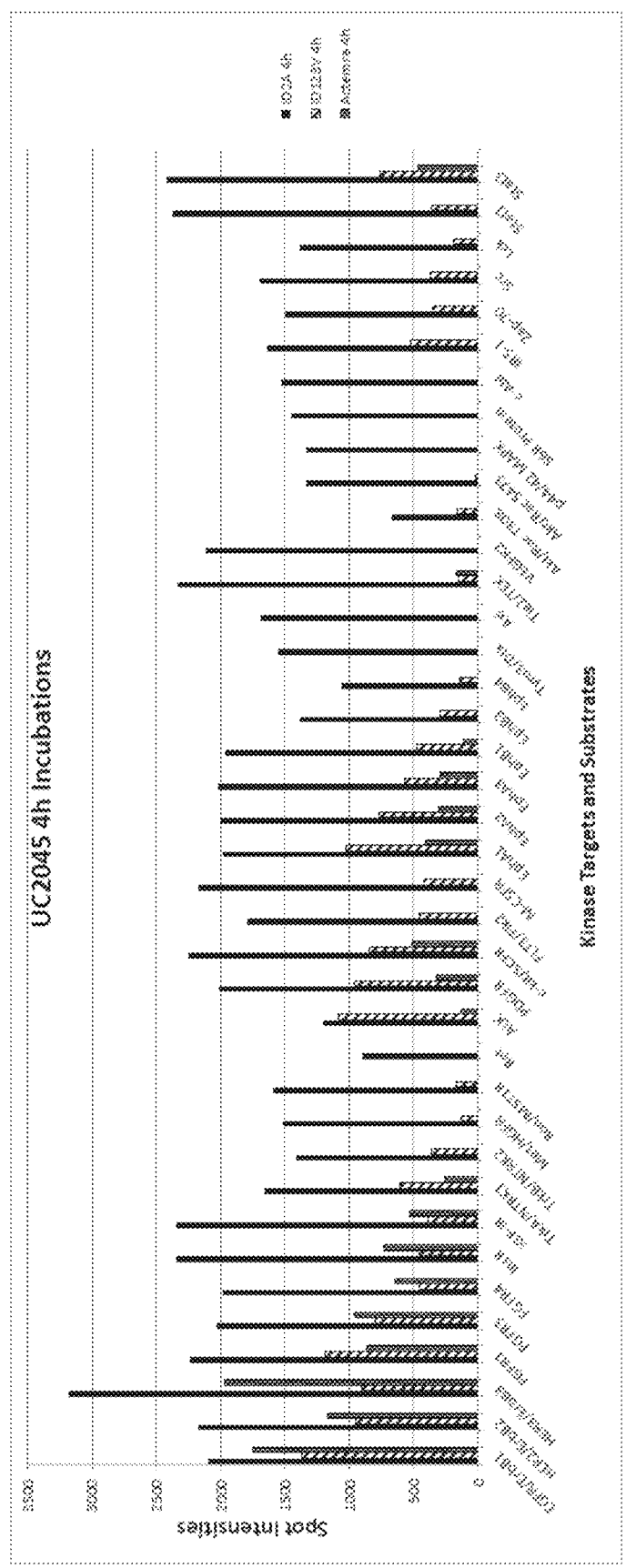
FIG. 7—Phosphoprotein signals for UC2045, 4 hour incubation (ID-123V)
Figure 8:
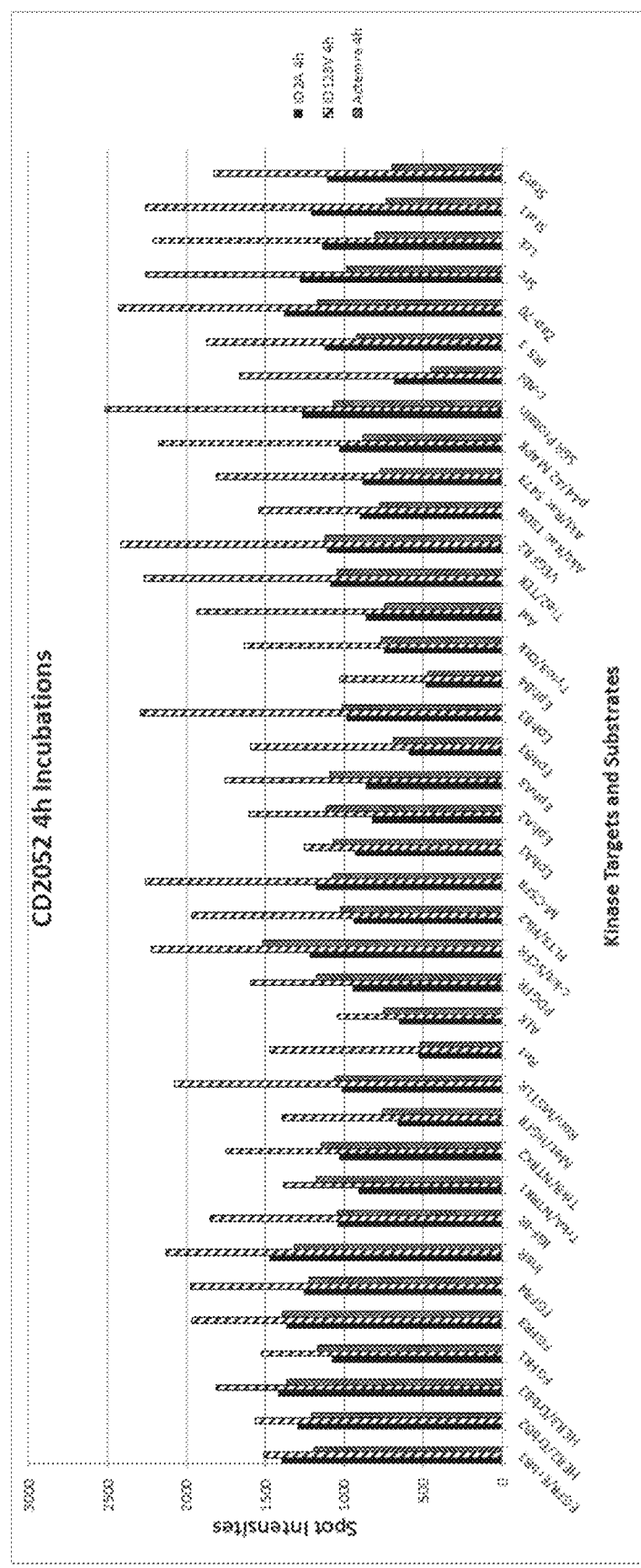
FIG. 8—Phosphoprotein signals for CD2052, 4 hour incubation (ID-123V)
Figure 9:
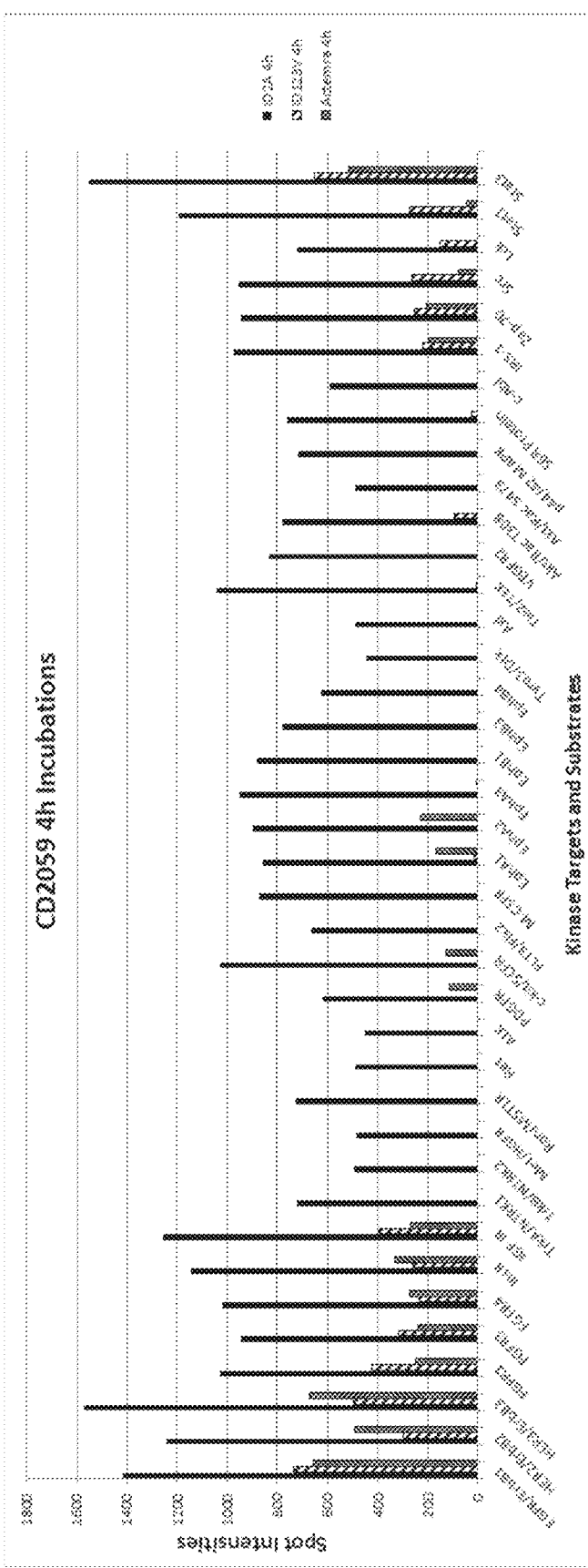
FIG. 9—Phosphoprotein signals for CD2059, 4 hour incubation (ID-123V)
Figure 10:
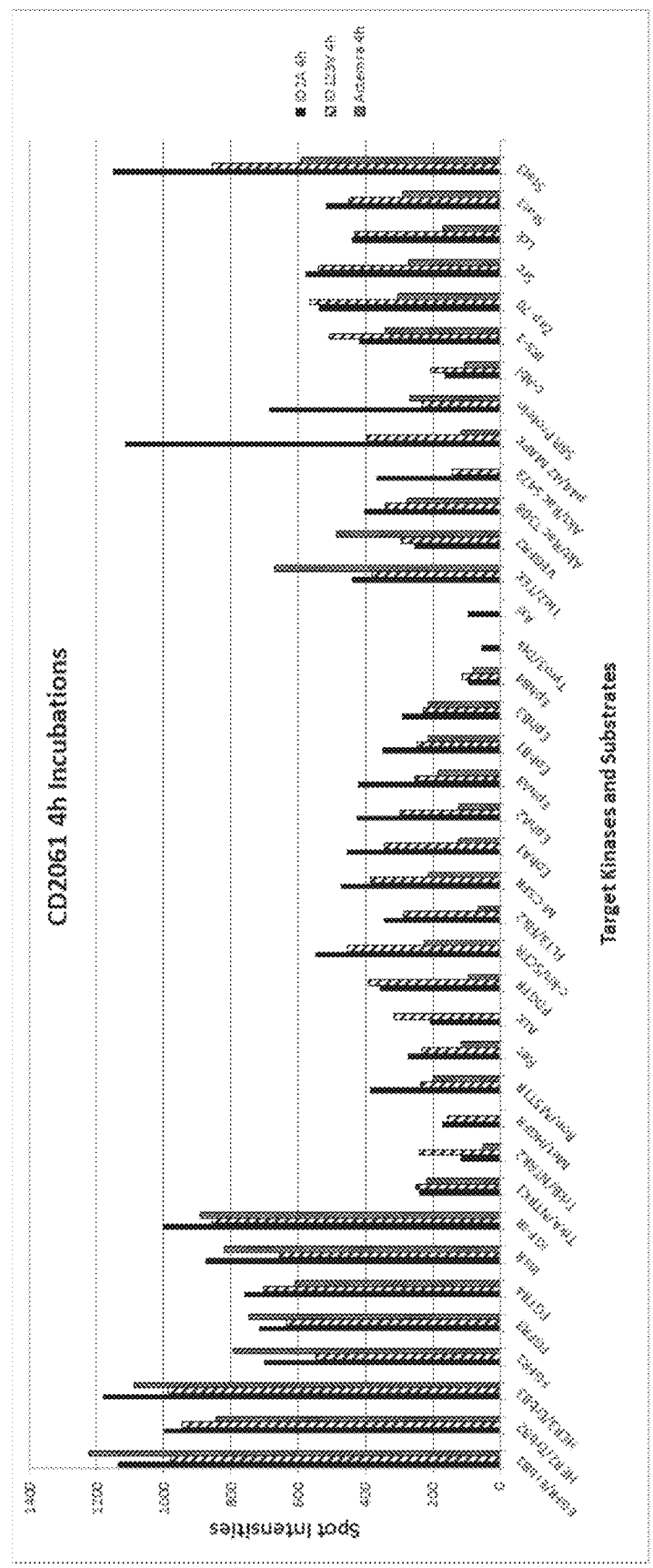
FIG. 10—Phosphoprotein signals for CD2061, 4 hour incubation (ID-123V)
Figure 11:
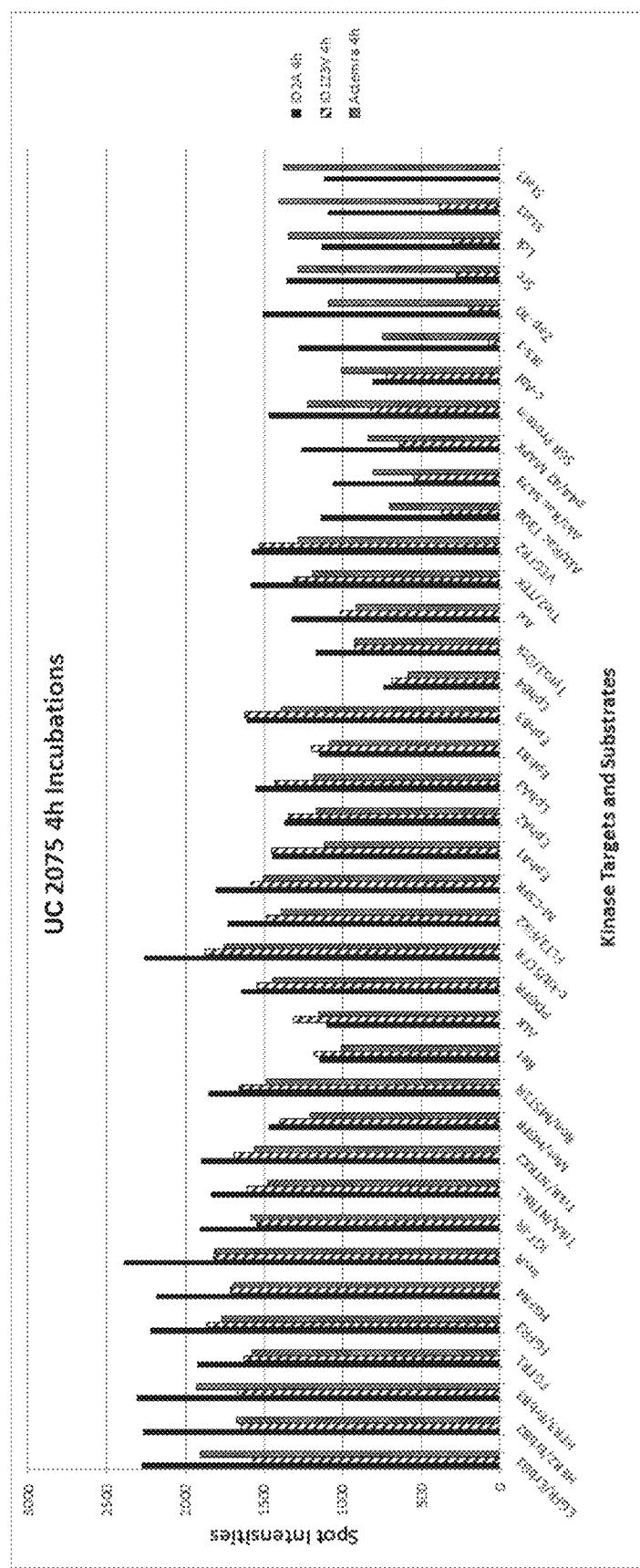
FIG. 11—Phosphoprotein signals for UC2075, 4 hour incubation (ID-123V)
Figure 12:
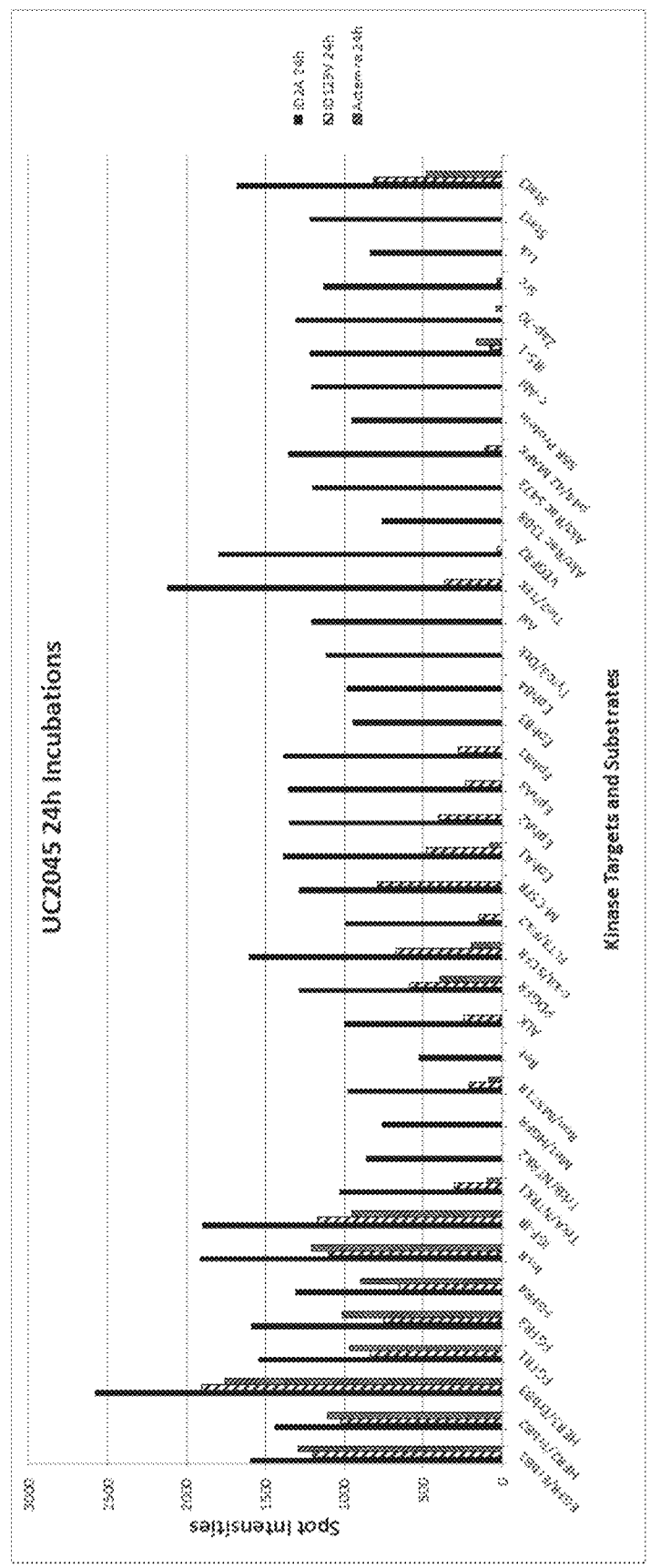
FIG. 12—Phosphoprotein signals for UC2045, 24 hour incubation (ID-123V)
Figure 13:
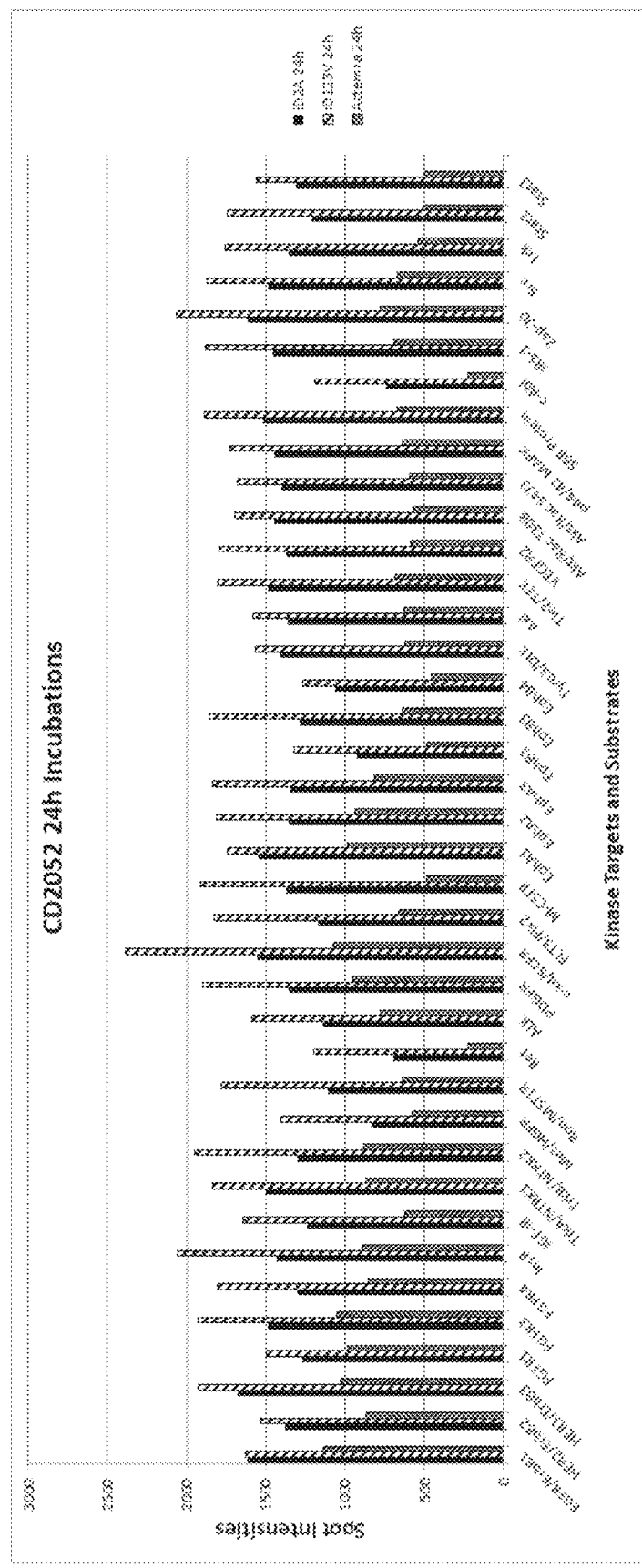
FIG. 13—Phosphoprotein signals for CD2052, 24 hour incubation (ID-123V)
Figure 14:
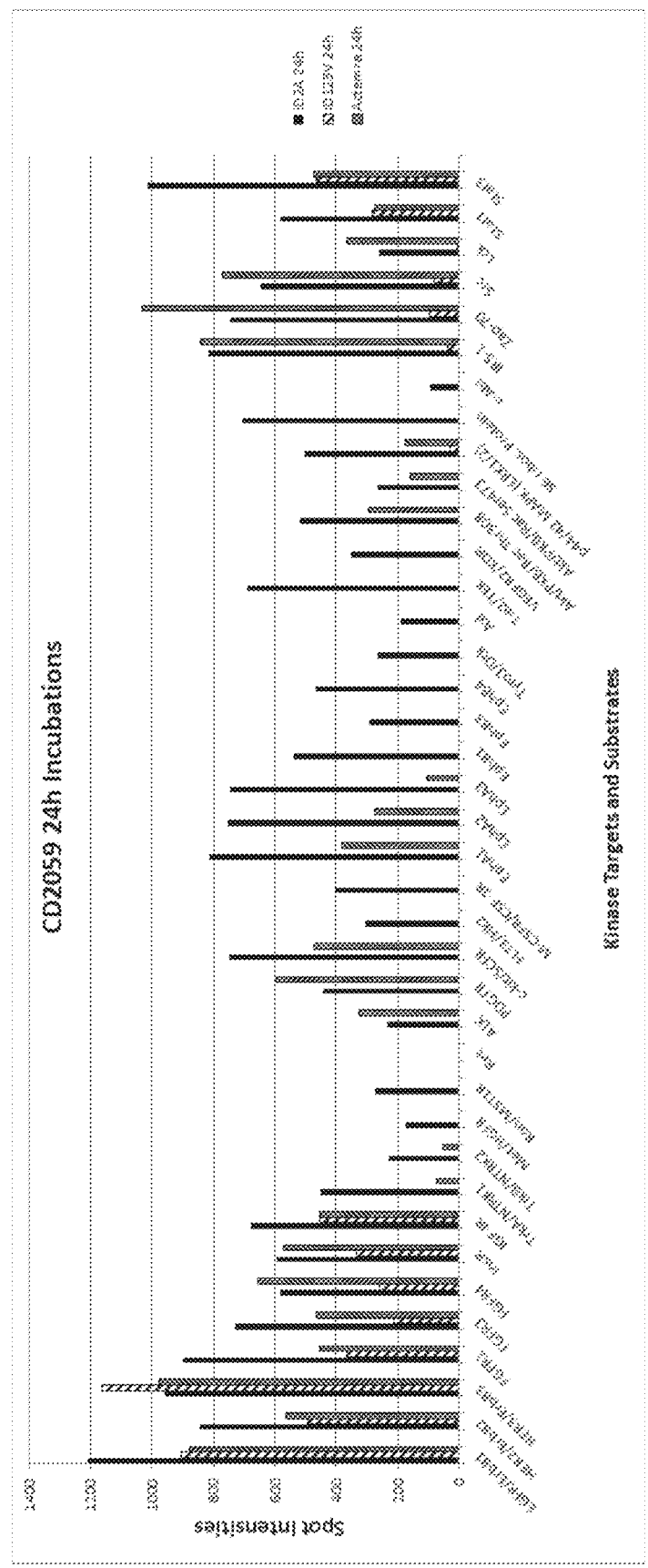
FIG. 14—Phosphoprotein signals for CD2059, 24 hour incubation (ID-123V)
Figure 15:
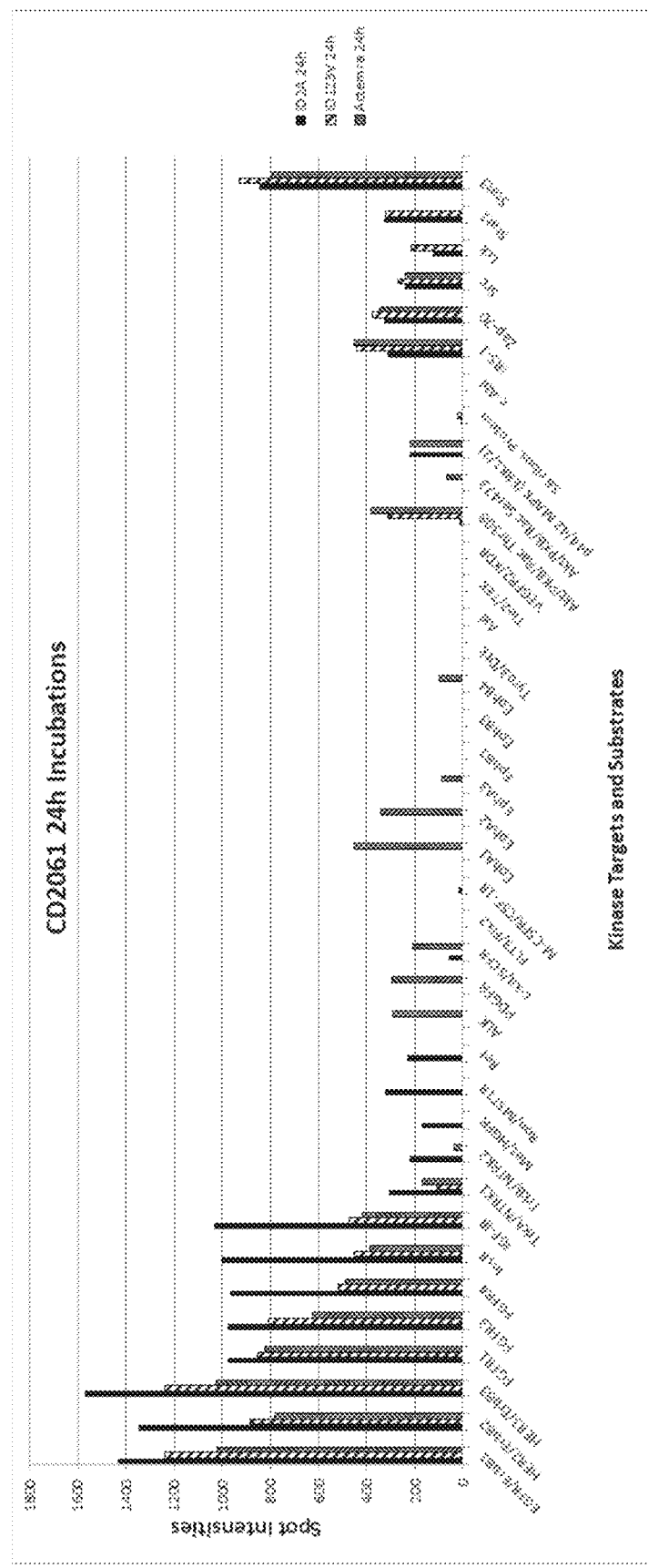
FIG. 15—Phosphoprotein signals for CD2061, 24 hour incubation (ID-123V)
Figure 16:
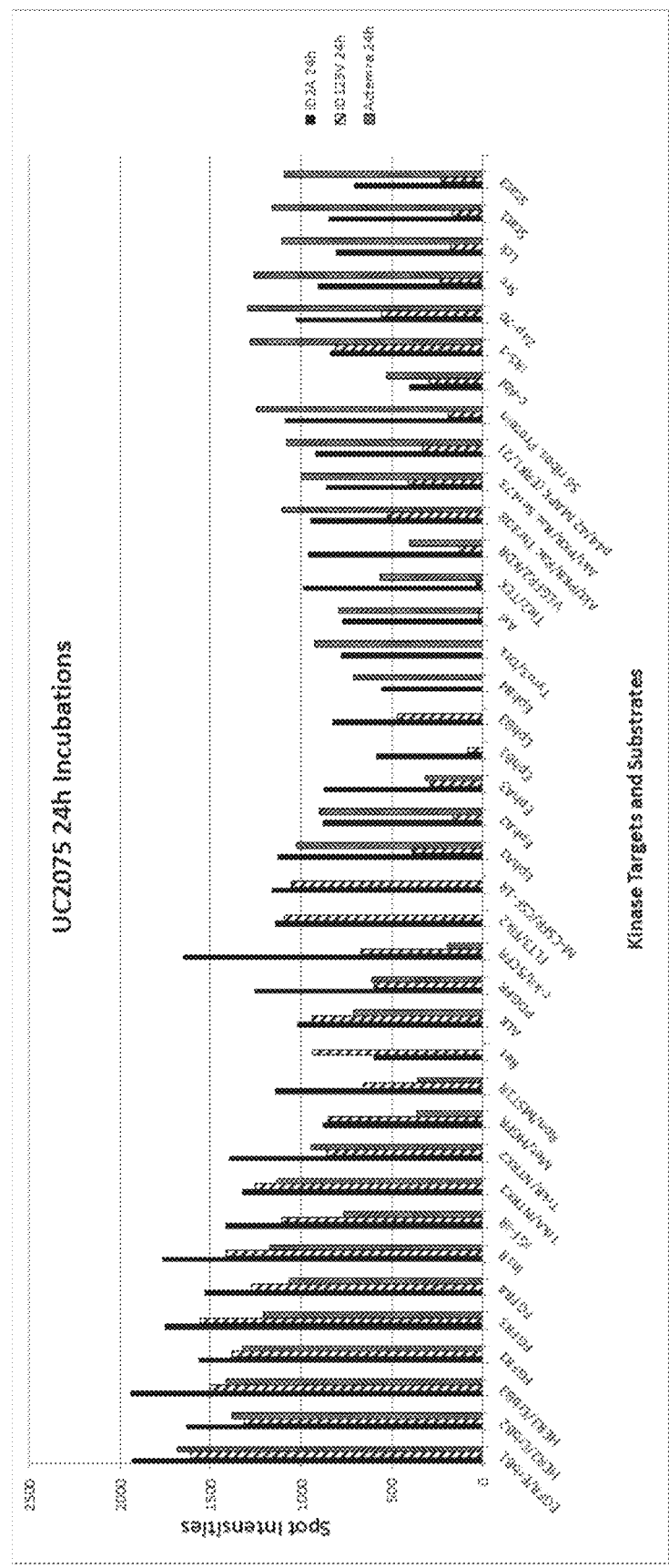
FIG. 16—Phosphoprotein signals for UC2075, 24 hour incubation (ID-123V)

A separate assay on 7F6 and 21E6 was performed using a similar protocol to that used above. In this assay, low level GM-SCF contamination increased the background assay signal. Regardless, dose response curves were calculable. The fluorescence measured at different ICVD concentrations was plotted (see FIG. 6), inhibition curves were produced (not shown) and IC50 values obtained as described above. The results are shown in Table 4.5.

TABLE 4.5

IC50 values of 7F6 and 21E6 in TF1 assay

| Anti-IL-6R ICVD | IC50 (nM) |
|---|---|
| 7F6 | 3 |
| 21E6 | 11 |

Due to differences in this assay from the previous iteration, the calculated IC50s are not directly comparable with those previously recorded. Despite this, the pairwise comparison between 7F6 and 21E6 assayed on the same plate indicate that 21E6 can still be considered a potent ICVD.

Example 5: Evaluation of the Intestinal Stability of Purified *E. coli* Recombinant ICVDs Stability of Purified *E. coli* Recombinant Anti-IL-6R ICVDs in Human Faecal Extract ICVDs were digested in pooled human faecal extract for 6 h each as detailed in 'the standard human faecal extract digestion assay'. The digested samples were then analysed as detailed in 'the standard anti-IL-6R gp130 ELISA performed on samples previously exposed to proteolytic material'. Any protocol deviations are described below. These assays can be found above under the heading 'Stability'.

Briefly, Maxisorp 96-well plates were coated overnight with 50 µl/well 0.5 µg/ml gp130 then blocked. ICVDs were serially diluted on ice and mixed 1:1 with 200 ng/ml recombinant human IL-6, then 1:1 with 20 ng/ml recombinant human sIL-6R and incubated for 10 mins before adding to the gp130-coated plates. Bound IL-6R was detected with 50 µl/well 0.250 µg/ml BAF227 and then 50 µl/well 1/1000 Extravidin-HRP and the level of neutralisation by the ICVD of IL-6R binding to IL-6/gp130 was determined.

The amount of ICVD remaining in the 0 time point and the 6 h digested samples was interpolated from standard curves using the Graphpad Prism software package. The ICVD concentration in the 6 h sample is expressed as a % of that in the 0 h sample to give ICVD survival. The results are shown in Table 5.1.

TABLE 5.1

Assay 1 - Stability of ICVDs after 6 hours' incubation in pooled human faecal extract

| Name | 7F6 | 5G9 | 3C12 | 4D3 |
|---|---|---|---|---|
| % survival | 42 | 75 | 16 | 46 |

A separate assay on 21E6 was performed using the protocol as described for the 21E6 potency assays in the section "Inhibition of gp130/IL-6/IL-6R complex formation—potency in neutralising soluble human IL6R". The results of the assay are shown in Table 5.2.

TABLE 5.2

Assay 2 - Stability of 21E6 after 6 hours' incubation in pooled human faecal extract

| Name | 21E6 |
|---|---|
| % survival | 50.8 |

Stability of Purified *E. coli* Recombinant Anti-IL-6R ICVDs in Mouse Small Intestinal Supernatant ICVDs were digested in mouse small intestinal supernatant for 1 h each as detailed in 'the standard mouse small intestinal supernatant digestion assay'. The digested samples were then analysed as detailed in 'the standard anti-IL-6R gp130 ELISA performed on samples previously exposed to proteolytic material'. Any protocol deviations are described below. These assays can be found above under the heading 'Stability'.

Briefly, Maxisorp 96-well plates were coated overnight with 50 µl/well 0.5 µg/ml gp130 then blocked. ICVDs were serially diluted on ice and mixed 1:1 with 200 ng/ml recombinant human IL-6, then 1:1 with 20 ng/ml recombinant human sIL-6R and incubated for 10 mins before adding to the gp130-coated plates. Bound IL-6R was detected with 50 µl/well 0.250 µg/ml BAF227 and then 50 µl/well 1/1000 Extravidin-HRP and the level of neutralisation by the ICVD of IL-6R binding to IL-6/gp130 was determined.

The amount of ICVD remaining in the 0 time point and the 1 h digested samples was interpolated from standard curves using the Graphpad Prism software package. The ICVD concentration in the 1 h sample is expressed as a % of that in the 0 h sample to give ICVD survival. The results are shown in Table 5.3.

TABLE 5.3

Assay 1 - Stability of selected ICVDs after 1 hour incubation in mouse small intestinal supernatant

| Name | 7F6 | 5G9 | 4D3 |
|---|---|---|---|
| % survival | 18 | 23 | 46 |

A separate assay on 7F6 and 21E6 was performed using the same protocol as described for 21E6 human faecal digestions. The results of the assay are shown in Table 5.4.

TABLE 5.4

Assay 2 - Stability of 21E6 after 1 hour incubation in mouse small intestinal supernatant

| Name | 21E6 |
|---|---|
| % survival | 29.5 |

In summary, it was found that ICVDs 7F6, 5G9 and 21E6, which all share similar CDR3 sequences, are not only highly potent but also surprisingly stable to intestinal proteases.

Example 6: Overall Summary of Properties of Selected ICVDs

ICVDs have been identified with good potency in assays measuring neutralisation of human and cynomolgus monkey soluble IL-6R, membrane IL-6R and resistance to inactivation by intestinal proteases. These characteristics are summarised in Table 6.1, which incorporates data from both first and second rounds of assays.

TABLE 6.1

Potency and protease resistance characteristics of ICVDs

| Identifier | gp130 ELISA $EC_{50}$ (nM) (sIL-6R) | TF1 assay $EC_{50}$ (nM) (mIL-6R) | Binds cyno monkey sIL-6R | % Survival 1 hour mouse small intestinal supernatant | % Survival 6 hours human faecal extract |
|---|---|---|---|---|---|
| 3C12 | 1.89 | 44.6 | Yes | NT | 16 |
| 4D3 | 0.66 | 26.0 | Yes | 46 | 46 |
| 5G9 | 0.16 | 0.9 | Yes | 23 | 75 |
| 7F6 | 0.11 | 0.5 | Yes | 18 | 42 |
| 21E6 | 0.3 | 11 | NT | 29.5 | 50.8 |

(NT = not tested)

It can be seen that ICVDs 7F6, 5G9 and 21E6, which all share similar CDR3 sequences, are highly potent and highly stable to intestinal proteases. 4D3, which also has a distinct CDR3 sequence to 7F6, 5G9 and 21E6, has relatively poorer potency. 3C12, which has a distinct CDR3 sequence to 7F6, 5G9 and 21E6, has relatively poorer potency and relatively poorer protease stability.

Example 7: Epitope Analysis

The selected ICVDs were assayed for their ability to cross-compete with tocilizumab Fab for binding to IL-6R.

Four Nunc Maxisorp 96-well ELISA plates were coated with 1 µg/ml mouse anti-human IgG Fab fragment (abcam ab1927) in PBS and incubated overnight at 4° C. Plates were washed in wash buffer (0.05% Tween in 1× PBS) using an automatic plate washer and blocked in block buffer (1% BSA in PBS) for 1 hour. Stocks of 40 ng/ml IL-6R, 8 nM TCZ (tocilizumab) Fab, and 400 nM ICVDs were prepared in block buffer. ICVD solutions were made up from a masterplate of 5 µM stock solutions.

Solutions of purified ICVDs were transferred to a Dilution Plate, where they were serially diluted threefold in 1% BSA in PBS. 60 µl each diluted sample was mixed with 60 µl TCZ Fab. 85 µl of this mixture was subsequently mixed with 85 µl IL-6R solution and incubated on a shaking platform for 1 hour. This resulted in final concentrations of: 100-0.138 nM ICVD, 2 nM TCZ Fab, and 20 ng/ml IL-6R. Block buffer was removed from ELISA plates and 50 µl each sample was added to each well in triplicate. Samples were incubated on the assay plates for 2 hours. Plates were washed as above, and 50 µl per well of 0.25 µg/ml BAF227 anti-IL-6R (R&D Systems) in blocking buffer was added to the plate and incubated for 1 hour. The plates were washed as above and incubated with 50 µl/well of a 1/1000 dilution of ExtrAvidin peroxidase (Sigma E2886) in blocking buffer for 1 hour. Plates were washed as above, and 100 µl TMB Microwell Substrate (KPL) was added.

After 20 minutes, the reactions were stopped with 50 µl 0.5 M $H_2SO_4$ per well. $OD_{450}$ was measured using a BMG FluoStar Omega plate reader.

Analysis of data:

$OD_{450}$ values for the highest concentration of ICVD (100 nM) were used to represent the maximum level of tocilizumab competition, achievable by the ICVDs. The percentage competition with the tocilizumab Fab was calculated as a percentage of the maximum range of the assay, with this value calculated for a non-IL6R binding ICVD control (IRR) included in each masterplate subtracted:

$$\% \text{ tocilizumab competition} = \left( \frac{OD_{No\ VHH} - OD_{Sample}}{OD_{No\ VHH} - OD_{IL6R\ only}} \right) - \% \text{ competition of } IRR$$

Results

The ICVDs were sorted according to their ability to inhibit the binding of the tocilizumab Fab to IL-6R (% tocilizumab competition, as shown in Table 7.1.

TABLE 7.1

Calculated average OD450 values and % tocilizumab completion values ranked by % competition:

| ICVD | % competition |
|---|---|
| 20A11 (prior art comparative example) | 102.78 |
| 3C12 | 81.72 |
| 7F6 | 73.64 |
| 5G9 | 33.36 |

It can be seen from this competition analysis that 7F6 and particularly 5G9 may be expected to bind to a different epitope to that of tocilizumab or 20A11.

Example 8: Mutations to the 5G9 and 7F6 Sequences and Impact on Potency

Mutant 5G9 Sequences

Mutant 5G9 sequences were produced and tested for their potency in the standard gp130 ELISA. The standard gp130 ELISA has a final assay concentration of 10 ng/mL IL-6R and 50 ng/mL IL-6. The results are shown in Table 8.1 below.

TABLE 8.1

Potency of mutant 5G9-based sequences in the gp130 ELISA

| Name | Mutations | Mutation(s) | Potency |
|---|---|---|---|
| 5G9 | 'Wild type' | — | 0.09 |
| ID-52V | R105H F109H | CDR3/CDR3 | 0.24 |
| ID-53V | F109H | CDR3 | 0.30 |
| ID-54V | R105H | CDR3 | 0.15 |
| ID-55V | K23H | FR1 | 0.11 |
| ID-56V | F29S | FR1 | 0.07 |

TABLE 8.1-continued

Potency of mutant 5G9-based sequences in the gp130 ELISA

| Name | Mutations | Mutation(s) | Potency |
|---|---|---|---|
| ID-57V | F29I | FR1 | 0.31 |
| ID-58V | F65V | CDR2 | 0.36 |
| ID-59V | Y62D | CDR2 | 0.11 |

IC50s were increased by approximately threefold in the F29I and F65V mutants, but all mutants nonetheless maintained high potency in this assay.

Some of these sequences were also tested for their potency in the TF-1 assay. The results are shown in Table 8.2 below.

TABLE 8.2

Potency of mutant 5G9-based sequences in the TF-1 assay

| Name | Mutations | Mutation(s) | Potency |
|---|---|---|---|
| tocilizumab | — | — | 0.69 |
| 5G9 | 'Wild type' | — | 0.23 |
| ID-52V | R105H F109H | CDR3/CDR3 | 14.20 |
| ID-53V | F109H | CDR3 | 17.52 |
| ID-54V | R105H | CDR3 | 0.31 |
| ID-56V | F29S | FR1 | 0.33 |

The mutations were well tolerated in this assay.

Mutant 7F6 Sequences

Mutant 7F6 sequences were produced and tested for their potency in the standard gp130 ELISA. The results are shown in Table 8.3 below.

TABLE 8.3

Potency of mutant 7F6-based sequences in the gp130 ELISA

| Name | Mutations | Mutation(s) | Potency |
|---|---|---|---|
| 7F6 | 'Wild type' | — | 0.15 |
| ID-3V | R102H | CDR3 | 0.16 |
| ID-6V | F106H | CDR3 | 0.22 |
| ID-40V | R102H F106H | CDR3/CDR3 | 0.21 |
| ID-47V | F106I | CDR3 | 0.27 |
| ID-49V | F106T | CDR3 | 0.31 |
| ID-50V | F106V | CDR3 | 0.24 |

It can be seen that these substitutions in the FRs or CDRs of the 5G9 and 7F6 sequences can be tolerated without seriously impacting potency.

Example 9: Modification of Cis/Trans-Binding Profile of 5G9

Selectivity for antagonism of IL-6 trans-signalling over cis-signalling can be defined by inhibitory potency in the IL-6-sIL-6R-gp130 ELISA (surrogate for trans-signalling) compared to inhibitory potency in the membrane IL-6R dependent TF-1 cell assay (surrogate for cis-signalling).

It was noted that the introduction of the F109H mutation led to a marked shift in activity towards selective antagonism of IL-6 trans-signalling (see potency of ID-53V, incorporating F109H, compared to 'Wild type' 5G9, in the gp130 ELISA and the TF-1 assays in Example 8 above).

Accordingly, trans-selective versions of 5G9 (ID-122V, ID-123V) underwent further optimisation in parallel with the cis-trans potent versions of 5G9 (ID-112, ID-114) as detailed below.

Example 10: Optimisation of 5G9-Derived ICVDs for Yeast Production

Constructs were designed initially for production of ICVDs in *E. coli*, necessitating C-terminal Flag- and His-tags to aid purification of the recombinant proteins. 5G9-derived ICVDs were tested for production in yeast without an epitope tag and with an E1D amino acid substitution to reduce the potential for formation of N-terminal pyroglutamate and resultant heterogeneity of final product.

ICVDs ID-74V (5G9 but for E1D and R105H mutations) and ID-75V (5G9 but for E1D, F29S and R105H mutations) were cloned into the yeast integration vector pUR9013 and transformed into *S. cerevisiae*. Experiments were performed to confirm that the yeast-expressed. ICVDs retained the characteristics of the earlier *E. coli*-produced ICVDs. Yeast-produced ICVDs maintained substantially the same potency as *E. coli*-produced ICVDs in the standard gp130 ELISA. Protease resistance was also very similar between the yeast- and *E. coli*-produced ICVDs.

Example 11: Further Optimisation of 5G9

A selection of further mutations were introduced into 5G9-derived ICVDs in combination with the mutations identified above and the resultant sequences produced in *E. coli*.

These are shown in Table 11.1.

TABLE 11.1

| Optimised variant 5G9-based ICVDs | | | | |
|---|---|---|---|---|
| Construct | Expression | Antagonism | Mutations relative to 5G9 | C-terminus |
| ID-112V | *E. coli* | Cis/Trans | F29S; Q47G; K89R; R105H | FLAG-6xHis |
| ID-114V | *E. coli* | Cis/Trans | F29S; V81L; N82Y; R105H | FLAG-6xHis |
| ID-122V | *E. coli* | Trans | F29S; Q47G; K89R; R105H; F109H | FLAG-6xHis |
| ID-123V | *E. coli* | Trans | F29S; Q47G; N82Y; K89R; R105H; F109H | FLAG-6xHis |
| ID-141V | Yeast | Trans | E1D; F29S; Q47G; V81L; N82Y; K89R; R105H; F109H | Wild type |
| ID-142V | Yeast | Trans | E1D; F29S; Q47G; N82Y; K89R; R105H; F109H | Wild type |
| ID-143V | Yeast | Cis/Trans | E1D; F29S; Q47G; V81L; N82Y; K89R; R105H | Wild type |
| ID-144V | Yeast | Cis/Trans | E1D; F29S; Q47G; N82Y; K89R; R105H | Wild type |

A 'Wild type' C-terminus denotes the natural ending of a llama ICVD domain sequence. 6xHis-FLAG denotes the functionally inert affinity tag used for purification of *E. coli*-derived constructs. Labile residues are present between the His tag and the C terminus of the ICVD. Western blot analysis demonstrates that the His tag is completely cleaved from the ICVD before potency or stability analysis takes place.

It can be seen that ID-123V is equivalent to ID-142V except for ID-123V being produced in *E. coli* and therefore lacking the E1D mutation. ID-112V is equivalent to ID-144V except for (a) ID-112V lacking the N82Y mutation and (b) ID-112V being produced in *E. coli* and therefore lacking the E1D mutation.

Example 12: Potency of Optimised ICVDs Against Soluble and Membrane Human IL-6R in Various Assays The inhibitory potency and efficacy (maximal inhibition) of the *E. coli*-produced 5G9 derivatives were confirmed in vitro in the gp130 ELISA, TF-1 cell and M1 cell functional assays measuring responses mediated via human IL-6R. The potency of the *E-coli*-produced 5G9 derivatives in these assays is shown in Tables 12.1-12.7. The gp130 assays follow the standard protocol with a final assay concentration of 10 ng/mL IL-6R and 50 ng/mL IL-6.

gp130 ELISA Assays

TABLE 12.1

| Potency of 5G9 derivatives - gp130 ELISA assay - Experiment 1 | |
|---|---|
| Construct | gp130 ELISA $EC_{50}$ nM |
| ID-112V | 0.1496 |
| ID-114V | 0.1375 |

TABLE 12.2

Potency of 5G9 derivatives - gp130 ELISA assay - Experiment 2

| Construct | gp130 ELISA $EC_{50}$ nM |
|---|---|
| ID-122V | 0.489 |
| ID-123V | 0.498 |
| Tocilizumab (prior art comparative example) | 1.831 |
| 20A11 (prior art comparative example) | 0.220 |

TF-1 Cell Assays

TABLE 12.4

Potency of 5G9 derivatives - TF-1 cell assay - Experiment 1

| Construct | TF-1 cell assay $EC_{50}$ nM (5 ng/ml IL-6) |
|---|---|
| ID-112V | 0.18 |
| Tocilizumab (prior art comparative example) | 0.69 |

TABLE 12.5

Potency of 5G9 derivatives - TF-1 cell assay - Experiment 2

| Construct | TF-1 cell assay $EC_{50}$ nM (5 ng/ml IL-6) |
|---|---|
| ID-123V | 4.50 |
| Tocilizumab (prior art comparative example) | 1.12 |
| 20A11 (prior art comparative example) | 0.56 |

TABLE 12.6

Potency of 5G9 derivatives - TF-1 cell assay - Experiment 3

| Construct | TF-1 cell assay $EC_{50}$ nM (5 ng/ml IL-6) |
|---|---|
| ID-114V | 0.29 |

M1 Cell Assay

The M1 cell assay was developed to investigate the IL-6 trans-signalling neutralising potency of ICVDs specific for IL-6R. M1 cells respond to exogenous IL-6+IL-6R by inhibition of proliferation, by differentiation and eventually cell death, but this response can be negated by IL-6R specific ICVDs that prevent IL-6R-IL-6 binding.

The M1 assay measures the effect, in terms of cell behaviour, of ICVD blockade of IL-6 trans-signalling over a period of days. In assessment of ICVD trans selectivity, the TF-1 cell assay is used to measure cis IL-6 signalling; it is therefore appropriate when determining the degree of trans vs cis selectivity, to use data from another cellular assay, dependent on IL-6 trans signalling, such as the M1 cell assay, for comparison.

M1 cells from a rapidly growing stock culture were inoculated into 96-well assay plates in RPMI medium+3% FCS at $5\times10^4$ cells/50 µl/well. IL-6, IL-6R and concentration ranges of ICVDs were all prepared in the same medium at 6× the final assay concentration (20 ng/ml IL-6R, 100 ng/ml IL-6). 75 µl of each ICVD dilution was mixed with the same volume of 120 ng/ml IL-6R and incubated for 1 hour at room temperature, before addition of 75 µl of 600 ng/ml IL=6 to each of these mixtures. Finally, 50 µl of each ICVD/IL-6R/IL-6 mixture was added to four replicate wells of M1 cells, and the plates incubated undisturbed for 5 days. Viable cell mass was then measured by Alamar blue addition (10 µl/well), further incubated for 5 hours, and finally 50 µl 3% SDS solution was added, and fluorescence measured at 620 nm. IL-6 only and IL-6+IL-6R only controls represent 0% and 100% of the IL-6+IL-6R stimulated response. The results of the M1 cell assay are shown in Table 12.7 below.

TABLE 12.7

Potency of 5G9 derivatives - M1 cell assay

| Construct | M1 cellular assay $EC_{50}$ nM |
|---|---|
| ID-112V | 0.55 |
| ID-114V | 0.52 |
| ID-122V | 3.96 |
| ID-123V | 4.20 |
| Tocilizumab (prior art comparative example) | 5.36 |

Cynomolgous Monkey IL-6R Competition Assay

It was found that ID-123V was active in the cynomolgus monkey IL-6R competition assay.

Summary of Potency Assays Performed on 5G9 Derivatives

In summary, it can be seen that these 5G9-derived ICVDs maintained high potency in the various assays performed.

Example 13: Evaluation of the Intestinal Stability of Optimised ICVDs

Assessment in Mouse Small Intestinal Supernatant and Human Faecal Extract Assays Various 5G9 variants and 20A11, a comparative anti-IL-6R polypeptide of the prior art, were tested for their survival in the standard mouse small intestinal supernatant and human faecal extract assays. Survival was measured by the gp130 plate ELISA as laid out above under 'Stability'; 'the standard Anti-IL-6R gp130 ELISA performed on samples previously exposed to proteolytic material'.

The standard mouse small intestinal supernatant assay was performed on these polypeptides with 4 hours' and 7 hours' digestion and the standard human faecal extract assay was performed on these polypeptides with 16 hours' digestion (using 250 ug/mL in 0.1% BSA assay stocks diluted to 20 ug/mL in protease testing solution). % survival was established for these polypeptides as follows in Table 13.1.

TABLE 13.1

Mouse small intestinal supernatant and human faecal extract stability of 5G9 variants

| ICVD | Modifications | Mouse small intestinal supernatant 4 h % survival | Mouse small intestinal supernatant 7 h % survival | Human faecal extract 16 h % survival |
|---|---|---|---|---|
| 112V | F29S Q47G K89R R105H | 44 | NT | 74 |
| 114V | F29S V81L N82Y R105H | 82 | NT | 99 |
| 122V | F29S, Q47G; K89R; R105H, F109H | NT | 73 | 49 |
| 123V | F29S Q47G; N82Y K89R; R105H, F109H | NT | 85 | 95 |
| 142V | E1D; F29S; Q47G; N82Y; K89R; R105H; F109H | NT | 47 | 92 |
| 20A11 (prior art comparative example) | — | NT | 0 | 0 |

NT = not tested

It is recalled that in the earlier assays detailed above, 'wild type' 5G9 demonstrated 23% survival after 1 hour's exposure to mouse small intestinal supernatant and 75% survival after 6 hours' exposure to human faecal supernatant.

It can be seen that these mutations generated highly protease resistant ICVDs. This was particularly evident in the trans-selective ICVD ID-123V, which showed extremely high survival in the presence of intestinal proteases (85% after 7 h in mouse small intestinal extract and 95% after 16 h in human faecal supernatant). In contrast, it can be seen that 20A11 is highly unstable in the presence of intestinal proteases.

In addition, a less stringent 7 hour mouse small intestinal supernatant assay and a less stringent 16 hour human faecal extract assay were performed on ID-123V, ID-122V and 20A11. In these less stringent assays, the assay stocks were made up to 118 ug/mL in 0.1% BSA instead of 250 ug/mL in 0.1% BSA in the standard assay. % survival was established for these variant ICVDs as follows in Table 13.2.

TABLE 13.2

Mouse small intestinal supernatant and human faecal extract stability of 5G9 variants ID-123V, ID-122V and prior art anti-IL6R polypeptide 20A11

| ICVD | Modifications | After 7 h in Mouse SI extract % survival | After 16 h in Human Faecal Extract % survival |
|---|---|---|---|
| ID-123V | F29S Q47G; N82Y K89R; R105H, F109H | 99 | 80 |
| ID-122V | F29S, Q47G; K89R; R105H, F109H | 73 | 49 |
| 20A11 (prior art comparative example) | — | 0 | 0 |

As noted in the previous standard stability assays, these less stringent assays further confirm that ID-123V and ID-122V are highly protease resistant ICVDs. Furthermore, it can be seen that 20A11 is highly unstable in the presence of intestinal proteases.

Resistance to a Gastrointestinal Matrix Metalloproteases

Levels of activated matrix metalloproteases (MMPs) are increased in the inflamed mucosa of patients with intestinal bowel disease. These MMPs are able to digest native human IgG and therapeutic agents that contain a human IgG scaffold (Biancheri et al, 2015). In the case of the anti-TNFα therapy etanercept, this digestion causes a significant reduction in TNFα neutralising potency. To confirm that the optimised ICVDs described here are resistant to MMPs, ID-112V and ID-123V were incubated for 18 hours in the presence of activated recombinant human MMP3 and MMP12.

Following incubation, both ID-112V and ID-123V were fully potent at neutralising IL-6R, as measured using the IL-6-sIL-6R-gp130 functional ELISA. However, after the same incubation time, MMP3 and MMP12 digested full-length etanercept and tocilizumab (anti-IL-6R) to smaller fragments, as measured by Western blotting.

Mouse Digestive Transit and Survival

Results of the in vitro studies described above showed that optimised 5G9-derivatives were highly resistant to inactivation by proteases present in a supernatant extract prepared from mouse small intestinal contents. A subsequent study was performed to investigate the stability of trans-selective ID-123V during passage through the gastrointestinal system of the mouse. ID-123V was formulated with a further, unrelated ICVD in a milk and bicarbonate mixture to protect against denaturation at low pH and digestion by pepsin in the stomach. Following administration of the ICVDs to mice by oral gavage, concentrations of the ICVDs in stomach, small intestine, caecum and colon were determined at 3 hours post-dosing. In addition, the ICVD concentration in faecal pellets collected at hourly intervals was measured.

Four mice were tested. The transit and excretion of the ICVDs in faeces varied between the mice tested. In three of the mice, ID-123V was detected in faeces between 2 and 4 hours after dosing, suggesting that ID-123V can survive transit through the mouse GI tract.

Examining the concentrations of ID-123V in each compartment at 3 hours post-dose revealed ID-123V in the stomach and small intestine. It is expected therefore that the 5G9 derived ICVDs will have good stability in the human intestinal tract.

Example 14: Binding Affinity and Specificity for Human IL-6R

Biacore Estimation of Optimised ICVD—IL-6R Binding Affinity

The binding kinetics of the trans-selective ID-123V (*E. coli* produced version of ID-142V) and the cis/trans potent ID-112V (*E. coli* produced version of ID-144V, but for ID-112V lacking N82Y relative to ID-144V) were compared against tocilizumab in a Biacore study. The ICVDs were fixed to the Biacore sensor plate and soluble human IL-6R was flowed over the plate to detect binding. Tocilizumab and the trans-selective ID-123V had similar Kds of 0.39 and 1.1 nM, respectively, while ID-112V had a lower Kd of 40 pM. The results indicate that both the trans-selective and cis/trans potent ICVDs demonstrate strong binding to the antigen.

Specificity of Optimised ICVDs

The trans-selective 5G9 derivative ID-123V was tested for selectivity against proteins related to human IL-6R. Human IL-11R and CNTFR (ciliary neurotrophic factor receptor) were found to be the most closely related human proteins to IL-6R identified using the NCBI BLASTp tool, both with a sequence identity with IL-6R of 29%. In ELISA assays, none of human IL-11R, CNTFR, or IL-6 interfered with IL-6R binding to ID-123V, while addition of human IL-6R shifted the curve dramatically. This indicated that binding of 5G9-derived ICVDs such as ID-123V to off-target molecules would be very unlikely in humans.

Example 15A: Efficacy in Ex Vivo IBD Models (ID-123V)

The possibility of testing the efficacy of anti-IL-6R ICVDs in an in vivo preclinical animal model of inflammatory bowel disease was precluded by the lack of cross-species reactivity towards murine IL-6R and the absence of a suitable non-human primate model of IBD. Although humanised (human immune cell engrafted) NOG mice are available commercially, it is as yet unclear whether established methods (e.g. DSS-administration) would be effective for the induction of inflammatory colitis in these animals. Since murine non-haematopoietic cells may be expected to produce and/or respond to IL-6, the potential effectiveness of human-specific IL-6R antibodies in a NOG mouse colitis model is uncertain.

Phosphorylation of Signalling Proteins

Infliximab is effective for the treatment of IBD. Infliximab is thought to act primarily by neutralising the biological activity of TNF leading to inhibition of the downstream pro-inflammatory effects of the cytokine. Activation of the many different cell types present in diseased tissue by TNF and secondary inflammatory mediators involves multiple receptor signalling pathways resulting in the phosphorylation of receptors, protein kinases and transcription factors. Experiments have shown that (i) patterns of protein phosphorylation are altered in IBD vs normal intestinal tissue and that (ii) patterns of phosphorylation are sensitive to inhibitors of specific pro-inflammatory mechanisms.

Due to the lack of a suitable preclinical in vivo animal model of IBD, an alternative human ex vivo IBD tissue model that reproduces the inflammatory bowel disease tissue environment was used (see Vossenkamper et al, 2014). A study was conducted to investigate the activity of the 5G9-derived ICVD ID-123V (containing the same mutations as the yeast-produced trans-selective ICVD ID-142V, but for E1D) on protein phosphorylation patterns in this human ex vivo model.

ID-123V and controls (ID-2A (an anti *C. difficile* toxin ICVD) and tocilizumab) were tested in ex vivo cultures for their effects, after 4 hours and 24 hours incubation, on levels of phosphoproteins present in inflamed biopsy tissue obtained from five patients with active IBD (4 hour incubation results in FIGS. 7-11, 24 hour incubation results in FIGS. 12-16).

Based on a visual assessment of the phosphoprotein signal patterns (summarised in Table 15.1), responses to the IL-6R antagonist ICVD ID123V and tocilizumab were noted in tissues from 3/5 IBD patients. In tissues from two of the IBD patients (UC2045 and CD2059, FIGS. 7, 9, 12 and 14), the patterns of inhibition obtained with ID-123V and tocilizumab were very similar with marked suppression of a majority of the phosphoprotein levels. The lack of (or more restricted) responses to both ID-123V and tocilizumab in tissues from two other IBD cases (CD2052 and CD2061, FIGS. 8, 10, 13 and 15) may have reflected differences in IL-6 dependent disease activity or differences in the cellularity of the biopsies taken from these patients.

TABLE 15.1

Responses to anti-IL-6R agents

| Patient # | Anti-IL-6R | Effect of anti-IL-6R agent compared with negative Control: Effects on phospho-protein signals at 4 h | Effect of anti-IL-6R agent compared with negative Control: Effects on phospho-protein signals at 24 h |
|---|---|---|---|
| UC2045 | ID-123V | Substantial inhibition - most markers | Substantial inhibition - most markers |
| | Tocilizumab | Substantial inhibition - most markers | Substantial inhibition - most markers |
| CD2052 | ID-123V | No inhibition - stimulation most markers | Low level stimulation most markers |
| | Tocilizumab | Partial inhibition - few markers | Partial inhibition - most markers |
| CD2059 | ID-123V | Substantial/complete inhibition - most markers | Substantial/complete inhibition - most markers |
| | Tocilizumab | Substantial/complete inhibition - most markers | Substantial inhibition - most markers |
| CD2061 | ID-123V | Partial inhibition of a few markers | Partial inhibition of a few markers |
| | Tocilizumab | Partial inhibition of most markers | Partial inhibition of a few markers |
| UC2075 | ID-123V | Substantial inhibition - some markers | Substantial inhibition - >50% markers |
| | Tocilizumab | Some inhibition - a few markers | Some inhibition - a few markers |

Overall, it can be seen that ID-123V produced a response that was highly similar to the clinical anti-IL-6R monoclonal antibody tocilizumab in this complex disease model system.

Production of Proinflammatory and Anti-Inflammatory Cytokines

A further study was conducted to investigate the activity of ID-123V in a human ex vivo model, reproducing the inflammatory bowel disease tissue environment.

IL-6 is important for the activation of inflammatory processes that contribute to the pathology and chronicity of IBD. Many of these effects rely on the regulation of complex cytokine networks that in turn control the different cellular processes involved in inflammation and immune-regulation.

ID-123V, negative control (ID-2A, anti *C. difficile* toxin ICVD) and the monoclonal anti-IL-6R antibody tocilizumab were tested for their effects on spontaneous production of proinflammatory and anti-inflammatory cytokines over a period of 24 h.

Aims of the study were to (i) determine whether the IL-6R-antagonist activity of ID-123V can be demonstrated in ex vivo cultures of IBD tissue based on changes in the levels of tissue cytokine production (ii) to compare effects of ID-123V with the clinically effective anti-IL-6R mAb tocilizumab.

Figure 17:
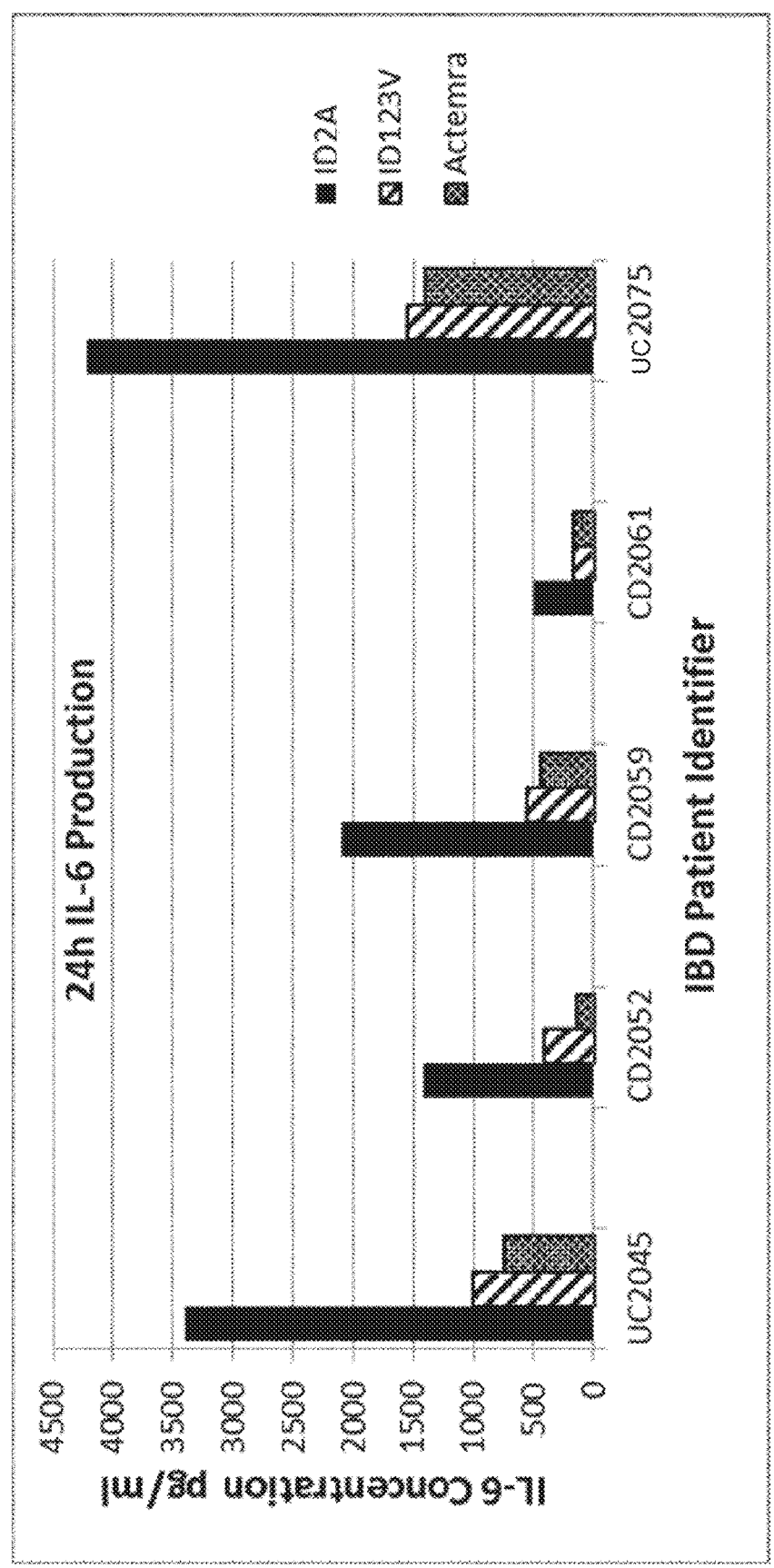
FIG. 17—IL-6 production for IBD patient tissue samples (ID-123V)
Figure 18:
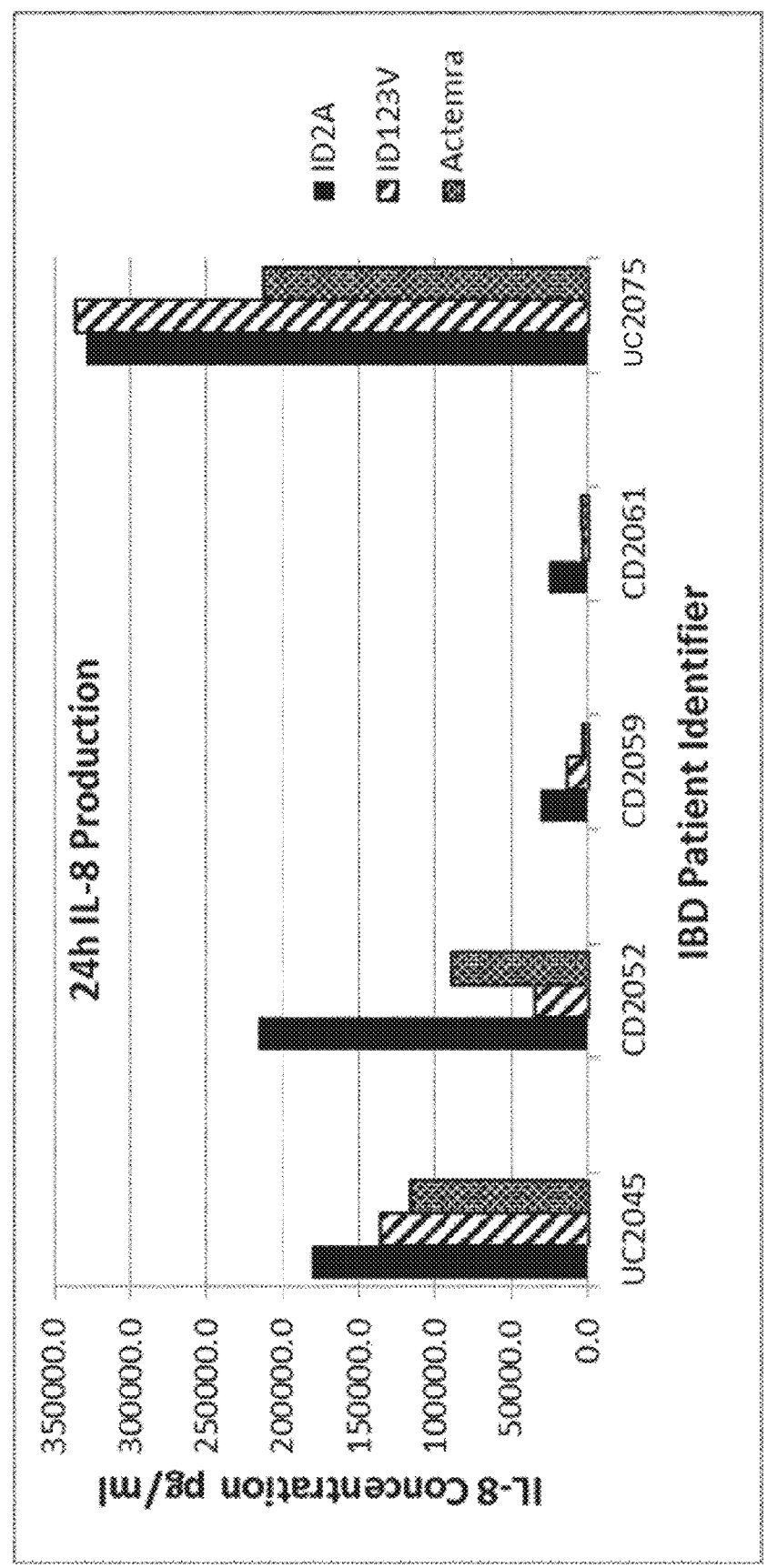
FIG. 18—IL-8 production for IBD patient tissue samples (ID-123V)
Figure 19:
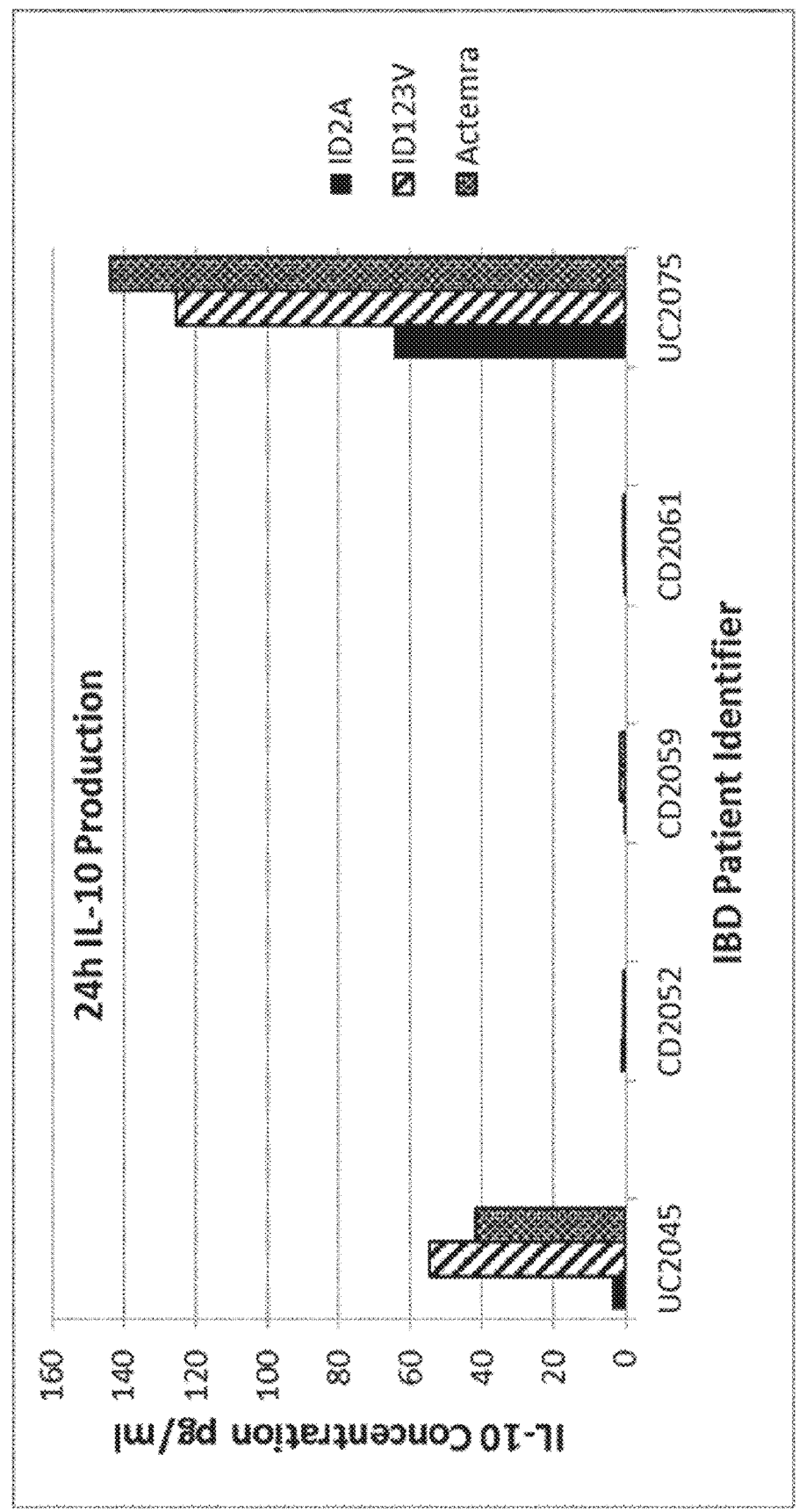
FIG. 19—IL-10 production for IBD patient tissue samples (ID-123V)

Mucosal biopsies taken from active IBD cases with inflamed mucosa were cultured (one biopsy per well) in 24-well plates (VWR International) in 300 µl serum-free HL-1 medium (Cambrex BioScience) supplemented with glutamine, 100 U/ml penicillin, 100 µg/ml streptomycin, 50 mg/mL gentamicin and cultured at 37° C., 5% $CO_2$. Biopsies were cultured for 24 h with the addition of the following agents; tocilizumab, ID-123V or ID-2A each at a final concentration of 70 nM. Supernatants collected at the end of the experiment (24 h) were snap-frozen and stored at −70° C. Samples of the culture supernatants were analysed for levels of IL-6, IL-8 and IL-10. The results are shown in FIGS. 17-19.

It can be seen that ID-123V inhibited spontaneous production of IL-6 and IL-8 from inflamed IBD tissues and stimulated production of IL-10 by biopsies from two UC patients. Overall, ID-123V demonstrated effects which were similar to those of tocilizumab.

Example 15B: Efficacy in Ex Vivo IBD Models (ID-142V)

Similar studies to those carried out in Example 15A were performed in respect of ID-142V.

Investigation of the Inhibitory Effects of ID-142V on the Phosphorylation of Signalling Proteins in Ex Vivo Cultured IBD Tissue IBD Tissue Endoscopic colonic mucosal biopsies were obtained from patients with active Inflammatory Bowel Disease (IBD). Patient characteristics are listed in Table 15.2.

TABLE 15.2

Details of IBD Patients, Disease Presentation and Medication

| Patient # | Presentation/ Biopsy | Medication | Sex; birth year |
|---|---|---|---|
| CD2241 | /colon | Azathioprine | M; 1976 |
| CD2244 | /colon | Azathioprine, Budesonide | M; 1982 |
| CD2250 | /colon | No meds; (on Humira 1 year ago) | M; 1992 |
| CD2256 | /terminal ileum | No meds | M; 1985 |
| UC2245 | mild pancolitis | Mesalazine oral and topical | M; 1955 |
| UC2249 | mayo 1-2 colitis left-sided | No meds | F; 1985 |

Organ Culture

Mucosal biopsies taken from active IBD cases (CD & UC) with inflamed mucosa were cultured (one biopsy per well) in 24-well plates (VWR International, Lutterworth, UK) in 300 µl serum-free HL-1 medium (Cambrex BioScience, Wokingham, UK) supplemented with glutamine, 100 µg/ml penicillin, 100 µg/ml streptomycin, 50 ug/mL gentamicin and cultured at 37° C., 5% $CO_2$. Biopsies were cultured for 24 h with the addition of ID-142V at a final concentration of 250 nM or ID-2A 500 nM (ID-2A is a negative control anti *C. difficile* toxin ICVD). Supernatants and tissue samples collected at the end of the experiment were snap-frozen and stored at −70° C.

Signalling Arrays and Data Analysis

For the analysis of phospho-protein content the IBD tissue samples were thawed, lysed in RIPA buffer (Sigma-Aldrich, St. Louis, Mo.) supplemented with phosphatase inhibitor cocktail 2 (Sigma-Aldrich) and protease inhibitor cocktail (Sigma-Aldrich), both at 1%. Protein concentrations of the lysates were determined by the Bio-Rad protein assay (Bio-Rad Laboratories, Hemel Hempstead, UK) and samples diluted to 1.0 mg/ml in Array Diluent Buffer.

Figure 20:
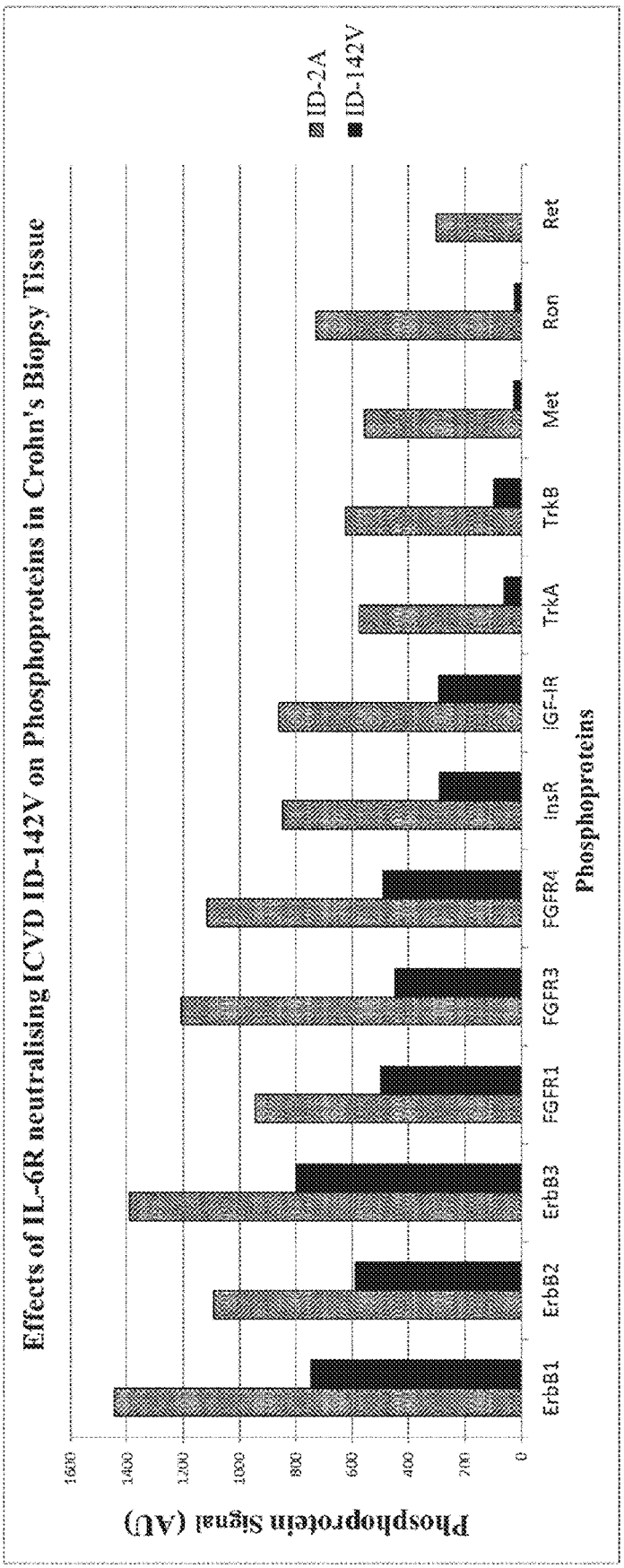
FIG. 20—Phosphoprotein signals in Crohn's disease biopsy tissue (ID-142V, phosphoproteins ErbB1 to Ret)
Figure 21:
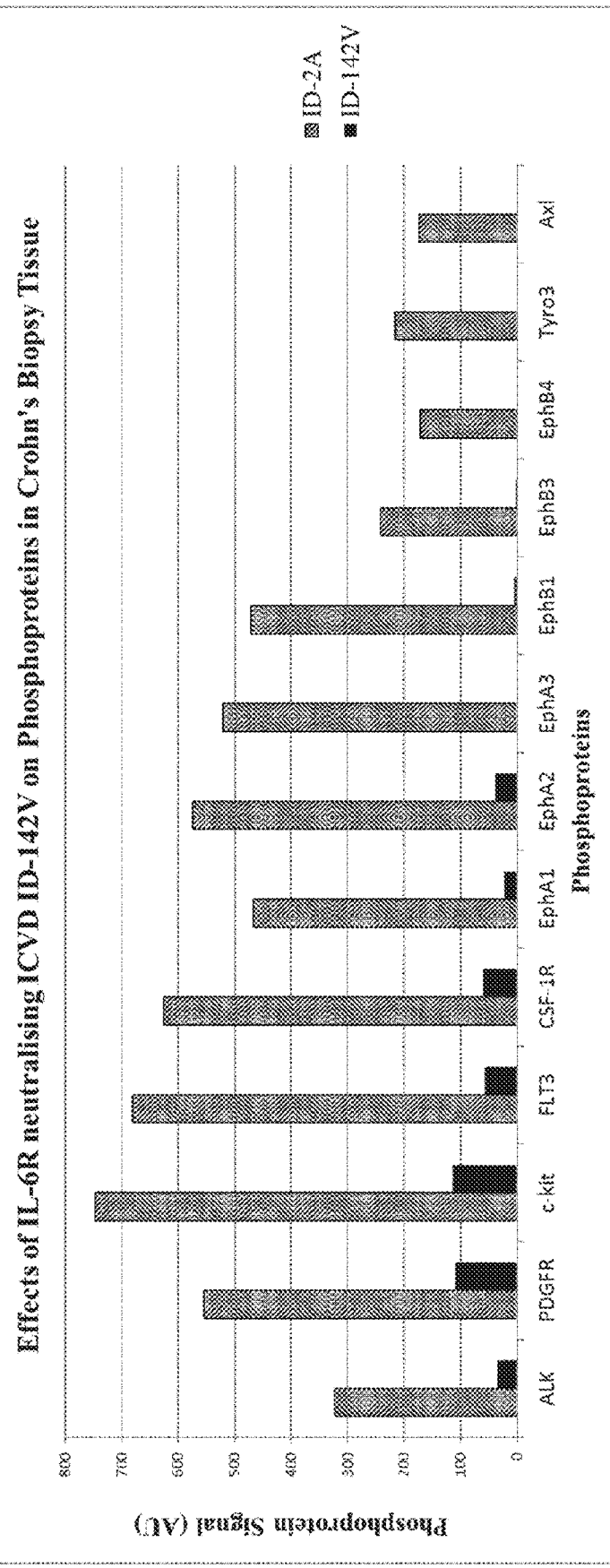
FIG. 21—Phosphoprotein signals in Crohn's disease biopsy tissue (ID-142V, phosphoproteins ALK to Axl)
Figure 22:
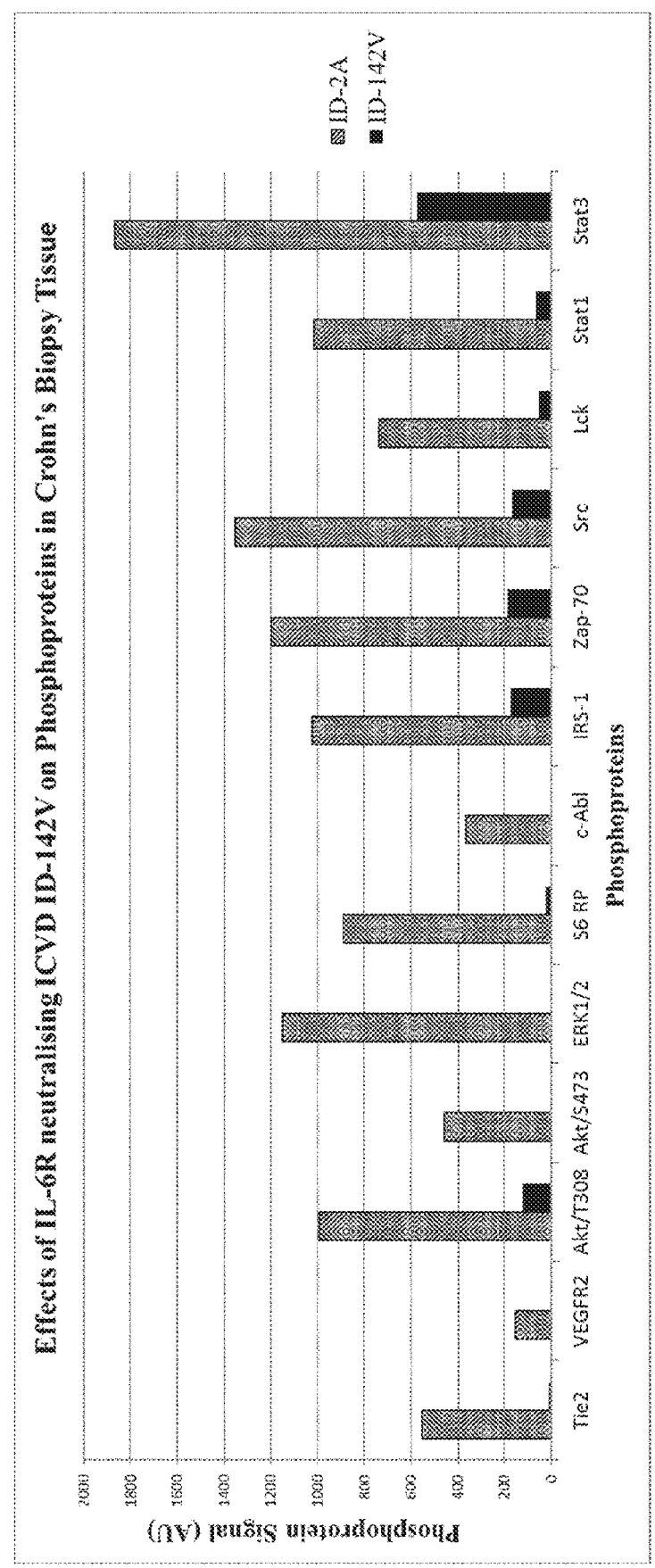
FIG. 22—Phosphoprotein signals in Crohn's disease biopsy tissue (ID-142V, phosphoproteins Tie2 to Stat3)
Figure 23:
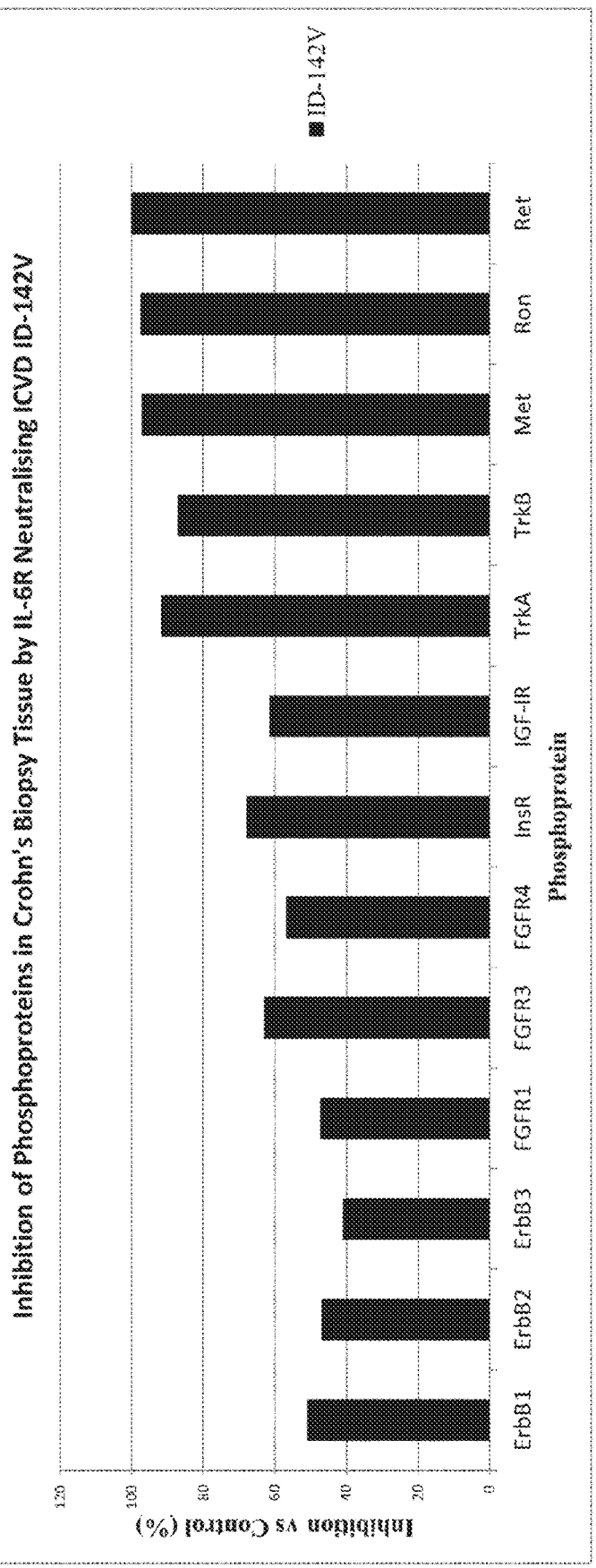
FIG. 23—Phosphoprotein signals (% inhibition vs control) in Crohn's disease biopsy tissue (ID-142V, phosphoproteins ErbB1 to Ret)
Figure 25:
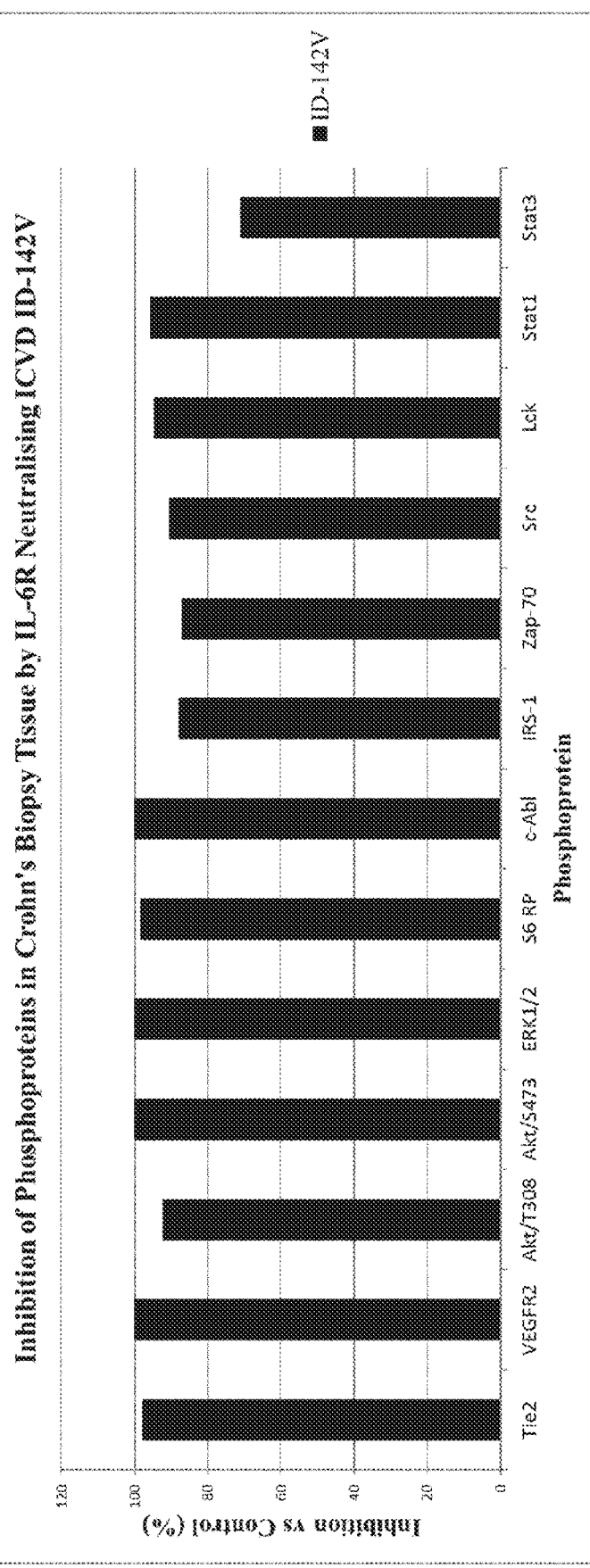
FIG. 25—Phosphoprotein signals (% inhibition vs control) in Crohn's disease biopsy tissue (ID-142V, phosphoproteins Tie2 to Stat3)

1. The phosphorylation status of receptor tyrosine kinases and signalling molecules was determined by using PathScan RTK signalling arrays (Cell Signalling Technology, Danvers, Mass.). The array kit allows for the simultaneous detection of 28 receptor tyrosine kinases and 11 important signalling nodes, when phosphorylated at tyrosine or other residues.
2. A total of 150 ug of protein from each biopsy tissue lysate was probed onto each array. For each CD and UC patient, the lysates prepared from the set of antibody-treated biopsies (ID-2A and ID-142V) were analysed on the same slide.
3. The chemiluminescent signals of all arrays were detected on X-ray films, and the pixel intensities were measured using ImageJ software.
4. For each antibody treatment (ID-2A or ID-142V), the phosphoprotein signals obtained from the four different patient biopsies (n=4 CD lysates) were used to calculate mean+/−SD pixel intensity values that are shown in FIGS. 20-22 (shown in 'AU'—arbitrary units). The intensity values for different phosphoproteins are displayed in each figure.
5. To account for differences between patients the pixel array data obtained for the experimental treatment were normalised against the pixel values obtained for the corresponding patient and ID-2A treatment control. Percentage inhibition of control values were calculated and presented in FIGS. 23-25. Values for the ID-142V treatment were derived from the analysis of lysates from four different CD patients.
6. For comparison, the treatment was repeated using inflamed biopsy tissue from two patients with ulcerative colitis. For each antibody treatment (ID-2A or ID-142V) the phosphoprotein pixel intensity values obtained from the two different patient biopsies (n=2 UC lysates) were used to calculate mean+/−SD pixel intensity values that are shown in FIGS. 26-28.

Results

When compared with the ID-2A controls, the pixel intensities measured for the Crohn's biopsies treated with ID-142V showed that ID-142V inhibited the phosphorylation levels of all the signalling proteins on the array (see FIGS. 20-22). When values for the experimental treated samples were normalised to the respective ID-2A Crohn's tissue control (FIGS. 23-25), the average percentage inhibition (n=4 CD patients) measured for all phosphoproteins on the array following ID-142V treatment was 59% (range 43% to 100%). Many of these proteins including CSF-1R, Tyro-3, Axl, Akt, ZAP-70, Lck, Stat1 and Stat3 are known to have functions involved in the regulation of inflammatory cells including macrophages and T cells that contribute to the immunopathology of Crohn's disease. The changes in phosphorylation are therefore consistent with the established anti-inflammatory effects of known IL-6R-neutralising antibodies.

Figure 26:
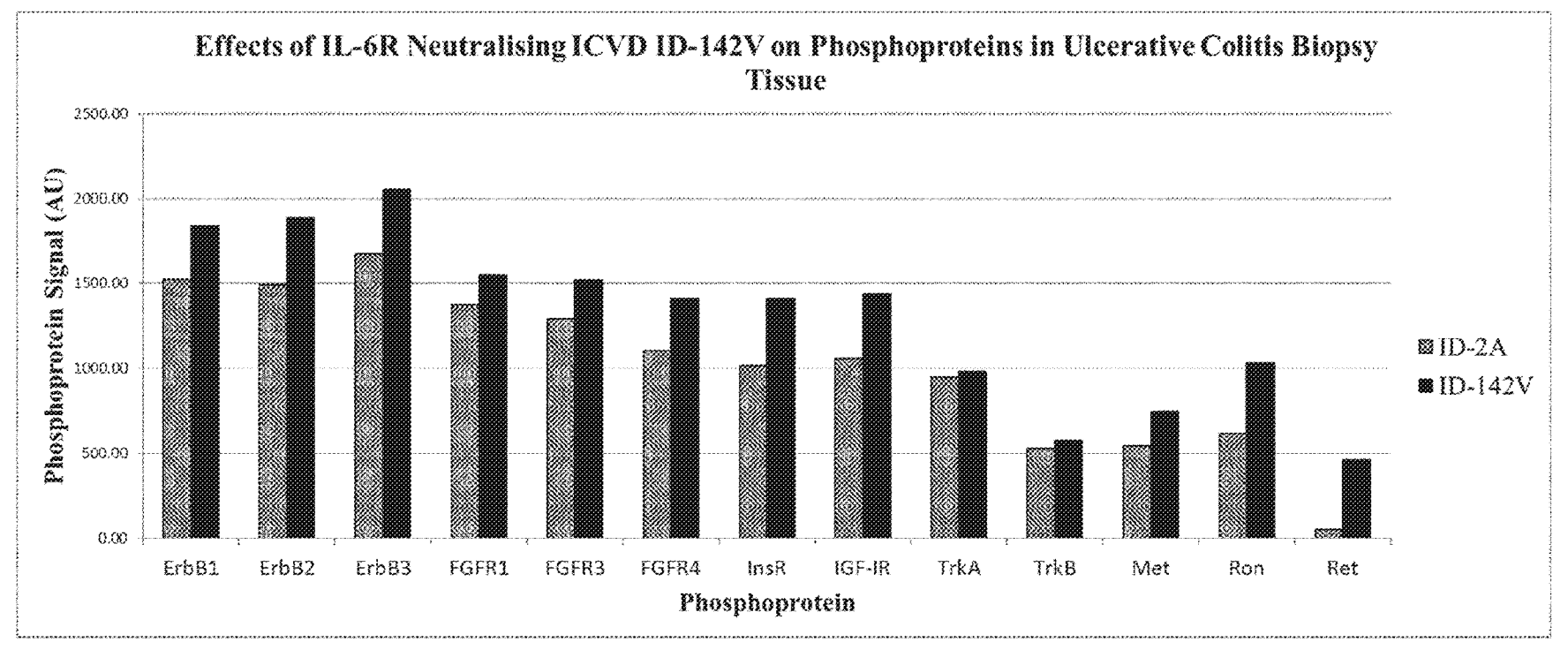
Figure 27:
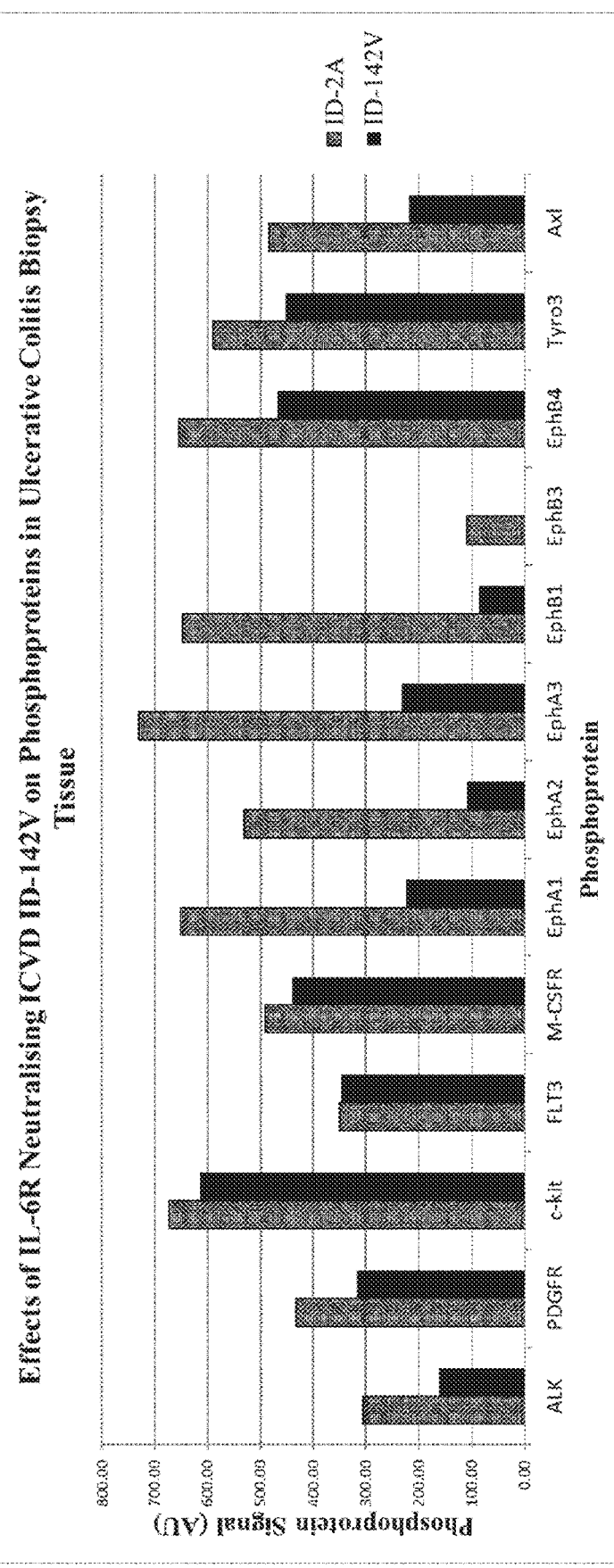
FIG. 27—Phosphoprotein signals in ulcerative colitis biopsy tissue (ID-142V, phosphoproteins ALK to Axl)
Figure 28:
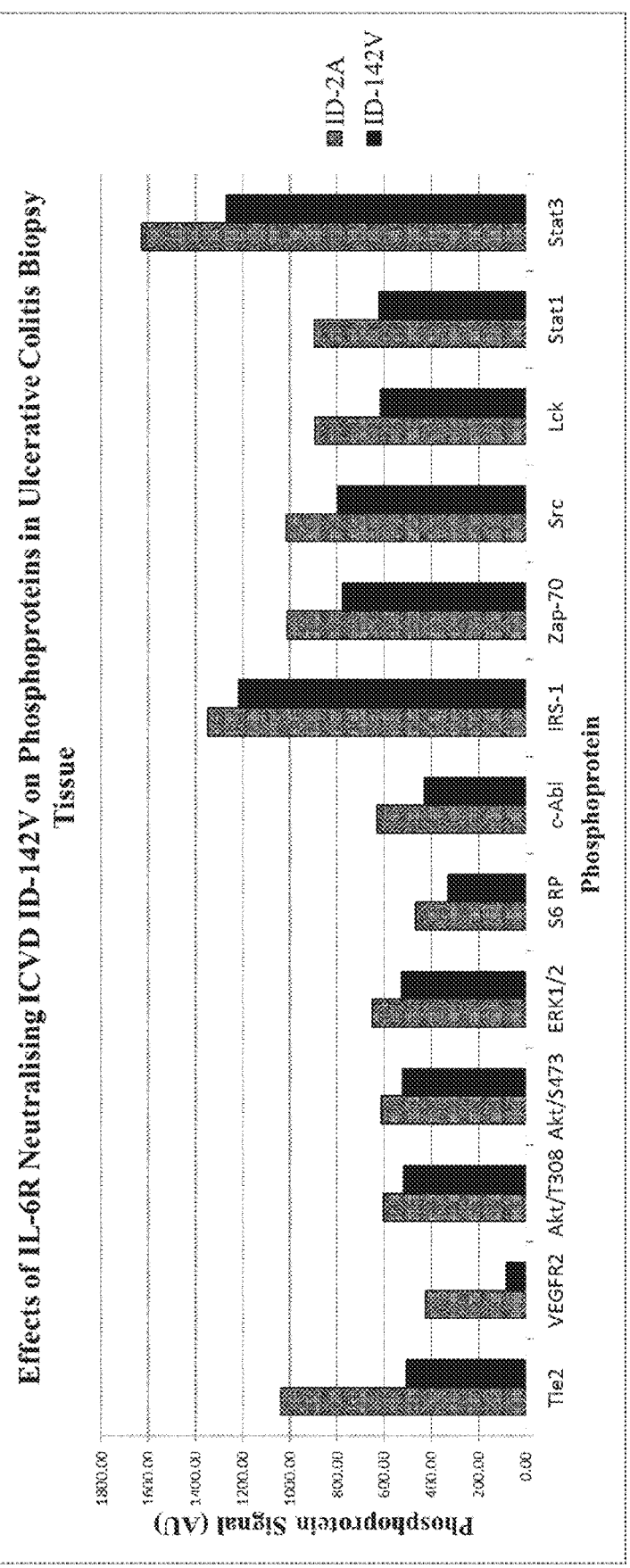
FIG. 28—Phosphoprotein signals in ulcerative colitis biopsy tissue (ID-142V, phosphoproteins Tie2 to Stat3)

The pixel intensity values for individual phosphoproteins and the pattern of intensities on the arrays found in the control ID-2A-treated UC biopsy tissue samples (average values for n=2 UC patients) were generally quite similar to those detected in the Crohn's tissue (FIGS. 26-28). However, the levels of phosphorylation of EphB4, Tyro3, Axl and VEGFR2 appeared to be higher while phosphorylation of Ret was lower in UC compared with CD tissue.

Investigation of the inhibitory effects of ID-142V on the production of cytokines in ex vivo cultures of IBD tissue IBD Tissue Endoscopic colonic mucosal biopsies were obtained from patients with active Inflammatory Bowel Disease (IBD). Patient characteristics are listed in Table 15.3.

TABLE 15.3

Details of IBD Patients. Disease Presentation and Medication

| Patient # | Presentation/ Biopsy | Medication | M/F |
|---|---|---|---|
| CD2241 | /colon | Azathioprine | M; 1976 |
| CD2244 | /colon | Azathioprine, Budesonide | M; 1982 |
| CD2250 | /colon | No meds; (on Humira 1 year ago) | M; 1992 |
| CD2254 | /ileum | Azathioprine, prednisolone | F; 1958 |
| CD2256 | /terminal ileum | No meds | M; 1985 |
| CD2259 | /colon | Azathioprine | M; 1975 |

Organ Culture

Mucosal biopsies (two biopsies per patient) were taken from six patients with active Crohn's disease. The inflamed mucosa biopsies were cultured (one biopsy per well) in 24-well plates (VWR International, Lutterworth, UK) in 300 µl serum-free HL-1 medium (Cambrex BioScience, Wokingham, UK) supplemented with glutamine, 100 µg/ml penicillin, 101 µg/ml streptomycin, 50 ug/mL gentamicin and cultured at 37° C., 5% $CO_2$. The biopsies (×2) from each patient were cultured for 24 h with the addition of ID-142V at a final concentration of 250 nM or ID-2A (ID-2A is a negative control anti C. difficile toxin ICVD) at a concentration of 500 nM. Supernatants and tissue samples collected at the end of the experiment were snap-frozen and stored at −70° C.

Multiplexed Cytokine Assays

The 24 h culture supernatants recovered from each of the two ICVD-treated biopsies (ID-2A and ID-142V) were analysed for each of the six CD patients. The frozen culture supernatants were thawed and analysed for levels of IFN-gamma, TNF-alpha, IL-10, IL-17A, IL-1-beta, IL-6 and IL-8 using multiplexed cytokine assay kits and R&D Systems MagPix technology.

1. Samples were diluted 1:2 in reagent diluent.
2. Standards (custom mix by R&D Systems) were re-suspended and 1:3 serial dilutions were prepared.
3. The pre-mixed micro-particle cocktail (custom mix by R&D) was prepared with reagent diluent.
4. Additions were made of 50 ul/well of standards and samples; both in duplicates, plus 50 ul of micro-particle cocktail/well.
5. The plate was sealed and incubated for 2 h at RT on a shaker
6. The plate was then attached to a magnet and washed using a multichannel pipette 3× with wash buffer.
7. 50 ul of biotin Ab cocktail (custom mix by R&D) was added per well. The plate was resealed and incubated on a shaker for 1 h at RT.
8. The wash step was repeated wash 3× using the magnet.
9. 50 ul of Streptavidin-PE mix was added/well and the plate incubated for a further 30 min at RT on a shaker.
10. After washing 3×, the microparticles were resuspended by adding 100 ul wash buffer/well, followed by incubation on a shaker for 2 minutes.
11. The plate was read using a Luminex analyser. The MagPix machine used was calibrated with R&D's calibration kit before each run.

Assay data obtained for cytokine standards were used to generate standard curves; cytokine concentrations present in the culture supernatants were then calculated from the respective standard curves.

Data Analysis

The 24 h culture supernatants recovered from the ICVD-treated biopsies (ID-2A and ID-142V) were analysed for each of the six CD patients. The cytokine concentrations were determined and the mean values (Mean+/−Standard Deviation) were calculated using the results obtained from the set of six donors. Results are summarised in FIGS. 29-31.

Differences in the levels of inflammation and/or cellular involvement in biopsies taken from different patients could potentially result in different levels of spontaneous cytokine production between patients. To allow treatment effects to be more clearly identified the cytokine concentration value obtained for the experimental treatment was normalised to the value obtained for the corresponding patient ID-2A treatment control. The normalised % control values obtained for each cytokine (IFN-gamma, TNF-alpha, IL-10, IL-17A, IL-1-beta, IL-6 and IL-8) measured for each patient were then combined and the mean values (Mean+/−SD; n=6 CD patients) calculated. Normalised (% control) cytokine values obtained for the treatment (ID-142V/ID-2A) are presented in FIG. 32.

Results

Figure 29:
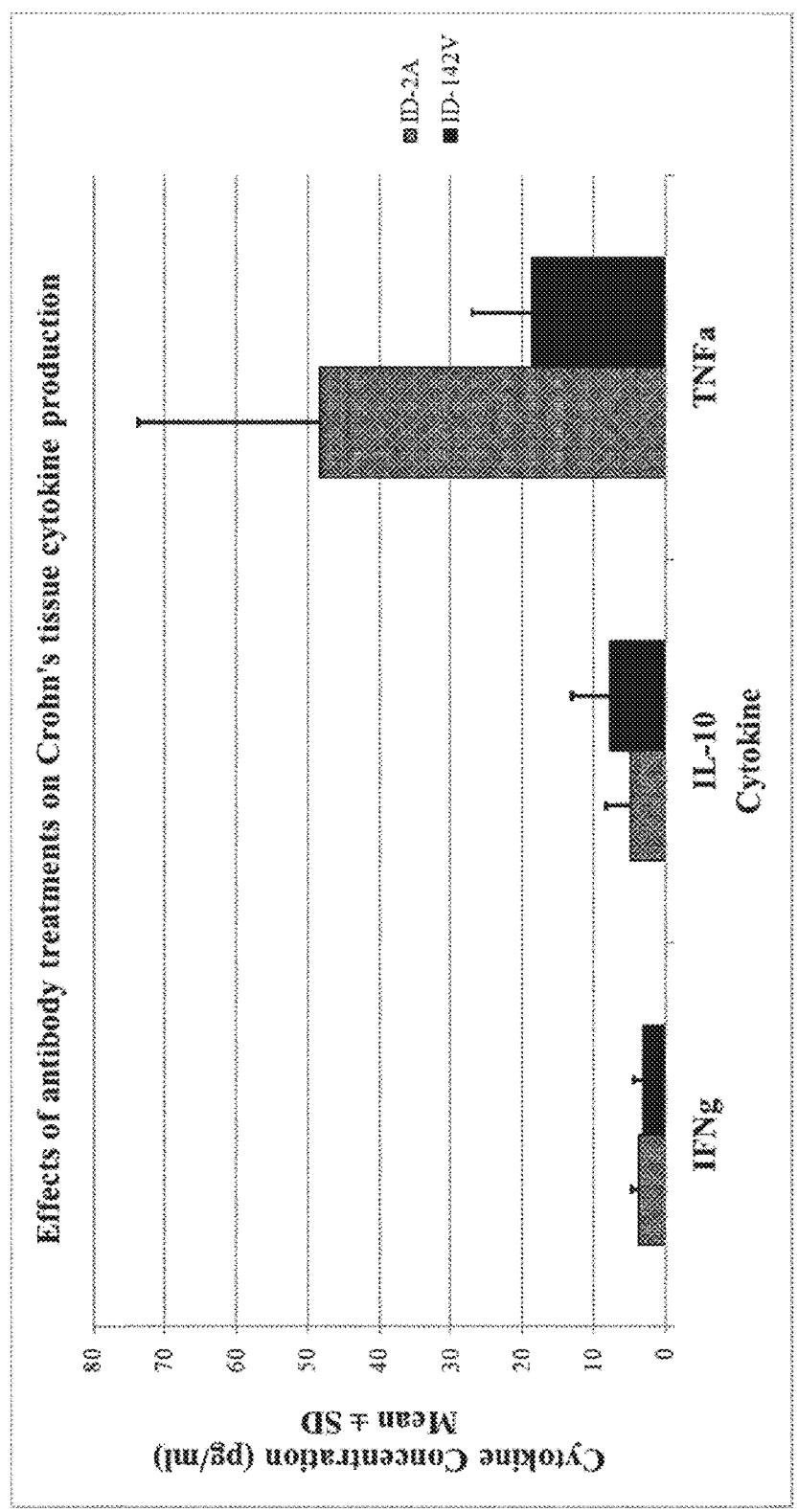
FIG. 29—Cytokine production in Crohn's disease biopsy tissue (ID-142V, cytokines IFNg, IL-10 and TNF-alpha)
Figure 30:
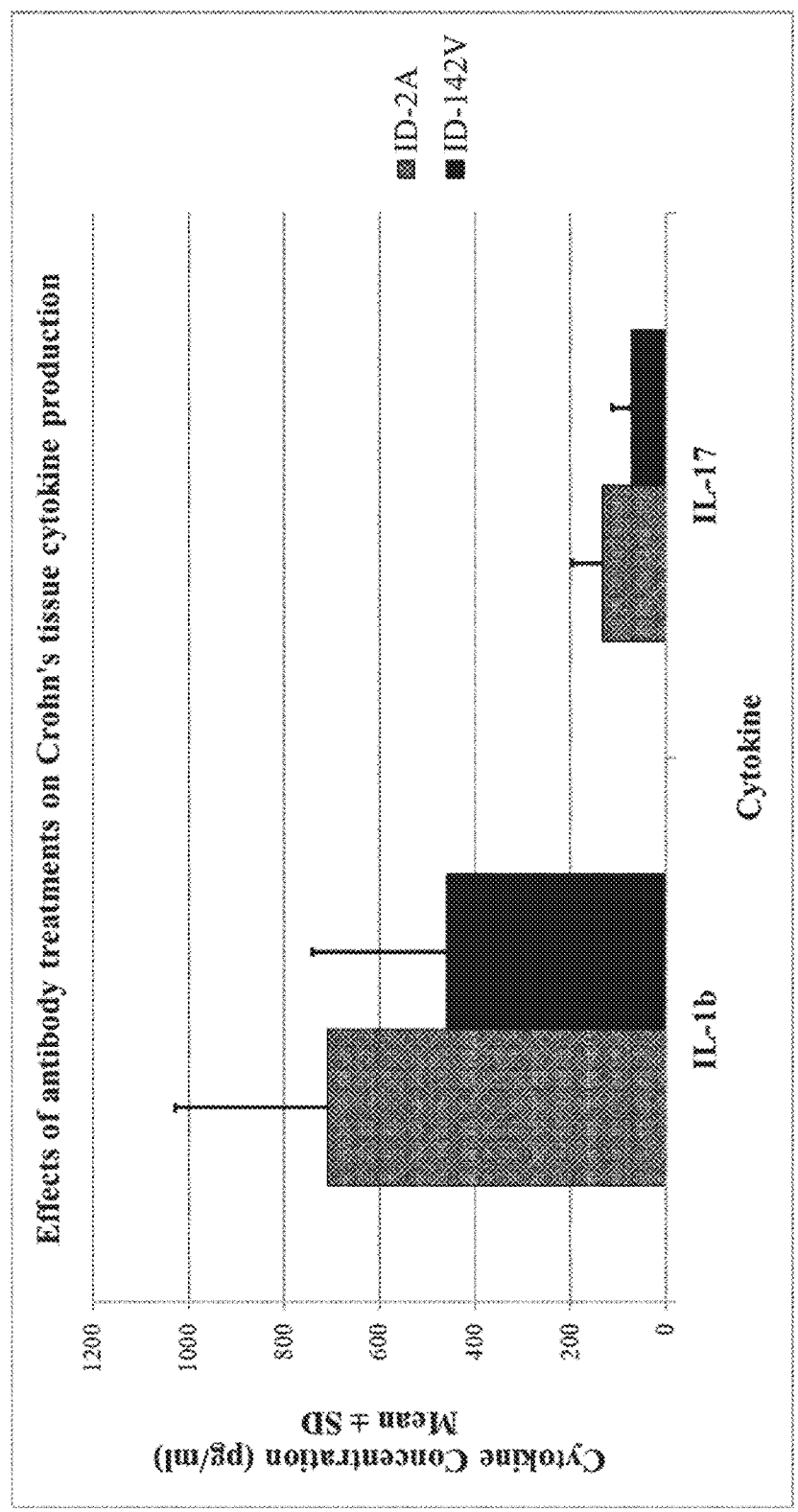
FIG. 30—Cytokine production in Crohn's disease biopsy tissue (ID-142V, cytokines IL-1b, and IL-17)
Figure 31:
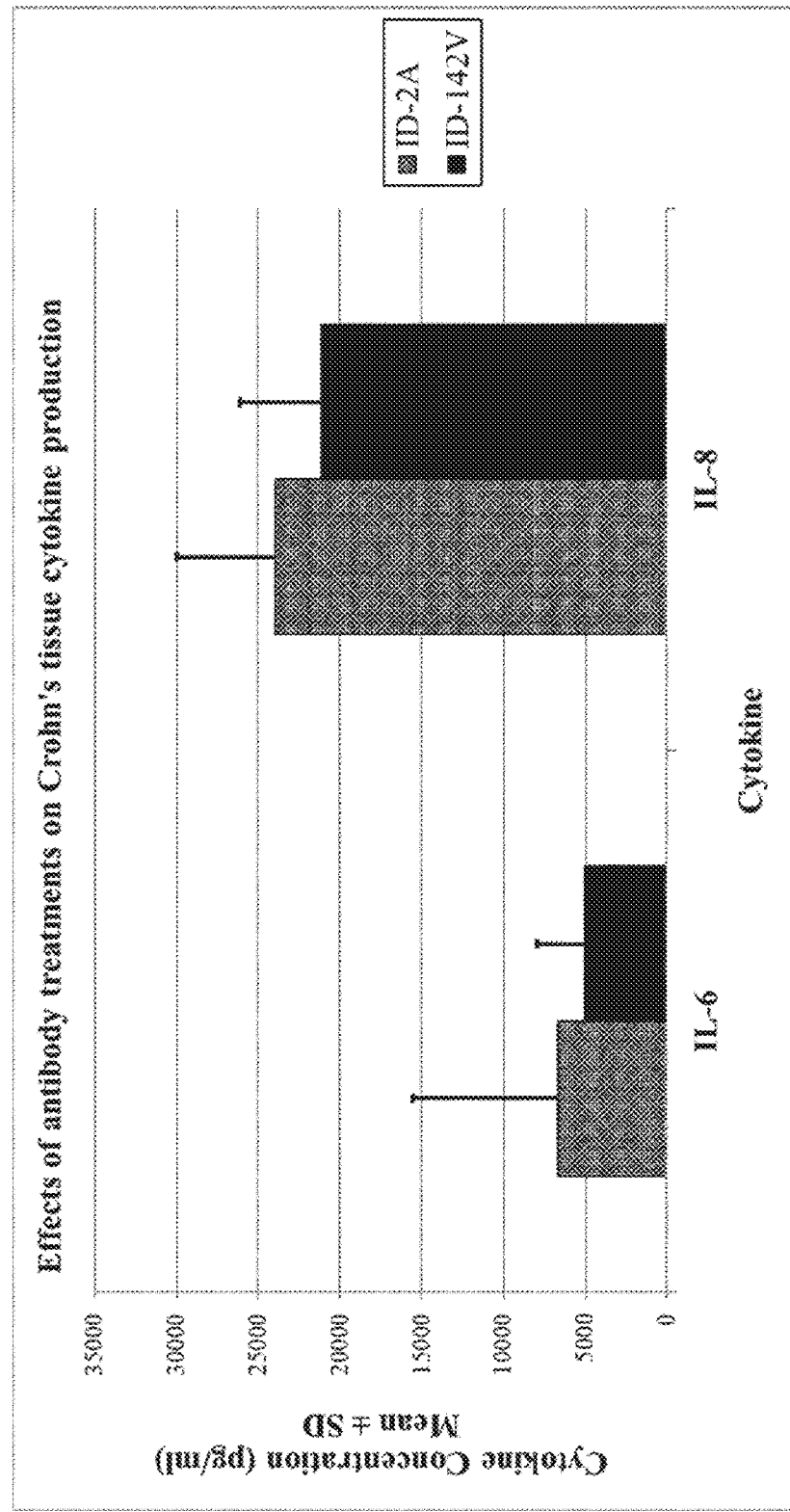
FIG. 31—Cytokine production in Crohn's disease biopsy tissue (ID-142V, cytokines IL-6 and IL-8)
Figure 32:
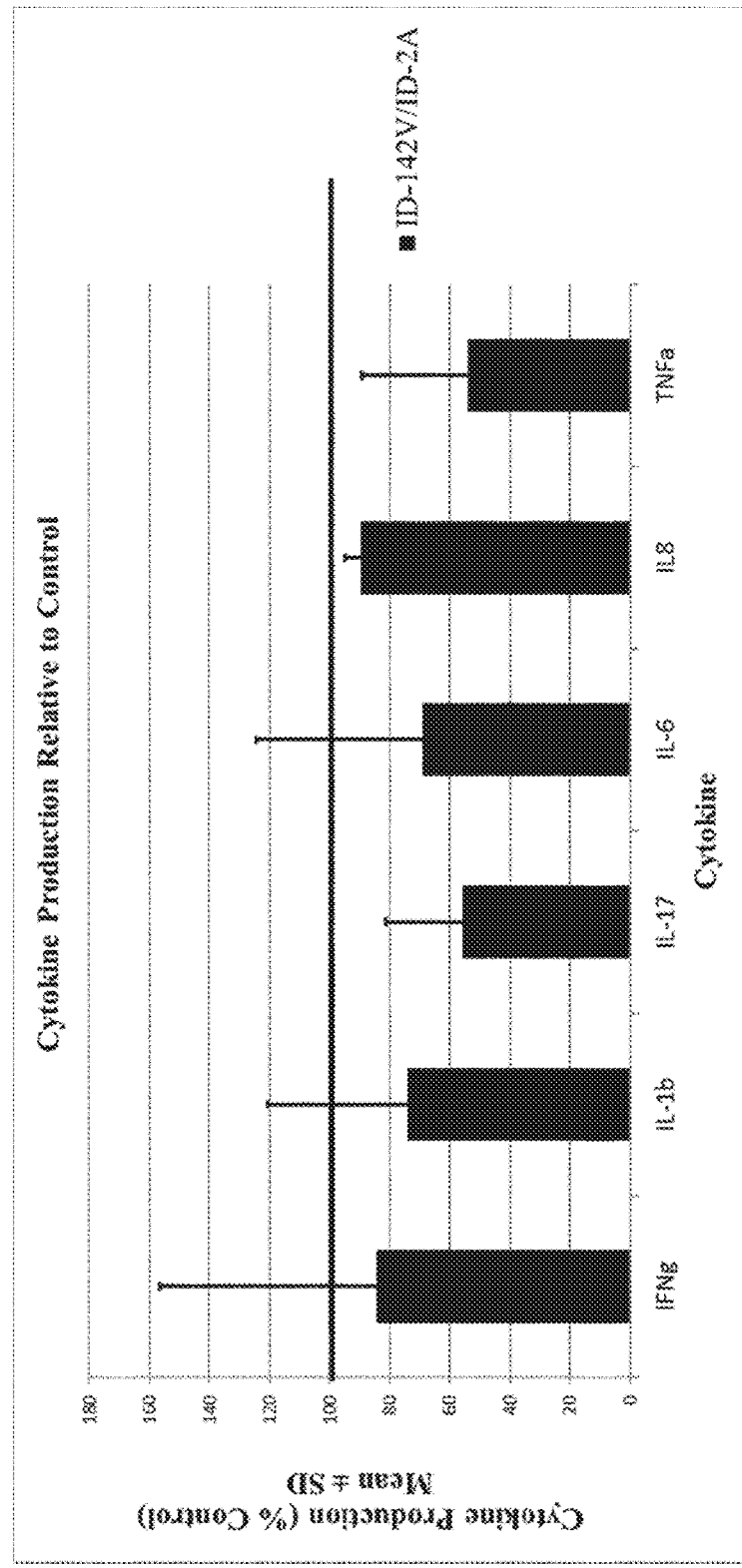
FIG. 32—Cytokine production in Crohn's disease biopsy tissue relative to control (ID-142V, pro-inflammatory cytokines)

When compared with the production levels of cytokines 'measured for the control ID-2A treated tissue, ID-142V treatment resulted' in some inhibition of each of the six pro-inflammatory cytokines (FIGS. 29-31). The spontaneous production of IL-17 and TNF-alpha were inhibited by ID-142V most strongly. The control-normalised cytokine data presented in FIG. 32 also show that ID-142V treatment was inhibitory (FIG. 32).

In contrast to the inhibitory effects of ID-142V on production of the pro-inflammatory cytokines, treatment with ID-142V increased production of the anti-inflammatory cytokine IL-10 relative to control ID-2A (FIG. 29).

Example 16: Local Delivery to the Intestinal Tract and Access to Lamina Propria Following Oral Administration Penetration of ID-123V into the lamina propria of mouse colons was assessed following oral dosing of dextran sulphate sodium (DSS).

DSS colitis was induced in mice using a standard protocol. 2% dextran suphate (MP biomedical) was administered in drinking water for 7 days, after which mice were kept for a further 3 days to allow peak development of disease.

On the day of peak disease, all mice received an initial pre-dose of bicarbonate+milk (vehicle) by oral gavage, followed 10 minutes later by further gavage of vehicle only, or vehicle+140 µg of ID-123V. At 1, 3, 5 and 7 hours post-dosing, pairs of animals were culled, the colons removed, and then colon segments were cryo-embedded for immunocytochemical analyses. Briefly, colon segments were cut and embedded in optimal cutting temperature compound (OCT) and snap frozen and stored at −80° C. until use. 6 urn sections were cut and were fixed in ice-cold acetone for 90 seconds. The sections were air dried and stored at −20 degrees C. until assayed. Two serial sections for each mouse were used to stain for each antibody set.

Figure 33:
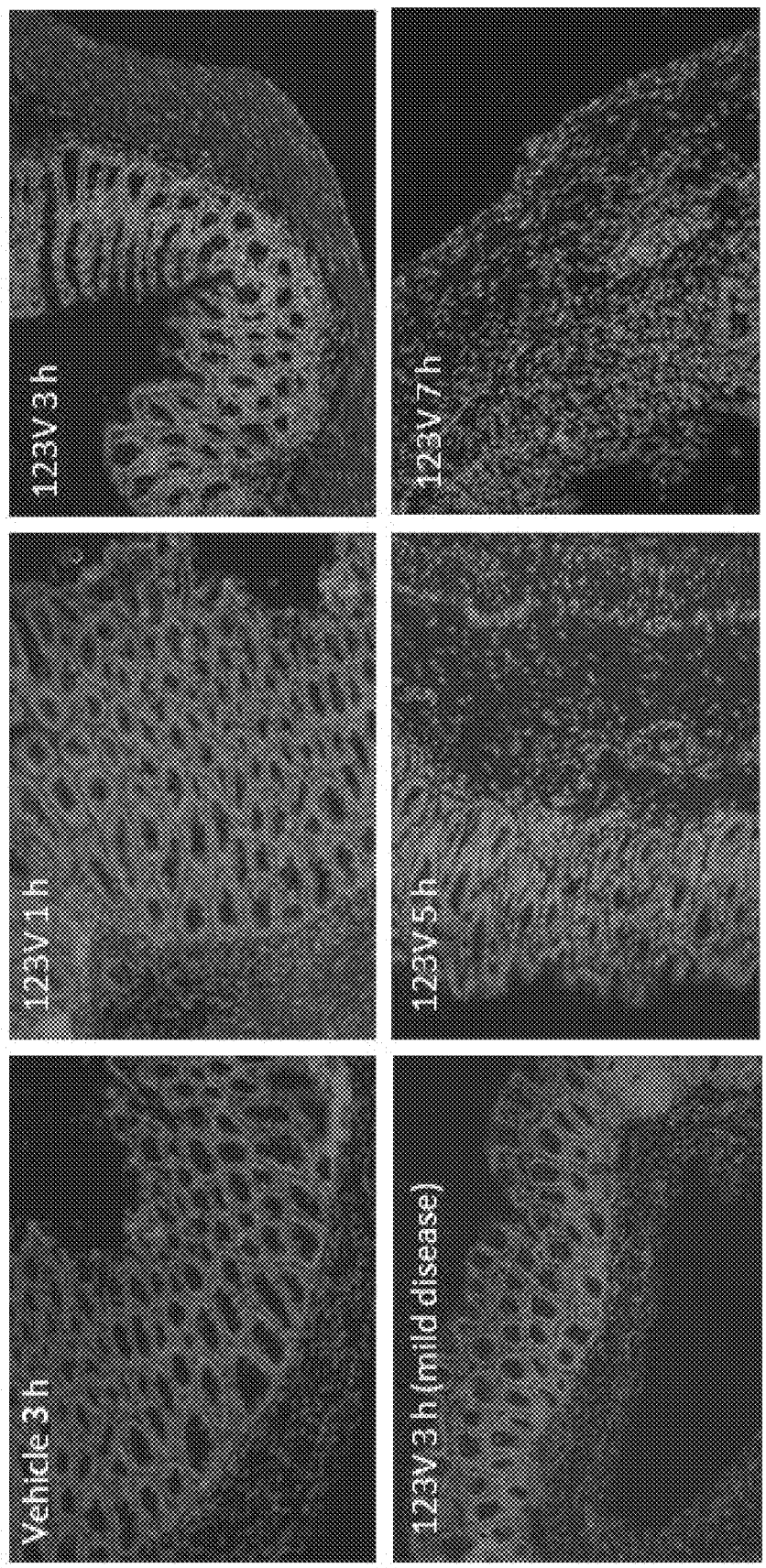
FIG. 33—Colon sample immunofluorescence displaying ID-123V

Colon sections were incubated with a rabbit anti-ICVD polyclonal antibody, followed by an Alexa 594-linked goat anti-rabbit antibody and Hoechst 33342 nucleic acid stain. ID-123V associated immunofluorescence within the colon at different times after dosing is shown in FIG. 33 (blue=cell nuclei, red=ID-123V staining).

After 1 hour post-dosing, ID-123V was observed throughout the lamina propria and in the muscularis mucosa and was also detected at 3 and 5 hours. Interestingly, ID-123V had accessed the muscularis mucosa in colons of mice with severe disease at 1 and 3 hours, but penetration was largely confined to the upper epithelium in mice with mild disease, with only very low levels detectable in the muscularis mucosa. The data show that the anti-IL-6R ICVD ID-123V is able to penetrate the colon epithelium and submucosa of colitis mice following oral dosing.

Bootstrapping is a computational technique for assessing the accuracy of a statistical estimate, and, when applied to a phylogenetic tree, it represents the confidence of a branch division. Bootstrapping re-samples the positions of the sequence of interest, rebuilds the tree, and tests whether the same node/tree structure is recovered. This is repeated multiple times (×1000 in this analysis), and the percentage at each node represents the support for that branch.

The phylogenetic trees suggested that 5G9 and 7F6 are most closely related to the VHH-V gene Vo (confidence of 96%). For the VHH-J amino acid region, 5G9 and 7F6 are most closely related to VHHJ6 family (confidence of 97%).

Further sequence analysis was carried out to determine how many ICVD polynucleotide sequences from the database originated from the Vo germline (or related V genes) and possess the same V mutations as 21E6, 5G9 or 7F6, with and without the same CDR3.

Methods

Calculating Germline Equivalent Sequences

All sequences in the database were aligned by the BLAST algorithm to the reference germline sequences, and hybrid sequences were generated where regions aligned to the reference germline sequences were combined with non-template regions of the ICVD sequences (Table 17.1). Note that 5G9 has a 3 amino acid insertion in framework 1 region compared to VHH Vo germline sequence

TABLE 17.1

Germline equivalents of ICVD sequences

| ID | VHHR sequence | Germline equivalent* |
|---|---|---|
| 7F6 | SGGGLVQAGGSTRLTCLASGSIS SINVIGVVYRQAPGKQRELVAMIG RGEGANYGDFAKGRFTISRDNSK NTVYLQMNSLKPEDTAVYYCYAD YEDRDSPFNGSWGQG (SEQ ID NO: 91) | sggglvqaggslrlscaasgsifsinamg wyrqapgkqrelvaaitsggstnyadsv kgrftisrdnakntvylqmnslkpedtavy ycnaDYEDRDSPFNGswgqg (SEQ ID NO: 94) |
| 5G9 | SGGGLVQAGGSTRLTCKASGSIF NINSNVMAVVYRQAPGKQRELVA IIGKGGGTNYADFVKGRFTISRDA AKNTVNLQMNSLKPEDTAVYYCY ADYEDRDSPFNGSWGQG (SEQ ID NO: 92) | sggglvqaggslrlscaasgsifNINsin amgwyrqapgkqrelvaaitsggstnya dsvkgrftisrdnakntvylqmnslkpedt avyycnaDYEDRDSPFNGswgqg (SEQ ID NO: 95) |
| 21E6 | SGGGLVLAGGSTRLTCLASGSIS SINVIGVVYRQAPGKQRELVAMIG RGEGANYGDFAKGRFTISRDNSK NTVYLQMNSLKPEDTAVYYCYAD YEDRDSPLNGSWGQG (SEQ ID NO: 93) | glvqaggslrlscaasgsifsinamgwyr qapgkqrelvaaitsggstnyadsvkgrft isrdnakntvylqmnslkpedtavyycna DYEDRDSPLNgswgqg (SEQ ID NO: 96) |

*Lower-case letters indicate regions that were germline encoded.

Example 17: Sequence Analysis

Using high throughput sequencing, the heavy chain repertoire of DNA sequences obtained in Example 1 was established and collated in a database. Sequence analyses were performed on this database.

To statistically identify the germline amino acid sequences which gave rise to 5G9 and 7F6, an alignment of each sequence with reference V and J sequences was performed using Mafft (Katoh and Standley, 2013), and then V and J phylogenetic trees were generated using maximum parsimony methods. This gave the relationships between the germline sequences and 5G9 and 7F6, where the statistical support can be determined by bootstrapping.

Particular conserved differences from the germline equivalent sequence (including non-template regions) were identified. These differences are provided in Table 17.2.

TABLE 17.2

Conserved sites in the ICVD sequences which differ from germline (position numbering according to Kabat)

| Amino acid position | Conserved amino acid | Germline amino acid(s) |
|---|---|---|
| 18 | T | L |
| 21 | T | S |
| 33 | V* | A |
| 52 | G* | T |

TABLE 17.2-continued

Conserved sites in the ICVD sequences which differ from germline (position numbering according to Kabat)

| Amino acid position | Conserved amino acid | Germline amino acid(s) |
|---|---|---|
| 56 | G* | S |
| 62 | F | S |
| 93 | Y* | N |

It is believed that the amino acids at the positions marked with an asterisk above are particularly important for maintaining optimal potency.

CLAUSES

A set of clauses defining the invention and its preferred aspects is as follows:
1. A polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein CDR3 comprises a sequence sharing 65% or greater sequence identity with SEQ ID NO: 3.
2. The polypeptide according to clause 1, wherein CDR3 comprises a sequence sharing 80% or greater sequence identity with SEQ ID NO: 3.
3. The polypeptide according to clause 1, wherein the sequence of CDR3 comprises any one of SEQ ID NO: 3, SEQ ID NO: 14, SEQ ID NO: 48 to 53 or SEQ ID NO: 55 to SEQ ID NO: 58.
4. The polypeptide according to any one of clauses 1 to 3, wherein CDR1 comprises a sequence sharing 50% or greater sequence identity with SEQ ID NO: 1.
5. The polypeptide according to any one of clauses 1 to 3, wherein CDR1 comprises a sequence sharing 40% or greater sequence identity with SEQ ID NO: 8.
6. The polypeptide according to any one of clauses 1 to 5, wherein CDR2 comprises a sequence sharing 50% or greater sequence identity with SEQ ID NO: 2.
7. The polypeptide according to any one of clauses 1 to 5, wherein CDR2 comprises a sequence sharing 50% or greater sequence identity with SEQ ID NO: 9.
8. The polypeptide according to clause 1 which comprises any one of SEQ ID NOs: 15-39, 43 or 44.
9. The polypeptide according to any one of clauses 1 to 8, wherein the polypeptide is an antibody.
10. The polypeptide according to any one of clauses 1 to 8, wherein the polypeptide is an antibody fragment.
11. The polypeptide according to any one of clauses 1 to 10, which is substantially resistant to one or more proteases.
12. The polypeptide according to any one of clauses 1 to 11 for use as a medicament.
13. The polypeptide according to clause 12 for use in the treatment of an autoimmune and/or inflammatory disease.
14. The polypeptide for use according to either clause 12 or 13, which is administered orally.
15. A polynucleotide encoding the polypeptide according to any one of clauses 1 to 14, especially wherein the polynucleotide comprises or consists of a sequence sharing 70% or greater sequence identity with any one of SEQ ID NOs: 59 to 80, more especially wherein the polynucleotide comprises or consists of any one of SEQ ID NOs: 59 to 80.

Miscellaneous

All references referred to in this application, including patent and patent applications, are incorporated herein by reference to the fullest extent possible.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The application of which this description and claims forms part may be used as a basis for priority in respect of any subsequent application. The claims of such subsequent application may be directed to any feature or combination of features described herein.

They may take the form of product, composition, process, or use claims and may include, by way of example and without limitation, the following claims.

| SEQUENCES |
|---|
| FR1(space)CDR1(space)FR2(space)CDR2(space)FR3(space)CDR3(space)FR4 |
| >5G9 (SEQ ID NO: 15)<br>EVQLVESGGGLVQAGGSLRLTCKASGSIFNINS INVMA WYRQAPGKQRELVA IIGKGGGTNYADFVKG RFTISRDAAKNTVNLQMNSLKPEDTAVYYCYA DYEDRDSPFNAS WGQGTQVTVSS |
| >ID-52V (5G9 + F109H, R105H) (SEQ ID NO: 16)<br>EVQLVESGGGLVQAGGSLRLTCKASGSIFNINS INVMA WYRQAPGKQRELVA IIGKGGGTNYADFVKG RFTISRDAAKNTVNLQMNSLKPEDTAVYYCYA DYEDRDSPHNAS WGQGTQVTVSS |
| >ID-53V (5G9 + F109H) (SEQ ID NO: 17)<br>EVQLVESGGGLVQAGGSLRLTCKASGSIFNINS INVMA WYRQAPGKQRELVA IIGKGGGTNYADFVKG RFTISRDAAKNTVNLQMNSLKPEDTAVYYCYA DYEDHDSPHNAS WGQGTQVTVSS |
| >ID-54V (5G9 + R105H) (SEQ ID NO: 18)<br>EVQLVESGGGLVQAGGSLRLTCHASGSIFNINS INVMA WYRQAPGKQRELVA IIGKGGGTNYADFVKG RFTISRDAAKNTVNLQMNSLKPEDTAVYYCYA DYEDRDSPHNAS WGQGTQVTVSS |
| >ID-55V (5G9 + K23H) (SEQ ID NO: 19)<br>EVQLVESGGGLVQAGGSLRLTCHASGSIFNINS INVMA WYRQAPGKQRELVA IIGKGGGTNYADFVKG RFTISRDAAKNTVNLQMNSLKPEDTAVYYCYA DYEDRDSPFNAS WGQGTQVTVSS |
| >ID-56V (5G9 + F29S) (SEQ ID NO: 20)<br>EVQLVESGGGLVQAGGSLRLTCKASGSISNINS INVMA WYRQAPGKQRELVA IIGKGGGTNYADFVKG RFTISRDAAKNTVNLQMNSLKPEDTAVYYCYA DYEDHDSPFNAS WGQGTQVTVSS |
| >ID-57V (5G9 + F29I) (SEQ ID NO: 21)<br>EVQLVESGGGLVQAGGSLRLTCKASGSIININS INVMA WYRQAPGKQRELVA IIGKGGGTNYADFVKG RFTISRDAAKNTVNLQMNSLKPEDTAVYYCYA DYEDRDSPFNAS WGQGTQVTVSS |
| >ID-58V (5G9 + F65V) (SEQ ID NO: 22)<br>EVQLVESGGGLVQAGGSLRLTCKASGSIFNINS INVMA WYRQAPGKQRELVA IIGKGGGTNYADVVKG RFTISRDAAKNTVNLQMNSLKPEDTAVYYCYA DYEDRDSPFNAS WGQGTQVTVSS |
| >ID-59V (5G9 + Y62Q) (SEQ ID NO: 23)<br>EVQLVESGGGLVQAGGSLRLTCKASGSIFNINS INVMA WYRQAPGKQRELVA IIGKGGGTNDADFVKG RFTISRDAAKNTVNLQMNSLKPEDTAVYYCYA DYEDRDSPFNAS WGQGTQVTVSS |
| >ID-112V (5G9 + F29S, Q47G, K89R, R105H) (SEQ ID NO: 24)<br>EVQLVESGGGLVQAGGSLRLTCKASGSISNINS INVMA WYRQAPGKGRELVA IIGKGGGTNYADFVKG RFTISRDAAKNTVNLQMNSLRPEDTAVYYCYA DYEDHDSPHNAS WGQGTQVTVSS |
| >ID-114V (5G9 + F29S, V81L, N82Y, R105H) (SEQ ID NO: 25)<br>EVQLVESGGGLVQAGGSLRLTCKASGSISNINS INVMA VVYRQAPGKQRELVA IIGKGGGTNYADFVKG RFTISRDAAKNTLYLQMNSLKPEDTAVYYCYA DYEDHDSPHNAS WGQGTQVTVSS |
| >ID-122V (5G9 + F29S, Q47G, K89R, R105H, F109H) (SEQ ID NO: 26)<br>EVQLVESGGGLVQAGGSLRLTCKASGSISNINS INVMA WYRQAPGKGRELVA IIGKGGGTNYADFVKG RFTISRDAAKNTVNLQMNSLRPEDTAVYYCYA DYEDHDSPHNAS WGQGTQVTVSS |
| >ID-123V (5G9 + F29S, Q47G, N82Y, K89R, R105H, F109H) (SEQ ID NO: 27)<br>EVQLVESGGGLVQAGGSLRLTCKASGSISNINS INVMA WYRQAPGKGRELVA IIGKGGGTNYADFVKG RFTISRDAAKNTVYLQMNSLRPEDTAVYYCYA DYEDHDSPHNAS WGQGTQVTVSS |
| >ID-141V (5G9 + E1D, F29S, Q47G, V81L, N82Y, K89R, R105H, F109H) (SEQ ID NO: 28)<br>DVQLVESGGGLVQAGGSLRLTCKASGSISNINS INVMA WYRQAPGKGRELVA IIGKGGGTNYADFVKG RFTISRDAAKNTLYLQMNSLRPEDTAVYYCYA DYEDHDSPHNAS WGQGTQVTVSS |
| >ID-142V (5G9 + E1D, F29S, Q47G, N82Y, K89R, R105H, F109H) (SEQ ID NO: 29)<br>DVQLVESGGGLVQAGGSLRLTCKASGSISNINS INVMA WYRQAPGKGRELVA IIGKGGGTNYADFVKG RFTISRDAAKNTVYLQMNSLRPEDTAVYYCYA DYEDHDSPHNAS WGQGTQVTVSS |
| >ID-143V (5G9 + E1D, F29S, Q47G, V81L, N82Y, K89R, R105H) (SEQ ID NO: 30)<br>DVQLVESGGGLVQAGGSLRLTCKASGSISNINS INVMA WYRQAPGKGRELVA IIGKGGGTNYADFVKG RFTISRDAAKNTLYLQMNSLRPEDTAVYYCYA DYEDHDSPHNAS WGQGTQVTVSS |

-continued

SEQUENCES

>ID-144V (5G9 + E1D, F29S, Q47G, N82Y, K89R, R105H) (SEQ ID NO: 31)
DVQLVESGGGLVQAGGSTRLTCKASGSTRLTCLASGSISS INVMA WYRQAPGKGRELVA IIGKGGGTNYADFVKG RFTISRDAAKNTVYLQMNSLRPEDTAVYYCYA DYEDHDSPFNAS WGQGTQVTVSS

>7F6 (SEQ ID NO: 32)
EVQLVESGGGLVQAGGSLRLTCLASGSIIS INVIG WYRQAPGKQRELVA MIGRGEGANYGDFAKG RFTISRDNSKNTVYLQMNSLKPEDTAVYYCYA DYEDHDSPFNGS WGQGTQVTVSS

>ID-3V (7F6 + R102H) (SEQ ID NO: 33)
EVQLVESGGGLVQAGGSTRLTCLASGSISS INVIG WYRQAPGKQRELVA MIGRGEGANYGDFAKG RFTISRDNSKNTVYLQMNSLKPEDTAVYYCYA DYEDHDSPFNGS WGQGTQVTVSS

>ID-6V (7F6 + F106H) (SEQ ID NO: 34)
EVQLVESGGGLVQAGGSTRLTCLASGSISS INVIG WYRQAPGKQRELVA MIGRGEGANYGDFAKG RFTISRDNSKNTVYLQMNSLKPEDTAVYYCYA DYEDHDSPHNGS WGQGTQVTVSS

>ID-40V (7F6 + R102H, F106H) (SEQ ID NO: 35)
EVQLVESGGGLVQAGGSTRLTCLASGSISS INVIG WYRQAPGKQRELVA MIGRGEGANYGDFAKG RFTISRDNSKNTVYLQMNSLKPEDTAVYYCYA DYEDHDSPHNGS WGQGTQVTVSS

>ID-47V (7F6 + F106I) (SEQ ID NO: 36)
EVQLVESGGGLVQAGGSTRLTCLASGSISS INVIG WYRQAPGKQRELVA MIGRGEGANYGDFAKG RFTISRDNSKNTVYLQMNSLKPEDTAVYYCYA DYEDRDSPINGS WGQGTQVTVSS

>ID-49V (7F6 + F106T) (SEQ ID NO: 37)
EVQLVESGGGLVQAGGSTRLTCLASGSISS INVIG WYRQAPGKQRELVA MIGRGEGANYGDFAKG RFTISRDNSKNTVYLQMNSLKPEDTAVYYCYA DYEDRDSPTNGS WGQGTQVTVSS

>ID-50V (7F6 + F106V) (SEQ ID NO: 38)
EVQLVESGGGLVQAGGSTRLTCLASGSISS INVIG WYRQAPGKQRELVA MIGRGEGANYGDFAKG RFTISRDNSKNTVYLQMNSLKPEDTAVYYCYA DYEDRDSPVNGS WGQGTQVTVSS

>21E6 (SEQ ID NO: 39)
EVQLVESGGGLVLAGGSTRLTCLASGSISS INVIG WYRQAPGKQRELVA MIGRGEGANYGDFAKG RFTMSRDNAKKTVYLQMNSLKPEDTAVYYCYA DYEDRDSPLNGS WGQGTQVTVSS

>4D3 (SEQ ID NO: 40)
EVQLVESGGGLAQLGGSLRLSCVASISTFS QNAMG WFRQAAGKRRESVA RISSSGNVGYTDAVKG RFTMSRDNAKTVYLQMNSLKPEDTAVYYCNA YSMSGELAAP WGQGTQVTVSS

>3C12 (SEQ ID NO: 41)
EVQLVESGGGLAQLGGSLRLSCVASGNIFS SNTAG WFRQAPGKQREWA GISIGGMPAYADSVKG RFTISRDNAKNTVYLQMNSLKPEDTAVYYCAT GGTEYDY WGQGTLVTVSS

>20A11 (SEQ ID NO: 42)
EVQLVESGGGLVQPGGSLRLSCAASGSVFK INVMA WYRQAPGKGRELVA GIISGGSTSYADSVKG RFTISRDNAKNTLYLQMNSLRPEDTAVYYCAF ITTESDYDLGRRY WGQGTLVTVSS

>ID-74V (5G9 + E1D, R105H) (SEQ ID NO: 43)
DVQLVESGGGLVQAGGSTRLTCKASGSIFNINS INVMA WYRQAPGKGRELVA IIGKGGGTNYADFVKG RFTISRDAAKNTVYLQMNSLRPEDTAVYYCYA DYEDHDSPFNAS WGQGTQVTVSS

>ID-75V (5G9 + E1D, F29S, R105H) (SEQ ID NO: 44)
DVQLVESGGGLVQAGGSTRLTCKASGSISNINS INVMA WYRQAPGKQRELVA IIGKGGGTNYADFVKG RFTISRDAAKNTVNLQMNSLKPEDTAVYYCYA DYEDHDSPFNAS WGQGTQVTVSS

REFERENCES

Arbabi-Ghahroudi et al *FEBS Lett* 1997 414:521-526
Blattler et al *Biochemistry* 1985 24:1517-1524
Biancheri et al *Gastroenterology* 2015 November; 149(6): 1564-1574
Chomezynnski et al *Anal Biochem* 1987 162:156-159
Faisst et al *J Virol* 1995 69:4538-4543
Frenken et al *J Biotech* 2000 78:11-21
Green and Sambrook *Molecular Cloning: A Laboratory Manual* 2012 4$^{th}$ Edition Cold Spring Harbour Laboratory Press
Griffiths et al *Antibodies* 2013 2:66-81
Grundstrom et al 1985 *Nucl. Acids Res* 13:3305-3316
Gustot et al *Gut* 2005; 54(4):488-95
Hamers-Casterman et al *Nature* 1993 363(6428):446-448
Harmsen et al *Gene* 1993 125:115-123
Harmsen et al *Appl Microbiol Biotechnol* 2007 77(1):13-22
Hendrickson et al *Clin Microbiol Rev* 2002 15(1):79-94
Hoogenboom et al *Nucl Acid Res* 1991 19:4133-4137
Hosokawa et al *J Gastroenterol Hepatol.* 1999; 14(10):987-96
Huse et al *Science* 1989 246 (4935):1275-1281
Ito et al *Gastroenterology* 2004; 126(4):989-96
Kabat et al Sequences of Proteins of Immunological Interest, *Fifth Edition U.S. Department of Health and Human Services*, 1991 NIH Publication Number 91-3242
Katoh and Standley 2013 *Molecular biology and evolution* 30:772-780
Koh et al *J Biol Chem* 2010 285(25):19116-19124
Köhler et al *Nature* 1975 256:495-497
Kusugami et al *Dig Dis Sci.* 1995; 40(5):949-59
Ling et al *Anal Biochem* 1997 254(2):157-178
McCoy et al *Retrovirology* 2014 11:83
Merchlinsky et al *J. Virol.* 1983 47:227-232
Miethe et al *J Biotech* 2013 163(2):105-111
Mitsuyama et al *Anticancer Res.* 2007; 27 (6A): 3749-56
Muyldermans et al *Protein Eng* 1994 7(9):1129-1135
Muyldermans *Annu Rev Biochem* 2013 82:775-797
Nambiar et al *Science* 1984 223:1299-1301
Nelson et al *Molecular Pathology* 2000 53(3):111-117
Nguyen et al *Adv Immunol* 2001 79:261-296
Ortonne, *Brit J Dermatol* 1999 140 (suppl 54):1-7
Padlan *Mol Immunol* 1994 31:169-217
Reimund et al *J Clin Immunol.* 1996; 16(3):144-50
Reinecker et al *Clin Exp Immunol.* 1993; 94(1):174-81
Rose-John *Int J Biol Sci.* 2012; 8(9):1237-47
Roux et al *Proc Natl Acad Sci USA* 1998 95:11804-11809
Sakamar et al *Nucl. Acids Res* 1988 14:6361-6372
Skerra et al *Science* 1988 240(4855):1038-1041
Tanha et al *J Immunol Methods* 2002 263:97-109
Thomassen et al *Enzyme and Micro Tech* 2002 30:273-278
Vandenbroucke et al *Mucosal Immunology* 2010 3(1):49-56
Verma et al *Annu Rev Biochem* 1998 67:99-134
Vossenkämper et al *Gastroenterology* 2014 147(1):172-83
Waetzig & Rose-John *Expert Opin Ther Targets* 2012; 16(2):225-36
Ward et al *Nature* 1989 341:544-546
Wells et al *Gene* 1985 34:315-323

The invention claimed is:

1. A polypeptide comprising an immunoglobulin chain variable domain which binds to IL-6R, wherein the immunoglobulin chain variable domain comprises three complementarity determining regions (CDR1-CDR3) and four framework regions (FR1-FR4), and wherein the polypeptide comprises:
    a CDR1 comprising SEQ ID NO: 1;
    a CDR2 comprising SEQ ID NO: 2; and
    a CDR3 comprising SEQ ID NO: 3.

2. The polypeptide according to claim 1 which comprises SEQ ID NO: 29.

3. The polypeptide according to claim 1, wherein the immunoglobulin chain variable domain is a VHH.

4. The polypeptide according to claim 1, which is substantially resistant to one or more proteases present in the stomach or the small or large intestine.

5. The polypeptide according to claim 1, wherein the polypeptide retains 10% or more of the original potency of the polypeptide after at least 16 hours' exposure to human fecal extract in the standard human fecal extract assay.

6. A pharmaceutical composition comprising the polypeptide according to claim 1 and one or more pharmaceutically acceptable diluents or carriers.

7. The pharmaceutical composition according to claim 6, wherein the composition is presented in enterically coated form.

8. A polypeptide comprising an immunoglobulin chain variable domain which binds to IL-6R, wherein the immunoglobulin chain variable domain comprises three complementarity determining regions (CDR1-CDR3) and four framework regions (FR1-FR4), wherein the polypeptide comprises:
   a CDR1 comprising SEQ ID NO: 1;
   a CDR2 comprising SEQ ID NO: 2; and
   a CDR3 comprising SEQ ID NO: 3;
   and wherein the immunoglobulin chain variable domain comprises one or more amino acids selected from V33, G52, G56 and Y93, and optionally one or more amino acids selected from T18, T21 and F62, according to Kabat numbering.

* * * * *

SEQUENCE LISTING

```
<160> NUMBER OF SEQ ID NOS: 96

<210> SEQ ID NO 1
<211> LENGTH: 5
<212> TYPE: PRT
<213> ORGANISM: Artificial Sequence
<220> FEATURE:
<223> OTHER INFORMATION: Polypeptide sequence of ID-142V CDR1

<400> SEQUENCE: 1

Ile Asn Val Met Ala
1               5

<210> SEQ ID NO 2
<211> LENGTH: 16
<212> TYPE: PRT
<213> ORGANISM: Artificial Sequence
<220> FEATURE:
<223> OTHER INFORMATION: Polypeptide sequence of ID-142V CDR2

<400> SEQUENCE: 2

Ile Ile Gly Lys Gly Gly Gly Thr Asn Tyr Ala Asp Phe Val Lys Gly
1               5                   10                  15

<210> SEQ ID NO 3
<211> LENGTH: 12
<212> TYPE: PRT
<213> ORGANISM: Artificial Sequence
<220> FEATURE:
<223> OTHER INFORMATION: Polypeptide sequence of ID-142V CDR3

<400> SEQUENCE: 3

Asp Tyr Glu Asp His Asp Ser Pro His Asn Ala Ser
1               5                   10
```

<210> SEQ ID NO 4
<211> LENGTH: 33
<212> TYPE: PRT
<213> ORGANISM: Artificial Sequence
<220> FEATURE:
<223> OTHER INFORMATION: Polypeptide sequence of ID-142V FR1

<400> SEQUENCE: 4

Asp Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
            20                  25                  30

Ser

<210> SEQ ID NO 5
<211> LENGTH: 14
<212> TYPE: PRT
<213> ORGANISM: Artificial Sequence
<220> FEATURE:
<223> OTHER INFORMATION: Polypeptide sequence of ID-142V FR2

<400> SEQUENCE: 5

Trp Tyr Arg Gln Ala Pro Gly Lys Gly Arg Glu Leu Val Ala
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Polypeptide sequence of ID-142V FR3

<400> SEQUENCE: 6

Arg Phe Thr Ile Ser Arg Asp Ala Ala Lys Asn Thr Val Tyr Leu Gln
1               5                   10                  15

Met Asn Ser Leu Arg Pro Glu Asp Thr Ala Val Tyr Tyr Cys Tyr Ala
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: Polypeptide sequence of ID-142V FR4

<400> SEQUENCE: 7

Trp Gly Gln Gly Thr Gln Val Thr Val Ser Ser
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Polypeptide sequence of ID-40V CDR1

<400> SEQUENCE: 8

Ile Asn Val Ile Gly
1               5

<210> SEQ ID NO 9
<211> LENGTH: 16
<212> TYPE: PRT
<213> ORGANISM: Artificial Sequence
<220> FEATURE:

<223> OTHER INFORMATION: Polypeptide sequence of ID-40V CDR2

<400> SEQUENCE: 9

Met Ile Gly Arg Gly Glu Gly Ala Asn Tyr Gly Asp Phe Ala Lys Gly
1               5                   10                  15

<210> SEQ ID NO 10
<211> LENGTH: 30
<212> TYPE: PRT
<213> ORGANISM: Artificial Sequence
<220> FEATURE:
<223> OTHER INFORMATION: Polypeptide sequence of ID-40V FR1

<400> SEQUENCE: 10

Glu Val Gln Leu Val Glu Ser Gly Gly Gly Leu Val Gln Ala Gly Gly
1               5                   10                  15

Ser Thr Arg Leu Thr Cys Leu Ala Ser Gly Ser Ile Ser Ser
            20                  25                  30

<210> SEQ ID NO 11
<211> LENGTH: 14
<212> TYPE: PRT
<213> ORGANISM: Artificial Sequence
<220> FEATURE:
<223> OTHER INFORMATION: Polypeptide sequence of ID-40V FR2

<400> SEQUENCE: 11

Trp Tyr Arg Gln Ala Pro Gly Lys Gln Arg Glu Leu Val Ala
1               5                   10

<210> SEQ ID NO 12
<211> LENGTH: 32
<212> TYPE: PRT
<213> ORGANISM: Artificial Sequence
<220> FEATURE:
<223> OTHER INFORMATION: Polypeptide sequence of ID-40V FR3

<400> SEQUENCE: 12

Arg Phe Thr Ile Ser Arg Asp Asn Ser Lys Asn Thr Val Tyr Leu Gln
1               5                   10                  15

Met Asn Ser Leu Lys Pro Glu Asp Thr Ala Val Tyr Tyr Cys Tyr Ala
            20                  25                  30

<210> SEQ ID NO 13
<211> LENGTH: 28
<212> TYPE: DNA
<213> ORGANISM: Artificial Sequence
<220> FEATURE:
<223> OTHER INFORMATION: Polynucleotide sequence of 3 primer

<400> SEQUENCE: 13
tcttaactag tgaggagacg gtgacctg                                      28

<210> SEQ ID NO 14
<211> LENGTH: 12
<212> TYPE: PRT
<213> ORGANISM: Artificial Sequence
<220> FEATURE:
<223> OTHER INFORMATION: Polypeptide sequence of ID-40V CDR3

<400> SEQUENCE: 14

Asp Tyr Glu Asp His Asp Ser Pro His Asn Gly Ser
1               5                   10

<210> SEQ ID NO 15

<211> LENGTH: 123
<212> TYPE: PRT
<213> ORGANISM: Artificial Sequence
<220> FEATURE:
<223> OTHER INFORMATION: Polypeptide sequence of 5G9

<400> SEQUENCE: 15

Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Phe Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp Arg Asp Ser Pro Phe Asn Ala Ser
            100                 105                 110

Trp Gly Gln Gly Thr Gln Val Thr Val Ser Ser
        115                 120

<210> SEQ ID NO 16
<211> LENGTH: 123
<212> TYPE: PRT
<213> ORGANISM: Artificial Sequence
<220> FEATURE:
<223> OTHER INFORMATION: Polypeptide sequence of ID-52V

<400> SEQUENCE: 16

Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Phe Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp His Asp Ser Pro His Asn Ala Ser
            100                 105                 110

Trp Gly Gln Gly Thr Gln Val Thr Val Ser Ser
        115                 120

<210> SEQ ID NO 17
<211> LENGTH: 123
<212> TYPE: PRT
<213> ORGANISM: Artificial Sequence
<220> FEATURE:
<223> OTHER INFORMATION: Polypeptide sequence of ID-53V

<400> SEQUENCE: 17

Glu Val Gln Leu Val Glu Ser Gly Gly Gly Leu Val Gln Ala Gly Gly
1               5                   10                  15

```
Ser Thr Arg Leu Thr Cys Lys Ala Ser Gly Ser Ile Phe Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp Arg Asp Ser Pro His Asn Ala Ser
            100                 105                 110

Trp Gly Gln Gly Thr Gln Val Thr Val Ser Ser
        115                 120
```

<210> SEQ ID NO 18
<211> LENGTH: 123
<212> TYPE: PRT
<213> ORGANISM: Artificial Sequence
<220> FEATURE:
<223> OTHER INFORMATION: Polypeptide sequence of ID-54V

<400> SEQUENCE: 18

```
Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Phe Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp His Asp Ser Pro Phe Asn Ala Ser
            100                 105                 110

Trp Gly Gln Gly Thr Gln Val Thr Val Ser Ser
        115                 120
```

<210> SEQ ID NO 19
<211> LENGTH: 123
<212> TYPE: PRT
<213> ORGANISM: Artificial Sequence
<220> FEATURE:
<223> OTHER INFORMATION: Polypeptide sequence of ID-55V

<400> SEQUENCE: 19

```
Glu Val Gln Leu Val Glu Ser Gly Gly Gly Leu Val Gln Ala Gly Gly
1               5                   10                  15

Ser Thr Arg Leu Thr Cys His Ala Ser Gly Ser Ile Phe Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80
```

Val Asn Leu Gln Met Asn Ser Leu Lys Pro Glu Asp Thr Ala Val Tyr
                85                  90                  95

Tyr Cys Tyr Ala Asp Tyr Glu Asp Arg Asp Ser Pro Phe Asn Ala Ser
            100                 105                 110

Trp Gly Gln Gly Thr Gln Val Thr Val Ser Ser
        115                 120

<210> SEQ ID NO 20
<211> LENGTH: 123
<212> TYPE: PRT
<213> ORGANISM: Artificial Sequence
<220> FEATURE:
<223> OTHER INFORMATION: Polypeptide sequence of ID-56V

<400> SEQUENCE: 20

Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp Arg Asp Ser Pro Phe Asn Ala Ser
            100                 105                 110

Trp Gly Gln Gly Thr Gln Val Thr Val Ser Ser
        115                 120

<210> SEQ ID NO 21
<211> LENGTH: 123
<212> TYPE: PRT
<213> ORGANISM: Artificial Sequence
<220> FEATURE:
<223> OTHER INFORMATION: Polypeptide sequence of ID-57V

<400> SEQUENCE: 21

Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ile Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp Arg Asp Ser Pro Phe Asn Ala Ser
            100                 105                 110

Trp Gly Gln Gly Thr Gln Val Thr Val Ser Ser
        115                 120

<210> SEQ ID NO 22
<211> LENGTH: 123
<212> TYPE: PRT
<213> ORGANISM: Artificial Sequence
<220> FEATURE:
<223> OTHER INFORMATION: Polypeptide sequence of ID-58V

<400> SEQUENCE: 22

Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Phe Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Val Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp Arg Asp Ser Pro Phe Asn Ala Ser
            100                 105                 110

Trp Gly Gln Gly Thr Gln Val Thr Val Ser Ser
        115                 120

<210> SEQ ID NO 23
<211> LENGTH: 123
<212> TYPE: PRT
<213> ORGANISM: Artificial Sequence
<220> FEATURE:
<223> OTHER INFORMATION: Polypeptide sequence of ID-59V

<400> SEQUENCE: 23

Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Phe Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Asp Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp Arg Asp Ser Pro Phe Asn Ala Ser
            100                 105                 110

Trp Gly Gln Gly Thr Gln Val Thr Val Ser Ser
        115                 120

<210> SEQ ID NO 24
<211> LENGTH: 123
<212> TYPE: PRT
<213> ORGANISM: Artificial Sequence
<220> FEATURE:
<223> OTHER INFORMATION: Polypeptide sequence of ID-112V

<400> SEQUENCE: 24

Glu Val Gln Leu Val Glu Ser Gly Gly Gly Leu Val Gln Ala Gly Gly
1               5                   10                  15

```
Ser Thr Arg Leu Thr Cys Lys Ala Ser Gly Ser Ile Ser Asn Ile Asn
            20                  25                  30

Ser Ile Asn Val Met Ala Trp Tyr Arg Gln Ala Pro Gly Lys Gly Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Arg Pro Glu Asp Thr Ala Val Tyr
                85                  90                  95

Tyr Cys Tyr Ala Asp Tyr Glu Asp His Asp Ser Pro Phe Asn Ala Ser
            100                 105                 110

Trp Gly Gln Gly Thr Gln Val Thr Val Ser Ser
        115                 120
```

<210> SEQ ID NO 25
<211> LENGTH: 123
<212> TYPE: PRT
<213> ORGANISM: Artificial Sequence
<220> FEATURE:
<223> OTHER INFORMATION: Polypeptide sequence of ID-114V

<400> SEQUENCE: 25

```
Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Leu Tyr Leu Gln Met Asn Ser Leu Lys Pro Glu Asp Thr Ala Val Tyr
                85                  90                  95

Tyr Cys Tyr Ala Asp Tyr Glu Asp His Asp Ser Pro Phe Asn Ala Ser
            100                 105                 110

Trp Gly Gln Gly Thr Gln Val Thr Val Ser Ser
        115                 120
```

<210> SEQ ID NO 26
<211> LENGTH: 123
<212> TYPE: PRT
<213> ORGANISM: Artificial Sequence
<220> FEATURE:
<223> OTHER INFORMATION: Polypeptide sequence of ID-122V

<400> SEQUENCE: 26

```
Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
            20                  25                  30

Ser Ile Asn Val Met Ala Trp Tyr Arg Gln Ala Pro Gly Lys Gly Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
```

```
                65                  70                  75                  80
Val Asn Leu Gln Met Asn Ser Leu Arg Pro Glu Asp Thr Ala Val Tyr
                    85                  90                  95

Tyr Cys Tyr Ala Asp Tyr Glu Asp His Asp Ser Pro His Asn Ala Ser
                    100                 105                 110

Trp Gly Gln Gly Thr Gln Val Thr Val Ser Ser
                    115                 120

<210> SEQ ID NO 27
<211> LENGTH: 123
<212> TYPE: PRT
<213> ORGANISM: Artificial Sequence
<220> FEATURE:
<223> OTHER INFORMATION: Polypeptide sequence of ID-123V

<400> SEQUENCE: 27

Glu Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
                20                  25                  30

Ser Ile Asn Val Met Ala Trp Tyr Arg Gln Ala Pro Gly Lys Gly Arg
            35                  40                  45

Glu Leu Val Ala Ile Ile Gly Lys Gly Gly Gly Thr Asn Tyr Ala Asp
        50                  55                  60

Phe Val Lys Gly Arg Phe Thr Ile Ser Arg Asp Ala Ala Lys Asn Thr
65                  70                  75                  80

Val Tyr Leu Gln Met Asn Ser Leu Arg Pro Glu Asp Thr Ala Val Tyr
                    85                  90                  95

Tyr Cys Tyr Ala Asp Tyr Glu Asp His Asp Ser Pro His Asn Ala Ser
                    100                 105                 110

Trp Gly Gln Gly Thr Gln Val Thr Val Ser Ser
                    115                 120

<210> SEQ ID NO 28
<211> LENGTH: 123
<212> TYPE: PRT
<213> ORGANISM: Artificial Sequence
<220> FEATURE:
<223> OTHER INFORMATION: Polypeptide sequence of ID-141V

<400> SEQUENCE: 28

Asp Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
                20                  25                  30

Ser Ile Asn Val Met Ala Trp Tyr Arg Gln Ala Pro Gly Lys Gly Arg
            35                  40                  45

Glu Leu Val Ala Ile Ile Gly Lys Gly Gly Gly Thr Asn Tyr Ala Asp
        50                  55                  60

Phe Val Lys Gly Arg Phe Thr Ile Ser Arg Asp Ala Ala Lys Asn Thr
65                  70                  75                  80

Leu Tyr Leu Gln Met Asn Ser Leu Arg Pro Glu Asp Thr Ala Val Tyr
                    85                  90                  95

Tyr Cys Tyr Ala Asp Tyr Glu Asp His Asp Ser Pro His Asn Ala Ser
                    100                 105                 110

Trp Gly Gln Gly Thr Gln Val Thr Val Ser Ser
                    115                 120
```

<210> SEQ ID NO 29
<211> LENGTH: 123
<212> TYPE: PRT
<213> ORGANISM: Artificial Sequence
<220> FEATURE:
<223> OTHER INFORMATION: Polypeptide sequence of ID-142V

<400> SEQUENCE: 29

```
Asp Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
            20                  25                  30

Ser Ile Asn Val Met Ala Trp Tyr Arg Gln Ala Pro Gly Lys Gly Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Tyr Leu Gln Met Asn Ser Leu Arg Pro Glu Asp Thr Ala Val Tyr
                85                  90                  95

Tyr Cys Tyr Ala Asp Tyr Glu Asp His Asp Ser Pro His Asn Ala Ser
            100                 105                 110

Trp Gly Gln Gly Thr Gln Val Thr Val Ser Ser
        115                 120
```

<210> SEQ ID NO 30
<211> LENGTH: 123
<212> TYPE: PRT
<213> ORGANISM: Artificial Sequence
<220> FEATURE:
<223> OTHER INFORMATION: Polypeptide sequence of ID-143V

<400> SEQUENCE: 30

```
Asp Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
            20                  25                  30

Ser Ile Asn Val Met Ala Trp Tyr Arg Gln Ala Pro Gly Lys Gly Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Leu Tyr Leu Gln Met Asn Ser Leu Arg Pro Glu Asp Thr Ala Val Tyr
                85                  90                  95

Tyr Cys Tyr Ala Asp Tyr Glu Asp His Asp Ser Pro Phe Asn Ala Ser
            100                 105                 110

Trp Gly Gln Gly Thr Gln Val Thr Val Ser Ser
        115                 120
```

<210> SEQ ID NO 31
<211> LENGTH: 123
<212> TYPE: PRT
<213> ORGANISM: Artificial Sequence
<220> FEATURE:
<223> OTHER INFORMATION: Polypeptide sequence of ID-144V

<400> SEQUENCE: 31

```
Asp Val Gln Leu Val Glu Ser Gly Gly Gly Leu Val Gln Ala Gly Gly
```

```
                1               5                   10                  15
Ser Thr Arg Leu Thr Cys Lys Ala Ser Gly Ser Ile Ser Asn Ile Asn
                20                  25                  30

Ser Ile Asn Val Met Ala Trp Tyr Arg Gln Ala Pro Gly Lys Gly Arg
            35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Tyr Leu Gln Met Asn Ser Leu Arg Pro Glu Asp Thr Ala Val Tyr
                85                  90                  95

Tyr Cys Tyr Ala Asp Tyr Glu Asp His Asp Ser Pro Phe Asn Ala Ser
            100                 105                 110

Trp Gly Gln Gly Thr Gln Val Thr Val Ser Ser
            115                 120

<210> SEQ ID NO 32
<211> LENGTH: 120
<212> TYPE: PRT
<213> ORGANISM: Artificial Sequence
<220> FEATURE:
<223> OTHER INFORMATION: Polypeptide sequence of 7F6

<400> SEQUENCE: 32

Glu Val Gln Leu Val Glu Ser Gly Gly Gly Leu Val Gln Ala Gly Gly
1               5                   10                  15

Ser Thr Arg Leu Thr Cys Leu Ala Ser Gly Ser Ile Ser Ile Asn
                20                  25                  30

Val Ile Gly Trp Tyr Arg Gln Ala Pro Gly Lys Gln Arg Glu Leu Val
            35                  40                  45

Ala Met Ile Gly Arg Gly Gly Ala Asn Tyr Gly Asp Phe Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Tyr Glu Asp Arg Asp Ser Pro Phe Asn Gly Ser Trp Gly Gln
            100                 105                 110

Gly Thr Gln Val Thr Val Ser Ser
            115                 120

<210> SEQ ID NO 33
<211> LENGTH: 120
<212> TYPE: PRT
<213> ORGANISM: Artificial Sequence
<220> FEATURE:
<223> OTHER INFORMATION: Polypeptide sequence of ID-3V

<400> SEQUENCE: 33

Glu Val Gln Leu Val Glu Ser Gly Gly Gly Leu Val Gln Ala Gly Gly
1               5                   10                  15

Ser Thr Arg Leu Thr Cys Leu Ala Ser Gly Ser Ile Ser Ile Asn
                20                  25                  30

Val Ile Gly Trp Tyr Arg Gln Ala Pro Gly Lys Gln Arg Glu Leu Val
            35                  40                  45

Ala Met Ile Gly Arg Gly Glu Gly Ala Asn Tyr Gly Asp Phe Ala Lys
    50                  55                  60
```

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Tyr Glu Asp His Asp Ser Pro Phe Asn Gly Ser Trp Gly Gln
            100                 105                 110

Gly Thr Gln Val Thr Val Ser Ser
        115                 120

<210> SEQ ID NO 34
<211> LENGTH: 120
<212> TYPE: PRT
<213> ORGANISM: Artificial Sequence
<220> FEATURE:
<223> OTHER INFORMATION: Polypeptide sequence of ID-6V

<400> SEQUENCE: 34

Glu Val Gln Leu Val Glu Ser Gly Gly Gly Leu Val Gln Ala Gly Gly
1               5                   10                  15

Ser Thr Arg Leu Thr Cys Leu Ala Ser Gly Ser Ile Ser Ser Ile Asn
            20                  25                  30

Val Ile Gly Trp Tyr Arg Gln Ala Pro Gly Lys Gln Arg Glu Leu Val
        35                  40                  45

Ala Met Ile Gly Arg Gly Glu Gly Ala Asn Tyr Gly Asp Phe Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Tyr Glu Asp Arg Asp Ser Pro His Asn Gly Ser Trp Gly Gln
            100                 105                 110

Gly Thr Gln Val Thr Val Ser Ser
        115                 120

<210> SEQ ID NO 35
<211> LENGTH: 120
<212> TYPE: PRT
<213> ORGANISM: Artificial Sequence
<220> FEATURE:
<223> OTHER INFORMATION: Polypeptide sequence of ID-40V

<400> SEQUENCE: 35

Glu Val Gln Leu Val Glu Ser Gly Gly Gly Leu Val Gln Ala Gly Gly
1               5                   10                  15

Ser Thr Arg Leu Thr Cys Leu Ala Ser Gly Ser Ile Ser Ser Ile Asn
            20                  25                  30

Val Ile Gly Trp Tyr Arg Gln Ala Pro Gly Lys Gln Arg Glu Leu Val
        35                  40                  45

Ala Met Ile Gly Arg Gly Glu Gly Ala Asn Tyr Gly Asp Phe Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Tyr Glu Asp His Asp Ser Pro His Asn Gly Ser Trp Gly Gln
            100                 105                 110

Gly Thr Gln Val Thr Val Ser Ser
        115                 120

<210> SEQ ID NO 36
<211> LENGTH: 120
<212> TYPE: PRT
<213> ORGANISM: Artificial Sequence
<220> FEATURE:
<223> OTHER INFORMATION: Polypeptide sequence of ID-47V

<400> SEQUENCE: 36

```
Glu Val Gln Leu Val Glu Ser Gly Gly Gly Leu Val Gln Ala Gly Gly
1               5                   10                  15

Ser Thr Arg Leu Thr Cys Leu Ala Ser Gly Ser Ile Ser Ser Ile Asn
            20                  25                  30

Val Ile Gly Trp Tyr Arg Gln Ala Pro Gly Lys Gln Arg Glu Leu Val
        35                  40                  45

Ala Met Ile Gly Arg Gly Glu Gly Ala Asn Tyr Gly Asp Phe Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Tyr Glu Asp Arg Asp Ser Pro Ile Asn Gly Ser Trp Gly Gln
            100                 105                 110

Gly Thr Gln Val Thr Val Ser Ser
        115                 120
```

<210> SEQ ID NO 37
<211> LENGTH: 120
<212> TYPE: PRT
<213> ORGANISM: Artificial Sequence
<220> FEATURE:
<223> OTHER INFORMATION: Polypeptide sequence of ID-49V

<400> SEQUENCE: 37

```
Glu Val Gln Leu Val Glu Ser Gly Gly Gly Leu Val Gln Ala Gly Gly
1               5                   10                  15

Ser Thr Arg Leu Thr Cys Leu Ala Ser Gly Ser Ile Ser Ser Ile Asn
            20                  25                  30

Val Ile Gly Trp Tyr Arg Gln Ala Pro Gly Lys Gln Arg Glu Leu Val
        35                  40                  45

Ala Met Ile Gly Arg Gly Glu Gly Ala Asn Tyr Gly Asp Phe Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Tyr Glu Asp Arg Asp Ser Pro Thr Asn Gly Ser Trp Gly Gln
            100                 105                 110

Gly Thr Gln Val Thr Val Ser Ser
        115                 120
```

<210> SEQ ID NO 38
<211> LENGTH: 120
<212> TYPE: PRT
<213> ORGANISM: Artificial Sequence
<220> FEATURE:
<223> OTHER INFORMATION: Polypeptide sequence of ID-50V

<400> SEQUENCE: 38

-continued

Glu Val Gln Leu Val Glu Ser Gly Gly Gly Leu Val Gln Ala Gly Gly
1               5                   10                  15

Ser Thr Arg Leu Thr Cys Leu Ala Ser Gly Ser Ile Ser Ile Asn
            20                  25                  30

Val Ile Gly Trp Tyr Arg Gln Ala Pro Gly Lys Gln Arg Glu Leu Val
        35                  40                  45

Ala Met Ile Gly Arg Gly Glu Gly Ala Asn Tyr Gly Asp Phe Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Tyr Glu Asp Arg Asp Ser Pro Val Asn Gly Ser Trp Gly Gln
            100                 105                 110

Gly Thr Gln Val Thr Val Ser Ser
        115                 120

<210> SEQ ID NO 39
<211> LENGTH: 120
<212> TYPE: PRT
<213> ORGANISM: Artificial Sequence
<220> FEATURE:
<223> OTHER INFORMATION: Polypeptide sequence of 21E6

<400> SEQUENCE: 39

Glu Val Gln Leu Val Glu Ser Gly Gly Gly Leu Val Leu Ala Gly Gly
1               5                   10                  15

Ser Thr Arg Leu Thr Cys Leu Ala Ser Gly Ser Ile Ser Ile Asn
            20                  25                  30

Val Ile Gly Trp Tyr Arg Gln Ala Pro Gly Lys Gln Arg Glu Leu Val
        35                  40                  45

Ala Met Ile Gly Arg Gly Glu Gly Ala Asn Tyr Gly Asp Phe Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Ala Asp Tyr Glu Asp Arg Asp Ser Pro Leu Asn Gly Ser Trp Gly Gln
            100                 105                 110

Gly Thr Gln Val Thr Val Ser Ser
        115                 120

<210> SEQ ID NO 40
<211> LENGTH: 118
<212> TYPE: PRT
<213> ORGANISM: Artificial Sequence
<220> FEATURE:
<223> OTHER INFORMATION: Polypeptide sequence of 4D3

<400> SEQUENCE: 40

Glu Val Gln Leu Val Glu Ser Gly Gly Gly Ser Val Gln Ala Gly Glu
1               5                   10                  15

Ser Leu Thr Leu Ser Cys Val Ala Ser Ile Ser Thr Phe Ser Gln Asn
            20                  25                  30

Ala Met Gly Trp Phe Arg Gln Ala Ala Gly Lys Arg Arg Glu Ser Val
        35                  40                  45

Ala Arg Ile Ser Ser Ser Gly Asn Val Gly Tyr Thr Asp Ala Val Lys
    50                  55                  60

```
Gly Arg Phe Thr Met Ser Arg Asp Asn Ala Lys Lys Thr Val Tyr Leu
65                  70                  75                  80

Gln Met Asn Ser Leu Lys Pro Glu Asp Thr Ala Val Tyr Tyr Cys Asn
                85                  90                  95

Ala Tyr Ser Met Ser Gly Glu Leu Ala Ala Pro Trp Gly Gln Gly Thr
            100                 105                 110

Gln Val Thr Val Ser Ser
        115

<210> SEQ ID NO 41
<211> LENGTH: 115
<212> TYPE: PRT
<213> ORGANISM: Artificial Sequence
<220> FEATURE:
<223> OTHER INFORMATION: Polypeptide sequence of 3C12

<400> SEQUENCE: 41

Glu Val Gln Leu Val Glu Ser Gly Gly Gly Leu Ala Gln Leu Gly Gly
1               5                   10                  15

Ser Leu Arg Leu Ser Cys Val Ala Ser Gly Asn Ile Phe Ser Ser Asn
                20                  25                  30

Thr Ala Gly Trp Phe Arg Gln Ala Pro Gly Lys Gln Arg Glu Trp Val
            35                  40                  45

Ala Gly Ile Ser Ile Gly Gly Met Pro Ala Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95

Thr Gly Gly Thr Glu Tyr Asp Tyr Trp Gly Gln Gly Thr Gln Val Thr
            100                 105                 110

Val Ser Ser
        115

<210> SEQ ID NO 42
<211> LENGTH: 121
<212> TYPE: PRT
<213> ORGANISM: Artificial Sequence
<220> FEATURE:
<223> OTHER INFORMATION: Polypeptide sequence of 20A11

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Ser Val Phe Lys Ile Asn
                20                  25                  30

Val Met Ala Trp Tyr Arg Gln Ala Pro Gly Lys Gly Arg Glu Leu Val
            35                  40                  45

Ala Gly Ile Ile Ser Gly Gly Ser Thr Ser Tyr Ala Asp Ser Val Lys
        50                  55                  60

Gly Arg Phe Thr Ile Ser Arg Asp Asn Ala Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Phe Ile Thr Thr Glu Ser Asp Tyr Asp Leu Gly Arg Arg Tyr Trp Gly
            100                 105                 110

Gln Gly Thr Leu Val Thr Val Ser Ser
```

-continued 115   120

<210> SEQ ID NO 43
<211> LENGTH: 123
<212> TYPE: PRT
<213> ORGANISM: Artificial Sequence
<220> FEATURE:
<223> OTHER INFORMATION: Polypeptide sequence of ID-74V

<400> SEQUENCE: 43

Asp Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Phe Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp His Asp Ser Pro Phe Asn Ala Ser
            100                 105                 110

Trp Gly Gln Gly Thr Gln Val Thr Val Ser Ser
        115                 120

<210> SEQ ID NO 44
<211> LENGTH: 123
<212> TYPE: PRT
<213> ORGANISM: Artificial Sequence
<220> FEATURE:
<223> OTHER INFORMATION: Polypeptide sequence of ID-75V

<400> SEQUENCE: 44

Asp Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
            20                  25                  30

Ser Ile Asn Val Met Ala Trp Tyr Arg Gln Ala Pro Gly Lys Gln Arg
        35                  40                  45

Glu Leu Val Ala Ile Ile Gly Lys Gly Gly Thr Asn Tyr Ala Asp
    50                  55                  60

Phe Val Lys Gly Arg Phe Thr Ile Ser Arg Asp Ala Ala Lys Asn Thr
65                  70                  75                  80

Val Asn Leu Gln Met Asn Ser Leu Lys Pro Glu Asp Thr Ala Val Tyr
                85                  90                  95

Tyr Cys Tyr Ala Asp Tyr Glu Asp His Asp Ser Pro Phe Asn Ala Ser
            100                 105                 110

Trp Gly Gln Gly Thr Gln Val Thr Val Ser Ser
        115                 120

<210> SEQ ID NO 45
<211> LENGTH: 111
<212> TYPE: PRT
<213> ORGANISM: Artificial Sequence
<220> FEATURE:
<223> OTHER INFORMATION: Polypeptide sequence of ID-2A

<400> SEQUENCE: 45

-continued

Asp Val Gln Leu Gln Glu Ser Gly Gly Gly Leu Val Gln Ala Gly Gly
1               5                   10                  15

Ser Leu Arg Leu Ser Cys Val Ile Ser Gly Met Asp Phe Ser His Lys
            20                  25                  30

Pro Ala Gly Trp Phe Arg Gln Ala Pro Gly Lys Glu Arg Glu Phe Val
        35                  40                  45

Ala Ser Ile Thr Thr Arg Ala Ser Thr His Tyr Ala Asp Ser Val Lys
    50                  55                  60

Gly Arg Phe Thr Ile Ser Arg Asp Asn Ala Lys Asn Thr Val Tyr Leu
65              70                  75                  80

Glu Met Asn Ser Leu Lys Pro Glu Asp Thr Ala Val Tyr Ser Cys Asn
                85                  90                  95

Ser Glu Tyr Tyr Trp Gly Gln Gly Thr Gln Val Thr Val Ser Ser
            100                 105                 110

<210> SEQ ID NO 46
<211> LENGTH: 16
<212> TYPE: PRT
<213> ORGANISM: Artificial Sequence
<220> FEATURE:
<223> OTHER INFORMATION: Polypeptide sequence of ID-58V CDR2

<400> SEQUENCE: 46

Ile Ile Gly Lys Gly Gly Gly Thr Asn Tyr Ala Asp Val Val Lys Gly
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Polypeptide sequence of ID-59V CDR2

<400> SEQUENCE: 47

Ile Ile Gly Lys Gly Gly Gly Thr Asn Asp Ala Asp Phe Val Lys Gly
1               5                   10                  15

<210> SEQ ID NO 48
<211> LENGTH: 12
<212> TYPE: PRT
<213> ORGANISM: Artificial Sequence
<220> FEATURE:
<223> OTHER INFORMATION: Polypeptide sequence of CDR3 of multiple ICVDs
      including 5G9

<400> SEQUENCE: 48

Asp Tyr Glu Asp Arg Asp Ser Pro Phe Asn Ala Ser
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Polypeptide sequence of ID-53V CDR3

<400> SEQUENCE: 49

Asp Tyr Glu Asp Arg Asp Ser Pro His Asn Ala Ser
1               5                   10

<210> SEQ ID NO 50
<211> LENGTH: 12
<212> TYPE: PRT

<213> ORGANISM: Artificial Sequence
<220> FEATURE:
<223> OTHER INFORMATION: Polypeptide sequence of CDR3 of multiple ICVDs including ID-143V

<400> SEQUENCE: 50

Asp Tyr Glu Asp His Asp Ser Pro Phe Asn Ala Ser
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Polypeptide sequence of 7F6 CDR3

<400> SEQUENCE: 51

Asp Tyr Glu Asp Arg Asp Ser Pro Phe Asn Gly Ser
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Polypeptide sequence of ID-3V CDR3

<400> SEQUENCE: 52

Asp Tyr Glu Asp His Asp Ser Pro Phe Asn Gly Ser
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Polypeptide sequence of ID-6V CDR3

<400> SEQUENCE: 53

Asp Tyr Glu Asp Arg Asp Ser Pro His Asn Gly Ser
1               5                   10

<210> SEQ ID NO 54
<211> LENGTH: 1407
<212> TYPE: DNA
<213> ORGANISM: Artificial Sequence
<220> FEATURE:
<223> OTHER INFORMATION: Polynucleotide sequence encoding human IL-6R

<400> SEQUENCE: 54

```
atgctggccg tcggctgcgc gctgctggct gccctgctgg ccgcgccggg agcggcgctg      60
gccccaaggc gctgccctgc gcaggaggtg caagaggcg tgctgaccag tctgccagga     120
dacagcgtga ctctgacctg cccggggta gagccggaag acaatgccac tgttcactgg     180
gtgctcagga agccggctgc aggctcccac ccagcagat gggctggcat gggaaggagg     240
ctgctgctga ggtcggtgca gctccacgac tctggaaact attcatgcta ccgggccggc     300
cgcccagctg gactgtgca cttgctggtg gatgttcccc ccgaggagcc ccagctctcc     360
tgcttccgga agagccccct cagcaatgtt gtttgtgagt ggggtcctcg gagcacccca     420
tccctgacga caaaggctgt gctcttggtg aggaagtttc agaacagtcc ggccgaagac     480
ttccaggagc cgtgccagta ttcccaggag tcccagaagt tctcctgcca gttagcagtc     540
ccggagggag acagctcttt ctacatagtg tccatgtgcg tcgccagtag tgtcgggagc     600
```

```
aagttcagca aaactcaaac ctttcagggt tgtggaatct tgcagcctga tccgcctgcc    660
aacatcacag tcactgccgt ggccagaaac ccccgctggc tcagtgtcac ctggcaagac    720
ccccactcct ggaactcatc tttctacaga ctacggtttg agctcagata tcgggctgaa    780
cggtcaaaga cattcacaac atggatggtc aaggacctcc agcatcactg tgtcatccac    840
gacgcctgga gcggcctgag gcacgtggtg cagcttcgtg cccaggagga gttcgggcaa    900
ggcgagtgga gcgagtggag cccggaggcc atgggcacgc cttggacaga atccaggagt    960
cctccagctg agaacgaggt gtccaccccc atgcaggcac ttactactaa taaagacgat   1020
gataatattc tcttcagaga ttctgcaaat gcgacaagcc tcccagtgca agattcttct   1080
tcagtaccac tgcccacatt cctggttgct ggagggagcc tggccttcgg aacgctcctc   1140
tgcattgcca ttgttctgag gttcaagaag acgtggaagc tgcgggctct gaaggaaggc   1200
aagacaagca tgcatccgcc gtactctttg gggcagctgg tcccggagag gcctcgaccc   1260
accccagtgc ttgttcctct catctcccca ccggtgtccc ccagcagcct ggggtctgac   1320
aatacctcga gccacaaccg accagatgcc agggacccac ggagccctta tgacatcagc   1380
aatacagact acttcttccc cagatag                                        1407
```

<210> SEQ ID NO 55
<211> LENGTH: 12
<212> TYPE: PRT
<213> ORGANISM: Artificial Sequence
<220> FEATURE:
<223> OTHER INFORMATION: Polypeptide sequence of ID-47V CDR3

<400> SEQUENCE: 55

Asp Tyr Glu Asp Arg Asp Ser Pro Ile Asn Gly Ser
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Polypeptide sequence of ID-49V CDR3

<400> SEQUENCE: 56

Asp Tyr Glu Asp Arg Asp Ser Pro Thr Asn Gly Ser
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Polypeptide sequence of ID-50V CDR3

<400> SEQUENCE: 57

Asp Tyr Glu Asp Arg Asp Ser Pro Val Asn Gly Ser
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Polypeptide sequence of 21E6 CDR3

<400> SEQUENCE: 58

Asp Tyr Glu Asp Arg Asp Ser Pro Leu Asn Gly Ser
1               5                   10

<210> SEQ ID NO 59
<211> LENGTH: 369
<212> TYPE: DNA
<213> ORGANISM: Artificial Sequence
<220> FEATURE:
<223> OTHER INFORMATION: Polynucleotide sequence encoding 5G9

<400> SEQUENCE: 59

| gaggtgcagc tggtggagtc tgggggaggt ttggtgcagg ctgggggtc aacgagactc | 60 |
| acctgtaaag cctctggaag tatcttcaat atcaacagta tcaacgtcat ggcatggtac | 120 |
| cgccaggctc cagggaagca gcgcgaattg gtcgcaatta ttggtaaagg tggtgggaca | 180 |
| aactacgcag acttcgtgaa gggccgattc accatttcca gagatgctgc caagaacacg | 240 |
| gtaaatctgc aaatgaacag cttgaaacct gaggacacgg ccgtctatta ctgttatgcg | 300 |
| gattatgaag atcgggattc cccgtttaac gcttcctggg gccaggggac ccaggtcacc | 360 |
| gtctcctca | 369 |

<210> SEQ ID NO 60
<211> LENGTH: 369
<212> TYPE: DNA
<213> ORGANISM: Artificial Sequence
<220> FEATURE:
<223> OTHER INFORMATION: Polynucleotide sequence encoding 5G9 (codon
       optimised)

<400> SEQUENCE: 60

| gaagtccaat tggttgaatc tggtggtggt ttggttcaag ccggtggttc tactagattg | 60 |
| acttgtaaag cttccggttc catcttcaac atcaactcca ttaacgttat ggcctggtat | 120 |
| agacaagctc caggtaaaca aagagaattg gttgccatta ttggtaaggg tggtggtact | 180 |
| aattatgccg attttgttaa gggtagattc accatttcta gagatgctgc taagaacacc | 240 |
| gttaacttgc aaatgaattc cttgaagcca gaagataccg ctgtttatta ctgttacgct | 300 |
| gactacgaag atagagactc cccttttaat gcttcttggg gtcaaggtac tcaggtcacc | 360 |
| gtttcttct | 369 |

<210> SEQ ID NO 61
<211> LENGTH: 360
<212> TYPE: DNA
<213> ORGANISM: Artificial Sequence
<220> FEATURE:
<223> OTHER INFORMATION: Polynucleotide sequence encoding 7F6

<400> SEQUENCE: 61

| gaggtgcagc tggtggagtc tgggggaggt ttggtgcagg ctgggggtc tacgaggctc | 60 |
| acctgtttag cctctggaag tatcagcagt atcaatgtca taggatggta ccgccaggct | 120 |
| ccagggaagc agcgcgagtt ggtcgcaatg attggtagag gtgaaggcgc aaactatgga | 180 |
| gacttcgcga agggccgatt caccatctcc agagacaata gcaagaacac ggtgtatctg | 240 |
| caaatgaaca gcttgaaacc tgaggacacg gccgtctatt actgttatgc agattatgaa | 300 |
| gatcgggatt tccgtttaa tggttcctgg ggccagggga cccaggtcac cgtctcctca | 360 |

<210> SEQ ID NO 62
<211> LENGTH: 360
<212> TYPE: DNA
<213> ORGANISM: Artificial Sequence
<220> FEATURE:
<223> OTHER INFORMATION: Polynucleotide sequence encoding 21E6

```
<400> SEQUENCE: 62
gaggtgcagc tggtggagtc tgggggaggt tggtgctcg ctggggggtc tacgaggctc      60
acctgtttag cctctggaag tatcagcagt atcaatgtca taggatggta ccgccaggct    120
ccagggaagc agcgcgagtt ggtcgcaatg attggtagag gtgaaggcgc aaactatgga    180
gacttcgcga agggccgatt caccatctcc agagacaata gcaagaacac ggtgtatctg    240
caaatgaaca gcttgaaacc tgaggacacg gccgtctatt actgttatgc agattatgaa    300
gatcgggatt ctccgctcaa tggttcctgg ggccagggga cccaggtcac cgtctcctca    360

<210> SEQ ID NO 63
<211> LENGTH: 369
<212> TYPE: DNA
<213> ORGANISM: Artificial Sequence
<220> FEATURE:
<223> OTHER INFORMATION: Polynucleotide sequence encoding ID-52V

<400> SEQUENCE: 63
gaggtgcagc tggtggagtc tgggggaggt tggtgcagg ctgggggtc aacgagactc       60 acctgtaaag cctctggaag tatcttcaat atcaacagta tcaacgtcat ggcatggtac    120
cgccaggctc agggaagca gcgcgaattg gtcgcaatta ttggtaaagg tggtgggaca    180
aactacgcag acttcgtgaa gggccgattc accatttcca gagatgctgc caagaacacg    240
gtaaatctgc aaatgaacag cttgaaacct gaggacacgg ccgtctatta ctgttatgcg    300
gattatgaag atcatgattc cccgcacaac gcttcctggg gccaggggac ccaggtcacc    360
gtctcctca                                                            369

<210> SEQ ID NO 64
<211> LENGTH: 369
<212> TYPE: DNA
<213> ORGANISM: Artificial Sequence
<220> FEATURE:
<223> OTHER INFORMATION: Polynucleotide sequence encoding ID-53V

<400> SEQUENCE: 64
gaggtgcagc tggtggagtc tgggggaggt tggtgcagg ctgggggtc aacgagactc       60 acctgtaaag cctctggaag tatcttcaat atcaacagta tcaacgtcat ggcatggtac    120
cgccaggctc agggaagca gcgcgaattg gtcgcaatta ttggtaaagg tggtgggaca    180
aactacgcag acttcgtgaa gggccgattc accatttcca gagatgctgc caagaacacg    240
gtaaatctgc aaatgaacag cttgaaacct gaggacacgg ccgtctatta ctgttatgcg    300
gattatgaag atcgggattc cccgcataac gcttcctggg gccaggggac ccaggtcacc    360
gtctcctca                                                            369

<210> SEQ ID NO 65
<211> LENGTH: 369
<212> TYPE: DNA
<213> ORGANISM: Artificial Sequence
<220> FEATURE:
<223> OTHER INFORMATION: Polynucleotide sequence encoding ID-54V

<400> SEQUENCE: 65
gaggtgcagc tggtggagtc tgggggaggt tggtgcagg ctgggggtc aacgagactc       60 acctgtaaag cctctggaag tatcttcaat atcaacagta tcaacgtcat ggcatggtac    120
cgccaggctc agggaagca gcgcgaattg gtcgcaatta ttggtaaagg tggtgggaca    180
```

```
aactacgcag acttcgtgaa gggccgattc accatttcca gagatgctgc caagaacacg    240
gtaaatctgc aaatgaacag cttgaaacct gaggacacgg ccgtctatta ctgttatgcg    300
gattatgaag atcatgattc cccgtttaac gcttcctggg gccaggggac ccaggtcacc    360
gtctcctca                                                            369
```

<210> SEQ ID NO 66
<211> LENGTH: 369
<212> TYPE: DNA
<213> ORGANISM: Artificial Sequence
<220> FEATURE:
<223> OTHER INFORMATION: Polynucleotide sequence encoding ID-55V

<400> SEQUENCE: 66

```
gaggtgcagc tggtggagtc tggggggaggt ttggtgcagg ctggggggtc aacgagactc     60
acctgtcatg cctctggaag tatcttcaat atcaacagta tcaacgtcat ggcatggtac    120
cgccaggctc cagggaagca gcgcgaattg gtcgcaatta ttggtaaagg tggtgggaca    180
aactacgcag acttcgtgaa gggccgattc accatttcca gagatgctgc caagaacacg    240
gtaaatctgc aaatgaacag cttgaaacct gaggacacgg ccgtctatta ctgttatgcg    300
gattatgaag atcgggattc cccgtttaac gcttcctggg gccaggggac ccaggtcacc    360
gtctcctca                                                            369
```

<210> SEQ ID NO 67
<211> LENGTH: 369
<212> TYPE: DNA
<213> ORGANISM: Artificial Sequence
<220> FEATURE:
<223> OTHER INFORMATION: Polynucleotide sequence encoding ID-56V

<400> SEQUENCE: 67

```
gaggtgcagc tggtggagtc tggggggaggt ttggtgcagg ctggggggtc aacgagactc     60
acctgtaaag cctctggaag tatctctaat atcaacagta tcaacgtcat ggcatggtac    120
cgccaggctc cagggaagca gcgcgaattg gtcgcaatta ttggtaaagg tggtgggaca    180
aactacgcag acttcgtgaa gggccgattc accatttcca gagatgctgc caagaacacg    240
gtaaatctgc aaatgaacag cttgaaacct gaggacacgg ccgtctatta ctgttatgcg    300
gattatgaag atcgggattc cccgtttaac gcttcctggg gccaggggac ccaggtcacc    360
gtctcctca                                                            369
```

<210> SEQ ID NO 68
<211> LENGTH: 369
<212> TYPE: DNA
<213> ORGANISM: Artificial Sequence
<220> FEATURE:
<223> OTHER INFORMATION: Polynucleotide sequence encoding ID-57V

<400> SEQUENCE: 68

```
gaggtgcagc tggtggagtc tggggggaggt ttggtgcagg ctggggggtc aacgagactc     60
acctgtaaag cctctggaag tatcattaat atcaacagta tcaacgtcat ggcatggtac    120
cgccaggctc cagggaagca gcgcgaattg gtcgcaatta ttggtaaagg tggtgggaca    180
aactacgcag acttcgtgaa gggccgattc accatttcca gagatgctgc caagaacacg    240
gtaaatctgc aaatgaacag cttgaaacct gaggacacgg ccgtctatta ctgttatgcg    300
gattatgaag atcgggattc cccgtttaac gcttcctggg gccaggggac ccaggtcacc    360
gtctcctca                                                            369
```

<210> SEQ ID NO 69
<211> LENGTH: 369
<212> TYPE: DNA
<213> ORGANISM: Artificial Sequence
<220> FEATURE:
<223> OTHER INFORMATION: Polynucleotide sequence encoding ID-58V

<400> SEQUENCE: 69

```
gaggtgcagc tggtggagtc tgggggaggt ttggtgcagg ctggggggtc aacgagactc      60
acctgtaaag cctctggaag tatcttcaat atcaacagta tcaacgtcat ggcatggtac     120
cgccaggctc cagggaagca gcgcgaattg gtcgcaatta ttggtaaagg tggtgggaca     180
aactacgcag acgttgtgaa gggccgattc accatttcca gagatgctgc caagaacacg     240
gtaaatctgc aaatgaacag cttgaaacct gaggacacgg ccgtctatta ctgttatgcg     300
gattatgaag atcgggattc cccgtttaac gcttcctggg gccaggggac ccaggtcacc     360
gtctcctca                                                            369
```

<210> SEQ ID NO 70
<211> LENGTH: 369
<212> TYPE: DNA
<213> ORGANISM: Artificial Sequence
<220> FEATURE:
<223> OTHER INFORMATION: Polynucleotide sequence encoding ID-59V

<400> SEQUENCE: 70

```
gaggtgcagc tggtggagtc tgggggaggt ttggtgcagg ctggggggtc aacgagactc      60
acctgtaaag cctctggaag tatcttcaat atcaacagta tcaacgtcat ggcatggtac     120
cgccaggctc cagggaagca gcgcgaattg gtcgcaatta ttggtaaagg tggtgggaca     180
aacgatgcag acttcgtgaa gggccgattc accatttcca gagatgctgc caagaacacg     240
gtaaatctgc aaatgaacag cttgaaacct gaggacacgg ccgtctatta ctgttatgcg     300
gattatgaag atcgggattc cccgtttaac gcttcctggg gccaggggac ccaggtcacc     360
gtctcctca                                                            369
```

<210> SEQ ID NO 71
<211> LENGTH: 369
<212> TYPE: DNA
<213> ORGANISM: Artificial Sequence
<220> FEATURE:
<223> OTHER INFORMATION: Polynucleotide sequence encoding ID-74V

<400> SEQUENCE: 71

```
gatgtgcagc tggtggagtc tgggggaggt ttggtgcagg ctggggggtc aacgagactc      60
acctgtaaag cctctggaag tatcttcaat atcaacagta tcaacgtcat ggcatggtac     120
cgccaggctc cagggaagca gcgcgaattg gtcgcaatta ttggtaaagg tggtgggaca     180
aactacgcag acttcgtgaa gggccgattc accatttcca gagatgctgc caagaacacg     240
gtaaatctgc aaatgaacag cttgaaacct gaggacacgg ccgtctatta ctgttatgcg     300
gattatgaag atcacgattc cccgtttaac gcttcctggg gccaggggac ccaggtcacc     360
gtctcctca                                                            369
```

<210> SEQ ID NO 72
<211> LENGTH: 369
<212> TYPE: DNA
<213> ORGANISM: Artificial Sequence
<220> FEATURE:

<223> OTHER INFORMATION: Polynucleotide sequence encoding ID-75V

<400> SEQUENCE: 72

| gatgtgcagc tggtggagtc tgggggaggt ttggtgcagg ctggggggtc aacgagactc | 60 |
| acctgtaaag cctctggaag tatcagcaat atcaacagta tcaacgtcat ggcatggtac | 120 |
| cgccaggctc cagggaagca gcgcgaattg gtcgcaatta ttggtaaagg tggtgggaca | 180 |
| aactacgcag acttcgtgaa gggccgattc accatttcca gagatgctgc caagaacacg | 240 |
| gtaaatctgc aaatgaacag cttgaaacct gaggacacgg ccgtctatta ctgttatgcg | 300 |
| gattatgaag atcacgattc cccgtttaac gcttcctggg gccaggggac ccaggtcacc | 360 |
| gtctcctca | 369 |

<210> SEQ ID NO 73
<211> LENGTH: 369
<212> TYPE: DNA
<213> ORGANISM: Artificial Sequence
<220> FEATURE:
<223> OTHER INFORMATION: Polynucleotide sequence encoding ID-112V

<400> SEQUENCE: 73

| gaagttcagc tggttgaaag cggtggtggt ctggttcagg caggcggtag cacccgtctg | 60 |
| acctgtaaag caagcggtag cattagcaat attaacagca ttaatgtgat ggcctggtat | 120 |
| cgtcaggcac cgggtaaagg tcgtgaactg gttgcaatta ttggtaaagg tggtggcacc | 180 |
| aattatgccg attttgtgaa aggtcgtttt accattagcc gtgatgcagc aaaaaatacc | 240 |
| gttaacctgc agatgaatag cctgcgtccg gaagataccg cagtgtatta ttgttatgcg | 300 |
| gattatgaag atcacgacag cccgtttaat gcaagctggg gtcagggcac ccaggtcacc | 360 |
| gttagcagc | 369 |

<210> SEQ ID NO 74
<211> LENGTH: 369
<212> TYPE: DNA
<213> ORGANISM: Artificial Sequence
<220> FEATURE:
<223> OTHER INFORMATION: Polynucleotide sequence encoding ID-114V

<400> SEQUENCE: 74

| gaagttcagc tggttgaaag cggtggtggt ctggttcagg caggcggtag cacccgtctg | 60 |
| acctgtaaag caagcggtag cattagcaat attaacagca ttaatgtgat ggcctggtat | 120 |
| cgtcaggcac cgggtaaaca gcgtgaactg gttgcaatta ttggtaaagg tggtggcacc | 180 |
| aattatgccg attttgttaa aggtcgtttt accattagcc gtgatgcagc aaaaaatacc | 240 |
| ctgtacctgc agatgaatag cctgaaaccg gaagataccg cagtgtatta ttgttatgcg | 300 |
| gattatgaag atcacgacag cccgtttaat gcaagctggg gtcagggcac ccaggtcacc | 360 |
| gttagcagc | 369 |

<210> SEQ ID NO 75
<211> LENGTH: 369
<212> TYPE: DNA
<213> ORGANISM: Artificial Sequence
<220> FEATURE:
<223> OTHER INFORMATION: Polynucleotide sequence encoding ID-122V

<400> SEQUENCE: 75

| gaagttcagc tggttgaaag cggtggtggt ctggttcagg caggcggtag cacccgtctg | 60 |
| acctgtaaag caagcggtag cattagcaat attaacagca ttaatgtgat ggcctggtat | 120 |

```
cgtcaggcac cgggtaaagg tcgtgaactg gttgcaatta ttggtaaagg tggtggcacc      180
aattatgccg attttgtgaa aggtcgtttt accattagcc gtgatgcagc aaaaaatacc      240
gttaacctgc agatgaatag cctgcgtccg gaagataccg cagtgtatta ttgttatgcg      300
gattatgagg atcatgacag tccgcataat gcaagctggg gtcagggcac ccaggtcacc      360
gttagcagc                                                             369
```

<210> SEQ ID NO 76
<211> LENGTH: 369
<212> TYPE: DNA
<213> ORGANISM: Artificial Sequence
<220> FEATURE:
<223> OTHER INFORMATION: Polynucleotide sequence encoding ID-123V

<400> SEQUENCE: 76

```
gaagttcagc tggttgaaag cggtggtggt ctggttcagg caggcggtag cacccgtctg      60
acctgtaaag caagcggtag cattagcaat attaacagca ttaatgtgat ggcctggtat     120
cgtcaggcac cgggtaaagg tcgtgaactg gttgcaatta ttggtaaagg tggtggcacc     180
aattatgccg attttgtgaa aggtcgtttt accattagcc gtgatgcagc aaaaaatacc     240
gtttacctgc agatgaatag cctgcgtccg gaagataccg cagtgtatta ttgttatgcg     300
gattatgagg atcatgacag tccgcataat gcaagctggg gtcagggcac ccaggtcacc     360
gttagcagc                                                             369
```

<210> SEQ ID NO 77
<211> LENGTH: 369
<212> TYPE: DNA
<213> ORGANISM: Artificial Sequence
<220> FEATURE:
<223> OTHER INFORMATION: Polynucleotide sequence encoding ID-141V

<400> SEQUENCE: 77

```
gatgtgcagc tggtggagtc tgggggaggt ttggtgcagg ctgggggggtc aacgagactc      60 acctgtaaag cctctggaag tatcagcaat atcaacagta tcaacgtcat ggcatggtac     120
cgccaggctc cagggaaggg tcgcgaattg gtcgcaatta ttggtaaagg tggtgggaca     180
aactacgcag acttcgtgaa gggccgattc accatttcca gagatgctgc caagaacacg     240
ttgtatctgc aaatgaacag cttgagacct gaggacacgc cgtctatta ctgttatgcg      300 gattatgaag atcacgattc cccgcataac gcttcctggg gccaggggac ccaggtcacc     360
gtctcctca                                                             369
```

<210> SEQ ID NO 78
<211> LENGTH: 369
<212> TYPE: DNA
<213> ORGANISM: Artificial Sequence
<220> FEATURE:
<223> OTHER INFORMATION: Polynucleotide sequence encoding ID-142V

<400> SEQUENCE: 78

```
gatgtgcagc tggtggagtc tgggggaggt ttggtgcagg ctgggggggtc aacgagactc      60 acctgtaaag cctctggaag tatcagcaat atcaacagta tcaacgtcat ggcatggtac     120
cgccaggctc cagggaaggg tcgcgaattg gtcgcaatta ttggtaaagg tggtgggaca     180
aactacgcag acttcgtgaa gggccgattc accatttcca gagatgctgc caagaacacg     240
gtatatctgc aaatgaacag cttgagacct gaggacacgg ccgtctatta ctgttatgcg     300
```

```
gattatgaag atcacgattc cccgcataac gcttcctggg gccaggggac ccaggtcacc    360
gtctcctca                                                           369

<210> SEQ ID NO 79
<211> LENGTH: 369
<212> TYPE: DNA
<213> ORGANISM: Artificial Sequence
<220> FEATURE:
<223> OTHER INFORMATION: Polynucleotide sequence encoding ID-143V

<400> SEQUENCE: 79
gatgtgcagc tggtggagtc tgggggaggt ttggtgcagg ctggggggtc aacgagactc     60
acctgtaaag cctctggaag tatcagcaat atcaacagta tcaacgtcat ggcatggtac    120
cgccaggctc cagggaaggg tcgcgaattg gtcgcaatta ttggtaaagg tggtgggaca    180
aactacgcag acttcgtgaa gggccgattc accatttcca gagatgctgc caagaacacg    240
ttgtatctgc aaatgaacag cttgagacct gaggacacgg ccgtctatta ctgttatgcg    300
gattatgaag atcacgattc cccgtttaac gcttcctggg gccaggggac ccaggtcacc    360
gtctcctca                                                           369

<210> SEQ ID NO 80
<211> LENGTH: 369
<212> TYPE: DNA
<213> ORGANISM: Artificial Sequence
<220> FEATURE:
<223> OTHER INFORMATION: Polynucleotide sequence encoding ID-144V

<400> SEQUENCE: 80
gatgtgcagc tggtggagtc tgggggaggt ttggtgcagg ctggggggtc aacgagactc     60
acctgtaaag cctctggaag tatcagcaat atcaacagta tcaacgtcat ggcatggtac    120
cgccaggctc cagggaaggg tcgcgaattg gtcgcaatta ttggtaaagg tggtgggaca    180
aactacgcag acttcgtgaa gggccgattc accatttcca gagatgctgc caagaacacg    240
gtatatctgc aaatgaacag cttgagacct gaggacacgg ccgtctatta ctgttatgcg    300
gattatgaag atcacgattc cccgtttaac gcttcctggg gccaggggac ccaggtcacc    360
gtctcctca                                                           369

<210> SEQ ID NO 81
<211> LENGTH: 468
<212> TYPE: PRT
<213> ORGANISM: Artificial Sequence
<220> FEATURE:
<223> OTHER INFORMATION: Polypeptide sequence of human IL-6R

<400> SEQUENCE: 81

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95
```

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
    370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
        435                 440                 445

Asp Ala Arg Asp Pro Arg Ser Pro Tyr Asp Ile Ser Asn Thr Asp Tyr
    450                 455                 460

Phe Phe Pro Arg
465

<210> SEQ ID NO 82
<211> LENGTH: 449
<212> TYPE: PRT
<213> ORGANISM: Artificial Sequence
<220> FEATURE:

<223> OTHER INFORMATION: Polypeptide sequence of mature human IL-6R (cleaved at L20)

<400> SEQUENCE: 82

| | | | | | | | | | | | | | | |
|---|---|---|---|---|---|---|---|---|---|---|---|---|---|---|
| Leu | Ala | Pro | Arg | Arg | Cys | Pro | Ala | Gln | Glu | Val | Ala | Arg | Gly | Val | Leu |
| 1 | | | | 5 | | | | | 10 | | | | | 15 | |
| Thr | Ser | Leu | Pro | Gly | Asp | Ser | Val | Thr | Leu | Thr | Cys | Pro | Gly | Val | Glu |
| | | | 20 | | | | | 25 | | | | | 30 | | |
| Pro | Glu | Asp | Asn | Ala | Thr | Val | His | Trp | Val | Leu | Arg | Lys | Pro | Ala | Ala |
| | | | 35 | | | | | 40 | | | | | 45 | | |
| Gly | Ser | His | Pro | Ser | Arg | Trp | Ala | Gly | Met | Gly | Arg | Arg | Leu | Leu | Leu |
| | | 50 | | | | | 55 | | | | | 60 | | | |
| Arg | Ser | Val | Gln | Leu | His | Asp | Ser | Gly | Asn | Tyr | Ser | Cys | Tyr | Arg | Ala |
| 65 | | | | | 70 | | | | | 75 | | | | | 80 |
| Gly | Arg | Pro | Ala | Gly | Thr | Val | His | Leu | Leu | Val | Asp | Val | Pro | Pro | Glu |
| | | | | 85 | | | | | 90 | | | | | 95 | |
| Glu | Pro | Gln | Leu | Ser | Cys | Phe | Arg | Lys | Ser | Pro | Leu | Ser | Asn | Val | Val |
| | | | 100 | | | | | 105 | | | | | 110 | | |
| Cys | Glu | Trp | Gly | Pro | Arg | Ser | Thr | Pro | Ser | Leu | Thr | Thr | Lys | Ala | Val |
| | | | 115 | | | | | 120 | | | | | 125 | | |
| Leu | Leu | Val | Arg | Lys | Phe | Gln | Asn | Ser | Pro | Ala | Glu | Asp | Phe | Gln | Glu |
| | | 130 | | | | | 135 | | | | | 140 | | | |
| Pro | Cys | Gln | Tyr | Ser | Gln | Glu | Ser | Gln | Lys | Phe | Ser | Cys | Gln | Leu | Ala |
| 145 | | | | | 150 | | | | | 155 | | | | | 160 |
| Val | Pro | Glu | Gly | Asp | Ser | Ser | Phe | Tyr | Ile | Val | Ser | Met | Cys | Val | Ala |
| | | | | 165 | | | | | 170 | | | | | 175 | |
| Ser | Ser | Val | Gly | Ser | Lys | Phe | Ser | Lys | Thr | Gln | Thr | Phe | Gln | Gly | Cys |
| | | | 180 | | | | | 185 | | | | | 190 | | |
| Gly | Ile | Leu | Gln | Pro | Asp | Pro | Pro | Ala | Asn | Ile | Thr | Val | Thr | Ala | Val |
| | | | 195 | | | | | 200 | | | | | 205 | | |
| Ala | Arg | Asn | Pro | Arg | Trp | Leu | Ser | Val | Thr | Trp | Gln | Asp | Pro | His | Ser |
| | | 210 | | | | | 215 | | | | | 220 | | | |
| Trp | Asn | Ser | Ser | Phe | Tyr | Arg | Leu | Arg | Phe | Glu | Leu | Arg | Tyr | Arg | Ala |
| 225 | | | | | 230 | | | | | 235 | | | | | 240 |
| Glu | Arg | Ser | Lys | Thr | Phe | Thr | Thr | Trp | Met | Val | Lys | Asp | Leu | Gln | His |
| | | | | 245 | | | | | 250 | | | | | 255 | |
| His | Cys | Val | Ile | His | Asp | Ala | Trp | Ser | Gly | Leu | Arg | His | Val | Val | Gln |
| | | | 260 | | | | | 265 | | | | | 270 | | |
| Leu | Arg | Ala | Gln | Glu | Glu | Phe | Gly | Gln | Gly | Glu | Trp | Ser | Glu | Trp | Ser |
| | | 275 | | | | | 280 | | | | | 285 | | | |
| Pro | Glu | Ala | Met | Gly | Thr | Pro | Trp | Thr | Glu | Ser | Arg | Ser | Pro | Pro | Ala |
| | | 290 | | | | | 295 | | | | | 300 | | | |
| Glu | Asn | Glu | Val | Ser | Thr | Pro | Met | Gln | Ala | Leu | Thr | Thr | Asn | Lys | Asp |
| 305 | | | | | 310 | | | | | 315 | | | | | 320 |
| Asp | Asp | Asn | Ile | Leu | Phe | Arg | Asp | Ser | Ala | Asn | Ala | Thr | Ser | Leu | Pro |
| | | | | 325 | | | | | 330 | | | | | 335 | |
| Val | Gln | Asp | Ser | Ser | Val | Pro | Leu | Pro | Thr | Phe | Leu | Val | Ala | Gly | Gly |
| | | | 340 | | | | | 345 | | | | | 350 | | |
| Gly | Ser | Leu | Ala | Phe | Gly | Thr | Leu | Leu | Cys | Ile | Ala | Ile | Val | Leu | Arg |
| | | | 355 | | | | | 360 | | | | | 365 | | |
| Phe | Lys | Lys | Thr | Trp | Lys | Leu | Arg | Ala | Leu | Lys | Glu | Gly | Lys | Thr | Ser |
| | | 370 | | | | | 375 | | | | | 380 | | | |
| Met | His | Pro | Pro | Tyr | Ser | Leu | Gly | Gln | Leu | Val | Pro | Glu | Arg | Pro | Arg |
| 385 | | | | | 390 | | | | | 395 | | | | | 400 |

```
Pro Thr Pro Val Leu Val Pro Leu Ile Ser Pro Val Ser Pro Ser
            405                 410                 415

Ser Leu Gly Ser Asp Asn Thr Ser Ser His Asn Arg Pro Asp Ala Arg
            420                 425                 430

Asp Pro Arg Ser Pro Tyr Asp Ile Ser Asn Thr Asp Tyr Phe Phe Pro
            435                 440                 445

Arg

<210> SEQ ID NO 83
<211> LENGTH: 346
<212> TYPE: PRT
<213> ORGANISM: Artificial Sequence
<220> FEATURE:
<223> OTHER INFORMATION: Polypeptide sequence of soluble human IL-6R
      isoform produced by differential mRNA splicing

<400> SEQUENCE: 83

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
        35                  40                  45

Gly Ser His Pro Ser Arg Trp Ala Gly Met Gly Arg Arg Leu Leu Leu
    50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Ala Asn Ile Thr Val Thr Ala Val
        195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300
```

```
Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Gly Ser Arg Arg Arg Gly Ser Cys Gly Leu
            340                 345

<210> SEQ ID NO 84
<211> LENGTH: 338
<212> TYPE: PRT
<213> ORGANISM: Artificial Sequence
<220> FEATURE:
<223> OTHER INFORMATION: Polypeptide sequence of soluble human IL-6R
      isoform produced by protease shedding

<400> SEQUENCE: 84

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
                20                  25                  30

Pro Glu Asp Asn Ala Thr Val His Trp Val Leu Arg Lys Pro Ala Ala
            35                  40                  45

Gly Ser His Pro Ser Arg Trp Ala Gly Met Gly Arg Arg Leu Leu Leu
        50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
    130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
    210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
    290                 295                 300

Glu Asn Glu Val Ser Thr Pro Met Gln Ala Leu Thr Thr Asn Lys Asp
```

```
305                 310                 315                 320
Asp Asp Asn Ile Leu Phe Arg Asp Ser Ala Asn Ala Thr Ser Leu Pro
                325                 330                 335

Val Gln

<210> SEQ ID NO 85
<211> LENGTH: 468
<212> TYPE: PRT
<213> ORGANISM: Artificial Sequence
<220> FEATURE:
<223> OTHER INFORMATION: Polypeptide sequence of predicted full length
      precursor cynomolgous monkey IL-6R

<400> SEQUENCE: 85

Met Leu Ala Val Gly Cys Ala Leu Leu Ala Ala Leu Leu Ala Ala Pro
1               5                   10                  15

Gly Ala Ala Leu Ala Pro Gly Gly Cys Pro Ala Gln Glu Val Ala Arg
                20                  25                  30

Gly Val Leu Thr Ser Leu Pro Gly Asp Ser Val Thr Leu Thr Cys Pro
            35                  40                  45

Gly Gly Glu Pro Glu Asp Asn Ala Thr Val His Trp Val Leu Arg Lys
50                  55                  60

Pro Ala Val Gly Ser His Leu Ser Arg Trp Ala Gly Val Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Pro Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Leu Ser Lys Thr Gln Thr Phe
            195                 200                 205

Gln Gly Cys Gly Ile Leu Gln Pro Asp Pro Pro Ala Asn Ile Thr Val
        210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Thr Gln Ala Pro Thr Thr
```

```
                    325                 330                 335

Asn Lys Asp Asp Asp Asn Ile Leu Ser Arg Asp Ser Ala Asn Ala Thr
            340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
    370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
    450                 455                 460

Phe Phe Pro Arg
465

<210> SEQ ID NO 86
<211> LENGTH: 33
<212> TYPE: PRT
<213> ORGANISM: Artificial Sequence
<220> FEATURE:
<223> OTHER INFORMATION: Polypeptide sequence of FR1 of ID-141V,
      ID-142V, ID-143V and ID-144V

<400> SEQUENCE: 86

Asp Val Gln Leu Val Glu Ser Gly Gly Gly Leu Val Gln Ala Gly Gly
1               5                   10                  15

Ser Thr Arg Leu Thr Cys Lys Ala Ser Gly Ser Ile Ser Asn Ile Asn
            20                  25                  30

Ser

<210> SEQ ID NO 87
<211> LENGTH: 14
<212> TYPE: PRT
<213> ORGANISM: Artificial Sequence
<220> FEATURE:
<223> OTHER INFORMATION: Polypeptide sequence of FR2 of ID-141V,
      ID-142V, ID-143V and ID-144V

<400> SEQUENCE: 87

Trp Tyr Arg Gln Ala Pro Gly Lys Gly Arg Glu Leu Val Ala
1               5                   10

<210> SEQ ID NO 88
<211> LENGTH: 32
<212> TYPE: PRT
<213> ORGANISM: Artificial Sequence
<220> FEATURE:
<223> OTHER INFORMATION: Polypeptide sequence of FR3 of ID-141V and
      ID-143V

<400> SEQUENCE: 88

Arg Phe Thr Ile Ser Arg Asp Ala Ala Lys Asn Thr Leu Tyr Leu Gln
1               5                   10                  15

Met Asn Ser Leu Arg Pro Glu Asp Thr Ala Val Tyr Tyr Cys Tyr Ala
            20                  25                  30
```

<210> SEQ ID NO 89
<211> LENGTH: 32
<212> TYPE: PRT
<213> ORGANISM: Artificial Sequence
<220> FEATURE:
<223> OTHER INFORMATION: Polypeptide sequence of FR3 of ID-142V and
      ID-144V

<400> SEQUENCE: 89

Arg Phe Thr Ile Ser Arg Asp Ala Ala Lys Asn Thr Val Tyr Leu Gln
1               5                   10                  15

Met Asn Ser Leu Arg Pro Glu Asp Thr Ala Val Tyr Tyr Cys Tyr Ala
            20                  25                  30

<210> SEQ ID NO 90
<211> LENGTH: 11
<212> TYPE: PRT
<213> ORGANISM: Artificial Sequence
<220> FEATURE:
<223> OTHER INFORMATION: Polypeptide sequence of FR4 of ID-141V,
      ID-142V, ID-143V and ID-144V

<400> SEQUENCE: 90

Trp Gly Gln Gly Thr Gln Val Thr Val Ser Ser
1               5                   10

<210> SEQ ID NO 91
<211> LENGTH: 107
<212> TYPE: PRT
<213> ORGANISM: Artificial Sequence
<220> FEATURE:
<223> OTHER INFORMATION: Polypeptide VHHR sequence of 7F6

<400> SEQUENCE: 91

Ser Gly Gly Gly Leu Val Gln Ala Gly Gly Ser Thr Arg Leu Thr Cys
1               5                   10                  15

Leu Ala Ser Gly Ser Ile Ser Ser Ile Asn Val Ile Gly Trp Tyr Arg
            20                  25                  30

Gln Ala Pro Gly Lys Gln Arg Glu Leu Val Ala Met Ile Gly Arg Gly
        35                  40                  45

Glu Gly Ala Asn Tyr Gly Asp Phe Ala Lys Gly Arg Phe Thr Ile Ser
    50                  55                  60

Arg Asp Asn Ser Lys Asn Thr Val Tyr Leu Gln Met Asn Ser Leu Lys
65                  70                  75                  80

Pro Glu Asp Thr Ala Val Tyr Tyr Cys Tyr Ala Asp Tyr Glu Asp Arg
                85                  90                  95

Asp Ser Pro Phe Asn Gly Ser Trp Gly Gln Gly
            100                 105

<210> SEQ ID NO 92
<211> LENGTH: 110
<212> TYPE: PRT
<213> ORGANISM: Artificial Sequence
<220> FEATURE:
<223> OTHER INFORMATION: Polypeptide VHHR sequence of 5G9

<400> SEQUENCE: 92

Ser Gly Gly Gly Leu Val Gln Ala Gly Gly Ser Thr Arg Leu Thr Cys
1               5                   10                  15

Lys Ala Ser Gly Ser Ile Phe Asn Ile Asn Ser Ile Asn Val Met Ala
            20                  25                  30

Trp Tyr Arg Gln Ala Pro Gly Lys Gln Arg Glu Leu Val Ala Ile Ile

```
                35                  40                  45
Gly Lys Gly Gly Gly Thr Asn Tyr Ala Asp Phe Val Lys Gly Arg Phe
         50                  55                  60

Thr Ile Ser Arg Asp Ala Ala Lys Asn Thr Val Asn Leu Gln Met Asn
 65                  70                  75                  80

Ser Leu Lys Pro Glu Asp Thr Ala Val Tyr Tyr Cys Tyr Ala Asp Tyr
                 85                  90                  95

Glu Asp Arg Asp Ser Pro Phe Asn Gly Ser Trp Gly Gln Gly
            100                 105                 110

<210> SEQ ID NO 93
<211> LENGTH: 107
<212> TYPE: PRT
<213> ORGANISM: Artificial Sequence
<220> FEATURE:
<223> OTHER INFORMATION: Polypeptide VHHR sequence of 21E6

<400> SEQUENCE: 93

Ser Gly Gly Gly Leu Val Leu Ala Gly Gly Ser Thr Arg Leu Thr Cys
 1               5                  10                  15

Leu Ala Ser Gly Ser Ile Ser Ser Ile Asn Val Ile Gly Trp Tyr Arg
             20                  25                  30

Gln Ala Pro Gly Lys Gln Arg Glu Leu Val Ala Met Ile Gly Arg Gly
         35                  40                  45

Glu Gly Ala Asn Tyr Gly Asp Phe Ala Lys Gly Arg Phe Thr Ile Ser
         50                  55                  60

Arg Asp Asn Ser Lys Asn Thr Val Tyr Leu Gln Met Asn Ser Leu Lys
 65                  70                  75                  80

Pro Glu Asp Thr Ala Val Tyr Tyr Cys Tyr Ala Asp Tyr Glu Asp Arg
                 85                  90                  95

Asp Ser Pro Leu Asn Gly Ser Trp Gly Gln Gly
            100                 105

<210> SEQ ID NO 94
<211> LENGTH: 107
<212> TYPE: PRT
<213> ORGANISM: Artificial Sequence
<220> FEATURE:
<223> OTHER INFORMATION: Polypeptide germline equivalent sequence of 7F6

<400> SEQUENCE: 94

Ser Gly Gly Gly Leu Val Gln Ala Gly Gly Ser Leu Arg Leu Ser Cys
 1               5                  10                  15

Ala Ala Ser Gly Ser Ile Phe Ser Ile Asn Ala Met Gly Trp Tyr Arg
             20                  25                  30

Gln Ala Pro Gly Lys Gln Arg Glu Leu Val Ala Ala Ile Thr Ser Gly
         35                  40                  45

Gly Ser Thr Asn Tyr Ala Asp Ser Val Lys Gly Arg Phe Thr Ile Ser
         50                  55                  60

Arg Asp Asn Ala Lys Asn Thr Val Tyr Leu Gln Met Asn Ser Leu Lys
 65                  70                  75                  80

Pro Glu Asp Thr Ala Val Tyr Tyr Cys Asn Ala Asp Tyr Glu Asp Arg
                 85                  90                  95

Asp Ser Pro Phe Asn Gly Ser Trp Gly Gln Gly
            100                 105

<210> SEQ ID NO 95
<211> LENGTH: 110
```

```
<212> TYPE: PRT
<213> ORGANISM: Artificial Sequence
<220> FEATURE:
<223> OTHER INFORMATION: Polypeptide germline equivalent sequence of 5G9

<400> SEQUENCE: 95

Ser Gly Gly Gly Leu Val Gln Ala Gly Gly Ser Leu Arg Leu Ser Cys
1               5                   10                  15

Ala Ala Ser Gly Ser Ile Phe Asn Ile Asn Ser Ile Asn Ala Met Gly
            20                  25                  30

Trp Tyr Arg Gln Ala Pro Gly Lys Gln Arg Glu Leu Val Ala Ala Ile
        35                  40                  45

Thr Ser Gly Gly Ser Thr Asn Tyr Ala Asp Ser Val Lys Gly Arg Phe
    50                  55                  60

Thr Ile Ser Arg Asp Asn Ala Lys Asn Thr Val Tyr Leu Gln Met Asn
65                  70                  75                  80

Ser Leu Lys Pro Glu Asp Thr Ala Val Tyr Tyr Cys Asn Ala Asp Tyr
                85                  90                  95

Glu Asp Arg Asp Ser Pro Phe Asn Gly Ser Trp Gly Gln Gly
            100                 105                 110

<210> SEQ ID NO 96
<211> LENGTH: 104
<212> TYPE: PRT
<213> ORGANISM: Artificial Sequence
<220> FEATURE:
<223> OTHER INFORMATION: Polypeptide germline equivalent sequence of
      21E6

<400> SEQUENCE: 96

Gly Leu Val Gln Ala Gly Gly Ser Leu Arg Leu Ser Cys Ala Ala Ser
1               5                   10                  15

Gly Ser Ile Phe Ser Ile Asn Ala Met Gly Trp Tyr Arg Gln Ala Pro
            20                  25                  30

Gly Lys Gln Arg Glu Leu Val Ala Ala Ile Thr Ser Gly Gly Ser Thr
        35                  40                  45

Asn Tyr Ala Asp Ser Val Lys Gly Arg Phe Thr Ile Ser Arg Asp Asn
    50                  55                  60

Ala Lys Asn Thr Val Tyr Leu Gln Met Asn Ser Leu Lys Pro Glu Asp
65                  70                  75                  80

Thr Ala Val Tyr Tyr Cys Asn Ala Asp Tyr Glu Asp Arg Asp Ser Pro
                85                  90                  95

Leu Asn Gly Ser Trp Gly Gln Gly
            100
```